(12) United States Patent
Burmeister

(10) Patent No.: US 7,267,954 B2
(45) Date of Patent: Sep. 11, 2007

(54) METHODS FOR THE DETECTION OF VARIANT CAYMAN ATAXIA NUCLEIC ACIDS

(75) Inventor: Margit Burmeister, Ann Arbor, MI (US)

(73) Assignee: Regents of the University of Michigan, Ann Harbor, MI (US)

( * ) Notice: Subject to any disclaimer, the term of this patent is extended or adjusted under 35 U.S.C. 154(b) by 260 days.

(21) Appl. No.: 10/699,941

(22) Filed: Nov. 3, 2003

(65) Prior Publication Data
US 2004/0146900 A1 Jul. 29, 2004

Related U.S. Application Data

(60) Provisional application No. 60/424,973, filed on Nov. 8, 2002, provisional application No. 60/422,971, filed on Nov. 1, 2002.

(51) Int. Cl.
*C07H 21/04* (2006.01)
*C12Q 1/68* (2006.01)

(52) U.S. Cl. ............. 435/6; 435/91.1; 435/91.2; 536/23.1; 536/24.3

(58) Field of Classification Search ............ None
See application file for complete search history.

(56) References Cited

U.S. PATENT DOCUMENTS

2003/0092019 A1* 5/2003 Meyer et al. ............ 435/6

OTHER PUBLICATIONS

Nystuen et al. (Human Mol. Genetics, vol. 5, No. 4, pp. 525-531, 1996).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Nagase et al. (Genbank Accession No. AB058775, Jun. 2001).*
Nagase et al. (DNA Research, vol. 8, pp. 85-95, 2001).*
Johnson et al., Neurology 28:352 [1978].
Brown et al., Neurology 34:273 [1984].
Nystuen et al., Hum. Mol. Genet. 5:525 [1996].
Brusadelli et al., Int J Dev Neurosci. 18:317 [2000].
Zhang et al., Circ. Res. 90:1251 [2002].
Lee and McKinnon, Apoptosis 5:523 [2000].
Kapfhamer et al., Genomics 35:533 [1996].
Dietrich et al., Genetics 131:423 [1992.
Reese et al., J. Comput. Biol. 4:311 [1997].
Boyd et al., Cell 79:341 [1994].
Stocker et al., Structure (Camb) 10:1533 [2002.
Sha et al., Nature 391:506 [1998].
Ouhchi et al., Nat Genet. 9:141 [1995].

* cited by examiner

*Primary Examiner*—Jeanine A. Goldberg
(74) *Attorney, Agent, or Firm*—Medlen & Carroll, LLP

(57) ABSTRACT

The present invention relates to ataxia, in particular to protein and nucleic acids encoding proteins associated with ataxia. The present invention provides assays for the detection of ataxia polymorphisms and mutations associated with disease or disease carrier states.

6 Claims, 59 Drawing Sheets

Figure 1
SEQ ID NO:1

ACACAAAAGCAGCTTCCTCCACTATCTGAGGGAAAGACAGAGCCTCAGCCATCAGAAAGG
GAAAAGCCAGAGCCGCGGCAGGCCTGGGCTGCGATGGCAGGGGAAACAGTGACTAAAGGG
GGACAGGGGTGCTGCTACTAACCCACGGCGCCGCCTTCTACAGTTGGGCCGGACAGGTGT
GCTGTGGCCACGTCGCCCTGGGTGACCTTCCTCAGATGTGGACTTGGCCCTGAGCATCCT
TCCACCAGGCCCCTCGCCTGGGTACCATCGAGAAATGCCCGCCTTTGTGTCCAAGTGACA
GCGCAGAGGCAGCTTCCGCTACCGAGATCATCTTCTGGGTCACCCGAGTTTCCAGACCAC
TTCTCTTTCCAGCTCTCATGGGAACCACAGAAGCTACACTAAGGATGGAAAATGTGGACG
TGAGGGATGAATGGCAGGATGAGGATCTGCCCAGACCGCTCCCAGAAGACACCGGGGTGG
AGCGGCTGGGTGGCGCAGTGGAAGACTCCTCCTCACCTCCCTCCACCCTGAACTTGAGCG
GAGCACATCGAAAGAGAAAGACGCTGGTGGCTCCAGAGATCAACATCTCCCTGGACCAAA
GCGAGGGCTCTCTGCTGTCCGACGACTTCCTCGACACACCTGATGACCTGGACATCAATG
TGGACGACATTGAGACGCCAGATGAAACTGACTCT
CTGGAGTTCTTGGGAAATGGCAATGAACTTGAGTGGGAAGATGACAC
CCCAGTGGCCACCGCCAAAAACATGCCTGGTGACAGTGCGGACCTGTTTGGGGACGGCTC
TGCGGAAGACGGCAGTGCGGCCAACGGTCGTCTGTGGCGAACTGTCATCATAGGGGAGCA
AGAGCATCGCATCGACCTGCATATGATCCGGCCCTACATGAAGGTGGTCACCCATGGAGG
ATACTACGGGGAAGGTCTCAACGCCATCATCGTGTTTGCAGCCTGCTTCCTGCCAGATAG
CAGCTCCCCAGACTATCACTACATCATGGAGAATCTCTTCCTGTACGTCATCAGCAGCCT
TAAACTGCTCGTGGCTGAGGACTACATGATCGTGTATCTGAACGGCGCCACGCCCCGGAG
GAGGATGCCTGGCATTGGTTGGCTGAAGAAGTGTTACCACATGATTGACAGGAGACTGAG
GAAGAATCTAAAGTCCCTGATCATCGTCCACCCCTCCTGGTTCATTCGCACTGTGTTGGC
CATCTCCCGGCCATTCATCAGTGTCAAGTTCATCAGTAAAATTCAGTACGTGCACAGCCT
GGAAGAGCTGGAGCGACTGATTCCCATGGAACACGTGCAGCTGCCAGACTGTGTCCTGCA
ATATGAAGAGCAGAGACTCCGAGCCAAGAGGGAGAGCACACGGCCACCGCAGCCGGAGTT
CCTCCTTCCCAGGTCAGAAGAAAAGCCAGAGACTGTGGAAGAAGAGGACAGGGCAGCAGA
GGCAACAGAGGACCAGGAAACTAGCATGTCCTGATCTACCCAGAACCTAGACATGGACAG
AGATTATTCCCAACATCATGTAACCCTCATCCGAAGCCCTGGGAGCCCCGCCTTCATCGA
GCCTCCACCGCCTGAGGATGCCTGGCTCCACCATGTCCCTGCACCCGGGTCCTCTCACT
GCTTGAGTCCATTTCACTGTTTTATTTTGAAGAAGGCGGTATGAGCACATCTCGGAATG
GAGCAGGTTCTTGACCCTTTCACAGTCTGGGCTTGTGGATGCCAAAGGTGGATGTGG
GCAGTGCCACCCACGGTTACTCTTCCAGGCCTTGGCATCCCCAAGATGCCCTTCTCTGTC
CCAGCTAGGATAACACAGATATGCATTTGGGCTGACCCAATGAGAGACCCTTTGCTCGG
TTGCCACCTGTCCCTAGCTGGAGCCTCAGATGTCTGGTGGCCCTGGCTGCAGCTGCATCT
GCTTCTCTGTGGAATGTGACCCACTGTCCCCTCTCCTGCCACCCCAGGCAGGGTTGTGA
CTGCTGACCTCACATCTCCACCTGACATGCACTATTCTGCCATTTGACTGTCTTTGGGGG
CCTTCAAGCCCATTGCACATGTACTGATCAGCCTGGTGGTCAACAAACCCAACATTTTGA
GCTCCTTTAAAGTAGATGTGACTCCAAAAAAAAAAAAAAAAAAAAAAAA

Figure 2
SEQ ID NO:2

```
MGTTEATLRMENVDVRDEWQDEDLP
RPLPEDTGVERLGGAVEDSSSPPSTLNLSGAHRKRKTLVAPEINISLDQS
EGSLLSDDFLDTPDDLDINVDDIETPDETDSLEFLGNGNELEWEDDTPVA
TAKNMPGDSADLFGDGSAEDGSAANGRLWRTVIIGEQEHRIDLHMIRPYM
KVVTHGGYYGEGLNAIIVFAACFLPDSSSPDYHYIMENLFLYVISSLELL
VAEDYMIVYLNGATPRRRMPGIGWLKKCYHMIDRRLRKNLKSLIIVHPSW
FIRTVLAISRPFISVKFISKIQYVHSLEELERLIPMEHVQLPDCVLQYEE
QRLRAKRESTRPPQPEFLLPRSEEKPETVEEEDRAAEATEDQETSMS
```

Figure 3
SEQ ID NO:3

```
   1   gccgagcctc tgccagccct gagctgggaa gaagcagcta cctcggaggc agggcgcgca
  61   ggcgggcggc gatgagaggg ggcgcagccg cagccccgcg ctggggagcc caccgctaac
 121   cctgcacccc acccacccct gcacaaaaga gctggcgggc gctggccacg tcgccctggg
 181   tgaccttcct cggatgcaga atccgcccct gcgagcatcc tcttcctcct aggctctgaa
 241   ggcccgggga gcgtgagcga tgcccagctg cacccgggca gggctcgcct ttgtttgcca
 301   gtaaggagga gaggctgtct cagctgcaga ggggtcatcc ctgcttcaag ccagtgcctc
 361   ttcccagctc ccatggggac caccgaagcc acgctccgga tggaaaacgt ggacgtgaag
 421   gaggaatggc aggacgaaga tcttcccagg ccactcccag aagagacggg ggtggaactg
 481   cttggcagcc cggtggaaga cacatcctct cctcccaaca cgctaaattt caacggagcg
 541   catcgtaaga ggaagacgct ggtggcccca gagatcaaca tttctctgga tcagagtgag
 601   gggtccctgc tgtccgatga cttcttggat acccctgatg acctggatat taacgtggat
 661   gacatcgaga cccccgatga gaccgactcg ctggagttcc tggggaatgg caacgaactg
 721   gagtgggaag acgacacccc cgtggccacc gccaagaaca tgcccgggga gcgcgcggat
 781   ctatttgggg acggcacgac ggaggacggc agcgccgcca acgggcgcct gtggcggaca
 841   gtgatcatcg gggagcaaga gcaccgtata gacctgcaca tgatccggcc ttacatgaaa
 901   gtggtcaccc acggagggta ctacggcgaa ggcctcaacg ccatcatcgt cttcgcagcc
 961   tgcttccttc agacagcag cctccccgac taccactaca tcatggagaa cctcttcctg
1021   tacgtcatca gcagcttaga gctcctggtg gctgaggact acatgatcgt gtacctgaac
1081   ggtgccacgc cccggcggag gatgcctgga atcggctggc tgaagaagtg ctaccagatg
1141   atcgaccgga ggttgcggaa aaacctgaag tccttgatca tcgtccaccc ctcgtggttc
1201   attcggactg tgctggccat ctctcgccct ttcatcagcg tcaagttcat caacaagatc
1261   cagtacgtgc acagcttgga agacctggag caactcatcc ctatggaaca cgtccagatc
1321   ccagactgcg tcctgcaata cgaagaggaa agactgaagg ccaggaggga gagcgcgagg
1381   ccccagccgg agtttgtgct gcccaggtct gaagagaagc cagaggtggc accagtggaa
1441   aacaggtctg ctctggtctc agaagatcag gaaacaagca tgtcctgagg cgacgtgagc
1501   ataacaaagg acatggaaga agattccaga tgccagaaaa cctctgtcag acgcccactg
1561   gccccagatc tcatcctgcc tcatcctgag tcccaatctt ccaagggtgc agcccctcc
1621   gttcatctct gaaacccagc atccttttca gctgcttgaa acattgtat ttttttttt
1681   taacgatgca gtatttgtgc gttccagaaa agggcccagc tctgagcccc tcaccttcc
1741   acactcacga actctcagcc gaggaaggca agaagcgcag ggggtggccc gcgtggcgtc
1801   ggtggcctcc gctcctgctc gcagcccctg tggtcagagc tggatacaag attcaagacc
1861   cttctcttgc ttgtcacccg ctccaggttg gagccacaga cacccaccgc caccccggct
1921   gggtctgcgt cctttcctgt gcctttccct ccagaatgcg gcctcagacc tagaagctca
1981   acccccctat gagggccacg tcctggggta gtcctgacc tccgacctta tgtccaaatt
2041   tcacacccat ggttttcat ttgacccgcc ccttctcgc tcataatgac acccagctcc
2101   tttgagagga tcagagccca ttgcacaaga agagccgctg ccaaccatcc ttgtcctccg
2161   attgcaaaat gacaccccag taatctagaa cattctcaag cccctttaac tcagatgtca
2221   agccaccggg caaaccccgt caatacctcc caccaaggaa tgagatatgt ggacctcact
2281   gctcccccaa cccagcgtca ggctgggaca cgccaacgct gttccgggtt ggaacagcag
2341   aggctcagaa actggctctg aaataggcag acctagcaag aggaagatac agggtatcgg
2401   gcgtttgagt gtttcagaag tcattcggga agataaatcc agtgcgctgg ccgcagccac
2461   ctgcattcaa agcttggacc agcgggttct tgttcgggag gcaaatttcc ctaggaaaaa
2521   gaagacagac ttttctaatg tggtccaaat gcggatcact ggtcagatgg actctagaag
2581   cactgagctc cctgtctctg gaagtattta agaaaaggct gggccaggca cgatggctca
2641   cgcctgtaat cccagacttt gggaggccga ggcaggcgga tcacctgagg tgaggagttt
2701   gagaacagcc tggccaacat ggtgaaacct catctctact aaaaatacaa aaattagcca
2761   ggcgtggtgg caggtgcctg taatcccagc tacttgggag gctgaggcat gagaatcact
2821   taaacctgag aggcagaggt tacagtgagc caagatcgtg ccactgcatt ccagcctggg
2881   cgacagagca agactctgtc tcaaaaaaaa aaaaaaa
```

Figure 4
SEQ ID NO:4

MGTTEATLRMENVDVKEEWQDEDLPRPLPEETGVELLGS
PVEDTSSPPNTLNFNGAHRKRKTLVAPEINISLDQSEGSLLSDDFLDTPDDLDINVDD
IETPDETDSLEFLGNGNELEWEDDTPVATAKNMPGDSADLFGDGTTEDGSAANGRLWR
TVIIGEQEHRIDLHMIRPYMKVVTHGGYYGEGLNAIIVFAACFLPDSSLPDYHYIMEN
LFLYVISSLELLVAEDYMIVYLNGATPRRRMPGIGWLKKCYQMIDRRLRKNLKSLIIV
HPSWFIRTVLAISRPFISVKFINKIQYVHSLEDLEQLIPMEHVQIPDCVLQYEEERLK
ARRESARPQPEFVLPRSEEKPEVAPVENRSALVSEDQETSMS

Figure 6

```
                         91                                                                                                        180
1 huKIAA1872  MGTTEATLRMENVDV KEEWQDEDLPRPLPE ETGVELLGSPVEDTS SPPNTLNFNGAHRKR KTLVAPEINISLDQS EGSLLSDDFLDTPDD
2 Macaque     MGTTEATLRMENVDV KEEWQDEDLPRPLPE ETGVELLGSPVEDTS SPPNTLNFNGAHRKR KTLVAPDINISLDQS EGSLLSDDFLDTPDD
3 mujittery   MGTTEATLRMENIVV RDEWQDEDLPRPLPE DTGVERLGGAVEDSS SPPSTLNLSGAHRKR KTLVAPEINISLDQS EGSLLSDDFLDTPDD
4 huBNIP2     --------MEGVEL KEEWQDEDFPIPLPE DDSIEADILAITGPE DQPGSLEVN-GNKVR KKLMAPDISLTLDPS DGSVLSDDLDES---
5 muNIP2      --------MEGVEL KEEWQDEDFPIPLPE DDSIEADILAITGPE DQPGSLEVN-GNKVR KKLMAPDISLTLDPS DGSVLSDDLDES---

91                            106              121              136              151              165    166              180
1 huKIAA1872  LDINVDDIETPDETD SLEFLGNGNELEWED DTPVATAKNMPGDSA DLFGDGTTEDGSAAN GRLWRTVIIGEQEHR IDLHMIRPYMKVVTH
2 Macaque     LDINVDDIETPDETD SLEFLGNGNELEWGD DTPVATAKNMPGDSA DLFGDGTTEDGGAAN GRLWRTVIIGEQEHR IDLHMIRPYMKVVTH
3 mujittery   LDINVDDIETPDETD SLEFLGNGNELEWED DTPVATAKNMPGDSA DLFGDGSAEDGSAAN GRLWRTVIIGEQEHR IDLHMIRPYMKVVTH
4 huBNIP2     GEIDLDGLDTPSE-- ------NSNEFEWED DLPKPKTTEVIRKGS ITEYTAAEEK---ED GRRWRMFRIGEQDHR VDMKAIEPYKKVISH
5 muNIP2      GEIDLDGLDTPSE-- ------NSNEFEWED DLPKPKTTEVIRKGS ITEYTAAEEK---ED GRRWRMFRIGEQDHR VDMKAIEPYKKVISH 181              196              211              226              241              255    256              270
1 huKIAA1872  GGYYGEGLNAIIVFA ACFLPDSSLPDYHYI MENLFLYVISSLELL VAEDYMIVYLNGATP RRRMPGIGWLKKCYQ MIDRRLRKNLKSLII
2 Macaque     GGYYGEGLNAIIVFA ACFLPDSSLPDYHYI MENLFLYVISSLELL VAEDYMIVYLNGATP RRRMPGIGWLKKCYQ MIDRRLRKNLKSLII
3 mujittery   GGYYGEGLNAIIVFA ACFLPDSSSPDYHYI MENLFLYVISSLKLL VAEDYMIVYLNGATP RRRMPGIGWLKKCYH MIDRRLRKNLKSLII
4 huBNIP2     GGYYGDGLNAIVVFA VCFMPESSQPNYRYL MDNLFKYVIGTLELL VAENYMIVYLNGATT RRKMPSLGWLRKCYQ QIDRRLRKNLKSLII
5 muNIP2      GGYYGDGLNAIVVFA VCFMPESSQPNYRYL MDNLFKYVIGTLELL VAENYMIVYLNGATT RRKMPSLGWLRKCYQ QIDRRLRKNLKSLII 271              286              301              316              331              345    346              360
1 huKIAA1872  VHPSWFIRTVLAISR PFISVKFINKIQYVH SLEDLEQLIPMEHVQ IPDCVLQYEEERLKA RRESARP-QPEFVLP RSEEKPEVAPVENRS
2 Macaque     VHPSWFIRTVLAISR PFISVKFINKIQYVH SLEDLEQLIPMEHVQ IPDCVLQYEEERLKA RRESARP-QPEFVMP RSEEKPEVAPVENRS
3 mujittery   VHPSWFIRTVLAISR PFISVKFISKIQYVH SLEELERLIPMEHVQ LPDCVLQYEEQRLRA KRESTRPPQPEFLLP RSEEKPETVEEEDRA
4 huBNIP2     VHPSWFIRTLLAVTR PFISSKFSQKIRYVF NLAELAELVPMEYVG IPECIKQVDQELNGK QDEPKNEQ-------   ---------------
5 muNIP2      VHPSWFIRTLLAVTR PFISSKFSQKIRYVF NLAELAELVPMEYVG IPECIKQVDQELNGK QDEPKNEQ-------   ---------------

361              375
1 huKIAA1872  ALVSEDQETSMS 371
2 Macaque     APVTEDQETSMS 371
3 mujittery   AEATEDQETSMS 372
4 huBNIP2     ------------ 314
5 muNIP2      ------------ 314
```

Figure 8
SEQ ID NO:8

```
   1   gccgagcctc tgccagccct gagctgggaa gaagcagcta cctcggaggc agggcgcgca
  61   ggcgggcggc gatgagaggg ggcgcagccg cagccccgcg ctggggagcc caccgctaac
 121   cctgcacccc acccacccct gcacaaaaga gctggcgggc gctggccacg tcgccctggg
 181   tgaccttcct cggatgcaga atccgcccct gcgagcatcc tcttcctcct aggctctgaa
 241   ggcccgggga gcgtgagcga tgcccagctg cacccgggca gggctcgcct ttgtttgcca
 301   gtaaggagga gaggctgtct cagctgcaga ggggtcatcc ctgcttcaag ccagtgcctc
 361   ttcccagctc ccatggggac caccgaagcc acgctccgga tggaaaacgt ggacgtgaag
 421   gaggaatggc aggacgaaga tcttcccagg ccactcccag aagagacggg ggtggaactg
 481   cttggcagcc cggtggaaga cacatcctct cctcccaaca cgctaaattt caacggagcg
 541   catcgtaaga ggaagacgct ggtggcccca gagatcaaca tttctctgga tcagagtgag
 601   gggtccctgc tgtccgatga cttcttggat acccctgatg acctggatat taacgtggat
 661   gacatcgaga cccccgatga accgactcg ctggagttcc tggggaatgg caacgaactg
 721   gagtgggaag acgacacccc cgtggccacc gccaagaaca tgcccgggga cagcgcggat
 781   ctatttgggg acggcacgac ggaggacggc agcgccgcca cgggcgcct gtggcggaca
 841   gtgatcatcg gggagcaaga gcaccgtata gacctgcaca tgatccggcc ttacatgaaa
 901   gtggtcaccc acggagggta ctacggcgaa ggcctcaacg ccatcatcgt cttcgcagcc
 961   tgcttccttc cagacagcag cctccccgac taccactaca tcatggagaa cctcttcctg
1021   tacgtcatca gcagcttaga gctcctggtg gctgaggact acatgatcgt gtacctgaac
1081   ggtgccacgc cccggcggag gatgcctgga atcggctggc tgaagaagtg ctaccagatg
1141   atcgaccgga ggttgcggaa aaacctgaag tccttgatca tcgtccaccc ctcgtggttc
1201   attcggactg tgctggccat ctctcgccct ttcatcagcg tcaagttcat caacaagatc
1261   cagtacgtgc acaggttgga agacctggag caactcatcc ctatggaaca cgtccagatc
1321   ccagactgcg tcctgcaata cgaagaggaa agactgaagg ccaggaggga gagcgcgagg
1381   ccccagccgg agtttgtgct gccaggtct gaagagaagc cagaggtggc accagtggaa
1441   aacaggtctg ctctggtctc agaagatcag gaaacaagca tgtcctgagg cgacgtgagc
1501   ataacaaagg acatggaaga agattccaga tgccagaaaa cctctgtcag acgcccactg
1561   gccccagatc tcatcctgcc tcatcctgag tccaatctt caagggtgc cagccctcc
1621   gttcatctct gaaacccagc atccttttca gctgcttgaa acattgtat ttttttttttt
1681   taacgatgca gtatttgtgc gttccagaaa agggcccagc tctgagcccc tcacccttcc
1741   acactcacga actctcagcc gaggaaggca agaagcgcag ggggtggccc gcgtggcgtc
1801   ggtggcctcc gctcctgctc gcagcccctg tggtcagagc tggatacaag attcaagacc
1861   cttctcttgc ttgtcacccg ctccaggttg gagccacaga cacccaccgc caccccggct
1921   gggtctgcgt cctttcctgt gcctttcct ccagaatgcg gcctcagacc tagaagctca
1981   accccctat gagggccacg tcctggggta gctcctgacc tccgaccttca tgtccaaatt
2041   tcacacccat ggttttcat ttgacccgcc ccttctcgc tcataatgac acccagctcc
2101   tttgagagga tcagagccca ttgcacaaga agagccgctg ccaaccatcc ttgtcctccg
2161   attgcaaaat gacaccccag taatctgaga cattctcaag ccccttttaac tcagatgtca
2221   agccaccggg caaacccgt caatacctcc caccaaggaa tgagatatgt ggacctcact
2281   gctcccccaa cccagcgtca ggctgggaca cgccaacgct gttccgggtt ggaacagcag
2341   aggctcagaa actggctctg aaataggcag acctagcaag aggaagatac agggtatcgg
2401   gcgtttgagt gtttcagaag tcattcggga agataaatcc agtgcgctgg ccgcagccac
2461   ctgcattcaa agcttggacc agcgggttct tgttcgggag gcaaatttcc ctaggaaaaa
2521   gaagacagac ttttctaatg tggtccaaat gcggatcact ggtcagatgg actctagaag
2581   cactgagctc cctgtctctg gaagtattta agaaaaggct gggccaggca cgatggctca
2641   cgcctgtaat cccagacttt gggaggccga ggcaggcgga tcacctgagg tgaggagttt
2701   gagaacagcc tggccaacat ggtgaaacct catctctact aaaaatacaa aaattagcca
2761   ggcgtggtgg caggtgcctg taatcccagc tacttgggag gctgaggcat gagaatcact
2821   taaacctgag aggcagaggt tacagtgagc caagatcgtg ccactgcatt ccagcctggg
2881   cgacagagca agactctgtc tcaaaaaaaa aaaaaaa
```

Figure 9
SEQ ID NO:9

MGTTEATLRMENVDVKEEWQDEDLPRPLPEETGVELLGS
PVEDTSSPPNTLNFNGAHRKRKTLVAPEINISLDQSEGSLLSDDFLDTPDDLDINVDD
IETPDETDSLEFLGNGNELEWEDDTPVATAKNMPGDSADLFGDGTTEDGSAANGRLWR
TVIIGEQEHRIDLHMIRPYMKVVTHGGYYGEGLNAIIVFAACFLPDSSLPDYHYIMEN
LFLYVISSLELLVAEDYMIVYLNGATPRRRMPGIGWLKKCYQMIDRRLRKNLKSLIIV
HPSWFIRTVLAISRPFISVKFINKIQYVHRLEDLEQLIPMEHVQIPDCVLQYEEERLK
ARRESARPQPEFVLPRSEEKPEVAPVENRSALVSEDQETSMS

Figure 10-1

SEQ ID NO:10

```
  1 ggaagccgag cctctgccag ccctgagctg ggaagaagca gctacctcgg aggcagggcg
 61 cgcaggcggg cggcgatgag aggggggcgca gccgcagccc cgcgctgggg agcccaccgc
121 taaccctgca ccccacccac ccctgcacaa aagagctggc gggcgctggc cacgtcgccc
181 tgggtgacct tcctcggatg cagaatccgc ccctgcgagc atcctcttcc tcctaggctc
241 tgaaggcccg gggagcgtga gcgatgccca gctgcacccg ggcagggctc gcctttgttt
301 gccagtaagg aggagaggct gtctcagctg cagaggtgag tgcgcgcatc tccccttctc
361 ccaggataaa ccgtctccct ggaaggttta tccggcagcc tttgccgcct ctaaatccct
421 ttccagcaga tggggcgggt gggagcagag agccacggtc ttgtgactcc gtgaaggccc
481 tcacatccct gttcccggta ccagggaaaa ccgttccctg agctgcgccc agcaacacag
541 tttaccttcc gcgcgcaccg ttcccctcta agtgcaccat tttcaggaca cgctgagagc
601 tcgggcggat gaaaacctca gcttctctct gggacgctga aatagaccca tcctagccct
661 atgtatttcc tatttataac gctaggaagg ccaccagccg acgatttcgg gaaaaaaaaa
721 aaaaaaaaat ctaagtgtgt cgataaaggc tgtcctgtgg ggtggggagg aaggggggtgg
781 tttatggttt aagacacaga tgcctcctcc ttattggaac tcgtatgtga tttgttaata
841 atcagacatc agggctcaaa tgagcgcttc actcccgttc cttgatgtca ctgtcttctt
901 ttggccgtcc ccaaatgcga agccaggatc tgagtgcagg agtgtccggg gcccactgag
961 gacccacccc accccatcct tagaagactg tggagtcaac gcctgtggct gcagctggca
1021 gggggtgggg gtcgggggcg gggctggtgg gagtgttcct ggggctgag gtcaccccca
1081 gctcagtata aggaagggag aggcgaagac cccttcctcc ggagagcaaa tgcgtttcta
1141 ctgccgagga gaacttaccc tcgcgggaag ggcctggctg gctgctgcca ccgccccccc
1201 cccgacccca tagcatccag gagggatttt ttttttttcc atgctgcgtg ttactgtccc
1261 tcctccaagc atgaatgacg acattgagga cagagaatcg agtgagaaac gctcaccctg
1321 tacggggggag ggtctagttt tagccgtccc ctccccccac ttcctcatct ggctgaggct
1381 gcctctgggt ccttccttgc taagccacag tccctgtcc ccgatgcaaa cccgatatct
```

Figure 10-2

```
    1441 atgctggggg gctgcaggta acctactcca cagagaggca gcctggatgc
catgagagtt
    1501 gggggcctta gatgcttcat gtatttggtt tttttgagac agggtcttgc
tatcttgccc
    1561 gggctggtct taacctcctg tgctcaggcg atcctcgcaa agtgctggga
ttacacgtgt
    1621 gagccactgc cccagccag atgctttatc ttttatttta tttttttgaag
tagggtctct
    1681 gttgctcagg ctggaaagca gtggcatgat catagctcac tgcagtctcg
acctcctggt
    1741 ctcaagcgat cctccaactt cagcctcctg aatagctggg acttcaggca
ccaggcaccc
    1801 atcaccatgt ttggttaatt tttgtatttt tttttttta agagatgggg
acttgctatg
    1861 ttgcccaggc tggtcttgac cttccaggct caagcgatcc tcctatctca
gcctcccaaa
    1921 gtgctgggga ttacacgtgt gagccactgc cccagccag atgccttatt
ttattttatt
    1981 ttattttctg aaatagaacc tcactctgtt gctcaggctg gaatgtggtg
gcacaatcat
    2041 acctcactgc agcctccacc tcctgggctc aggcaatcct cccacctcag
cctcctgaac
    2101 agctgtgact tcaggcaccc accaaattta attaattttt gtttttgttt
ttgcttttcg
    2161 tagagatggt gtcttgctat gttgcccagg ctggtcttga ccttctgggc
tcaatcctcc
    2221 cacctcagcc tcctgaatag ctaagacctc aggcacccac cattgtgctt
ggttagtttt
    2281 tgtattttt tttttgagaga tggggtcttg ctgtgttgcc caggctggtc
tcgaacccct
    2341 ggtctcaagt gatctgccca aagtgctgga attccaggca tgcaccactg
cacccagccc
    2401 ctagacgctt taaaaagtgg atctagtggc ccggcagggt ggctcacacc
tgtaatccca
    2461 gcactttggg aggcaggtgg atcatgaggt caggagttcg agaccagcct
ggccaatata
    2521 gtgaaacccc atctctacta aaaatacaaa aattagctgg acgtggtggc
acgcgcctgt
    2581 agtccaagct actcaagagg tggaggttgc agtgagccga gatcgcacca
ctgcactcta
    2641 gcctgggcga cagagcgaga ctctgtctca aaaaaaaaat gacaacaaaa
aaagtggatc
    2701 tagctactcg gaagctgttg agagacagac agaggtaatg gaaggacaga
gtgtacaata
    2761 ctctataatg actgccggac acaggcctga aatcctttcg caaacacggg
aatgcacaca
    2821 gaaatgacta ttgcctttaa gacaaggttt ctccaccttg gatctatgga
tatttgggac
    2881 ccagtcattc ttggtcatgg gcggccatcc tgggcactgt aaggtgctga
gcagcacccc
    2941 tggcctgccc aggggggcact ccttcccctc agttgtgaca aaagtgcctc
tagacaatgc
    3001 caagtgtccc cttgcagcag gggaggcaga attgtccaca ggtgcaaagc
actggtttca
```

Figure 10-3

```
3061 aagcccaaaa cagatggggt tggttgagtc ataagatgct ggtatgttat
gtccaaaagg
3121 tatcttagag gtcatctcta attcaactct tttgtttaca gaaagggaaa
ctgagaccca
3181 gagagggaga tggtctgaga gtctgccatg ccccagagca gaccacaact
cagtctcacc
3241 tggcagctct gatcctggcc cccacccaga ctgctccccc ctgccctgcc
cctgcccctg
3301 cccccagtga gctcctcaga acaagaaaaa caaaactggt gtgggggtg
gggcggcaca
3361 gtggctcaca cctgtaatcc cagcgctctg ggaggctgag gcaagaggat
cacctgagcc
3421 cgaaagttca agaccagcct gggtgacata ccaagatcag agaaattagc
caggcatgat
3481 ggcacacact cgtggtccca gatacttggg aggctgaggc aggaggatcg
cttgagccca
3541 ggagttggag gctgtagtga gctgggatca caccactgca ctccagcctg
ggcgacagag
3601 caagaccccg tctctaaata aataaataaa taaataaagt ggcattttgt
ggtagtaaag
3661 atgagggtct cctttctaac cccagtctct ttccacactg ccttagtgag
ccctggagtc
3721 agaaagtcac taggacttgc ttgagggagg acagagaggc aggacaggtg
gcctggtaca
3781 tatggcagat agcgatgggt tagagcctac tggattctct ttgaacttgg
cattcccagc
3841 acggaagctg aagtatatca gccattcaca ctttagtatg aatgactgtt
tggatttctt
3901 gctttctagt tgaggtccaa ggcacaagag ggagggtaag tctatctggg
tcatggctca
3961 ccctggagaa ggtagatttc gaagtttcca agggagcagg acttgtatct
gaaggctcag
4021 cctctcgccc acgttcaaac tctgaacccc actgtgcatc ctaagctctc
tgtgcctctg
4081 ttttctcatc tgtaaaacag gggaacctca tggggctcgg tgatggttca
ataagaagtg
4141 ctggccgggc acagtggttt acccttgtaa tctcagcgct tagagaggcc
gaggcaggag
4201 gattgcttga gcccaagagt ttgagaccac cctggccaac atagcaagac
ccaatctctt
4261 aaaaaaagat tttaaaaaat tacccaggca tgatggtaca cacctgtggt
cacagctact
4321 ggtgggggc tgaggcagga ggattgctta agcccaggag ttcaaggctg
ccatgagcca
4381 tgattgtgcc cctgcactcc agcccaggca acagagcaag atcatgtttt
ttttttttaaa
4441 aaaaaaaaa aaaaaaaaa aaacagccaa gctcagtggc tcacccctgt
aatcccagca
4501 ctttgggagg ctgaggcggg tagaccgctt gagctcagga gtttgagacc
agcctggcca
4561 acacagtgaa accccgtctc tattaaaaat acaaaaatta gccgggtgtg
atggctcaag
4621 cctgtaatcc cagcactttg ggaggccaag gcaggaggat cacctgaggt
caggagttcg
```

Figure 10-4

```
    4681 agaccagcct ggccaacatg gcgaaaccct gtctctacta aaaatacaag
aattaaccag
    4741 gcgtggtgat gggtgcctgt aacccagct acttgggagg ctgaggcggg
agaatcgctt
    4801 gagcctggaa ggtggatgtt gcagtgagct gagatggcac cattgcacta
cagcctgggc
    4861 aacagagcaa gactccgtct caaaaaagaa gaagaagaag gagaaggaga
gaggagagga
    4921 gaaggagag aggggaggg gaaggggag gggagacgg aggggagtg
ggaggggga
    4981 gagctgcatg gggtagacga ttgtcattag gactattgtc cagtaaaacc
cattcctctg
    5041 cggcttcctt tcagggtca tccctgcttc aagccagtgc ctcttcccag
ctcccatcgg
    5101 gaccaccgaa gccacgctcc ggatggaaaa cgtggacgtg aaggaggaat
ggcaggacga
    5161 agatcttccc aggtaggact ccacatccc tgagtcaacc gttggggag
caggtgtctc
    5221 tcccaggtgg gacacaggag cggcccgggt ctctctctaa gtgggaaccg
cccggggctg
    5281 gcctggttcc atctccgcgt cctcctctcc cgcacactct gggaggcctg
aggccctgtg
    5341 tgcgagtctt ctctgtggcc tcacagtggg gtagtcctgg ccaggcacat
aatgggtatt
    5401 tgctcaatga tttaagattc atttctgtct tccctgcccc aaagctccaa
aggaccccc
    5461 accctacac cattttaaga gttcttaaca ttctggctgg gcgcggcggt
tcacgcctgt
    5521 aatcccagca ctttgggagg ccgaggtggg cggatcactt gaggtcagga
gttcgagacc
    5581 agcctggcca acatggcaaa accgcgtctc tactaaaact acaaaaatta
gctgggcatg
    5641 ccgggcgcag tgactcatgc ctgtaatccc agcactttgg gaggccgagg
cgggcggatc
    5701 atgaggtcag cagatggaaa ctatcctggc taacatggtg aaactccatc
tctactaaaa
    5761 atacaaaaat tagccgggtg tgtggcaggc gcctgtagtc ccagctactc
gggaggctga
    5821 ggcaggagaa tggcgtgaac ccaggaggcg gagcttgcag tgagccgaga
tcgcgccact
    5881 gcactccagc ctgggcgaca ggtgagactc catctcaaaa gaaaaaaaaa
aaaattagct
    5941 gggtatggtg tcatgcgcct ataattccag ctactcggga ggctgaggca
ccatggtgat
    6001 ttattagcag cctttaggag acacttacct cccctaacat gctgaacttt
ttttttttt
    6061 tttttgagtc tcactctgtc ccacaggctg gagtgcagtg cacgatctc
aggtcactgc
    6121 aacctccagg tcctgggttc cagtgattct ccttcctcat gccccgagt
agcttggatt
    6181 acaggcaccc gccaccacat ctggctgatt tttctatttt tagtagagac
cggatttcac
    6241 catgttggcc aggccagtct cgaactccga aagtgcttgg attccaggca
agagccaccg
```

Figure 10-5

```
      6301 cgcccggccc ctacgctgaa cattttgcag ggacatcttg tctacactct
gtctccccac
      6361 cacacggagc gccacaagag cagggtctt tgtttagctc actgctgtat
cccaacctaa
      6421 ggatagtgcc tggcatacag tcggcgctta acaaatattg ggtgacaggt
gctgatcact
      6481 ggtcagaata agaaatcaca ggggctgggc acggtggctc acgcctatga
tcccagcact
      6541 tacagaggct caggctgggg ggattgatag agctcaagag ttcgaaacca
gcctgggcaa
      6601 gatagtgaga ccccatttct accaaaaaaa aaaaaattag ctgggcatgg
tggtgtgcac
      6661 ctgcagtctt agctacttgg caggctgaga caggaggatc ccttgagccc
agaaggcaga
      6721 ggttgcagcg agccatgatt gcagccctgc actccagtct gggtgacaga
gcgagactct
      6781 gtctctattt tattttattt tttttatttt atttatttat ttatttattt
ttgagacaga
      6841 gtgtcgcttt gtcgcccagg ctggagtgca gtggcgcgat cttggctcac
tgcaagctcc
      6901 gcctcccggg ttcacgccat tctcctgcct cagcctcccg agtagctggg
actacgggca
      6961 cccgccacca cgcccggcta attttttgta ttttagtag gacggggtt
tcaccatgtt
      7021 agccaggatg gtctcgatcg tctgacctcg tgatccgccc acctcggcct
cccaaagtgc
      7081 tgggattaca ggcgtgagcc atcgcgccct accacctgtc tctatttaaa
aagagaggaa
      7141 aaaaaaaaaa aaggccggtc gctgtggctc aggtgtgtgt aatcccagca
ctttgggagg
      7201 ccaaggtggg cagatcacaa ggtcaggaat ttgagaccag cctggccgac
atagtgaaac
      7261 cctgtctcta ctaaaaataa aaattaaaaa aaattagctg ggcatggtgg
tgcacgcctg
      7321 taatccccag tactcgggag gctgaggcag gagaatccct tgaacccggg
aggcagaggt
      7381 tgcagtgagc cgagatgtgc caccgcactc cagcccgggt gacagtgtga
gactccgtct
      7441 caaaaaaaaa aaaatactac atggaaagga agctgtgcga atttgctgtt
gagacgtgtg
      7501 actctgattt gctggctaaa gatagctgct catccctctt cccttttcaga
accaggaatt
      7561 catccatccc ccaaacacaa tgcccaaggg tcagttatag aaactattgg
gtgaggttca
      7621 gtcaaaaaga ccaggtgtgt tccgcctgaa aaagagaatt ggaaaagaat
ctccaggccg
      7681 cgcacagtgg ctcacgtctg cagtcccaac agtttgggag gccgaggcgg
gcaaatcact
      7741 tgaggtcagg agttcgaggc cagcctggac aacatggtga aaccccgtct
ctactaaaaa
      7801 tacaaaaatt agtcgggcgt ggtggtgggc acctgtaatc ccagctactc
aggaggctga
      7861 ggcaggaaaa ctgctggaac tcgggaggcg aaggttgcag tgagccgaga
tcgcgccact
```

Figure 10-6

```
7921 ggactccagc ccgggcagta gagtgagtga gagtgtctca aaaaaacaga
atctccagtt
7981 ccaggaaaat ttcaatctga gagggttccg gagggcagaa cgaggccaaa
agaacgaact
8041 taaaagagaa tggggtttga aggagataca gaagaatgcc ttgaagtaat
cggtctcctt
8101 caaaatgagt caggctggtg tgggaggccg agagcttcct tcccattcat
gtccaggcag
8161 aaggaggact gttgaagacg gcatcttgat attcaagaac ttcagccctc
tcctgaatcc
8221 agtcattgcc aggcctctaa ggcccatgca cctgtctgtg tttctttgca
gcaggaggtc
8281 cctgttctca gaatagccga gaatcagaga atcacggctg ggagcggagg
ctgatgtctg
8341 taatcccagc tctttgggag gccaaggcgg gaggatcgct tgagcccagg
agtttgagat
8401 tagcctgggc aacatagcaa gacctcgtct cttaaaaaaa caaaaaacaa
acaaaaactg
8461 gctgggccta gtggctcaca cctataatcc tagcactttg ggaagccaag
gctggcagat
8521 cacctgaggt caggagtttg agaccagcct gaccaacatg gagaaacccc
gtctctacta
8581 aaaatacaaa attagccggg cgtggtggcc catgcctgta ataccagcta
ctcgggaagc
8641 tgaggaagga gaatcgcttg aacgcgggag gcggaggttg cagtgagcca
agatcgcacc
8701 actgaactcc agcctgggcg acagagtgag actccgtctc aaaataaata
aataaaaata
8761 aaaaataaaa aaaattagt caggtatgct ggtgtgcacc tgtagtttca
gctactcagg
8821 aggctgaggc aggaggattg tttggacttg ggacatcgca gcagtgagct
atgatcacac
8881 caccgcactc cagcctggac aacagagcaa gactgcatat ctaagaaaaa
taataataat
8941 tttaaaataa tgtcatttca agcagcacag cataaacaaa ggcgcataag
ctttggaatc
9001 ggacgcccat ggttcaaatc ccaattcccc agcaggtttg ctctgccacc
tgggctacct
9061 ctttgggcat ctcagtgcct ctgttttctg atctgtaaaa taggacaata
atctctcgcg
9121 caccaggtgg tcatgaaatt ttgataaaac agccgagatg ggctgtgcaa
atggcgaagg
9181 cagcacaaat aaataatcat ctccagcgtt attactatta ttagcttagc
tcccttttccc
9241 cctactgatt ttttttttatt tctttacttt tcttttcttt tttttttttt
gagacagagt
9301 ctcgctctgt cacccaggct ggggtgcagt ggcgccatct cagctcactg
caacctccac
9361 ctcctgggtt caagtgattc tcctgcttca gcctcccaag tagctggatt
acaggcatct
9421 gccaccacgc ccagctcatc tttgtatttt tagtagagac gaggtttcac
cgtgttggcc
9481 aggctggtct cgaactctca acctcaggtg atctgcccac ctcccaaagt
gctaggatta
```

Figure 10-7

```
     9541 caggtgtgag ccattgggcc cagctccacc tataattttt tttttttttt
tttttttttt
     9601 ttttttttgca gacaaagtct cactctgtca cctaagctgg agtgcagtgg
cgcgagttcg
     9661 gctcactgca acctccacct cccgggttca agcaattctc ccacctcagc
ctcccgagta
     9721 gctgggatta caggcacaca ccaccacacc cagctaattt ttgtatttt
ggtagagacg
     9781 gggtttcacc atgttggcca ggctggtctc gaactcccaa cctcaagtga
tccgcctacc
     9841 tcggtctccc aaagtgctgg gattacaggc gcaagccacc acaccggcc
tccaccgata
     9901 attttaaaag ctctcatctc acccaagcct tcttgagaca aaaaccaagg
ccgagcgcac
     9961 ctgcaaatgc aagctggagg cccttctgg aaggcgcgag gccagcggga
gcgggaggag
    10021 ggtgtgttc tggtggattt cttacagctg caaggcttct cgcccacccg
ctgcagcagc
    10081 tttgtgtttg caggacagtg gcctcgctgt gccagcctgg cccccacgag
ctacgccttt
    10141 gccaacagga cacttcctcc acgaggcttc tgtcttcctc gtctctggaa
gaactgagtc
    10201 ggctcctcgg tgcaggtcca gctgcggcca cacataacca cctctgtctg
ccgcaaaaca
    10261 gctcacaatt ctgtttcttc cagcccagcc atcccctccc ctggggactg
cagaagtggt
    10321 ctttgtactg cccttaaggg tgtcagacag agccctgcat ggcctctgcc
cttctagcac
    10381 tttttttttt tttttggag acagagtctc agtgtatcac ccaggctgga
gtgcagtggt
    10441 gcaacctcag ctcactgcaa cctccacttc ctggtttcga gcaattctct
tgcctcagcc
    10501 tcccaagtag ctgggattac aggtacgcac caccatgcct ggctcatttt
tgtatttcg
    10561 ttagagacag ggtttcacca tgttggccag gctggtctcg aactcctaac
ctcaagtgat
    10621 tcgcctgcct cggcctccca aagtgctggg attacaggtg tgagccacgc
gcccggcctc
    10681 cttctagcat tttccttcac tctcacccctt ctgcagccta ctacggagct
agagctgaag
    10741 gcagcccgga gattgctgcc tcaatttctc cattcattca ttctgatgct
atgcgccaac
    10801 tgtataccag tcccttatag cctcacaacc caatacaagg tggcagctgg
gttcatggca
    10861 cttctgacca ggccaggag ggaaggggag ctgtgattct tggctgtgaa
gggtgaggag
    10921 ggatgagccg gggaaggaag tggggtgtag gggccccaca ttccaagcag
agagggcagc
    10981 atgtgcaaag gctctgggct cagtggaagc aggttgaggg actggggaag
gctgcgtggg
    11041 gaaactgagg acttggggga ggagcttacc cagggcatcc tagccaagga
gggtcagatg
    11101 cagggtgagc tgccccatag ctccctctac tctcttcccc tcacagctga
gtggctgcca
```

Figure 10-8

```
11161 gttttgtttg cttgcttgta acttttttctt tgtttgtttt gggttttctg gggggtttta
11221 tttatttatt tatttgaaac agagtctcgc tgcaacgccc aggctggaat gcaatgacgt
11281 gacctcggct cgctgcaacc tccacttccc aggttccagc aattctcctg cctcagcctc
11341 ccaaatagct gagtttacag gcgcccacca ccacgcccag ctaattttg tatttttagc
11401 agagatgggg tttcaccata ttggtcaggc tggtctcgaa ctactgacct caagtgatcc
11461 acccgcctca gcttcccaaa gtgctgggat tacaggcgtg agccaccatg cccagctgct
11521 tgtaactttt taattttttt tttttttcca gacggggtct tgctctgtca cccaggctgg
11581 agtgcagtgg tgcgatcata gctcactaca gcctccacat cccaggctga ggcgatcctc
11641 ccactgcagc cccctgaata cctgggacca caggcatatg ccaccacacc cagctatgtt
11701 ttatttctg tagagacagg gtctcactgt gttgcccagg ttggtctcaa actcctgggt
11761 tcaaatgatc ctcccacctc agcctcccaa aatgctggga ttacaggcat gagccactgc
11821 gcctggccta tttgatatac ttccaaactt ggaaaaaaat tacaagaatg atataaagaa
11881 tatctgcata cctttagtag gattatacaa ttgttaacat tttgctcctt ttatatcaaa
11941 gtcagccctc agggctgggt gcggtgactc acatctgtaa tcccagcact tgggaggcc
12001 aaggcaggtg gatcacctga ggtcgggagt tcaagaccag cctaggccaa catggtgaaa
12061 ccccgtctct actaaaaata caaaaatcaa ctgggtgtgg tggcgggcac ctgtaatccc
12121 agctactggg gaggctgaag caggagaatt gcttaaaccc aggaggcaga agttgcaatg
12181 agcccagatt gtgccgccac actctagcct gagcaacaca gcaagactct gtctccaaaa
12241 aaaaaatttt accctcaatt gtaccgataa tgtcccatgt ccctatttag ctaatgcccc
12301 tgccccaaac cctgggtcca agacccaatc tggcaccact cattgcatca ggttgagtat
12361 actgggttgt gtgtttactg gggtatgtgt ctcaccaggc actgggactt aaacttatct
12421 cttttagggg aacacgatcc aacccacctc agcaggacga agccacgctg tgcatcttgc
12481 atgtggggggg gaccccact ttttttttt ttttttttg agacggagac ttgctctgtc
12541 gcccaggctg gagtgcagta gcatgatctc agctcactgc aacctccgcc tcctgggttc
12601 aagcgactct cctgcctcag cctcccaagt agctgtagct gggaccacag gcatgtgcca
12661 ccatgccagg ctaatttag tatttttagt agagacgggg tttcaccatg ttggccaggc
12721 tggtcttgat cgcttgacct tatgatccac ctgcctcggc ctcgcaaagt gctgggatta
```

Figure 10-9

```
12781 caggtgtgag ccaccatgcc cggctaggat ttccactttt tacctggatt
gcccatcatg
12841 gactttgaga gccggctctg cagagggcta agtggatata ttataccca
gggccacgga
12901 ggggatctcc aagtctggag agtctgcggt tctcctggag cttgcggaag
taacaggatc
12961 tcacctgacc ttggaaactg cagctccatg aacaggcggg gagagcttgc
tccacccatg
13021 ttccagagca gtgggtcttc cttcagggag cctggagccc tgccaggtcg
gcttctccag
13081 ttctgcatga tcttaaacct ttcctgaaca tccactgcaa ctggcagctc
agcctcagga
13141 cctcatccca tccccgaggc actgcctctc cctggccctc cctccctacc
ctccatcctc
13201 caaccactcc ctcctccccc actgctctct ctgcgccagg caccctgagt
ctgctttctg
13261 atctgccctt gaacttggca agcttattcc agtcccggag cctgggcctc
tgcagtgcct
13321 tccatctgga gtgctcttgc ctggtctctg caggacgcca acatcatgct
taaaagtcta
13381 cacttaaaag tcgcttccag ccaggcacag tggctcactc ctgtaatccc
agcactctgg
13441 gaggccaagg cgggaggatc acttgagccc aggagttcaa gaccagcctg
caagacccca
13501 tctgcagaaa aatataaaaa ttagctgggt ggccgggcgc ggtggctcac
gtctgtaatc
13561 ccagcacttt gggaggccga ggcgggcagg tcacgaggtc aggagatcga
gaccatcctg
13621 gctaacacgg tgaaacccg tctctactaa aaatacaaaa aattagctgg
gcgtggtggc
13681 aggcgcctgt agtcccagct actcgggagg ctgaggcagg agaatggcgt
gaacccggga
13741 ggcggagctt gcagtgacct gagatcgcgc cactgcactc cagcctgggt
gacagagtga
13801 gactccgtct caaaaaaaaa aaaaaaaaaa aattagctgg acatagtagt
gtgtgctggt
13861 agtcccagct acttgagagg ctgaggtagg aggattgctt gagcccaaga
atttgagacc
13921 agcctgggca acatggcgag accctgtgtc tgcaaaaaaa aaaaaaaaa
aaaactgtaa
13981 aaacctgaaa aattaaccag gtgtggcagc tcactcctgt aatcccatca
ctttaggaag
14041 ctgaggcagg agaattgctt gaaatgtgaa gttcaagacc agcctaggca
ccacagtaag
14101 accctgtctc tacaaaaaat tttataatta gccgggtgtg gtggtgcaca
cctagggtcc
14161 cagctactca gaagactgag acaggaggat cccttgagcc caggaatttg
aggctgcagt
14221 gagctatgat ttcactactg tgctctaggc tgggcaacag agcaagaccc
tgtctcaaaa
14281 aaaaaaaaaa aaaaaaaag ctgcctcctc aatgaggcct tccctgacca
ccccacagat
14341 ttttttctct ctctctcctc tcctttattt cattcatttt ctttgccgta
agcatcacta
```

Figure 10-10

```
14401 tctgccttgt tcacttattt gcttattgtc ttcctttata tacatggtct
caagccagga
14461 attgctttgc acaatcctgg gaaccaccaa gtccaaaatc cacagggcag
gctggaaact
14521 gtcaggtaag agctaatgct gcagtttttg tttttgtttt tgagacggag
tctcactctg
14581 tcgccaggct ggagtgcaat ggcacgatct cagctcactg caacctccgc
ttcctgggtt
14641 caagccattc tcttgcctca gcctcctgag tagctggggt tacaggcatg
caccaccaca
14701 cccagctaat ttttgtattt ttagtagaga tggggtttca ccacgttggc
caggctggtc
14761 tcgaactcct gacctcaggt gatctgcccg cctcggcctc ccaaagtgct
gggattacag
14821 gtgtgagcca ccgcgcctgg cccccatttt agtcatgagg aaaacagagg
ctcagggagg
14881 agaaggcacc acccagactc gtagcgctgg atggagtggc agggctggga
gttgtgctca
14941 gactctctga gactctctta ggcattccca cccttctcc tgctttcctc
actttcccag
15001 tatgtgcagc tgagatgctt tcttttttc tttcttttct tttcttttt
ttttttttt
15061 ttgatagact cttgctctgt tgctcaggcg ggagtgcagt ggtgccaatc
acagctcact
15121 gcagcctcaa actcccggac tcaaacgatc ctcctgcctc agcctcctta
gtagctggga
15181 ttacaagtgc atgccaccat gcctggctaa tatgttgtat tttttgtaga
gatggggtct
15241 cactatgttg cccaggctag tctcgaactc ctagtctcaa gagatcctcc
cacctcagcc
15301 tgctgagtag ctgggatcac aggcatgagc catcatgctg ggctaatttt
taaattttta
15361 gtagtgatgg ggtcttgctg tgtgggccag gcttgtcttc aactcttggg
cttaagtgat
15421 cctccctcct cagcctccca aagtgctgtg attaccggca tgagcccctg
cgcccagtct
15481 gagatgcttt ctacagcttc acatttcagc tgcagcccag cagtggtcca
cctagttcac
15541 agccaatgta gaatctgtgt ggaccatcca atgttgtgag gttgaatcac
atcccttttt
15601 ttttttttt ctcgagacag agtctcactc tgtcactcag gctggagtgc
agtggcacgg
15661 tctcagctca ctgcaacctc cacctcccgg gttcaagcga ttctcttgcc
tcagcctccc
15721 gagtagctga gattacaggc acgtgccacc acccagct aatttgtgt
ttttagtaga
15781 gacggggttt caccatgttg gccaggctgg tcttgaactc ttggcctcag
atgatccacc
15841 tgcctcggcc tcccaaagtg ccgggattac aggcatgagc ccctgcgccc
ggcctgagat
15901 gctttctaca gcttcatatt tcagctgcag cccagcaatg gtccactcag
ttcacagcct
15961 acgtagagtc tgtgtggacc gtccaaggtt atgaggctaa atcacatctt
gagaatcgaa
```

Figure 10-11

```
16021 ggcagtgccg gctgcaaagc aatggggctt tcctctggcg ggaggagatg
gtggctggac
16081 agggaccctg gctgggcaag tggttgtttg tttgtttgtt ttgagacgga
gtctcgctct
16141 gttgcccagg ctggagtgca gtgtcacgat ctcggctcac tgcaacctcc
acctcccagg
16201 ttcaagcgat tctcctgcct cagcctcacc aatagctggg attacaggcg
cccgccacca
16261 tgcccggcta atttttgtgt ttttattaga gacagggttt tgccatgctg
accaggctgg
16321 tctcgaactc ctgacctcag atgatccacc cgcctcagcc tcccaaagcg
ctgggattac
16381 tgaggcatga gccaccacgc ccagccagaa atctagactt tttgcatctc
ttcttcgaca
16441 gcaaatggaa aatgttttta aatgctgcat gggtgggaca taactaggct
tggtgcatca
16501 gccatcagcc tgcaattttg cagcgctggt ttgggttaac cttctgaatg
agcaggtcag
16561 ttcattcttc agtcctttct ttgaagtttg ctatatatat atatatatat
agcaaaatct
16621 atatctatat ctatatctat atctatctat atcgcctcgc tctgtcatcc
aggctggagt
16681 gcagtggctc gatcatggct cactgcagcc ttgacctcct gggctcagct
gatcctccca
16741 ccttggcttc ccaaatagct gggactacag gacacgcca ccatgcctgg
cttttttattt
16801 tttatagaga tggagtctcg ctgtgttgcc caggctgatc tcaaactcct
gggctcaagg
16861 gatcctccca cctcagcctc ccaaagtgct gggattacaa gcgtgtgcca
cctcatgccc
16921 agccaaagct tgcttttaa aaaattgagg tgaggccaag tacagtggct
cacgcatgta
16981 atctcagcac tttgggaggc cgaggcaggt ggatctcctg agctcaggag
ttcgagacca
17041 gcctggccaa cgtggtgaaa ccccatctct actaaaaaca caaaaatcag
ctgagcatgg
17101 tggtgggcgc ctataatcac agctactctg gaggctgagg cacaagaatc
gcctaaaccc
17161 gggagatgga ggttgcagtg agccaagatt gtgccactgc actccagcct
gggcaaaaga
17221 gtgaaactcc gtctcaaaaa ttaaataagt aaaataaaat ttaaaaaata
taaaaaattg
17281 aggtggaatt ctcataacat gaattcatca ttttaaagtt catgattcag
tggcagagtc
17341 cattcataat gttctgcaac cccacatcta tctaatttga agacattttc
atcaccgtga
17401 gaggaaatcc tatctactaa gtcagcccca ttttcatccc tctcccccaa
ccccagtgac
17461 cacacatcta cttcctgtga gaatttacgt gttctaaaca tctcttttt
ttttctttc
17521 ttttctgttt tgagcagggt gtcactcttt cacctaggct ggagtgcagt
ggtgcaatca
17581 tagctcactg cagcctcgac ctcccaagtt agagcaatcc tcctgcctca
gcctcctgag
```

Figure 10-12

```
17641 tacttggaac tagacgtgta ccaccacacc cagctaattg ttttgtattt
ttagtagaga
17701 cgggctttcg ccatgttgcc ccgactggtc ttgaactcct gggctcaatg
aacccgcccg
17761 catcagcctt tcaaagtgct gggattacag gcataagcca ccacactcag
ccaacatttc
17821 atgtaattgg aatcacacac tgtgtggcct tttgtgtctg gcatctctca
ctgagcatga
17881 tgtcctcaag gtgcatccat gctgtggtct gtgtcagagc cctgttcctt
ttcagggcta
17941 aatagtattc cattgaatgg atataccaca tttgttgatc cagtcagctg
ttaatggact
18001 ggtgttgttt gtttgtttgt ttgtttttga gacagagtct cactctgtcc
ccaggctgga
18061 gtgtagtggc gtgacttcag ctcactgcaa cttccacctc ccaggttcaa
gtgatcctct
18121 tgcctcagcc tcccaagtag ctaggattat aggcatgcgc caccatgtcc
agctaatttt
18181 tgtatttta gtacagacag ggtttcatcg tgttggccag gatggtctca
atctcttggc
18241 ctcatgatgt gccctcctcg gcctcccaaa gtgccaggat gacaggcgtg
agccaccgcg
18301 cctggccgtc aatggactct tgaattgttt ccacttttg gtttttatga
attatgttca
18361 ttcaagtatg agttttcgtg tgaacagatg ttttcatttc ctttgggaat
ccgctccatt
18421 ttgatctttg ccatgaacag gaggagggtg acatctgatt cctcctttac
ctccaagccc
18481 catagatgca ctggagacgc agtggttacg caaaaacatt tgatgaatag
agaaaagaga
18541 gggagggaaa gggagaggga aaaagcataa atagattccg ccccaaaaag
gttaacagct
18601 catgccctaa gtggaacaga atgagggaa taaatctttt ttttttttt
tttttttttg
18661 agagagagtc tcactttgtt gcccaggctg gagtgcaatg gcacgatctc
ggctcaccgc
18721 aacctccgcc tcagggttc aagtgattct cctgcctcag cctccccagt
agctgagact
18781 gcaagcacgc accaccacgc ccagataatt tttgtatttt tcagtagaga
ctgggtttca
18841 ccattttggc caggctagtc ttgaactcct gacctcaggt gatccgcccg
cctcggcctc
18901 cctaagtgcc aggattacag gcatgagcca ccacgcccgg ccaataaatc
atttttttaa
18961 aggaaaggaa catgcattcc accgcccttc catctaaaca gcttgccttg
cagctgagcc
19021 aggaatgctg agttacagag acgaattaag ctgtagcctg gctttccgga
gtcagcacgc
19081 cctgccgcta ggacctctgg cagccccgtg caaaatgttc tgcccggaat
ggaatatttc
19141 ccagggtagc caaggagcca gtgctcctgg gtcaaactcg ggcagcacgg
gctgcggctt
19201 caagaagtga tctggggccg ggtgcggtgg ctcatgctgt aattccagca
tttctgtctc
```

Figure 10-13

```
19261 aaaaagaaag aaaaagttgc aaagttagta cagataattc ctgtagactg
ggaacctagt
19321 ttctcccata attaacatct tatattagct gtgtatattt tatatttgtc
acaattgatg
19381 aatcaatatt gatactattg gttattgata atcaacattg atcaataaca
atattgatca
19441 atattggtta ttagttacca aagtccatgc tttttttagat tttcaaagtt
tttcctaatg
19501 tcctcttttt ttttcttttc tctctttttt tttttaagag acagggtctc
actctgtcat
19561 ccaggctggg gtgcagtggt gccatcatac ctcactgcag cctccgcctc
ccaggctcaa
19621 gcagtcctcc cacctcagcc tccagagtag ctgggactac aggcaccacc
acgtccagct
19681 aatctttgta attttttgtag agacagagtt acgccatgtt gcccaggctg
gcctaatgtc
19741 cttttccttc tgccccacaa ccccatccag gatccagat gacatttagt
tatcacatct
19801 cctgacactc ctctggactg tggcagtctc cctgtctttc ttgtttttgat
gcccttgata
19861 gttttgtttg tttgtttgtt ttgagatgga gtctcactct gtcacccagg
ctggagagca
19921 gtggcacgat ctcggctcac tgcaacctcc gcctcccggg ttcaagcgat
tctcctgcct
19981 cagcctcctg atagctggga ttacaggtgt cctccaccat gcctgcctaa
tttttgtatt
20041 tttagtagag atggcgtttc accatgttgt ccaggctggt ctcgaattcc
tgagctcaag
20101 tgatcctcct gcctcagcct cccaaagtgc tgggattaca ggcgtgagct
gctgcgcctg
20161 gcccatcctg tattttttgg aatgacatca ctatacacag cctacacaga
gttatccttc
20221 atctttttttt ttttttttttt ttttttgag acagagtctt gctctgtggc
ccaggctgga
20281 gtgcagtggc acgatctcgg ctcactgcaa gctccgcctc ctgggttcat
gccattctcc
20341 tgcctcagcc tcctgagtag ctgggactac aggcacctgc caccacgccc
cgctatttt
20401 tttgtacttt tagtagagac ggggtttcac catgttagcc aggatggtct
cgatctcctg
20461 acctcgtgat ccgcacgcct cggcctccca aagtgctggg attacaggcg
tgagccaccg
20521 cacccggcct atccttcatc ttcttgaggg cagaactgta cataaactat
ttccaattct
20581 tctgcacaag aaatgtgtct cttctctcct gtttatttgt tcagtgactt
atttatatcc
20641 gtatggactc atagacattt attttacatc ttgggttata attcaatatt
tcattattta
20701 tttggttgca caaactgttc cagcattgac atagagatct cttctggttg
actcaggttt
20761 ttgtgggggt tttatctatt tatttatttt taatactttt tgctgcattt
gagagtcaac
20821 aactcatcag agaccaaatc ccacagggtc gccctagaga gaattcaact
tactaactta
```

Figure 10-14

```
20881 tttcaaagtt tttgaagtca tgtgatgctg gggaaaaacc ttcattctcc
tcaagccgtg
20941 caaaaatctc caaaaggctt aatataaatt tgattatcta aaagaagccc
ttcagccctg
21001 atgcgttata attttcttcc tctgctaaag aaaaaacatg ctgggcgggc
gcggtggctc
21061 atgcctgtaa tcccagcact tgagaggcc gaggtgggca gatcacaagg
tcaggagttc
21121 cagaccagcc tggccaatat ggtgaaaccc cgtctctact aaaaatacaa
aaattagccg
21181 ggcatggtag cgggcacctg tagtcccagt ttacttagga ggctgaggca
gaagaatggc
21241 ctgaacccgg gaggcggagg ttgccgtgag ccgagatcat gccactctac
tccatccagc
21301 ctgggcgaca gagcgagact ctgtctcaaa agaaaaaaat aaaagaaaaa
gaaaaaacat
21361 gcgcttgtgg tggctcacgc ccgtaatccc aacactttgg gaggctgagg
tgggaagatg
21421 gcttgagccc aggagttcaa gagcaacctg gcaacatag tgagacccca
tctctacaaa
21481 aaaccaaaaa actacaaaaa ttagccagcc gtggtggtgt gcacctgtag
tcccagctac
21541 tcaggaggct gaggcaggag gatctcttga gcccaggagg ttgaggctgc
agtgagccat
21601 gatcacgcta ctgcactcca gcctgggcga tacagtgagg ctctgtctcc
aaaaaaatgt
21661 atatatttag gtccagtgat tctccagaac taaatgtgtt ttgcttttgt
tcttgtctga
21721 ctcgcctggc tggacctgtc tgggccactc cactgtcctc tgcctgaatc
tctggtgccc
21781 ggcgactgat gcctgttcct ggatgggtcc gcaggccact cccagaagag
acggggtgg
21841 aactgcttgg cagcccggtg aagacacat cctgtaagtt tccacgtcca
cagaagggcg
21901 gaaacaggct cagtgtttcc gggtttcagc cctgcctggg gctgtaactg
tagaaatgtc
21961 agaggccaca caccgtgggt agaatgttct gtcctggggt ctatggtgga
agtggccgtg
22021 gtgggtgaga gacacaatgg atgatggcgc tctcatgaag ccagcacgct
gtgttgctgt
22081 gtgtccctgt gctagtcact cagcctctct gtgccccaat gcctcatcta
ctaaatgtag
22141 gtagcgagct tctcgcagag ggggcatgta aggattaaat gaggtgatgc
caaatgccct
22201 ggaggcacaa agtcagcaca gccaagggtg cactgggagg ctctgctatc
tggagctcta
22261 aacatataca ttttaatgtg taataccta tattagaccc aaatatatac
attttttggg
22321 agaccgggtc acactctgtc atccaggctg gagtgcagtg gcgtgatcat
ggctcactgc
22381 agcctcaacc tccagggctc aagagatcct cctgcctcag ccttctgagt
agctgggact
22441 acaggtgcac accaccatgg ctggctaatt ttggtagttt ttgtagaaat
gggatctagc
```

Figure 10-15

```
22501 tatgttgccc aggctgctct tgaactcctg ggctcaagcc atcttcttgc
ctcagcctcc
22561 caaagtgctg ggattacggg cgtgagccac cacgcctggc atgtttttc
ttcagcagag
22621 gaaaaaaatc ataatgtatc aggctctgaa gccccagatc ccggggatgg
gagtcctggg
22681 cggccagagg agagttttag ccgtaacctg gcgattgcaa cgtgcctccg
gaggcaggga
22741 aagggcccag gttggcaccg tggggagagg tggggtctgg ggaggacctg
gcagccagcc
22801 ccacttaacg acattcagtt aagcagaata tggaaaataa acctgtgagg
gccaaacaaa
22861 atttttttgg agacagagcc tcactgtatc gcccaggctg gagtgcagta
gcgtgatcat
22921 ggctcactgc agcctcaacc tctgggctc aagagatcct cctgcctcag
cctcctgagt
22981 agctgggact acaggtacac accaccatgg ctggttaatt tttgtagttt
tttgtagaga
23041 tggggtctca ctatgttgcc caggctgctc ttgaactcct gggctcaagc
catcttccca
23101 ccttggcctc ccaaagtgtt gggattacgg gcgtgagcca ctgcacccgg
ccgcctgtct
23161 ctatttaaaa agaaaaaaaa aaaaggcagg tcaccgtggc tcacgcctgt
aatcccagca
23221 ctttgggagg ccgaggcggg cagatcacga ggtcaggagt ttgagaccaa
cctggccaac
23281 atggtgaagc cccgtctcta ctaaagatac aaaaaaaaaa aaaaaaaaaa
attagccggg
23341 cattgtggca cttgcctgta atcccagtca ctcaggaggc tgaggcatga
ggatcgcttg
23401 aacccaggag acggaggttg cagcaagctg agattgtgcc attgcactcc
agcctgggtg
23461 acaaggcgag actctgtcta aacaaacaa acaaaaaaa gattagtcgg
gcttggtggc
23521 gcatgcctgt aatcccagct acttgggagg ctgaggtggg agaatcactt
gaacctggga
23581 ggcggaggtt gcagtgagct gagatcctac cattgtactc cagcctgggt
aacggagtga
23641 gactccatct caaaaaaata aatacataaa taaaacaaaa taaattagca
gactttggat
23701 taaagcaggc agccatctgt gatgtgggtg ggcctcatct aatcagttga
aggttttaag
23761 agaaacagac tgaggttccc ccaggcagag acaattctgc ctgcggacgg
ttttgcaaca
23821 tcaactcttc cctaggcgtc ccgcctgctg gcctgccctg ccgattgagg
acttgtcagt
23881 ctctgtgatc acacgagcta attccttaaa ataaatttct ccctctctct
ttttttccat
23941 acatatagga aaaaatatg tatacacaca cacacacaca cacacgtc
ctattggatt
24001 tgtttccctg gagcactctg attaaaatag gagactatcc tggatcctgt
attatccagg
24061 tggcctgaca tcgttacagg atcctcatga gtggagacag gagggtgaga
gtcagagaaa
```

Figure 10-16

```
    24121 gcctagaaga agatgggctg ctttcacaat ttgtctgcac aagagatatg
tctcttctcc
    24181 tttatttatt tatttattta tttttgagat agagtttcac tctgtcaccc
aggctggagt
    24241 gcaatggtac gatcttggct cactgtaacc tccgcctcct gggctcaagt
gattctcctg
    24301 cctcagactc ccaagcagct gggattacag gcgccaccac tgtgcccggc
taattttat
    24361 attttagta gagatggggt ttcgccatgt tggccaggct ggtctcgaac
tcctgacctc
    24421 aggtgatctg cccgcctcgg cctccaaagt gctgggatta caggcgtgag
ccaccgcacc
    24481 cggcccaaag tcaggctttg aactcatgtc tgcccaatgt ccaagcatcc
atcccttaa
    24541 tctctgaggc ttgcccacag gacagaggtt ataacattca ccctgtcag
gatgatgtcg
    24601 gtttaattct gcccacccc gccaatggca tggatacaga agggagccca
ccctctcttc
    24661 ccattcctgc atgatgaaac agcttccacc aggtaggaaa atgggggaa
ggtaaaagag
    24721 agaaagcaaa gatgttttcc attttctca tttccctgca gctcctccca
acacgctaaa
    24781 tttcaacgga gcgcatcgta agaggaagac gctggtggcc ccagagatca
acatttctct
    24841 ggatcagagt gagggtccc tgctgtccga tgacttcttg gataccctg
atgacctgga
    24901 tattaacgtg gatgacatcg agaccccga tgagaccgac tcgctggagt
tcctggggaa
    24961 tggcaacgaa ctggagtggg aaggtaaagt tcagggtctc tctggggcct
gctggagccc
    25021 acccccccca ccccacctt ccgtctctgg attcccatag gctcagagag
tcacaagtgg
    25081 ggcaggggct ctaagcagtc tagccttaaa cccaggagat caagactgca
gtgagacgtg
    25141 atcatgccac tgcactccag cctggacaac agagtgagac cctgtctcaa
aaataaaatt
    25201 tttaaaaaag agagaggtgg ctgggcgcag tggctcatgc ctgtaatcct
agcactttgg
    25261 gaggccgagg cgggcagatc acgaggtcag gagatcgaga ccatcctggc
tgacacagtg
    25321 aaacccccgtc tctactaaaa tacaaaaaat tagccaggca tggtggcggg
cacctgaagt
    25381 cccagctact caggaggctg aggcaggaga acggtgtgaa cccaggaggc
cgagcttgcg
    25441 gtgagccaag attgtgccac tgcactccag cctgggcgac agagcgagac
tccgtctcaa
    25501 aaaaaaaaa aaagagagag agaggttggt gaatgggtac caacatacag
ttagacagaa
    25561 ggaataagtt ctattgttcg atagcagaat aggaggggtg ccaggaggag
ggtccatccg
    25621 ctcctgcgac tgttttttt tttttttga gacagagtct cactctgttg
cccaggctgg
    25681 agtgcagtgg tgtgatctca gctcactgca tcctccacct cccgggttca
agcgattctt
```

Figure 10-17

```
25741 ttgcctcagc ctcccgagta gctgggatta caggcatgca ctaccacttc
cggctgatgt
25801 ttatattttt agtagagatg gggttttccc atgttgccca ggctggtctc
aaactcctga
25861 cttcaagtga tacacccacc tcggcctccc aaagtgctgg gatcacaggt
gtgagccacg
25921 gcgcccagcc tgcccctgca atttgatgca tattttctt gtgggcttgt
gaattttct
25981 gcagaacgtg gctttcatca gaatctcaaa ggcgaccaag atcccaacaa
actgccctcg
26041 atgtatgcaa caaatacttt ttgaccattt actccagggc aagtcctgat
tcaggcgtgg
26101 ggtatatggc agggctatga taagaagaga tggtcctggt ccctacctgc
acacacagat
26161 catcagaaag acagaccacg aaaggccagg cgcagtgact cacgcctgta
atcccagcac
26221 tttgggaggc tgaggtgggc agatcacctg aggtcaggag tttgagacca
gcctggccaa
26281 catggtgaag ctccatctct actaaaaata cagaaattag ccgggcatgg
tggcgtgcgt
26341 agtcccagct actcgggagg ctgaggcagg agaatcgctt gaactctgga
ggcagaggct
26401 gcagtgagca gagatcgcac cactccactc cagcctgggc gatggaacaa
gactctctca
26461 aaaaaaaaa agaaagaaaa aaaaaatta aggacaatgt agtggctcat
tcctgtaatc
26521 ccagagcttc gggaggccag ggtaggagga tcgcttaagg ccaggagttt
gagaccagcc
26581 tgggcaacat attgaaaccc catctctaca aaaatataaa aattagctgg
gtgtggtggt
26641 gcacaactgt agtcccaggt atctgggagg ctgaggcagg aggactgctc
tctgtgtgcc
26701 aggctcctgg gagagtaaaa accaagcatg catgccccga gtatcctcgt
ggtttgatga
26761 agcagatgca ttcaccagct ctgagaagct ccaggacaca ggtccttaac
caacagagtg
26821 ccctgggagg ccagcaaagg gaatgtccag aaaggcttcc tggaggaggc
ggcatttgag
26881 ccaggccttg aaaggggagt aggagaggaa aatgggtcag cagggcagcc
aggtggggag
26941 aagcgaagga cttgtgggtc ccggcagcga gggaggtggg agaggggaag
gaaggctgag
27001 caggagggca ggagatatcc ggactctggc gtccatgcga ctctccgcca
cctgcttcta
27061 gacgacaccc ccgtggccac cgccaagaac atgcccgggg acagcgcgga
tctatttggg
27121 gacggcacga cggaggacgg cagcgccgcc aacgggcgcc tgtggcggac
agtgatcatc
27181 ggggagcaag agcaccgtat agacctgcac atgatccggc cttacatgaa
agtggtcacc
27241 cacggaggtg agacccgccc cccggtgccc ccttggggct ccagcccggc
ccactgggca
27301 acagggggtt cgtcagtgcc cctctctgat gcacggggat gttaagccgt
caactcgctt
```

Figure 10-18

```
27361 cggtggacg gactgtgggc aaggcgtgca tggtcaggga ggcgcactgg
gggcccctga
27421 tggtcgctgt cactcctcag cgaaggcaga gactggctaa ggggtcgccg
gctgctgtgg
27481 ctcggagcca tgccctcccg agcgtgtggg caccgggacg tggtgggtgg
tgcgcgggag
27541 gcagctcagg gctgggagag gactctgacg ttgccgatcg gctgcctctc
ctcagggtac
27601 tacggcgaag gcctcaacgc catcatcgtc ttcgcagcct gcttccttcc
agacagcagc
27661 ctccccgact accactacat catggagaac ctcttcctgt gagtccccgc
ccgcggcgag
27721 cagcctcggg ccagctctga tgcctccctg gccacagggg caccaggctg
caaggattgc
27781 attgtggccc taggaagcct gcctggcacc agggaagggc gtggtggcca
cagaccttga
27841 tctgagtccc tgctggccct gaggctcaca gtggccttcc ctctgggcca
ccctgttctc
27901 ctccccgtcc tcctcctcct cctcttcctc ctccttcccc tcctcctcac
tgtcctcctc
27961 ctcctcccct tcttcctccc ccttcccctt tcttctcctc cttctcctcc
ccttcttcct
28021 cccccctcct cctcccttt ctcctcctcc tccccttccc tctcctcctc
ccctcttcc
28081 ccttccctct cctcctcccc cctcttcctt ctcctcctct tcctcccctt
tctccacctc
28141 atcctctttc tcttcctccc ctttctcccc ccttcctcct ccttctcctc
cttccctcat
28201 cttcctctcc ttccctctcc tccccctccc catcctcctc ctccccatcc
tcttcccctt
28261 cctcctcctc ttcccgctct gagatggcac cactgcactc cagcctgggt
gacagagtga
28321 gaacctgtct caaaaaaaaa aaaaaaaaaa aaagcaagg cctagagacc
agcctggcca
28381 acatagtgaa atcctgcctc tactaaaact acaatttagc tgggctcggt
ggcaggcgcc
28441 tgtaatccca gctactaggg aggctgtggc aggagaatgg cgtgaacctg
ggaggcggag
28501 cttgcagtga gccgagatcg caccactgca ctctagcctg gcaacagag
cgagattccg
28561 tctcaaaaaa aaaaaacgac tcaataaaag agtaactgcc ctatgaggat
gcccgctgac
28621 actcatgtgg agtgtgctgg gatcatccac gtcctctccc accctgcagt
ccgccaggac
28681 agcagacaac acctggacca gtggggctga cccagccagc ggcaggagtg
gaggcaggca
28741 gggtcggcac cgcaggtgtc ctgaccctgg accctccat gttgggtccc
tgccttctgt
28801 gccccgtgag caggtacgtc atcagcagct tagagctcct ggtggctgag
gactacatga
28861 tcgtgtacct gaacggtgcc acgccccggc ggaggatgcc tggaatcggc
tggctgaaga
28921 agtgctacca gatgatcgac cggaggtgag gtggggatgc ctcaggaagc
acagtggggg
```

Figure 10-19

```
28981 catgaaaatc acacagggg ctggacatgg tggctcacac ctggaatccc
agcacttcgg
29041 gaggctgagg tgggaaggtc ccttgagccc aggagtttga gaccagcctg
ggcaacgcag
29101 caagacgctg tctctacaga aaacttta ggccgggcaa ggggctcac
acctctaatc
29161 ccagcacttt gggaggccaa ggtgggtgga tcacctgagg tcaggagttc
aagaccagcc
29221 cggccaacat atagtgaaac cccatctcta ctaaaaaaat tcaaaaatta
gctgggcgtg
29281 gtggcgcatg cctgtagtcc cagctacttg ggaagctgag gcaggagaat
cacttgaacc
29341 caggaggtgg aggttgcagt gagccgagat catgccactg cacttcagcc
tgggcaacag
29401 agcgagactc tgtccccatg aaacactcac tccctattcc ttctcccag
gctccggcac
29461 cccccatcct actttctgtc tctgtaaatc tgatgactct agggacctcc
taggactgga
29521 atcacacagg atttgtcctt ttgtgtctgg ctttcctcac tgagtgtgat
gtcctcaggg
29581 tgcatccaca ttgtagcctg tgtcagagcc tccttccttt tcatggctgc
ataatattcc
29641 actgtatgga cataccacat ttggtttgtc cattccattc atctcttgat
ggacatgggt
29701 tgcttccacc cctgagttat tgtaaatagc ctcagagtga cattaaaatt
gagccagcca
29761 atccatcctt gcacccaggt tagtggaggg aggctccaag gacaggctgg
tccctcctag
29821 ggcattaggt ggtgaaaata caatcttggc tgctcaaata actaccaacc
tggttcacct
29881 gctctgcacc atgggtctc tacctacctc atccacctga gggtcttagg
gactcaaagg
29941 gtgtgtcttt atcccaccat aggacccca tgtcttggat gggggcaggg
atttgacagg
30001 tacctggaga ccacacgtgg aatgagcaga gtgacgaatg cttgcttgtg
gctctcccgt
30061 cccacccagc tcctccctcc ccagggctcg cccaggagc ccatcttgct
tcctttgcgg
30121 ccccacacag gttgcggaaa aacctgaagt ccttgatcat cgtccacccc
tcgtggttca
30181 ttcggactgt gctggccatc tctcgccctt tcatcaggtg agacggggag
gctgcaaccc
30241 aagtccagtg gcctcagtgt gcgtgtgtgc gtgtgtgtat gcatgcattt
gtgtgtgcat
30301 gtgtgcacgt gtgtgcgtgt gtgcatctgt gtgtgtgtgc atccatgtgt
gtgtttgatg
30361 tgcatgttcc agcttctcta tgatgaatac atattattgc tttaaacagt
tttaaattgc
30421 acacagccag gcacagtggc tgacacctgt aatcccagct actcagaagg
ctgaggtggg
30481 aggatcgttt gaggccagcc tgagcaacat agcaaaaccc ccatctctac
aaaaaataca
30541 aaaattagca ggacgtggtg gtgcacacct gtagtttcag ctacttggga
ggctcacgtg
```

Figure 10-20

```
30601 ggaggatggc ttgagcccag gagatcaagg ctgcaatgag ccgtgatcga
gccactgtac
30661 tccagcctgg atgacagagt gagaccctgt ctcaaaagaa aatcagtcat
gcatggcatc
30721 acatgcctgt agtcccagct actcaggagg ctgaggcagg aggatcactt
gagcccagga
30781 ggtagaggct gcagtgagct atgatcactc cactgcactc cagcctggga
gacagagcaa
30841 aacaaccctg tctctaaaaa taaaatatat atatatgtat gtataaataa
ataaataata
30901 tgactaataa atttaaaatt taaaactaca tatattctat aatgtatatc
atatatagtt
30961 actatattaa acatatagta aaacagatca agtgaaataa aattaggcat
gttaaatgcc
31021 ctattcaatc caataaaatg tcatgcaaat ttaatttaat ctaatgcaaa
acattgaatt
31081 gaataaagat tcctaatgtt cacgttccca gttacaaatc tgggatgagc
gaaagagacg
31141 agggcttcac tttcccttga acaacaggac acattcacag caggcccgat
tttcaaggaa
31201 gactctttaa acatgctgtt tcaaggact gctaagtacc ctgaaggggc
ttatttgcat
31261 attagcgaaa tgagatgagg aatacactaa ttatggatca ttttagctaa
taatgaatca
31321 acaggcaaaa cggtaaacac gcatttcagt ctaagataat tgcatttgct
cctctatatt
31381 ccagaattca gtaacataga ctacctttgc ctttaatgta gatattagga
tggtgcaaaa
31441 ataattgagg ttcttgccat attttcatta caaaaactgc aatcactctt
gcacgaaccc
31501 aataattctg tcactcttca ccggtcgcca tggctcacac ctgtaatccc
aacactttgg
31561 aaggtcgaga tgaggatc gcttgagccc gggagttcga gaccagcctg
ggtgacatag
31621 cgagaccctg tctctacaaa aaaaaatttt ttttttttc agacggagtc
tcactctgtc
31681 gcccaggctg gagtgcagtg gcgcgatctc agctcactgc aagctccgcc
tcccgggttc
31741 acgctattct gcctcagcct cccgagcagc tgggactaca ggcgcccgcc
accaggccca
31801 gctaactttt tgtattttta gtagagatgg ggtttcatcg tgttagccag
gatggtctcg
31861 atctcctgac ttcgtgatcc gctgccttg gcctcccaaa gtgaaaaaaa
tttttttta
31921 aatacggcca ggtgtggtga cccaggcttg taatcccagc actttgggag
accgaggcag
31981 gaggatcgct tgaggccagg agttgaagac cagtctggc aacatagcaa
gacctccatc
32041 tctacaaaaa aaatttttt ttaattagcc aggcctggtg gcgcgcacct
gtgatcccag
32101 ctactcagag gctgagggag gaggatcact tgagcccagg aggtcgaggc
tgtagtgagc
32161 catgattaca ccactgcact ccagcctggg tgacagagtg agactctgtc
tcttaaaaaa
```

Figure 10-21

```
32221 aaaataccat gaagtgctgg tgatgaaaca ccacatggta tcagatggcc
agaattcagg
32281 attggaaggg aaagaaggga aagaaccatt catccctgaa aaacagagaa
ttgggccagg
32341 cagggtagct catgactgta atcccagcac tttgggagtt agaggcaggc
agatcacatg
32401 aggtcaggag ttggagacta gcctggccaa catgatgaaa ccccatctcc
attaaaaata
32461 caaaattagc cgagagtggt ggtgcatgcc tgtagtccca gctactcggg
aggctgaggc
32521 agggaaaatc gcttgaaccg gggaggcgga ggtggcagtg agccgagatc
acaccactgc
32581 actccagcct gggtgaagag caagactctg tgtcaaaaaa taacaataac
agagaatcaa
32641 tgggcagccc cgtgtgcccc cttcttgtgc ccagctgagt gttggctgtg
ccgtcctgtg
32701 cggtgacatg gagagaaagc atccctggga aaaattaaca cagaggagca
acttttagag
32761 atgatgggaa aacagcctgt agagtctaag acaatctccc cacctcctga
cttccttcca
32821 acaagatcct cattgcaggg acccatgtca ggtgcatggc cctgcttgca
agggcctcgg
32881 cgcagacccg gggtctccac tccatgcatg gggtgcaaga taattaaggc
tgtcatcggg
32941 cgggagggag gtgtcgtcgt ctgcactggg gcatcctgga gtggggtcct
gtggggatcc
33001 ctgtcgccat ggctctgtct ggacctaggt aaccccacc ccatgggttg
catttcagac
33061 ctctccctcc ttctccccc gccagcgtca agttcatcaa caagatccag
tacgtgcaca
33121 gcttggaaga cctggagcaa ctcatcccta tggaacacgt ccagatccca
gactgcgtcc
33181 tgcagttagt ggccccacag tccaccccgc cgtattagtc tgttttcgtg
ctgctgataa
33241 agacacacct gagacagggc aatttacaaa agaggtttaa ggggccgggc
gcggtggctc
33301 ctgcctgtaa tcccagcact ttgggaggct gaggcgggcg gatcacgagg
tcagggggatc
33361 gagaccatcc tggctaacat ggtgaaaccc cgtctctact aaaaatacaa
aaaattagcc
33421 gggcgtggtg gcgggcgcct gtagtcccag ctactcagga ggctgaggca
ggagaatggc
33481 gtgaaccccg gaggcggagg ttgcagtaag ctgagatcgc gccactgcac
tccagcctgg
33541 gccacagagc gagactccat cgcaaaaaaa aaaaaaaagg gctaacggac
tcacaattcc
33601 atgtggctgg caacgcctcc caatcacggt ggaaggcaaa aggcacgtct
cccatggcgg
33661 cagagaagag aaggaaattt gtacaggcaa attcccottt ataaaccat
cagatctcat
33721 gagacttact cactgtcgcg agaatagcac aggaaagacc tgcccccatg
attcagtgac
33781 ctcccaccag gtcactccca caacaggagg gaattatggg agctacaatt
caagatgaga
```

Figure 10-22

```
    33841 tttgggtgaa gagaccaggc aaggtggctc acacctataa tcccagcact
gtaatcccag
    33901 catttttgaga ggctgagaca ggcagatcac ttgaggtcag gagttcgaga
ctagcctggc
    33961 caagatggtg aaaccctgtc tctcctaaaa atacaaaaat tagccaggtg
tggtggtgca
    34021 tgcctgtaat cccagatact gaggaggctg aggcaggaga atcgcttgaa
cctgggaggc
    34081 agaggttgtg gtgagccgag atcgcaccac tgcactccag cctgggcaac
aagagtgaaa
    34141 ctccgtctca agaaaaaaaa aaaaagattt gggtggagat acagtcaaac
cctgtcaccc
    34201 ccaacacccc cccaccgggt cccctggct accaggagcc agcaatgagg
ggaaacgcag
    34261 acttggaagg gaggaactag aacccaccca ttttatttcc tggagcccct
cagggacccc
    34321 ccggagcttg gggaagggat gggcagcttc aagtcctgtt gttttcact
gaatgtcata
    34381 tcatcggcac ctcccctagg ttcatgctgc aaaaatctcc ttaaacgtac
attttttat
    34441 tgtggtaaaa tacacgtaac atagaacttc ccatcttagc cattcctttt
ttaattttat
    34501 ttatttattt attttttgag aaggagtttc actcttgttg cccaggctgg
agtgcaatgg
    34561 cgccatctcg gctcaccaca acctccgcct cccgggttca agcgattctc
ctgcctcagc
    34621 ctcccaacta gctgggatta caggcatgag ccgccatgcc tggctaattt
ttttttttt
    34681 ttttgtattt ttagtagaga cagggtttct ccatgttcgt caagctggtc
tcaaacccct
    34741 gacctcagat gatctaccgg cctcggcctc ccaaagtgct gggattacag
gcgtgagcca
    34801 ctgcgcccgg cctatcttag ccatttctaa aagcacattc gcatatttgt
gcagccatca
    34861 ccaccatcct ctccagacct ttcttttttt ttttttgag atggagtctt
gctctgttgc
    34921 ccaggctgga gtgcagtggc acgatctcgg gtcactgcaa cctccacctc
ctgggttcaa
    34981 gtgattctcc tgcctcagcc tccccagtag ctgggattaa ggcacccacc
accatgccca
    35041 gctaatttt tttttttttt tttttgagat ggagtttaac tcttgttgcc
caggctggtc
    35101 tcgaactccc gacctcaggt gatccgccca cctcagcctc ccaaagtgct
gggattacag
    35161 gcgtgagcca ccacgcctgg ccgattttg tatttttagt agagacggag
ttttgtcatg
    35221 ttggccaggc tggtcttgaa ctcctgacct cagttgatct gcctggctcg
gcctcacaaa
    35281 gtgctgggat tacaggcatg agccactgca cccggccctc tccagaacgt
tctcatcttc
    35341 ccaaactgaa actctgtctc catcaaacac tcactcccca ttccacatcc
caaccctgg
    35401 cagccccat cctactttct gtctctggga gtctgacgac tctagggacc
tcctaggaat
```

Figure 10-23

```
35461 ggatccacac aggatttgtc cttttgtgtc tgacgtctct cactgagcgt
gacatcctca
35521 aggtgcatcc acattgtagc ctgtgtcaga atgtccttcc ttttcatggc
tgaataatat
35581 tccattgcgt gaatggacca cattttgtca atccatttgt ccatcaatgg
acaattgggt
35641 tgtttccacc ttttggctct tgtgaatagt catgttattt atatgctact
cacctatgac
35701 cgtagatgta caaatatctc tgtaagaccc tactttcaat tctaatgagt
atatacccaa
35761 aagtggaatt gctgataatt ctgtttttt gaggaaccac catactgttt
tgttttgttt
35821 tgctttgctt tgcttttttg agacggagtc tcactctgtc acccaggctg
gagtgcagtg
35881 gcgctatctt ggctcgctgc aacctccacc tcccgggttc aagcaactct
cctgcctcag
35941 cctcccgagt agctgggact acaggcgccc accaccacac ccagataatt
ttttgtatt
36001 tttagtagag atggggtttc accatgttgg cctggctggt ctcaaactcc
ccacctcagc
36061 ctcccaaagt gctgggatta caggcgtgag ccatcgcacc cagcctgttt
tttgttgttg
36121 ttgttttgtt ggggttttc tggtttttt tttagacag agtctcactc
tgttgcctac
36181 gctggaacgc aatggcgcaa tctcggctca ccatatcctc cagcttctac
gttcaaggga
36241 ttctcgtgcc tcagcctccc gaatagctgg gattacaggc acctgccacc
acgcccagct
36301 aattttgta ttttagtag atagggtt tcaccatgtt ggccaggatg
gtctcagtct
36361 cctgaactca gtgatctgcc cgcctcggcc tccaaagtt ctgggattat
aggcgtgagc
36421 caccgtgctc agccaannnn nnnnnnnnnn nnnnnnnnnn nnnnnnnnnn
nnnnnnnnnn
36481 nnnnnnnnnn nnnnnnnnnn nnnnnnnnnn nnnnnnnnnn nnnnnnnnnn
nnnnnnaaaa
36541 tgcatctatg ggccaggtgt ggtggctcat gcctgtaatc ccagcacttt
gggaggctga
36601 ggccagagga tcgcttgagc ccaggagttg gaggctacaa gtgagttcat
gccactgcac
36661 tccagtctgg gctatgacag aatgagaacc tgtctaaaaa aaagagaaga
ggccgggcgc
36721 ggtggttcgc gcctgtaatc ccagcacttt gggaggccga ggtgggtgga
tcatgaggtc
36781 aggagtttga gaccagccag gccaacatag gaaaccccg tctgtactaa
aaatacaaaa
36841 aattagctgg gcgtggtagc aggtgcctgt aagtcccagc tactccggag
gctgaggcag
36901 cagaatcact caaaccgggg aggtggaggt tgcagtgagc caagatcgca
ccactgcact
36961 ccagcttggg cgacagtgca agactccatc tcaaaaaaaa aaaaaaaaaa
aaaaaaaagg
37021 aagaagaaga agaagaaag aagaaaaaa gagagcttgt ttctctgctt
gaaaaggaaa
```

Figure 10-24

```
37081 gggatttccc caaaaagtat atctcagggg aaaggaaggt tgtgtctgac
atcttttct
37141 ttctttcaga tacgaagagg aaagactgaa ggccaggagg gagaggtgtg
tgcagagtgg
37201 tttctgctgg ggctgggtcg gggcagcggg gggctgagct gaactctcag
ttagggcaac
37261 ccggtgactt ctgggcagca gggaccattg tcctgtgcag ggctcaagac
gctgcccttc
37321 tggcaaggac tttaaactca gacctgggtt caaatactgg ctcccgcatt
gagctgcaag
37381 gtaacattaa gcaaataaaa agctaacaac caccttggag gttattgtgc
aagatgaggc
37441 acccttggca aaaaggttg agcacagact tcacgctcca taaagcataa
aagtcaagac
37501 gggcgcggtg gctcacccag cactttgaga ggctgtaatc ccagcacttt
gggaggctga
37561 ggcaggagga ttgtgtgagg tcaggagttg gagaacaacc tggacaacat
ggcgtaactc
37621 cgtctctacc aaaaatacaa aaattagcca ggcgtggtgg tgcgtgcctg
taatcccagc
37681 tacttgggag gctgagccag gagaatcact tgaacctggg aggcggaggt
tgcagtgagc
37741 cgagatcatg ccactgcact ccagcgtggg tgacagagca agactctgtc
tcaaaaaaaa
37801 aaaaaaataa attagccagg tgtggtggca tgcgcctgta gttcagctac
ttgcagggag
37861 actgaatcgg gacgactgct tgagcccagg aagttgaggc tgcagtgagc
catgattgta
37921 ccattgcact ccagcctggg caacagagca agatcctgtc tcaaaaaaaa
aaacaaaaaa
37981 aaacagcctt tatcatgcca ggtccaatgc cagctttgag ggaaacagag
gcaaataaga
38041 cagagtcttg gtcccagaag ttttctcaaa tagcaaaggc agggaacatc
tcactggttt
38101 ggaaaacagg tcccagggga caggaaaacc agagaggcca gtactagctg
agagcccacc
38161 ccttggcctg gctgggctag tcaccttgt cacctcgttc tctctgtcca
cagcgcgagg
38221 ccccagccgg agtttgtgct gcccaggtct gaagagaagc cagaggtggc
accagtggaa
38281 aacaggtagg tgtgcagggg accatgggca gagagctgac agtcacggga
ggctgcctac
38341 tcccttgggg gaggctagag aggaagatgg gtccttgttc agggacagaa
aatggaacta
38401 agtggccggc catggtggct cacgcctgta atcccagcac tttgggaggc
cgaggtgggc
38461 agatcacatg aggtcaggag ttcgagacca gcctggccag catggtgaaa
cctcatctct
38521 actaaaaata caaaaattag ctggacatgg tggctcacat ctgtaatccc
agctacttgg
38581 gaggccgagg caggagattc gcttgaaccc aggggggcaga ggttgcagtg
agccgagata
38641 gtaccactgc actcggcgac aaagtgagac tccatctcaa aaaataaat
aaacaaataa
```

Figure 10-25

```
38701 aataaaaata aaaattatcg gccgggtgtg gtggctcacg cctgtaatcc
cagtagtttg
38761 ggaggctgag gtgggccgat cacaaggcca agagatcgag accagcctgg
ccaacatggt
38821 gaaacccat ctcttctaaa aatacaaaaa ttagctgggc atggtggctc
gtgcctgtag
38881 tcccacctac ttggaaggct gaggcaggag aatcacttga acctgggagg
cggaggttgc
38941 agtgagccga gatcagacca ctgcactcca gcctggcgac agaatgagat
tctgtctcaa
39001 aaataaataa ataaataaat atcatccagg tgtggtgatg tacacctcta
gtccagctac
39061 tcagaagggt gaggcaggca gatggctgga gccaggagg tcaaggctac
agcaagctat
39121 gactgcactc cagcctgggc aacagagcaa gaccctgtct caaaaaaaaa
aaaaaagtta
39181 tcatgatgtt ctcatattat cgcaatctca atgttatcat aatgatgaaa
ggtgaccttt
39241 gtccaggtcc cagcaggtag attcagactc ccccaatcca gtagaccctg
agcaacatta
39301 ttggcttcat tttatgttag tgaagggcct tggccaattt cctcaaaact
gtctgtttgg
39361 gctcatttgt tacgcagcag atgcacgctg acatctgttt tgtaccagat
acagcagtgt
39421 cggtcctcat agggcttaca gcctccacga acaggtagaa aatgcccaag
aatgggcact
39481 gtggctcacg cctgtaatcc cagcactttc ggaggccaaa gcaggaggac
catttgaggt
39541 caggagttcg agaccaactt gggcaacata ttgagactcc atctctacaa
aaagtttaaa
39601 agttagccag gcatgatggt gtataccttg tagtcccagc tacttgggag
gctgaggtgg
39661 gaggatcact tgagcccgga gctggaagct gcagtgagcc atgattgcac
cactgccctc
39721 cagcctgggc aacataacaa gaccctgtat cttttttttt ttttttaagac
agattttcac
39781 tcttgtcgcc caggggccag agtgcaatgg tgcgatcttg gctcactgca
acctccacct
39841 cccgggttca agcgattctc ctgcctcagc ctcccgagta gctgggatta
caggcaccca
39901 ccaccacacc cggctaattt ttgtatttt agtagagaca gggttttacc
atgttggcca
39961 ggctggtctc gaactcctga cctcaagtga tccacccacc tcagcctccc
aaagtgctgg
40021 gattataggc atgagccact gcacccagcc aagacctgt atcttaataa
taataaataa
40081 ataaaaataa aataagttaa agaaaaaaaa gggaaaatgc ccaggctccc
aaaaataagc
40141 aaataacgcc cagtctccgt ctctcctcca caggtctgct ctggtctcag
aagatcagga
40201 aacaaggtgg gtgtgatgca gagtggtctt cgtgctgttt tcaaaatgtc
cttcatggac
40261 ctgtattagt cagggttctc tagaaggaca gaaaatcaaa ccagctgcca
gcaaatataa
```

Figure 10-26

```
40321 agcaggcagg gatcctaatc ccaggaaaac tgccccatga cttatcggga
gtgggggata
40381 cggcaccggg aaggcaggga ggtagtggtt cccttaacca gtcaggccgt
ccttgcacaa
40441 ctccagggg gcaccattac ctagaccagg atgcaaatga ggccccagag
ttatgcagtg
40501 gagcggccct cagggaaaaa cccacacaga gccaagctcc ctgaagccca
ggatatgata
40561 ccacaaaagg gtagactgtc cacgctctgc ctccgattct ccacctggtt
ctggatgcca
40621 agaaaagcct ccctgtggcc gggcgcagcg tctcacgcct gtaatcccag
cactttggga
40681 ggccgaggca ggcggatcat ttgaggtcag gagttcaaga ccagcctggg
caacatggca
40741 agaccccgtc cctaaaaaaa atacaaaaat tagccaggtg agccaagatc
gtaccactgc
40801 actccacagc ctgggcaata gggctagact ttgtctcaaa aaaagaaaaa
aaaaaggaaa
40861 gaaaagaaaa gcctccctgt gtgttgatgt ccaagggtat cctcaggcac
aatggtttgc
40921 cagaaggact cacagagctc agcaaagctg tcatactcac agttatggtt
tatcacagtg
40981 gcatggttta ttacagtaga agggtacagt taaaaatcag cagagttggg
tgtggtggct
41041 catgcctgta atcccagcac tttgggaggc cgaggcaggt ggatcacttg
aaatcaggaa
41101 ttcaagacca gcctggccaa tatggtgaaa ccccatctct actaaaaata
taaaattagc
41161 tgggtgtggt ggcacacacc tgtagtccca gctactcagg aggctgaggc
aagagaattg
41221 cttgaacctg ggaggcggag gttgcagtga gctgagattg caccattgca
ttccagcctg
41281 ggcaacagag caagactctg tttaaaaaaa aaaaacaaa aaaacaaaaa
acttaacaaa
41341 aggaagaggt gcatagggct ggatccagga gagatcgggt ggaagcctgc
aagtgtcctc
41401 tcccagtggg gttgtgtgga cagcctttat ttctcccagc agggatgtgt
ggcaaaacac
41461 acaaagtgct gccaactaga gaagctgacc caagcctttc tagccagggt
gtttatagac
41521 agtcaactac atacacctgg ctgactgtct gcatggcttt tcttagcctc
cagcccctgc
41581 acagatcaag ctgatgccac gtggcccaag ttccaaccct aagtcacgtt
gtgagtgtta
41641 ttagtccatt ctcatgctgc tatgaagaaa tacccaagac cgggtaaatt
ataagaaaa
41701 gaggtttaat tgactcacag ttctgcatgg ctggggaggc cccgggaaat
ttataatcct
41761 gcggaagcc acctcttcac caggcagcag gagcgagaag tgctgagcaa
agggggaaa
41821 gccccttata aaaccatcag atctcgtgag aactcactac cacgagaaca
gcatggaggt
41881 agccgccccc atggttcagt tacctcccac tgagtaccgc ccacgacaag
tggggttatg
```

Figure 10-27

```
41941 ggaactacaa ttcaagatga gatttgggtg gggacacagc ccaaccatat
cagttagcat
42001 agactatctg gcatgaccca catagacact ccagccagga tgctccaaga
gtttagaagt
42061 taatcccagg agccagggaa ggaccaaact tttctttaga atgtgtggga
tttatccttg
42121 accacacagt ttttttgttt tgttttgttt ttgttgttgt tgttgttttt
gagatggagt
42181 ctcgctctgt cgcccaggct ggagtgcagt ggcatgatct tggctcactg
caagctccgc
42241 ctcccaggt cactccagtc tcttgcctca gcctcccaag tagctgggac
tacaggcgtc
42301 tgccaccaca cccagctaat ttttgtatt ttttagtaga gacgggttt
caccatgtta
42361 gccgggatgg tctcgatctc ctgacctcgt gatccacccg cttcggcctc
ccaaagtgct
42421 gagattacag gcgtgagcca ccatgcccag ctgaccacac agttttatac
aaatctataa
42481 gatggcctgg ccacatgcct tactacccat gtgacccagg aagctccaag
ctaagaaata
42541 aacatcaaaa atggccttag accagtgctg cttaaggggc actgagtaaa
agttctcaat
42601 gtatttctga aaagaccacc tcaacccaag ctctctggag atgagttcac
atatacagac
42661 agaaaacaca aggaaatcat ccaccatgag caaaagacag cagagacaac
aaacagcaga
42721 attagatctt gcctggagat ccttaggtgg ataagatata ataagcatgt
tttaacaatt
42781 aaaaacacaa aagaaggaat tgtaagaagc aatagatgaa tggatgaatg
gataggtgga
42841 taaatggatg gatggatgga tgagtggatg gatggaagga tgtttggatg
atgggtggat
42901 agatagatga atgaatgagt ggagggatgg gaggatagat ggatgatagg
tggatggatg
42961 gatggataaa tggatggatg gatggatggg tgaaggttnn nnnnnnnnn
nnnnnnnnn
43021 nnnnnnnnnn nnnnnnnnnn nnnnnnnnnn nnnnnnnnnn nnnnnnnnnn
nnnnnnnnnn
43081 nnnnnnnnnn nnnnnnnnga gtgggtgggt ggatggatgg atggatggat
ggatggatgg
43141 atggacagat ggatgagtgg gtggatggat gggtgggcag atggatcaat
ggataggtgg
43201 gtggatggat ggatggatgg ttgaatagat ggatgagtgg agggatggat
ggatgaatgg
43261 atggatgtgt gggtgggtgg atgggtggat ggacggatga gtgagtggct
ggatgggtgg
43321 gcagagggat gaatggatcc ctccattgag tgaatggatg ggtgagtgag
tgtgtggatg
43381 gatggatgga tggatggatg gatggatgga tgggtggatg gatagatgtg
tgggtggttg
43441 tatggttggt tagttggggg gtgggttgaa gcctccctcc aggctgattg
aggttgccag
43501 tctccagggc ctgttctgct gaggcaccag gaaggaggcc ctcagagcca
cacttagaaa
```

Figure 10-28

```
43561 gtgggtggca ggagccgggc cctgaagggc atgtgccact cttgctgctg
ggagttcacc
43621 cacgctggt gggatcattg ttttggatta catacatgta gaagcgcatt
ttgcactttt
43681 aacattaaca gcaataactt ggcctgtgtc tttccctccc tagcatgtcc
tgaggcgacg
43741 tgagcataac aaaggacatg gaagaagatt ccagatgcca gaaaacctct
gtcagacgcc
43801 cactggcccc agatctcatc ctgcctcatc ctgagtccca atcttccaag
ggtgccagcc
43861 cctccgttca tctctgaaac ccagcatcct tttcagctgc ttgaaaacat
tgtatttttt
43921 tttttttaacg atgcagtatt tgtgcgttcc agaaaagggc ccagctctga
gcccctcacc
43981 cttccacact cacgaactct cagccgagga aggcaagaag cgcaggggt
ggcccgcgtg
44041 gcgtcggtgg cctccgctcc tgctcgcagc ctctgtggtc agagctggat
acaagattca
44101 agacccttct cttgcttgtc acccgctcca ggttggagcc acagacaccc
accgccaccc
44161 cggctgggtc tgcgtccttt cctgtgcctt tccctccaga atgcggcctc
agacctagaa
44221 gctcaacccc cctatgaggg ccacgtcctg gggtagctcc tgacctccga
ccttatgtcc
44281 aaatttcaca cccatggttt ttcatttgac ccgccccctt ctcgctcata
atgacaccca
44341 gctcctttga gaggatcaga gcccattgca caagaagagc cgctgccaac
catccttgtc
44401 ctccgattgc aaaatgacac cccagtaatc tagaacattc tcaagcccct
ttaactcaga
44461 tgtcaagcca ccgggcaaac cccgtcaata cctcccacca aggaatgaga
tatgtggacc
44521 tcactgctcc cccaacccag cgtcaggctg gacacgcca acgctgttcc
gggttggaac
44581 agcagaggct cagaaactgg ctctgaaata ggcagaccta gcaagaggaa
gatacagggt
44641 atcggcgtt tgagtgtttc agaagtcatt cgggaagata aatccagtgc
gctggccgca
44701 gccacctgca ttcaaagctt ggaccagcgg gttcttgttc gggaggcaaa
tttccctagg
44761 aaaaagaaga cagacttttc taatgtggtc caaatgcgga tcactggtca
gatggactct
44821 agaagcactg agctccctgt ctctggaagt atttaagaaa aggctgggcc
aggcacgatg
44881 gctcacgcct gtaatcccag actttgggag gccgaggcag gcggatcacc
tgaggtgagg
44941 agtttgagaa cagcctggcc aacatggtga aacctcatct ctactaaaaa
tacaaaaatt
45001 agccaggcgt ggtggcaggt gcctgtaatc ccagctactt gggaggctga
ggcatgagaa
45061 tcacttaaac ctgagaggca gaggttacag tgagccaaga tcgtgccact
gcattccagc
45121 ctgggcgaca gagcaagact ctgtctcaaa aaaaataaaa aataatcagg
gcacagtggc
```

Figure 10-29

```
45181 tcatgcctgt aatcccagca ctctgggagg ctgaggtggg tggatcacct
gaggtcagga
45241 gttcaagacc agcctggtga acatggcgaa accccgtctc taataaaaat
acaaaaatta
45301 gccgggcatg gtggtgcatg cctgtaatcc cagctactcg ggaggctgag
gcaggagaac
45361 tgcttgaacc caggaggcag aggttgcagt gatccaagat catgccactg
cactccagcc
45421 tgggcaacaa gagcaaaact ccgtctcaaa ataaaagaa aagaaaagaa
tggacagtgt
45481 ttgcagagag ttgctcacga gtttccctct aatcctaaat gtcttcatgt
ctatcagtct
45541 gagcagacgg tgagtagggc gggcacattc tccaggccct tcttcctagc
tctgtggttg
45601 acctctcagc aagtgctatc caggctgggc aaccagacc cacaattaac
tgagcctcag
45661 tgaaagcgtc cagtgcatct tgacctgaga cagcaaggaa ttgcatttgg
ggttattcca
45721 acgatgatgg cagggaactg gtggtattta gtgctgaggg gcagtgatac
agaaagattt
45781 gccctgtggg acagggtcct gcgcgagtcc catccccaaa agccagcagc
tcctgccatg
45841 aggaagacgg ggtttctgag caggcttatg cctgcaggtt cctgtggagc
caccggctgt
45901 gacgggacac ctctgggtct cagcattgcc ctggggaggc tgggacattt
agggacatgg
45961 tagggtttta acatttgttt cccaaatgtc aaatcccggg cacagggca
agaccctgtc
46021 ccgaattccc accccagtga atggtgtcgc tgccaaagcc aacacaagat
gacaaaagtg
46081 gctgggtacg gtggctcacg cctataatcc cagcactttg ggagaccgag
acaggtggat
46141 cacctgaggt caggagttcg agaccaggct ggccaacatg gtgaaacccc
atctctacta
46201 aaaatacaaa aattagctgg gtgtggtggc gcgcacctgt agtcccagct
actcaggagg
46261 ctgaggtaga agaatagctg gaacccagga ggcagagatt gcagtcagcc
gagattgcac
46321 cactgcactc cagcctggga gacagagcaa gactgactca aaagaaaaaa
aatgacagaa
46381 gcctgattat cagactgccc ggaggagaca ggctccagca gatagatgcc
agccaggccc
46441 agctgccacg atttgtccca ggtgaccaaa ggcacgcagc tccagcatga
atcgttctaa
46501 cccaacagtg acaagaactg ctgggcctta accgtcatgg aagactgcgg
ccgcttccaa
46561 gtcacagaca ggagacgggg acaggaaaga actcattcca cccaatcgga
cacctaataa
46621 ttgagtgtct acagcagcaa tcaagtgaca agtgaggccc tacctgaccc
agaaggtgcc
46681 tgccggctaa acattctgcc cccaccagaa actccagggg gtccgcccgt
tatgccgtgg
46741 cccacccacg cccctttgga tcaccagcag tcacagacaa caggcaggcg
aaactgaaga
```

Figure 10-30

```
46801 ccccaactca gccccagcgg accctccaga gcaaaagagg cccccggcga
ggccacctgt
46861 cggcaggcat gccgaggtca aacagccggg gccaccgttc ccagctgggc
cacgacctgc
46921 accgtccaca gatgggcttt gagatggatt tgtatcaggg tgggggggtgt
ggtttggcca
46981 aaatgcaatg gaccccgacc cctcctcgta aaggatgtt gggtttccct
ctggtgacac
47041 atgggatgcg tcataaaccc tcccccaaag tcctggtcag cagcccatcc
ttccaacgat
47101 gagttttgcg gtttttcaga acagaaatga tcactacgat tgacgacggt
cgtgatgtta
47161 agacgtcgtc tccatgagct ttgggggggac ttttatgtgg aataaagaaa
ctatcactg
```

Figure 11-1

SEQ ID NO:11

```
cccaccatcaggggtcagtgccctccacactcgaatgttgctgccccctg
cccagtcgggaaacttccaggtctctgccttctcctcctccagcaatcg
gggattaacgccctctgccttccctcctcctgcccagccagacaccc
tcccaggtctgaattctctcccctaccagcaatcggggtcagctccgct
ctagctctcccctgtccagccagacaccctccaggtttctgtcttctc
tcttaccccatcaggggccaattcctcaccctcgactgtggcttcctc
ctgcccagccaggaaccctcgctgatctctgttttctcctccctacaag
taatcggggtcagctacctctgtccatcccctgcccggccaggcacc
ctccaggtctgtgtcttctcctcccccgcaatcgggggtcaatgcccc
tctgcccttccctcctcctgcccagccagacaccctctaggtctgtgt
cttctcttccctaccagcaatcaggggtcagctcccctctgcccatccc
cacccactcccggccaggcacctccaggtctcctccctgcattgggtc
agttccgtcccctccctcctcggtcagaccacccaccccccgccgggt
ctgtccctctcgctgcctcctcgtggcgcccatcaggggctgaccc
ccccgaccccgcacaggcccaggcccaaacccaggcccctcccacttca
ggagcccctcccgctcccgccgacagacaccgttggctgcagagacgtc
tcagccggagccccggagccgcatcccgccggtgcctaacctgaggcc
gccccgcctgcttctcccggcgccgcggcttccctcaggccggggttcca
ggttggggctgggactggggccgggccgggcgcacgcggcgggagaaggg
gtaggcggggtcccggccaggctgcaggggccgggactggcgggggctgg
cgcggcgggcagttacctgtactgcgggccgccgccctgcgcgaagtcg
aaatactgactcgtcgccatcttggcgtcttccccgagcctggcggaccc
gcgacgtcacccgccccgccccgagccgcgtgccgctcgcgcctggcca
cgcgccccaagctccgcccctgcgcgaagccctcaccttctcgcttcct
tctcttaggctagggagacaccgccccgcgaccacacctgccccgaggcc
ccgcctcctacgcagagcccgccctcctcttaaccactcaaatgtggag
gtctctgctcaagccccgccatgctagaagccctgcctctttctcggag
ccccacattccctttaaccactcagatgtggtggtatctgatcaagtccc
gcccatgctacaagccccgcctcttactcagagccctgccttccctttac
ccactcagatgtgatctctgctcaaccccacccatgccacaagcccgc
cttttttggaaccgtaccttccctttaaccattcaggtgtggaggtctc
tgctcaagccccacccatgccacaagccccgcctctttctcggagccccg
ccttcccttacctgctcagatatggtctctgcacaagccctacctctgt
ctccgagccccaccttctctttaaccactcagatgtggaggtctctgctc
aagccccaccaccaccacagccagctaattttttaaatttttttgtagagac
agtgtcttgctatgttgcccaggctgatgttgaactcctggcctcaaata
atcttgccttggcctccaaaagtgctgggattacagacgtgagccactgc
atctagcctcagaatgactcttcagaaggcccccatggtctctgcctcct
gtgttcacaacgtgatataaataaatgataggccgggcacagtggctcac
gtctgtaatcccaacatttgagaggcggaggcaggaggatcttgagccc
taggactttgagactagcctgggcaacatagcaagacctgtttctacaa
tttttttttaattagctggtcatggtggtacatgcctgtggtcccagcta
ctcaggaggctaaggtggaggatcacttgagcctgggctgtcaaggctg
cagtgatctgtgactgtaccactgcactccagagtgagaccctgtctcaa
aaaagagaaaagaaagaaagggctgggcgtggtggctcacgcctgtaatc
ccagcactttgggaaggcgaggtgggcagctcacccaaggtcaggagttc
aagagcagcctagccaacatggcaaaccctgtctctactaaaaatacaa
```

Figure 11-2

```
aaaaaaaaattagccaggcgtggtggggcacacctgtaatcccagctact
cgggaggctgaggcaggagaattacctaacccaggaggtggaggatgcag
cgagccgagatcacaccactgtactccagcctgggcaacagagcaataca
ccgtctcaaaaaataaaaaataaaaaataaaaaaataaataaataaat
aataaaagaggagagggagaggagcagggagggagggaagggaaggaaag
aagagagagagagagagagagagaaagaattgaatgaataaacaaataaa
tggaggcaaacagacaaatctcttatgcagaagaattcctaatttgtgta
gctacactgcgcttaaggagatagagagtaactctacacctcttgagtgt
gggttgtgcatagtgacttccttcccaagactgcagcctggaaggaggggg
gagggagagtcacttgacagtattgaaacctgacaagcagcagcgtgttt
ggcggtcccgcggatccgtctcttgcttccacagtgtttggatggaacag
atccgggaactcacttccagcctccgaccacccgctgatttcctctcttc
ttgcaacctccagGAGCATCGGCTCAGCCATCTCCTGCTTCTCGGACCAA
CCAACGCCGTTTTTTTGGTTAGCTCCTTCTTGCCGACCAACCATGAGCTC
CCAGATTCGTCAGAATTATTCCACCGCGGTGGAGGCAGCCGTCAACCGCC
TGgtcagtttgcacctgcgggcctcctacacctcctccctctgcgggttt
ttttttttttttttttgcttgttttttttttgagacggagtctggctctg
tcgcccaggctggagtgcagtggtgcgatctctgctcactgcaagctccg
cctcctaggttcacgccattctcccgcctcagcctcccgagtagctggga
ctacaggcgcccaccaccacgcctggctaattttttttgtattttttagtag
agacggggtttcaccgtgttagccaggatggtctcgatctcccgacctca
tgatccgcctgcctcggcctcccaaagtgctgggattacaggcgtgagcc
atcgtctgcgcttctatttcgatcaccaagatgtggctccggaatgcggg
gcttacttcttccatgaattggccaaggagaagcgcaagggtgttgagcg
tctcctgaagatgcaaaaccagcgtggtggccctgctgtcttccagGACA
TCCTGAAGCCAGGTCAAGATGAGTGGGGTAAAACCCTGGAAGCCATGGAA
GCCGCCATGGCCCCGGGGAAAAATCTCAACCAGAGTCTTTTGGATCTTCA
TGCACTGGGTTCCGCCCCTACAGACCCCCATCTCTGTGACTTCCTGGAGA
GTCACTTCCGAGATGAGGAgtgggctgcacgcggtggctcacacctgta
atccctgcactttgggagaccgaggcaggcagatcacctgaggtcaggag
tttgagaccagcctggccaacatggcgaaactccagttcttctaaaaata
caaaaattagccgggcgtggtgagctactaagaggctgaggcatgagaa
tcgcttgaacccaagaggcagggggatgcagtgagccgagatcacgctact
gcactccagcctggggaatagagtgaggctctccaaaaaaaaaagaagaa
gaagatgggtgaccacctgaccaacctccacaggctggccggcccggaag
ctgggggcccagaggctgggctgcatgagtatctcttagaaaagccgac
tctcaaacacggctaggaacctactgagcccagcgacttctgaagggccc
cacgtaaagtaacggggcttctgcctaagcctttccctccattcactagg
cagcttttttgtttatttgtttgttggtttgtttgttttgttttgagaa
ggaatctcgctctgtcgctggagtgcaatagcacaatttcagctcactgc
aacctccgcctcccaggctttggcgatcctccaacctcagcctcccgagt
agctgggattactggcatgcgccaccacacccggctaattttgtatttt
tagtagagacggggtttcaccatgttggccaggctggtatcaaactcctg
agctcaggtgatccacccgcctcggtctcccaaagtgctgggattatagg
cgtgagccactgcgcctggctttgttatagcacctgaacagactaagac
gcccactttgaacactagattccaaaaagcatcatagaagtcttgggctt
ctgttagataggcatggtggcaggtgcctgtggtcccagctactcaggag
gctgaggcgggaggatcacttgagcccaggaggcagaggttacagtgagc
caagatctcaccactgcactccagcctgggtgacagagccagacccccgt
ctcaaaacaaacaaacaaacaaaaaacataaaaggggcctggcgcagtgg
ctcatgcctgtaatcccagcactttgggaggctgaggcgggcggatcacc
tgaggtcacgagttcaagacgagcctggtcaacatggtgaaaccctgtct
ctactaaaaatacaaaaattagccaggcaaggtggcgggtgactgtagt
cccagctactcgggaggccaaggcaggagaattgcttgaacctgggaggc
agatgttgcagtgagccgagatcgcgccactgcactccagcccaggtgac
```

Figure 11-3

```
ggagtgagactcagtctcaaaacaaaacaaaacaaacaaaaaggaagtc
ttgggtcttgggcatctatgaacttttgctttgctgaagtctttcaaatc
agttggcttttttgacaatggagtattacgagagcattaaagtaagaagtg
cattcagcagatacagggctactaattcttggacaggctccatggagagc
ccagggtgctgagggaagccacatttggtgatttagcggatggcactctt
ccatctgtaactccatgaccatgtgtggccaccaggaatggtctggtggg
tctggccagtgcagctctccctgccatgccctggctaaagtccaacaagg
taattaattgcacacggcctctctccaagtccctgccgttctaattaggt
aatgaaggctgtgtctctttacaaaggatctgttgtagtgttttctctgg
gttgcatttttctattatttactgcaaggattgtgctaaatgctttaca
tgcaaaatgtgatctagttcccacaacagccttcagaaggccgggcatgg
tggcttacacctgtaatcccagcactttgggaggccgaggttgggagttc
aagaccagcctggctaacatagtgaaaccctgtctctattaaaaatacaa
aaaaattagctgggcgtggtggtagttgcctataatcccagctactcagg
aggctgaggcaggagaactgcttgaacctggagggcagaggttgcagtga
gttgagatcacaccactgcactccagcctgggtgaaagagtgaaactctg
tctcaaaacaaaaaaaaaaccaaaaaaaaaaaaaacagccttcagaagta
gaaacaggcatagtggctcataccagtaaccccagctacttcggaggcca
aggcaggaggattgcttgagcccaggagtttgagaccagtctgggcaaca
tagggagaccccatctctacaaaatacaaaaattagctggatgtggttgt
gtgtgcctgtagtcctagccacttaggaggctgaggtgggaggatcgctt
gagcccaggaggtggaggctgcagtgagccataagtgtaccactgcattc
cagtctgggtgacacagcaagacccagtctaaaaaaaagaaagaaagaa
aagaaaagaaaaagaggccaggcgtggtggctcacacctataatcccag
cactttgggaggccaaggcaggcagatcatgaggtcaggagatggagacc
atcctggctaacacagtgaaaccccgtctctactaaaaatacaaaaaat
tagcaaggcatggtggcacctgtagtcccagctactcgggaggctgaggc
agaagaatggcatgaacccgggaggcggagcttgcagtgagccgagattg
caccactgcactccagcctgggcgacacagcaagactccgtcccccaaaa
aaaaaaaaaaagaagtagacacagtcgattctcattaattctgttctct
aaagtcaataccaagctcactaatactgaccatcgctcctaagagaaaca
cgaggttgagttcctgtgagcctctagtcacagtgtttgcatcaaccatc
aatacacgacctcggccagtgcagtggctcacgcctgtaatcccagcact
ttgagaggatgaggagggcggatcaactgaggtcaggagttcgagacccg
cctgaccaacatctctactaaaaatacaaaattcgccaggagtggtggtg
catgcctgtaatctcagctactcaggaggctgaggcaggagaatcactt
aacccaggacgtggaggttgcagtgagctgagattgcgtcattgcactcc
aacctgggcaataagagcgaaactccgtctcaaaaaaaaaaaaaagaaa
aaaagaaagttcaaatgtctagccaaccgggattagttcagattgtgtg
acccgaccccggccaatggggaaagggcacaggggcaggacttgcctcag
gaataaaggctctcatgccccttttgttcaggtgcgctctcatgacgactg
gacaaagaaaaacacctctctgcgcagaagtaaaattgctttgctaaaat
cccttttgtttgtgtattcaatcttcttaggattttgagcgttattcccaa
caaatagacatggttgattcattcacattgaactcatagcactttttactc
atatctgaagttctctaacacactgcttttcttcttggagctttcttttt
tttttttttttgagatggagtcttgctctgttgcccaggccagactgaagt
ggcgcgatcttggctcactgcaagctccgcctcccgggttcacgccattc
tcctgcctcagcctcccgagtagctgggaccacaggcgcccgccaccacg
cccggctaattttttgtattttagtagagacggggtattgccgtgttag
ccaggctggtctcgatgtcctgaccttgtgatccgcccacctcagcctcc
caaagtgctgggattacaggcgtgagccaccgcgcccggcctctccttgg
agctttcttgcacttaggaagactagacagtgcttcagcatgaagcttgg
aagtcatttatttatggatttatttatttattttgagacagagtctt
gctctttcacccaggctggagtgcagtggcgcagtctcagctcactgcaa
cctccgcctccctggttcaagcaattctcctgcctcagcctcctgaatag
```

Figure 11-4

```
ctgggattgcaggcgcgtgccaccacgcccggctaattttgtatttta
gtacagacggggtttcaccatgttggccaggctggtcttgaacttctgac
ctcctgaccacccactttggcctcccaaagtgctgggattatacgcgtga
gccacattgcctggcctgtatcaagcattcttttagggcagaattttct
tgctcagtaccgtggacattgggaccagattattctctggggcggagcca
tcctgggcactgcagggtgctgagcagcgtccctggcccccatccactcc
ataacaggagtatcccccagtcgcaacaaacacaagtgtcccagaaatc
gtccggtgtccgctgcgggcaggatcaccaccccccaggtgacagccac
tggtgtaggggttaaagatacagggtgacaggccgggattacacctgtaa
tcccagcactgagcccagcactcctggcctcaagtgatccacccgcctca
gactcccaaagtgctgggattacaggtgtgagccactgcacccagcccac
aagaaattttctacaagctcaccttcagaaaagtttcaagatcctacaa
aatctagccctttgtgcatttccaaacgaattcctcagggatggccggc
agaataatggcccctaaagatatccacacccactgggtgtggtatgtttg
cctgggaaaaatagtgagacccatctctacaaaaaattgtcaaattaac
caagtgtgatggcatacacctgtagtcccagctgccagggaggctgagat
aggaggatcacttgagcccaggaggttgaggctgcagtgagccatgatca
caccccgcactccagcctgggctacagagcaagaacctgtctcaaaaaa
attaaattaaattttttccattttaaaattaaaataaaacgaaat
gaaaacagacagaggccagctgcagtggctcacacctgtgatcacagcac
tttgggaggccaaggtaagcggatcacctgaggtcaggagtttgagacca
gcctggccaacatggtgaaacccgtctctactaaaaatacaaaaattag
cctggcgtggtggtgggtgcctgtaatcccagctactcgggaggctgagg
cagaaaaatcgcctgaacctgggaggtagaggttgcagtgagccgagatc
gcaccagcctgggtgacagagcaagcctctgtctcaaagggaaaaaaaaa
cagggaaccaagcttaggtcacacgctgtggctcctcggtggtggctgta
gcaccatggacagctcccaggctttggtggactggggagaagctgttgct
ctttaaatgccagtctgggcaggcctgtctgtccagaatatgccttcctc
cctcttttttattcatctaactccactcactcctcaggggtctcactcat
gcagtcgccacctctgtgccccaccaggaaacctccccaacggtccccca
acctgcaccactccaaagatgtctctagatcagcccagactctgttgtcc
acctgtttctctcaactgaatgggaattatttatttttttttttttgag
atggagtctcactctgtcaccccacctggaatgcagtggctcaatctggg
ctcactgcaacctccacctcccgggttcaagcgattctcctgcctcagtc
tcccgagtagctggaattacaggcgcccaccgccacgtctgaccaatttt
tgtattttagtagaggcggggtttcaccatgttgtccaggctggtctca
aacccccaacctcaagttatctgcccgcctcagcctcccaaagtgctgag
attacaggtgtgagcggcctcccaaagtgctgggattacatgcctggcct
caactgaatggtcattctaagagaattcccaatcctgcacacaaaacag
cataaattaactgaattagggaagccacgcctctgccagccgtgagctgg
gaagaagcagatacctcagaggcagggagcgcaggcgggtgatgatgaga
ggggccacagccgcagcccacgcaggggagcccaccactaaccctgcac
ccccaccctgcacaaaagagctggtgggcactagccatatcgccttgca
accttcctcggatgcagaatccactccttcaggcatcctcttcctccaat
gctctgaaggcctggggagcctgagagatgcccgctgcacccaggcaggg
ctcgcctttgtttgccagtaatgggaattactcatatcttgtgcccagtg
cccagcacagggactcatcgaatccacccctcagttaacacaagtgtctc
ttacaagacctccatttctccagccaggagatgggaagtcccaaccttg
tgctaaagtctctggggcctctgcttccccatcagggctttctgcctctg
ctgtgggcagGTTACCTTTATGCCTCGGAAGAGTGCAGACCTCCATGCAG
CGGgtgaggctgccagcctaggtggggtgtcattgaatgtcatgaaggga
gccagccttcatgcactctgcctgcgtctcctgaacagctttggaccagg
agttgctaccttgtgcggagaacgtgtggtgcataagaacaaccgagcct
ctgctcttcgaaaatgtatattctggccaggtgcggtggctcacgcctgt
aatcccaacactttgggaggccaaggtgggcaggttgcctgaggtcagga
```

Figure 11-5 gtttaagaccagcctggccaacatggtgaaacccgtttctaccaaaat
aaaaaaaatagctgggtgtggtggtgcatgcctgtagtcccagatgcttg
ggaggctgaggcatgagaatcgcttgaacctgagaggaggaggaggttgc
ggtgagctgagatcacaccactgcactccagcctgggaaacagagcaagt
ctctgtctcaaaacaaaacaaaacaaaacaaaacccagtatattctaata
aggaggagcagagaatcaacaacaacaacaaaaaagtgtaaataatttca
attaatagtaagtgctgtgggtcaggcacggtggctcacacctataatcc
caacatttttcgaggctgagatgagaggctcacttgagcccaagaattca
agaccagcctgggcaatagagagatacccctatttctacaaaaattacaca
gattagcagggcgtggtggtaggagcctgtagtctcaaccactggagaga
aagaggtgtaaggatcacctgagcccgggagttcaagactgcagcgagct
gtgattgtgccattgcactccagcctggatgacagggaaaactcctgttt
cttaaaaaaataagtaaataaaataaacattaaaaacagcaatagcaaga
aatacatataggccgagcacagtgattcgcacctctaatcccagcacttt
gggaggccaaggtgggcggatcacctgaagtcaggagttcgagaccagcc
tggccaacatgttgaaacccgcctctactaaaaatacaaaaaaaaaatt
agccaggtgtggtggtgtgtgcctgtaatcccagctacttgggaggctga
gggaggagaaccacttgaacctgggagtcggaggttgcagtgagccaaga
tcgcaccactgtactccagcctggcaacagagcgagactccacctaaaaa
aaaaaaaaaagaaagaaagaaagaaagaaagaaagaaagaaagaaagaa
agaaagaaagaaagaaagagaaagaaacacatagggagcttttcttgtgc
cccagcactgtgtttagtgctgtctatgcattatctcataatgtggaaaa
gccatagcggctccatttcacagatgagaaaaactgaggcccgcaggtga
gatcactcatgccactggtctgccagctggggagtggctgggctagagt
tcaaacccacttccagtccgactgcacggcctgcactctccaccctacca
tcttccacagtctccttgaattcctccagggcgaggccacgccagcgcac
aactgcaggggcgccgttcccacagcagccctgcaaagtgagtgtgcct
gagaaacttccgcctcccctgcacccagccctgtttagggcacgaggctg
aatcaatggtaagtgaccatctaatggacccacaacacggtgacctgggg
acagtcatttctttcttttttttttttttctttgagacagagtctccct
ctgccgcccaggctgcagtgcagtggcgccatctcggctcactgcaacct
ccgcctcccaggttcaagcgattctcctgcctcagcctcccgagtagctg
ggattacaggcgcacgccaccacgcctggctaattttttgtattttcagta
gaaacggggtttcaccatgttggccaggctggtatcgaactcctgacttc
aggtgatcctcctcctcggcctccgaaagtgctgggattacaggcgtga
gccatggcatccgacctggggacagtcatttctttgcctgcacagacttt
ttgggggatgccacccctcacccctgctccctttgcaaggagaagtgcca
agaagacctttcccaactcccccaccccccattctctaaggaatgaggcc
atcttgccatttatttatttatttgtccgttgttttgttttaaatctct
gatgcgccatcagaaaattatttctgcctctgcccctggcgtggctttcg
gagatgcttgtctgtcagccaatggggaggatcggattctggcaggggc
tgtgcttttccgtcaggccgccaccccccaccccctcctccctgcacaca
aaagcagcataaattaaccgtcttcg

```
ggaagccgag  cctctgccag  ccctgagctg  ggaagaagca  gctacctcgg  aggcagggcg
cgcaggcggg  cggcgatgag  aggggcgca   gccgcagccc  cgcgctgggg  agcccaccgc
taaccctgca  ccccacccac  ccctgcacaa  aagagctggc  gggcgctggc  cacgtcgccc
tgggtgacct  tcctcggatg  cagaatccgc  ccctgcgagc  atcctcttcc  tcctaggctc
tgaaggcccg  gggagcgtga  gcgatgccca  gctgcacccg  gcagggctc   gcctttgttt
gccagtaagg  aggagaggct  gtctcagctg  cagaggtgag  tgcgcgcatc  tccccttctc
ccaggataaa  ccgtctccct  ggaaggttta  tccggcagcc  tttgccgcct  ctaaatccct
ttccagcaga  tggggcgggt  gggagcagag  agccacggtc  ttgtgactcc  gtgaaggccc
tcacatccct  gttcccggta  cagggaaaa   ccgttccctg  agctgcgccc  agcaacacag
tttaccttcc  gcgcgcaccg  ttccctcta   agtgccacat  tttcaggaca  cgctgagagc
tcgggcggat  gaaaacctca  gcttctctct  gggacgctga  aatagaccca  tcctagccct
atgtattttcc tatttataac  gctaggaagg  ccaccagccg  acgattcgg   gaaaaaaaa
```

Figure 11-6

```
aaaaaaaaat ctaagtgtgt cgataaaggc tgtcctgtgg ggtggggagg aagggggtgg
tttatggttt aagacacaga tgcctcctcc ttattggaac tcgtatgtga tttgttaata
atcagacatc agggctcaaa tgagcgcttc actcccgttc cttgatgtca ctgtcttctt
ttggccgtcc ccaaatgcga agccaggatc tgagtgcagg agtgtccggg gcccactgag
gacccacccc accccatcct tagaagactg tggagtcaac gcctgtggct gcagctggca
gggggtgggg gtcggggcg gggctggtgg gagtgttcct gggggctgag gtcacaccca
gctcagtata aggaagggag aggcgaagac cccttcctcc ggagagcaaa tgcgtttcta
 ctgccgagga gaacttaccc tcgcgggaag ggcctggctg gctgctgcca ccgccccccc
cccgacccca tagcatccag gagggatttt tttttttttcc atgctgcgtg ttactgtccc
tcctccaagc atgaatgacg acattgagga cagagaatcg agtgagaaac gctcaccctg
tacgggggag ggtctagttt tagccgtccc ctccccccac ttcctcatct ggctgaggct
gcctctgggt ccttccttgc taagccacag tccctgtcc ccgatgcaaa cccgatatct
atgctggggg gctgcaggta acctactcca cagagaggca gcctggatgc catgagagtt
gggggcctta gatgcttcat gtatttggtt ttttttgagac agggtcttgc tatcttgccc
gggctggtct taacctcctg tgctcaggcg atcctcgcaa agtgctggga ttacacgtgt
gagccactgc ccccagccag atgctttatc ttttattta tttttgaag tagggtctct
 gttgctcagg ctggaaagca gtggcatgat catagctcac tgcagtctcg acctcctggt
ctcaagcgat cctccaactt cagcctcctg aatagctggg acttcaggca ccaggcaccc
atcaccatgt ttggttaatt tttgtatttt ttttttttta agagatgggg acttgctatg
ttgcccaggc tggtcttgac cttccaggct caagcgatcc tcctatctca gcctcccaaa
gtgctgggga ttacacgtgt gagccactgc ccccagccag atgccttatt ttatttatt
ttattttctg aaatagaacc tcactctgtt gctcaggctg gaatgtggtg gcacaatcat
acctcactgc agcctccacc tcctgggctc aggcaatcct cccacctcag cctcctgaac
agctgtgact tcaggcaccc accaaattta attaattttt gtttttgttt ttgcttttcg
tagagatggt gtcttgctat gttgcccagg ctggtcttga ccttctgggc tcaatcctcc
cacctcagcc tctgaatag ctaagacctc aggcacccac cattgtgctt ggttagtttt
tgtatttttt ttttgagaga tggggtcttg ctgtgttgcc caggctggtc tcgaacccct
ggtctcaagt gatctgccca agtgctgga attccaggca tgcaccactg cacccagccc
ctagacgctt taaaaagtgg atctagtggc ccggcagggt ggctcacacc tgtaatccca
gcactttggg aggcaggtgg atcatgaggt caggagttcg agaccagcct ggccaatata
gtgaaacccc atctctacta aaaatacaaa aattagctgg acgtggtggc acgcgcctgt
agtccaagct actcaagagg tggaggttgc agtgagccga atcgcacca ctgcactcta
gcctgggcga cagagcgaga ctctgtctca aaaaaaaaat gacaacaaaa aaagtggatc
tagctactcg gaagctgttg agagacagac agaggtaatg gaaggacaga gtgtacaata
ctctataatg actgccggac acaggcctga aatcctttcg caaacacggg aatgcacaca
gaaatgacta ttgcctttaa gacaaggttt ctccaccttg gatctatgga tatttgggac
ccagtcattc ttggtcatgg gcggccatcc tgggcactgt aaggtgctga gcagcacccc
tggcctgccc aggggcact cctccccctc agttgtgaca aaagtgcctc tagacaatgc
caagtgtccc cttgcagcag gggaggcaga attgtccaca ggtgcaaagc actggtttca
aagcccaaaa cagatggggt tggttgagtc ataagatgct ggtatgttat gtccaaaagg
tatcttagag gtcatctcta attcaactct tttgtttaca gaaagggaaa ctgagaccca
gagagggaga tggtctgaga gtctgccatg cccagagca gaccacaact cagtctcacc
tggcagctct gatcctggcc cccacccaga ctgctccccc ctgccctgcc cctgccctg
cccccagtga gctcctcaga acaagaaaaa caaaactggt gtgggggtg gggcggcaca
gtggctcaca cctgtaatcc cagcgctctg ggaggctgag gcaagaggat cacctgagcc
cgaaagttca agaccagcct gggtgacata ccaagatcag agaaattagc caggcatgat
ggcacacact cgtggtccca gatacttggg aggctgaggc aggaggatcg cttgagccca
ggagttggag gctgtagtga gctgggatca caccactgca ctccagcctg ggcgacagag
caagaccccg tctctaaata aataaataaa taaataaagt ggcattttgt ggtagtaaag
atgagggtct cctttctaac cccagtctct ttccacactg ccttagtgag ccctggagtc
agaaagtcac taggacttgc ttagggagg acagagaggc aggacaggtg gcctggtaca
tatggcagat agcgatgggt tagagcctac tggattctct ttgaacttgg cattcccagc
acggaagctg aagtatatca gccattcaca ctttagtatg aatgactgtt tggatttctt
gctttctagt tgaggtccaa ggcacaagag ggagggtaag tctatctggg tcatggctca
ccctggagaa ggtagatttc gaagtttcca agggagcagg acttgtatct gaaggctcag
```

Figure 11-7

```
cctctcgccc acgttcaaac tctgaacccc actgtgcatc ctaagctctc tgtgcctctg
ttttctcatc tgtaaaacag gggaacctca tgggctcgg tgatggttca ataagaagtg
ctggccgggc acagtggttt acccttgtaa tctcagcgct tagagaggcc gaggcaggag
gattgcttga gcccaagagt ttgagaccac cctggccaac atagcaagac ccaatctctt
aaaaaaagat tttaaaaaat tacccaggca tgatggtaca cacctgtggt cacagctact
ggtgggggc tgaggcagga ggattgctta agcccaggag ttcaaggctg ccatgagcca
tgattgtgcc cctgcactcc agcccaggca acagagcaag atcatgtttt ttttttaaa
aaaaaaaaa aaaaaaaaa aaacagccaa gctcagtggc tcaccctgt aatcccagca
ctttgggagg ctgaggcggg tagaccgctt gagctcagga gtttgagacc agcctggcca
acacagtgaa accccgtctc tattaaaaat acaaaaatta gccgggtgtg atggctcaag
cctgtaatcc cagcactttg ggaggccaag gcaggaggat cacctgaggt caggagttcg
agaccagcct ggccaacatg gcgaaaccct gtctctacta aaaatacaag aattaaccag
gcgtggtgat gggtgcctgt aaccccagct acttgggagg ctgaggcggg agaatcgctt
gagcctggaa ggtggatgtt gcagtgagct gagatggcac cattgcacta cagcctgggc
aacagagcaa gactccgtct caaaaagaa gaagaagaag gagaaggaga gaggagagga
gaaggagag aggggaggg gaaggggag gggagacgg aggggagtg ggagggaa
gagctgcatg gggtagacga ttgtcattag gactattgtc cagtaaaacc cattcctctg
cggcttcctt tcaggggtca tccctgcttc aagccagtgc ctcttcccag ctcccatggg
gaccaccgaa gccacgctcc ggatggaaaa cgtggacgtg aaggaggaat ggcaggacga
agatcttccc aggtaggact tccacatccc tgagtcaacc gttgggggag caggtgtctc
tcccaggtgg gacacaggag cggcccgggt ctctctctaa gtgggaaccg cccggggctg
gcctggttcc atctccgcgt cctcctctcc cgcacactct gggaggcctg aggccctgtg
tgcgagtctt ctctgtggcc tcacagtggg gtagtcctgg ccaggcacat aatgggtatt
tgctcaatga tttaagattc atttctgtct tccctgcccc aaagctccaa aggacccccc
accctacac cattttaaga gttcttaaca ttctggctgg gcgcggcggt tcacgcctgt
aatcccagca ctttgggagg ccgaggtggg cggatcactt gaggtcagga gttcgagacc
agcctggcca acatggcaaa accgcgtctc tactaaaact acaaaaatta gctgggcatg
ccggcgcag tgactcatgc ctgtaatccc agcactttgg gaggccgagg cgggcggatc
atgaggtcag cagatggaaa ctatcctggc taacatggtg aaactccatc tctactaaaa
atacaaaaat tagccgggtg tgtggcaggc gcctgtagtc ccagctactc gggaggctga
ggcaggagaa tggcgtgaac ccaggaggcg gagcttgcag tgagccgaga tcgcgccact
gcactccagc ctgggcgaca ggtgagactc catctcaaaa gaaaaaaaaa aaaattagct
gggtatggtg tcatgcgcct ataattccag ctactcggga ggctgaggca ccatggtgat
ttattagcag cctttaggag acacttacct cccctaacat gctgaacttt tttttttttt
tttttgagtc tcactctgtc ccacaggctg gagtgcagtg cacgatctc aggtcactgc
aacctccagg tcctgggttc cagtgattct ccttcctcat gcccccgagt agcttggatt
acaggcaccc gccaccacat ctggctgatt tttctatttt tagtagagac cggatttcac
catgttggcc aggccagtct cgaactccga aagtgcttgg attccaggca agagccaccg
cgcccggccc ctacgctgaa cattttgcag ggacatcttg tctacactct gtctccccac
cacacggagc gccacaagag cagggtctt tgtttagctc actgctgtat cccaacctaa
ggatagtgcc tggcatacag tcggcgctta acaaatattg ggtgacaggt gctgatcact
ggtcagaata agaaatcaca ggggctgggc acggtggctc acgcctatga tcccagcact
tacagaggct caggctgggg ggattgatag agctcaagag ttcgaaacca gctgggcaa
gatagtgaga ccccatttct accaaaaaaa aaaaattag ctgggcatgg tggtgtgcac
ctgcagtctt agctacttgg caggctgaga caggaggatc ccttgagccc agaaggcaga
ggttgcagcg agccatgatt gcagccctgc actccagtct gggtgacaga gcgagactct
gtctctattt tattttattt ttttattttt atttatttat ttatttattt ttgagacaga
gtgtcgcttt gtcgcccagg ctggagtgca gtggcgcgat cttggctcac tgcaagctcc
gcctcccggg ttcacgccat tctcctgcct cagcctcccg agtagctggg actacgggca
cccgccacca cgcccggcta attttttgta ttttagtag acggggtt tcaccatgtt
agccaggatg gtctcgatcg tctgacctcg tgatccgccc acctcggcct cccaaagtgc
tgggattaca ggcgtgagcc atcgcgccct accacctgtc tctatttaaa aagagaggaa
aaaaaaaaa aaggccggtc gctgtggctc aggtgtgtgt aatcccagca ctttgggagg
ccaaggtggg cagatcacaa ggtcaggaat tgagaccag cctggccgac atagtgaaac
cctgtctcta ctaaaaataa aaattaaaaa aaattagctg gcatggtgg tgcacgcctg
```

Figure 11-8

```
taatccccag tactcgggag gctgaggcag gagaatccct tgaacccggg aggcagaggt
tgcagtgagc cgagatgtgc caccgcactc cagcccgggt gacagtgtga gactccgtct
caaaaaaaaa aaaatactac atggaaagga agctgtgcga atttgctgtt gagacgtgtg
actctgattt gctggctaaa gatagctgct catccctctt ccctttcaga accaggaatt
catccatccc ccaaacacaa tgcccaaggg tcagttatag aaactattgg gtgaggttca
gtcaaaaaga ccaggtgtgt tccgcctgaa aaagagaatt ggaaaagaat ctccaggccg
cgcacagtgg ctcacgtctg cagtcccaac agtttgggag gccgaggcgg gcaaatcact
tgaggtcagg agttcgaggc cagcctggac aacatggtga aaccccgtct ctactaaaaa
tacaaaaatt agtcgggcgt ggtggtgggc acctgtaatc ccagctactc aggaggctga
ggcaggaaaa ctgctggaac tcgggaggcg aaggttgcag tgagccgaga tcgcgccact
ggactccagc ccgggcagta gagtgagtga gagtgtctca aaaaaacaga atctccagtt
ccaggaaaat ttcaatctga gagggttccg gagggcagaa cgaggccaaa agaacgaact
taaaagagaa tggggtttga aggagataca gaagaatgcc ttgaagtaat cggtctcctt
caaaatgagt caggctggtg tgggaggccg agagcttcct tcccattcat gtccaggcag
aaggaggact gttgaagacg gcatcttgat attcaagaac ttcagccctc tcctgaatcc
agtcattgcc aggcctctaa ggcccatgca cctgtctgtg tttctttgca gcaggaggtc
cctgttctca gaatagccga gaatcagaga atcacggctg ggagcggagg ctgatgtctg
taatcccagc tctttgggag gccaaggcgg gaggatcgct tgagcccagg agtttgagat
tagcctgggc aacatagcaa gacctcgtct cttaaaaaaa caaaaaacaa acaaaaactg
gctgggccta gtggctcaca cctataatcc tagcactttg ggaagccaag gctggcagat
cacctgaggt caggagtttg agaccagcct gaccaacatg gagaaacccc gtctctacta
aaaatacaaa attagccggg cgtggtggcc catgcctgta ataccagcta ctcgggaagc
tgaggaagga gaatcgcttg aacgcgggag gcggaggttg cagtgagcca agatcgcacc
actgaactcc agcctgggcg acagagtgag actccgtctc aaaataaata aataaaaata
aaaaataaaa aaaaattagt caggtatgct ggtgtgcacc tgtagtttca gctactcagg
aggctgaggc aggaggattg tttggacttg ggacatcgca gcagtgagct atgatcacac
caccgcactc cagcctggac aacagagcaa gactgcatat ctaagaaaaa taataataat
tttaaaataa tgtcatttca agcagcacag cataaacaaa ggcgcataag ctttggaatc
ggacgcccat ggttcaaatc ccaattcccc agcaggtttg ctctgccacc tgggctacct
ctttgggcat ctcagtgcct ctgttttctg atctgtaaaa taggacaata atctctcgcg
caccaggtgg tcatgaaatt ttgataaaac agccgagatg ggctgtgcaa atggcgaagg
cagcacaaat aaataatcat ctccagcgtt attactatta ttagcttagc tcccttccc
cctactgatt ttttttatt tctttacttt tcttttcttt ttttttttt gagacagagt
ctcgctctgt cacccaggct ggggtgcagt ggcgccatct cagctcactg caacctccac
ctcctgggtt caagtgattc tcctgcttca gcctcccaag tagctggatt acaggcatct
gccaccacgc ccagctcatc tttgtatttt tagtagagac gaggtttcac cgtgttggcc
aggctggtct cgaactctca acctcaggtg atctgcccac ctcccaaagt gctaggatta
caggtgtgag ccattgggcc cagctccacc tataattttt ttttttttt ttttttttt
tttttttgca gacaaagtct cactctgtca cctaagctgg agtgcagtgg cgcgagttcg
gctcactgca acctccacct cccgggttca agcaattctc ccacctcagc ctcccgagta
gctgggatta caggcacaca ccaccacacc cagctaattt ttgtattttt ggtagagacg
gggtttcacc atgttggcca ggctggtctc gaactcccaa cctcaagtga tccgcctacc
tcggtctccc aaagtgctgg gattacaggc gcaagccacc acacccggcc tccaccgata
attttaaaag ctctcatctc acccaagcct tcttgagaca aaaaccaagg ccgagcgcac
ctgcaaatgc aagctggagg ccctttctgg aaggcgcgag gccagcggga gcgggaggag
ggtgtgtttc tggtggattt cttacagctg caaggcttct cgcccacccg ctgcagcagc
tttgtgtttg caggacagtg gcctcgctgt gccagcctgg ccccacgag ctacgccttt
gccaacagga cacttcctcc acgaggcttc tgtcttcctc gtctctggaa gaactgagtc
ggctcctcgg tgcaggtcca gctgcggcca cataacca cctctgtctg ccgcaaaaca
gctcacaatt ctgtttcttc cagcccagcc atcccctccc ctggggactg cagaagtggt
ctttgtactg cccttaaggg tgtcagacag agccctgcat ggcctctgcc cttctagcac
tttttttttt tttttggag acagagtctc agtgtatcac ccaggctgga gtgcagtggt
gcaacctcag ctcactgcaa cctccacttc ctggtttcga gcaattctct gcctcagcc
tcccaagtag ctgggattac aggtacgcac caccatgcct ggctcatttt tgtatttcg
ttagagacag ggtttcacca tgttggccag gctggtctcg aactcctaac ctcaagtgat
```

Figure 11-9

```
tcgcctgcct cggcctccca aagtgctggg attacaggtg tgagccacgc gcccggcctc
cttctagcat tttccttcac tctcacccct ctgcagccta ctacggagct agagctgaag
gcagcccgga gattgctgcc tcaatttctc cattcattca ttctgatgct atgcgccaac
tgtataccag tcccttatag cctcacaacc caatacaagg tggcagctgg gttcatggca
cttctgacca ggccagggag ggaaggggag ctgtgattct tggctgtgaa gggtgaggag
ggatgagccg gggaaggaag tggggtgtag gggccccaca ttccaagcag agagggcagc
atgtgcaaag gctctggct cagtggaagc aggttgaggg actggggaag gctgcgtggg
  gaaactgagg acttggggga ggagcttacc caggcatcc tagccaagga gggtcagatg
  cagggtgagc tgccccatag ctccctctac tctcttcccc tcacagctga gtggctgcca
  gttttgtttg cttgcttgta acttttttctt tgtttgtttt gggttttctg gggggtttta
  tttatttatt tatttgaaac agagtctcgc tgcaacgccc aggctggaat gcaatgacgt
  gacctcggct cgctgcaacc tccacttccc aggttccagc aattctcctg cctcagcctc
  ccaaatagct gagtttacag cgcccacca ccacgcccag ctaattttg tattttagc
  agagatgggg tttcaccata ttggtcaggc tggtctcgaa ctactgacct caagtgatcc
  acccgcctca gcttcccaaa gtgctgggat tacaggcgtg agccaccatg cccagctgct
  tgtaactttt taattttttt ttttttccca gacggggtct tgctctgtca cccaggctgg
agtgcagtgg tgcgatcata gctcactaca gcctccacat cccaggctga ggcgatcctc
  ccactgcagc ccctgaata cctgggacca caggcatatg ccaccacacc cagctatgtt
  ttattttctg tagagacagg gtctcactgt gttgcccagg ttggtctcaa actcctgggt
  tcaaatgatc ctcccacctc agcctcccaa aatgctggga ttacaggcat gagccactgc
  gcctggccta tttgatatac ttccaaactt ggaaaaaaat tacaagaatg atataaagaa
  tatctgcata cctttagtag gattatacaa ttgttaacat tttgctcctt ttatatcaaa
  gtcagccctc agggctgggt gcggtgactc acatctgtaa tcccagcact ttgggaggcc
  aaggcaggtg gatcacctga ggtcgggagt tcaagaccag cctaggccaa catggtgaaa
cccgtctct actaaaaata caaaaatcaa ctgggtgtgg tggcgggcac ctgtaatccc
  agctactggg gaggctgaag caggagaatt gcttaaaccc aggaggcaga agttgcaatg
  agcccagatt gtgccgccac actctagcct gagcaacaca gcaagactct gtctccaaaa
  aaaaaaattt accctcaatt gtaccgataa tgtcccatgt ccctatttag ctaatgcccc
  tgccccaaac cctgggtcca agacccaatc tgggaccact cattgcatca ggttgagtat
  actgggttgt gtgtttactg gggtatgtgt ctcaccaggc actgggactt aaacttatct
  cttttagggg aacacgatcc aacccacctc agcaggacga agccacgctg tgcatcttgc
  atgtgggggg gacccccact tttttttttt ttttttttg agacggagac ttgctctgtc
  gcccaggctg gagtgcagta gcatgatctc agctcactgc aacctccgcc tctgggttc
  aagcgactct cctgcctcag cctcccaagt agctgtagct gggaccacag gcatgtgcca
  ccatgccagg ctaattttag tattttagt agagacgggg tttcaccatg ttggccaggc
  tggtcttgat cgcttgacct tatgatccac ctgcctcggc ctcgcaaagt gctgggatta
  caggtgtgag ccaccatgcc cggctaggat ttccactttt tacctggatt gcccatcatg
  gactttgaga gccggctctg cagagggcta agtggatata ttatacccca gggccacgga
  ggggatctcc aagtctggag agtctgcggt tctcctggag cttcggaag taacaggatc
  tcacctgacc ttggaaactg cagctccatg aacaggcggg gagagcttgc tccacccatg
  ttccagagca gtgggtcttc cttcagggag cctggagccc tgccaggtcg gcttctccag
  ttctgcatga tcttaaacct ttcctgaaca tccactgcaa ctgcagctc agcctcagga
  cctcatccca tccccgaggc actgctctc cctggccctc cctccctacc ctccatcctc
  caaccactcc ctcctccccc actgctctct ctgcgccagg caccctgagt ctgctttctg
  atctgccctt gaacttggca agcttattcc agtcccggag cctgggcctc tgcagtgcct
  tccatctgga gtgctcttgc ctggtctctg caggacgcca acatcatgct taaaagtcta
  cacttaaaag tcgcttccag ccaggcacag tggctcactc ctgtaatccc agcactctgg
  gaggccaagg cgggaggatc acttgagccc aggagttcaa gaccagcctg caagacccca
  tctgcagaaa aatataaaaa ttagctgggt ggccgggcgc ggtggctcac gtctgtaatc
  ccagcacttt gggaggccga ggcgggcagg tcacgaggtc aggagatcga gaccatcctg
  gctaacacgg tgaaacccg tctctactaa aaatacaaaa aattagctgg gcgtggtggc
  aggcgcctgt agtcccagct actcgggagg ctgaggcagg agaatggcgt gaacccggga
  ggcggagctt gcagtgacct gagatcgcgc cactgcactc cagcctggtg acagagtga
  gactccgtct caaaaaaaaa aaaaaaaaa aattagctgg acatagtagt gtgtgctggt
  agtcccagct acttgagagg ctgaggtagg aggattgctt gagcccaaga atttgagacc
```

Figure 11-10

```
agcctgggca acatggcgag accctgtgtc tgcaaaaaaa aaaaaaaaaa aaaactgtaa
aaacctgaaa aattaaccag gtgtggcagc tcactcctgt aatcccatca ctttaggaag
ctgaggcagg agaattgctt gaaatgtgaa gttcaagacc agcctaggca ccacagtaag
accctgtctc tacaaaaaat tttataatta gccgggtgtg gtggtgcaca cctagggtcc
cagctactca gaagactgag acaggaggat cccttgagcc caggaatttg aggctgcagt
gagctatgat ttcactactg tgctctaggc tgggcaacag agcaagaccc tgtctcaaaa
aaaaaaaaaa aaaaaaaaag ctgcctcctc aatgaggcct tccctgacca ccccacagat
ttttttctct ctctctcctc tcctttattt cattcatttt ctttgccgta agcatcacta
tctgccttgt tcacttattt gcttattgtc ttcctttata tacatggtct caagccagga
attgctttgc acaatcctgg gaaccaccaa gtccaaaatc cacagggcag gctggaaact
gtcaggtaag agctaatgct gcagtttttg ttttgttttt tgagacggag tctcactctg
tcgccaggct ggagtgcaat ggcacgatct cagctcactg caacctccgc ttcctgggtt
caagccattc tcttgcctca gcctcctgag tagctgggt tacaggcatg caccaccaca
cccagctaat ttttgtattt ttagtagaga tggggtttca ccacgttggc caggctggtc
tcgaactcct gacctcaggt gatctgcccg cctcggcctc ccaaagtgct gggattacag
gtgtgagcca ccgcgcctgg cccccatttt agtcatgagg aaaacagagg ctcagggagg
agaaggcacc acccagactc gtagcgctgg atggagtggc agggctggga gttgtgctca
gactctctga gactctctta ggcattccca cccttctcc tgctttcctc acttttccag
tatgtgcagc tgagatgctt tctttttttc tttcttttct tttcttttt tttttttt
ttgatagact cttgctctgt tgctcaggcg ggagtgcagt ggtgccaatc acagctcact
gcagcctcaa actcccggac tcaaacgatc ctcctgcctc agcctcctta gtagctggga
ttacaagtgc atgccaccat gcctggctaa tatgttgtat ttttgtaga gatggggtct
cactatgttg cccaggctag tctcgaactc ctagtctcaa gagatcctcc cacctcagcc
tgctgagtag ctgggatcac aggcatgagc catcatgctg gctaatttt taaattttta
gtagtgatgg ggtcttgctg tgtgggccag gcttgtcttc aactcttggg cttaagtgat
cctccctcct cagcctccca agtgctgtg attaccggca tgagccctg cgcccagtct
gagatgcttt ctacagcttc acatttcagc tgcagcccag cagtggtcca cctagttcac
agccaatgta gaatctgtgt ggaccatcca atgttgtgag gttgaatcac atcccttttt
ttttttttt ctcgagacag agtctcactc tgtcactcag gctggagtgc agtggcacgg
tctcagctca ctgcaacctc cacctcccgg gttcaagcga ttctcttgcc tcagcctccc
gagtagctga gattacaggc acgtgccacc acacccagct aatttttgtgt ttttagtaga
gacggggttt caccatgttg gccaggctgg tcttgaactc ttggcctcag atgatccacc
tgcctcggcc tcccaaagtg ccgggattac aggcatgagc cctgcgccc ggcctgagat
gcttttctaca gcttcatatt tcagctgcag cccagcaatg gtccactcag ttcacagcct
acgtagagtc tgtgtggacc gtccaaggtt atgaggctaa atcacatctt gagaatcgaa
ggcagtgccg gctgcaaagc aatgggcttt tcctctggcg ggaggagatg gtggctggac
agggaccctg gctgggcaag tggttgtttg tttgtttgtt ttgagacgga gtctcgctct
gttgcccagg ctggagtgca gtgtcacgat ctcggctcac tgcaacctcc acctcccagg
ttcaagcgat tctcctgcct cagcctcacc aatagctggg attacaggcg cccgccacca
tgcccggcta attttgtgt ttttattaga cagggttt tgccatgctg accaggctgg
tctcgaactc ctgacctcag atgatccacc cgcctcagcc tcccaaagcg ctgggattac
tgaggcatga gccaccacgc ccagccagaa atctagactt tttgcatctc ttcttcgaca
gcaaatggaa aatgttttta aatgctgcat gggtgggaca taactaggct tggtgcatca
gccatcagcc tgcaattttg cagcgctggt ttgggttaac cttctgaatg agcaggtcag
ttcattcttc agtcctttct ttgaagtttg ctatatatat atatatat agcaaaatct
atatctatat ctatatctat atctatctat atcgcctcgc tctgtcatcc aggctggagt
gcagtggctc gatcatggct cactgcagcc ttgacctcct gggctcagct gatcctccca
ccttggcttc ccaaatagct gggactacag ggacacgcca ccatgcctgg ctttttattt
tttatagaga tggagtctcg ctgtgttgcc caggctgatc tcaaactcct gggctcaagg
gatcctccca cctcagcctc ccaaagtgct gggattacaa gcgtgtgcca cctcatgccc
agccaaagct tgctttttaa aaaattgagg tgaggccaag tacagtggct cacgcatgta
atctcagcac tttgggaggc cgaggcaggt ggatcctg agctcaggag ttcgagacca
gcctggccaa cgtggtgaaa ccccatctct actaaaaaca caaaaatcag ctgagcatgg
tggtgggcgc ctataatcac agctactctg gaggctgagg cacaagaatc gcctaaaccc
gggagatgga ggttgcagtg agccaagatt gtgccactgc actccagcct gggcaaaaga
```

Figure 11-11

```
   gtgaaactcc gtctcaaaaa ttaaataagt aaaataaaat ttaaaaaata taaaaaattg
   aggtggaatt ctcataacat gaattcatca ttttaaagtt catgattcag tggcagagtc
   cattcataat gttctgcaac cccacatcta tctaatttga agacattttc atcaccgtga
   gaggaaatcc tatctactaa gtcagcccca ttttcatccc tctcccccaa ccccagtgac
   cacacatcta cttcctgtga gaatttacgt gttctaaaca tctctttttt ttttcttttc
   ttttctgttt tgagcagggt gtcactcttt cacctaggct ggagtgcagt ggtgcaatca
   tagctcactg cagcctcgac ctcccaagtt agagcaatcc tcctgcctca gcctcctgag
   tacttggaac tagacgtgta ccaccacacc cagctaattg ttttgtattt ttagtagaga
   cgggctttcg ccatgttgcc ccgactggtc ttgaactcct gggctcaatg aacccgcccg
   catcagcctt tcaaagtgct gggattacag gcataagcca ccacactcag ccaacatttc
   atgtaattgg aatcacacac tgtgtggcct tttgtgtctg gcatctctca ctgagcatga
   tgtcctcaag gtgcatccat gctgtggtct gtgtcagagc cctgttcctt ttcagggcta
   aatagtattc cattgaatgg atataccaca tttgttgatc cagtcagctg ttaatggact
   ggtgttgttt gtttgtttgt ttgttttttga gacagagtct cactctgtcc ccaggctgga
   gtgtagtggc gtgacttcag ctcactgcaa cttccacctc ccaggttcaa gtgatcctct
   tgcctcagcc tcccaagtag ctaggattat aggcatgcgc caccatgtcc agctaatttt
   tgtatttta gtacagacag ggtttcatcg tgttggccag gatggtctca atctcttggc
   ctcatgatgt gccctcctcg gcctcccaaa gtgccaggat gacaggcgtg agccaccgcg
   cctggccgtc aatggactct tgaattgttt ccacttttg gttttatga attatgttca
   ttcaagtatg agttttcgtg tgaacagatg ttttcatttc ctttgggaat ccgctccatt
   ttgatctttg ccatgaacag gaggagggtg acatctgatt cctccttac ctccaagccc
catagatgca ctggagacgc agtggttacg caaaaacatt tgatgaatag agaaaagaga
   gggagggaaa gggagaggga aaaagcataa atagattccg ccccaaaaag gttaacagct
   catgccctaa gtggaacaga atgagggaa taaatctttt tttttttttt tttttttttg
   agagagagtc tcactttgtt gcccaggctg gagtgcaatg gcacgatctc ggctcaccgc
   aacctccgcc tccagggttc aagtgattct cctgcctcag cctcccagt agctgagact
   gcaagcacgc accaccacgc ccagataatt tttgtatttt tcagtagaga ctgggtttca
   ccattttggc caggctagtc ttgaactcct gacctcaggt gatccgcccg cctcggcctc
   cctaagtgcc aggattacag gcatgagcca ccacgcccgg ccaataaatc atttttttaa
   aggaaaggaa catgcattcc accgccttc catctaaaca gcttgccttg cagctgagcc
aggaatgctg agttacagag acgaattaag ctgtagcctg gctttccgga gtcagcacgc
   cctgccgcta ggacctctgg cagccccgtg caaaatgttc tgcccggaat ggaatatttc
   ccagggtagc caaggagcca gtgctcctgg gtcaaactcg ggcagcacgg gctgcggctt
   caagaagtga tctggggccg ggtgcggtgg ctcatgctgt aattccagca tttctgtctc
   aaaaagaaag aaaaagttgc aaagttagta cagataattc ctgtagactg gaacctagt
   ttctcccata attaacatct tatattagct gtgtatattt tatatttgtc acaattgatg
   aatcaatatt gatactattg gttattgata atcaacattg atcaataaca atattgatca
   atattggtta ttagttacca aagtccatgc ttttttagat tttcaaagtt tttcctaatg
   tcctcttttt ttttcttttc tctcttttt ttttaagag acagggtctc actctgtcat
   ccaggctggg gtgcagtggt gccatcatac ctcactgcag cctccgcctc ccaggctcaa
   gcagtcctcc cacctcagcc tccagagtag ctgggactac aggcaccacc acgtccagct
   aatctttgta atttttgtag agacagagtt acgccatgtt gcccaggctg gcctaatgtc
   cttttccttc tgccccacaa ccccatccag gatcccagat gacatttagt tatcacatct
   cctgacactc ctctggactg tggcagtctc cctgtctttc ttgttttgat gcccttgata
   gttttgtttg tttgtttgtt ttgagatgga gtctcactct gtcacccagg ctggagagca
gtggcacgat ctcggctcac tgcaacctcc gcctcccggg ttcaagcgat tctcctgcct
   cagcctcctg atagctggga ttacaggtgt cctccaccat gctgcctaa ttttttgtatt
   tttagtagag atggcgtttc accatgttgt ccaggctggt ctcgaattcc tgagctcaag
   tgatcctcct gcctcagcct cccaaagtgc tgggattaca ggcgtgagct gctgcgcctg
   gccatcctg tattttttgg aatgacatca ctatacacag cctacacaga gttatccttc
   atcttttttt tttttttttt tttttgag acagagtctt gctctgtggc ccaggctgga
   gtgcagtggc acgatctcgg ctcactgcaa gctccgcctc ctgggtcat gccattctcc
tgcctcagcc tcctgagtag ctgggactac aggcacctgc caccacgccc cgctattttt
   tttgtacttt tagtagagac ggggtttcac catgttagcc aggatggtct cgatctcctg
   acctcgtgat ccgcacgcct cggcctccca aagtgctggg attacaggcg tgagccaccg
```

Figure 11-12

```
cacccggcct atccttcatc ttcttgaggg cagaactgta cataaactat ttccaattct
tctgcacaag aaatgtgtct cttctctcct gtttatttgt tcagtgactt atttatatcc
gtatggactc atagacattt attttacatc ttgggttata attcaatatt tcattattta
tttggttgca caaactgttc cagcattgac atagagatct cttctggttg actcaggttt
ttgtgggggt tttatctatt tatttatttt taatactttt tgctgcattt gagagtcaac
aactcatcag agaccaaatc ccacagggtc gccctagaga gaattcaact tactaactta
tttcaaagtt tttgaagtca tgtgatgctg gggaaaaacc ttcattctcc tcaagccgtg
caaaaatctc caaaaggctt aatataaatt tgattatcta aagaagccc ttcagccctg
atgcgttata attttcttcc tctgctaaag aaaaaacatg ctgggcgggc gcggtggctc
atgcctgtaa tcccagcact tgagaggcc gaggtgggca gatcacaagg tcaggagttc
cagaccagcc tggccaatat ggtgaaaccc cgtctctact aaaaatacaa aaattagccg
ggcatggtag cgggcacctg tagtcccagt ttacttagga ggctgaggca gaagaatggc
ctgaacccgg gaggcggagg ttgccgtgag ccgagatcat gccactctac tccatccagc
ctgggcgaca gagcgagact ctgtctcaaa agaaaaaaat aaaagaaaaa gaaaaaacat
gcgcttgtgg tggctcacgc ccgtaatccc aacactttgg gaggctgagg tgggaagatg
gcttgagccc aggagttcaa gagcaacctg ggcaacatag tgagacccca tctctacaaa
aaaccaaaaa actacaaaaa ttagccagcc gtggtggtgt gcacctgtag tcccagctac
tcaggaggct gaggcaggag gatctcttga gcccaggagg ttgaggctgc agtgagccat
gatcacgcta ctgcactcca gcctgggcga tacagtgagg ctctgtctcc aaaaaaatgt
atatatttag gtccagtgat tctccagaac taaatgtgtt ttgcttttgt tcttgtctga
ctcgcctggc tggacctgtc tgggccactc cactgtcctc tgcctgaatc tctggtgccc
ggcgactgat gcctgttcct ggatgggtcc gcaggccact cccagaagag acggggggtgg
aactgcttgg cagcccggtg gaagacacat cctgtaagtt tccacgtcca cagaagggcg
gaaacaggct cagtgtttcc gggtttcagc cctgcctggg gctgtaactg tagaaatgtc
agaggccaca caccgtgggt agaatgttct gtcctggggt ctatggtgga agtggccgtg
gtgggtgaga gacacaatgg atgatggcgc tctcatgaag ccagcacgct gtgttgctgt
gtgtccctgt gctagtcact cagcctctct gtgccccaat gcctcatcta ctaaatgtag
gtagcgagct tctcgcagag ggggcatgta aggattaaat gaggtgatgc caaatgccct
ggaggcacaa agtcagcaca gccaagggtg cactgggagg ctctgctatc tggagctcta
aacatataca ttttaatgtg taataccta tattagaccc aaatatatac attttttggg
agaccgggtc acactctgtc atccaggctg gagtgcagtg gcgtgatcat ggctcactgc
agcctcaacc tccagggctc aagagatcct cctgcctcag ccttctgagt agctgggact
acaggtgcac accaccatgg ctggctaatt ttggtagttt ttgtagaaat gggatctagc
tatgttgccc aggctgctct tgaactcctg ggctcaagcc atcttcttgc ctcagcctcc
caaagtgctg ggattacggg cgtgagccac cacgcctggc atgttttttc ttcagcagag
gaaaaaaatc ataatgtatc aggctctgaa gccccagatc ccggggatgg gagtcctggg
cggccagagg agagttttag ccgtaacctg gcgattgcaa cgtgcctccg gaggcaggga
aagggcccag gttggcaccg tggggagagg tggggtctgg ggaggacctg gcagccagcc
ccacttaacg acattcagtt aagcagaata tggaaaataa acctgtgagg gccaaacaaa
attttttttgg agacagagcc tcactgtatc gcccaggctg gagtgcagta gcgtgatcat
ggctcactgc agcctcaacc tcctgggctc aagagatcct cctgcctcag cctcctgagt
agctgggact acaggtacac accaccatgg ctggttaatt tttgtagttt tttgtagaga
tggggtctca ctatgttgcc caggctgctc ttgaactcct gggctcaagc catcttccca
ccttggcctc ccaaagtgtt gggattacgg gcgtgagcca ctgcacccgg ccgcctgtct
ctatttaaaa agaaaaaaaa aaaaggcagg tcaccgtggc tcacgcctgt aatcccagca
ctttgggagg ccgaggcggg cagatcacga ggtcaggagt ttgagaccaa cctggccaac
atggtgaagc ccgtctctca ctaaagatac aaaaaaaaaa aaaaaaaaaa attagccggg
cattgtggca cttgcctgta atcccagtca ctcaggaggc tgaggcatga ggatcgcttg
aacccaggag acggaggttg cagcaagctg agattgtgcc attgcactcc agcctgggtg
acaaggcgag actctgtcta aacaaacaa aacaaaaaaa gattagtcgg cttggtggc
gcatgcctgt aatcccagct acttgggagg ctgaggtggg agaatcactt gaacctggga
ggcggaggtt gcagtgagct gagatcctac cattgtactc cagcctgggt aacggagtga
gactccatct caaaaaaata aatacataaa taaaacaaaa taaattagca gactttggat
   taaagcaggc agccatctgt gatgtgggtg ggcctcatct aatcagttga aggttttaag
   agaaacagac tgaggttccc ccaggcagag acaattctgc ctgcggacgg ttttgcaaca
```

Figure 11-13

```
tcaactcttc cctaggcgtc ccgcctgctg gcctgccctg ccgattgagg acttgtcagt
ctctgtgatc acacgagcta attccttaaa ataaatttct ccctctctct tttttccat
acatatagga aaaaatatg tatacacaca cacacacaca cacacgtc ctattggatt
tgtttccctg gagcactctg attaaaatag gagactatcc tggatcctgt attatccagg
tggcctgaca tcgttacagg atcctcatga gtggagacag gagggtgaga gtcagagaaa
gcctagaaga agatgggctg ctttcacaat ttgtctgcac aagagatatg tctcttctcc
tttatttatt tatttattta tttttgagat agagtttcac tctgtcaccc aggctggagt
gcaatggtac gatcttggct cactgtaacc tccgcctcct gggctcaagt gattctcctg
cctcagactc ccaagcagct gggattacag gcgccaccac tgtgcccggc taatttttat
atttttagta gagatggggt ttcgccatgt tggccaggct ggtctcgaac tcctgacctc
aggtgatctg cccgcctcgg cctccaaagt gctgggatta caggcgtgag ccaccgcacc
cggcccaaag tcaggctttg aactcatgtc tgcccaatgt ccaagcatcc atcccttaa
tctctgaggc ttgcccacag gacagaggtt ataacattca cccctgtcag gatgatgtcg
gtttaattct gcccaccccc gccaatggca tggatacaga agggagccca ccctctcttc
ccattcctgc atgatgaaac agcttccacc aggtaggaaa atgggggaa ggtaaaagag
agaaagcaaa gatgttttcc attttttctca tttccctgca gctcctccca acacgctaaa
tttcaacgga gcgcatcgta agaggaagac gctggtggcc ccagagatca acatttctct
ggatcagagt gaggggtccc tgctgtccga tgacttcttg gatacccctg atgacctgga
tattaacgtg gatgacatcg agacccccga tgagaccgac tcgctggagt tcctggggaa
tggcaacgaa ctggagtggg aaggtaaagt tcaggtctc tctggggcct gctggagccc
acccccccca ccccaccttt ccgtctctgg attcccatag gctcagagag tcacaagtgg
ggcagggct ctaagcagtc tagccttaaa cccaggagat caagactgca gtgagacgtg
atcatgccac tgcactccag cctggacaac agagtgagac cctgtctcaa aaataaaatt
tttaaaaaag agagaggtgg ctgggcgcag tggctcatgc ctgtaatcct agcactttgg
gaggccgagg cgggcagatc acgaggtcag gagatcgaga ccatcctggc tgacacagtg
aaacccccgtc tctactaaaa tacaaaaaat tagccaggca tggtggcggg cacctgaagt
cccagctact caggaggctg aggcaggaga acgtgtgaa cccaggaggc cgagcttgcg
gtgagccaag attgtgccac tgcactccag cctgggcgac agagcgagac tccgtctcaa
aaaaaaaaaa aaagagagag agaggttggt gaatgggtac caacatacag ttagacagaa
ggaataagtt ctattgttcg atagcagaat aggaggggtg ccaggaggag ggtccatccg
ctcctgcgac tgttttttt tttttttga gacagagtct cactctgttg cccaggctgg
agtgcagtgg tgtgatctca gctcactgca tcctccacct cccgggttca agcgattctt
ttgcctcagc ctcccgagta gctgggatta caggcatgca ctaccacttc cggctgatgt
ttatatttt agtagagatg gggttttccc atgttgccca ggctggtctc aaactcctga
cttcaagtga tacacccacc tcggcctccc aaagtgctgg gatcacaggt gtgagccacg
gcgcccagcc tgcccctgca atttgatgca tattttctt gtgggcttgt gaattttct
gcagaacgtg gctttcatca gaatctcaaa ggcgaccaag atcccaacaa actgccctcg
atgtatgcaa caaatacttt ttgaccattt actccagggc aagtcctgat tcaggcgtgg
ggtatatggc agggctatga taagaagaga tggtcctggt ccctacctgc acacacagat
catcagaaag acagaccacg aaaggccagg cgcagtgact cacgcctgta atcccagcac
tttgggaggc tgaggtgggc agatcacctg aggtcaggag tttgagacca gcctggccaa
catggtgaag ctccatctct actaaaaata cagaaattag ccgggcatgg tggcgtgcgt
agtcccagct actcgggagg ctgaggcagg agaatcgctt gaactctgga ggcagaggct
gcagtgagca gagatcgcac cactccactc cagcctgggc gatggaacaa gactctctca
aaaaaaaaaa agaaagaaaa aaaaaatta aggacaatgt agtggctcat tcctgtaatc
ccagagcttc gggaggccag ggtaggagga tcgcttaagg ccaggagttt gagaccagcc
tggcaacat attgaaaccc catctctaca aaaatataaa aattagctgg gtgtggtggt
gcacaactgt agtcccaggt atctgggagg ctgaggcagg aggactgctc tctgtgtgcc
aggctcctgg gagagtaaaa accaagcatg catgccccga gtatcctcgt ggtttgatga
agcagatgca ttcaccagct ctgagaagct ccaggacaca ggtccttaac caacagagtg
ccctgggagg ccagcaaagg gaatgtccag aaaggcttcc tggaggaggc ggcatttgag
ccaggccttg aaaggggagt aggagaggaa aatgggtcag cagggcagcc aggtggggag
aagcgaagga cttgtgggtc ccggcagcga gggaggtggg agaggggaag gaaggctgag
caggagggca ggagatatcc ggactctggc gtccatgcga ctctccgcca cctgcttcta
gacgacaccc ccgtggccac cgccaagaac atgcccgggg acagcgcgga tctatttggg
```

Figure 11-14

```
         gacggcacga cggaggacgg cagcgccgcc aacgggcgcc tgtggcggac agtgatcatc
         ggggagcaag agcaccgtat agacctgcac atgatccggc cttacatgaa agtggtcacc
         cacggaggtg agacccgccc cccggtgccc ccttggggct ccagcccggc ccactgggca
         acaggggggtt cgtcagtgcc cctctctgat gcacggggat gttaagccgt caactcgctt
         cgggtggacg gactgtgggc aaggcgtgca tggtcaggga ggcgcactgg ggcccctga
         tggtcgctgt cactcctcag cgaaggcaga gactggctaa ggggtcgccg gctgctgtgg
         ctcggagcca tgccctcccg agcgtgtggg caccgggacg tggtgggtgg tgcgcgggag
         gcagctcagg gctgggagag gactctgacg ttgccgatcg gctgcctctc ctcagggtac
         tacggcgaag gcctcaacgc catcatcgtc ttcgcagcct gcttccttcc agacagcagc
         ctccccgact accactacat catggagaac ctcttcctgt gagtccccgc ccgcggcgag
         cagcctcggg ccagctctga tgcctccctg gccacagggg caccaggctg caaggattgc
         attgtggccc taggaagcct gcctggcacc agggaagggc gtggtggcca cagaccttga
         tctgagtccc tgctggccct gaggctcaca gtggccttcc ctctgggcca ccctgttctc
         ctccccgtcc tcctcctcct cctcttcctc ctccttcccc tcctcctcac tgtcctcctc
         ctcctcccct tcttcctccc ccttcccctt tcttctcctc cttctcctcc ccttcttcct
         cccccctcct cctcccttttt ctcctcctcc tccccttccc tctcctcctc cccctcttcc
         ccttccctct cctcctcccc cctcttcctt ctcctcctct tcctcccctt tctccacctc
         atcctctttc tcttcctccc cttttctcccc ccttcctcct ccttctcctc cttccctcat
         cttcctctcc ttccctctcc tccccctccc catcctcctc ctccccatcc tcttcccctt
         cctcctcctc ttcccgctct gagatggcac cactgcactc cagcctgggt gacagagtga
         gaacctgtct caaaaaaaaa aaaaaaaaaa aaaagcaagg cctagagacc agcctggcca
         acatagtgaa atcctgcctc tactaaaact acaatttagc tgggctcggt ggcaggcgcc
         tgtaatccca gctactaggg aggctgtggc aggagaatgg cgtgaacctg ggaggcggag
         cttgcagtga gccgagatcg caccactgca ctctagcctg ggcaacagag cgagattccg
         tctcaaaaaa aaaaaacgac tcaataaaag agtaactgcc ctatgaggat gcccgctgac
         actcatgtgg agtgtgctgg gatcatccac gtcctctccc accctgcagt ccgccaggac
         agcagacaac acctggacca gtggggctga cccagccagc ggcaggagtg gaggcaggca
         gggtcggcac cgcaggtgtc ctgaccctgg acccctccat gttgggtccc tgccttctgt
         gccccgtgag caggtacgtc atcagcagct tagagctcct ggtggctgag gactacatga
         tcgtgtacct gaacggtgcc acgcccggc ggaggatgcc tggaatcggc tggctgaaga
         agtgctacca gatgatcgac cggaggtgag gtggggatgc ctcaggaagc acagtggggg
         catgaaaatc acacaggggg ctggacatgg tggctcacac ctggaatccc agcacttcgg
         gaggctgagg tgggaaggtc ccttgagccc aggagtttga ccagcctg gcaacgcag
         ccagcactttt ggggaggccaa ggtgggtgga tcacctgagg tcaggagttc aagaccagcc
         cggccaacat atagtgaaac cccatctcta ctaaaaaaat tcaaaaatta gctgggcgtg
    gtggcgcatg cctgtagtcc cagctacttg ggaagctgag gcaggagaat cacttgaacc
         caggaggtgg aggttgcagt gagccgagat catgccactg cacttcagcc tgggcaacag
         agcgagactc tgtcccatg aaacactcac tccctattcc ttctccccag gctccggcac
         cccccatcct actttctgtc tctgtaaatc tgatgactct agggacctcc taggactgga
         atcacacagg atttgtcctt ttgtgtctgg cttttcctcac tgagtgtgat gtcctcaggg
         tgcatccaca ttgtagcctg tgtcagagcc tccttccttt tcatggctgc ataatattcc
         actgtatgga cataccacat ttggtttgtc cattccattc atctcttgat ggacatgggt
         tgcttccacc cctgagttat tgtaaatagc ctcagagtga cattaaaatt gagccagcca
         atccatcctt gcacccaggt tagtggaggg aggctccaag gacaggctgg tccctcctag
         ggcattaggt ggtgaaaata caatcttggc tgctcaaata actaccaacc tggttcacct
         gctctgcacc atggggtctc tacctacctc atccacctga gggtcttagg gactcaaagg
         gtgtgtcttt atcccaccat aggaccccca tgtcttggat gggggcaggg atttgacagg
    tacctggaga ccacacgtgg aatgagcaga gtgacgaatg cttgcttgtg gctctcccgt
         cccacccagc tcctccctcc ccagggctcg cccaggagc ccatcttgct tcctttgcgg
         ccccacacag gttgcgaaaa acctgaagt ccttgatcat cgtccacccc tcgtggttca
         ttcggactgt gctggccatc tctcgccctt tcatcaggtg agacggggag gctgcaaccc
         aagtccagtg gcctcagtgt gcgtgtgtgc gtgtgtgtat gcatgcattt gtgtgtgcat
         gtgtgcacgt gtgtgcgtgt gtgcatctgt gtgtgtgtgc atccatgtgt gtgtttgatg
         tgcatgttcc agcttctcta tgatgaatac atattattgc tttaaacagt tttaaattgc
         acacagccag gcacagtggc tgacacctgt aatcccagct actcagaagg ctgaggtggg
```

Figure 11-15

```
aggatcgttt gaggccagcc tgagcaacat agcaaaaccc ccatctctac aaaaaataca
aaaattagca ggacgtggtg gtgcacacct gtagtttcag ctacttggga ggctcacgtg
ggaggatggc ttgagcccag gagatcaagg ctgcaatgag ccgtgatcga gccactgtac
tccagcctgg atgacagagt gagaccctgt ctcaaaagaa aatcagtcat gcatggcatc
acatgcctgt agtcccagct actcaggagg ctgaggcagg aggatcactt gagcccagga
ggtagaggct gcagtgagct atgatcactc cactgcactc cagcctggga gacagagcaa
aacaaccctg tctctaaaaa taaaatatat atatatgtat gtataaataa ataaataata
tgactaataa atttaaaatt taaaactaca tatattctat aatgtatatc atatatagtt
actatattaa acatatagta aaacagatca agtgaaataa aattaggcat gttaaatgcc
ctattcaatc caataaaatg tcatgcaaat ttaatttaat ctaatgcaaa acattgaatt
gaataaagat tcctaatgtt cacgttccca gttacaaatc tgggatgagc gaaagagacg
agggcttcac tttcccttga acaacaggac acattcacag caggcccgat tttcaaggaa
gactctttaa acatgctgtt tcaaggact gctaagtacc ctgaaggggc ttatttgcat
attagcgaaa tgagatgagg aatacactaa ttatggatca ttttagctaa taatgaatca
acaggcaaaa cgtaaacac gcatttcagt ctaagataat tgcatttgct cctctatatt
ccagaattca gtaacataga ctacctttgc ctttaatgta gatattagga tggtgcaaaa
ataattgagg ttcttgccat attttcatta caaaaactgc aatcactctt gcacgaaccc
aataattctg tcactcttca ccggtcgcca tggctcacac ctgtaatccc aacactttgg
aaggtcgaga tgagaggatc gcttgagccc gggagttcga gaccagcctg ggtgacatag
cgagaccctg tctctacaaa aaaaaatttt ttttttttc agacggagtc tcactctgtc
gcccaggctg gagtgcagtg gcgcgatctc agctcactgc aagctccgcc tcccgggttc
acgctattct gcctcagcct cccgagcagc tgggactaca ggcgccgcc accaggccca
gctaactttt tgtattttta gtagagatgg ggtttcatcg tgttagccag gatggtctcg
atctcctgac ttcgtgatcc gcctgccttg gcctcccaaa gtgaaaaaa ttttttttta
aatacggcca ggtgtggtga cccaggcttg taatcccagc actttgggag accgaggcag
gaggatcgct tgaggccagg agttgaagac cagtctgggc aacatagcaa gacctccatc
tctacaaaaa aaaatttttt ttaattagcc aggcctggtg gcgcgcacct gtgatcccag
ctactcagag gctgagggag gaggatcact tgagcccagg aggtcgaggc tgtagtgagc
catgattaca ccactgcact ccagcctggg tgacagagtg agactctgtc tcttaaaaaa
aaaataccat gaagtgctgg tgatgaaaca ccacatggta tcagatggcc agaattcagg
attggaaggg aaagaaggga agaaccatt catccctgaa aaacagagaa ttgggccagg
cagggtagct catgactgta atcccagcac tttgggagtt agaggcaggc agatcacatg
aggtcaggag ttggagacta gcctggccaa catgatgaaa ccccatctcc attaaaaata
caaaattagc cgagagtggt ggtgcatgcc tgtagtccca gctactcggg aggctgaggc
agggaaaatc gcttgaaccg gggaggcgga ggtggcagtg agccgagatc acaccactgc
actccagcct gggtgaagag caagactctg tgtcaaaaaa taacaataac agagaatcaa
tgggcagccc cgtgtgcccc cttcttgtgc ccagctgagt gttggctgtg ccgtcctgtg
cggtgacatg gagagaaagc atccctggga aaaattaaca cagaggagca acttttagag
atgatgggaa aacagcctgt agagtctaag acaatctccc cacctcctga cttccttcca
acaagatcct cattgcaggg acccatgtca ggtgcatggc cctgcttgca agggcctcgg
cgcagacccg ggtctccac tccatgcatg gggtgcaaga taattaaggc tgtcatcggg
cgggagggag gtgtcgtcgt ctgcactggg gcatcctgga gtggggtcct gtggggatcc
ctgtcgccat ggctctgtct ggacctaggt aaccccacc ccatgggttg catttcagac
ctctccctcc ttctccccc gccagcgtca agttcatcaa caagatccag tacgtgcaca
gcttggaaga cctggagcaa ctcatcccta tggaacacgt ccagatccca gactgcgtcc
tgcagtgagt ggcccacag tccaccccgc cgtattagtc tgttttcgtg ctgctgataa
agacacacct gagacagggc aatttacaaa agaggtttaa ggggccgggc gcggtggctc
ctgcctgtaa tcccagcact tgggaggct gaggcgggcg gatcacgagg tcagggatc
gagaccatcc tggctaacat ggtgaaaccc cgtctctact aaaaatacaa aaaattagcc
gggcgtggtg gcgggcgcct gtagtcccag ctactcagga ggctgaggca ggagaatggc
gtgaacccg gaggcggagg ttgcagtaag ctgagatcgc gccactgcac tccagcctgg
gccacagagc gagactccat cgcaaaaaaa aaaaaaaagg ctaacggac tcacaattcc
atgtggctgg caacgcctcc caatcacggt ggaaggcaaa aggcacgtct cccatggcgg
cagagaagag aaggaaattt gtacaggcaa attcccctttt ataaaaccat cagatctcat
gagacttact cactgtcgcg agaatagcac aggaaagacc tgcccccatg attcagtgac
```

Figure 11-16

```
ctcccaccag gtcactccca caacaggagg gaattatggg agctacaatt caagatgaga
tttgggtgaa gagaccaggc aaggtggctc acacctataa tcccagcact gtaatcccag
cattttgaga ggctgagaca ggcagatcac ttgaggtcag gagttcgaga ctagcctggc
caagatggtg aaaccctgtc tctcctaaaa atacaaaaat tagccaggtg tggtggtgca
tgcctgtaat cccagatact gaggaggctg aggcaggaga atcgcttgaa cctgggaggc
agaggttgtg gtgagccgag atcgcaccac tgcactccag cctgggcaac aagagtgaaa
ctccgtctca agaaaaaaaa aaaaagattt gggtggagat acagtcaaac cctgtcaccc
ccaacacccc cccaccgggt ccccctggct accaggagcc agcaatgagg ggaaacgcag
acttggaagg gaggaactag aacccaccca ttttatttcc tggagcccct cagggacccc
ccggagcttg gggaagggat gggcagcttc aagtcctgtt gtttttcact gaatgtcata
tcatcggcac ctcccctagg ttcatgctgc aaaaatctcc ttaaacgtac atttttttat
tgtggtaaaa tacacgtaac atagaacttc catcttagc cattccttt ttaattttat
ttatttattt attttttgag aaggagtttc actcttgttg cccaggctgg agtgcaatgg
cgccatctcg gctcaccaca acctccgcct cccgggttca agcgattctc ctgcctcagc
ctcccaacta gctgggatta caggcatgag ccgccatgcc tggctaattt ttttttttt
ttttgtattt ttagtagaga cagggttct ccatgttcgt caagctggtc tcaaacccct
gacctcagat gatctaccgg cctcggcctc ccaaagtgct gggattacag gcgtgagcca
ctgcgcccgg cctatcttag ccatttctaa aagcacattc gcatatttgt gcagccatca
ccaccatcct ctccagacct ttcttttttt tttttttgag atggagtctt gctctgttgc
ccaggctgga gtgcagtggc acgatctcgg gtcactgcaa cctccacctc ctgggttcaa
gtgattctcc tgcctcagcc tccccagtag ctgggattaa ggcacccacc accatgccca
gctaattttt tttttttttt ttttgagat ggagtttaac tcttgttgcc caggctggtc
tcgaactccc gacctcaggt gatccgccca cctcagcctc ccaaagtgct gggattacag
gcgtgagcca ccacgcctgg ccgatttttg tatttttagt agagacggag ttttgtcatg
ttggccaggc tggtcttgaa ctcctgacct cagttgatct gcctggctcg gcctcacaaa
gtgctgggat tacaggcatg agccactgca cccggccctc tccagaacgt tctcatcttc
ccaaactgaa actctgtctc catgaaacac tcactcccca ttccacatcc caaccctgg
cagcccccat cctactttct gtctctggga gtctgacgac tctagggacc tcctaggaat
ggatccacac aggatttgtc cttttgtgtc tgacgtctct cactgagcgt gacatcctca
aggtgcatcc acattgtagc ctgtgtcaga atgtccttcc ttttcatggc tgaataatat
tccattgcgt gaatggacca cattttgtca atccatttgt ccatcaatgg acaattgggt
tgtttccacc ttttggctct tgtgaatagt catgttattt atatgctact cacctatgac
cgtagatgta caaatatctc tgtaagaccc tactttcaat tctaatgagt atatacccaa
aagtggaatt gctgataatt ctgttttttt gaggaaccac catactgttt tgttttgttt
tgctttgctt tgcttttttg agacggagtc tcactctgtc acccaggctg gagtgcagtg
gcgctatctt ggctcgctgc aacctccacc tcccgggttc aagcaactct cctgcctcag
cctcccgagt agctgggact acaggcgccc accaccacac ccagataatt ttttgtatt
tttagtagag atggggtttc accatgttgg cctggctggt ctcaaactcc ccacctcagc
ctcccaaagt gctgggatta caggcgtgag ccatcgcacc cagcctgttt tttgttgttg
ttgttttgtt ggggttttc tggttttttt ttttagacag agtctcactc tgttgcctac
gctggaacgc aatggcgcaa tctcggctca ccatatcctc cagcttctac gttcaaggga
ttctcgtgcc tcagcctccc gaatagctgg gattacaggc acctgccacc acgcccagct
aattttgta tttttagtag atagggtt tcaccatgtt ggccaggatg gtctcagtct
cctgaactca gtgatctgcc cgcctcggcc tcccaaagtt ctgggattat aggcgtgagc
caccgtgctc agccaannnn nnnnnnnnnn nnnnnnnnnn nnnnnnnnnn nnnnnnnnnn
nnnnnnnnnn nnnnnnnnnn nnnnnnnnnn nnnnnnnnnn nnnnnnnnnn nnnnnnaaaa
tgcatctatg gccaggtgt ggtggctcat gcctgtaatc ccagcacttt gggaggctga
ggccagagga tcgcttgagc ccaggagttg gaggctacaa gtgagttcat gccactgcac
tccagtctgg gctatgacag aatgagaacc tgtctaaaaa aaagagaaga ggccgggcgc
ggtggttcgc gcctgtaatc ccagcacttt ggaggccga ggtgggtgga tcatgaggtc
aggagtttga gaccagccag gccaacatag ggaaacccg tctgtactaa aaatacaaaa
aattagctgg gcgtggtagc aggtgcctgt aagtcccagc tactccggag gctgaggcag
cagaatcact caaaccgggg aggtggaggt tgcagtgagc caagatcgca ccactgcact
ccagcttggg cgacagtgca agactccatc tcaaaaaaaa aaaaaaaaaa aaaaaaaagg
aagaagaaga agaagaaaag aaagaaaaaa gagagcttgt ttctctgctt gaaaaggaaa
```

Figure 11-17

```
gggatttccc caaaaagtat atctcagggg aaaggaaggt tgtgtctgac atctttttct
ttctttcaga tacgaagagg aaagactgaa ggccaggagg gagaggtgtg tgcagagtgg
tttctgctgg ggctgggtcg gggcagcggg gggctgagct gaactctcag ttagggcaac
ccggtgactt ctgggcagca gggaccattg tcctgtgcag ggctcaagac gctgcccttc
tggcaaggac tttaaactca gacctgggtt caaatactgg ctcccgcatt gagctgcaag
 gtaacattaa gcaaataaaa agctaacaac caccttggag gttattgtgc aagatgaggc
accccttggca aaaaggttg agcacagact tcacgctcca taaagcataa aagtcaagac
gggcgcggtg gctcacccag cactttgaga ggctgtaatc ccagcacttt gggaggctga
ggcaggagga ttgtgtgagg tcaggagttg gagaacaacc tggacaacat ggcgtaactc
cgtctctacc aaaaatacaa aaattagcca ggcgtggtgg tgcgtgcctg taatcccagc
tacttgggag gctgagccag gagaatcact tgaacctggg aggcggaggt tgcagtgagc
cgagatcatg ccactgcact ccagcgtggg tgacagagca agactctgtc tcaaaaaaaa
aaaaaaataa attagccagg tgtggtggca tgcgcctgta gttcagctac ttgcagggag
actgaatcgg gacgactgct tgagcccagg aagttgaggc tgcagtgagc catgattgta
ccattgcact ccagcctggg caacagagca agatcctgtc tcaaaaaaaa aaacaaaaaa
aaacagcctt tatcatgcca ggtccaatgc cagctttgag ggaaacagag gcaaataaga
cagagtcttg gtcccagaag ttttctcaaa tagcaaggc agggaacatc tcactggttt
ggaaaacagg tcccagggga caggaaaacc agagaggcca gtactagctg agagcccacc
ccttggcctg gctgggctag tcacccttgt cacctcgttc tctctgtcca cagcgcgagg
ccccagccgg agtttgtgct gcccaggtct gaagagaagc cagaggtggc accagtggaa
aacaggtagg tgtgcagggg accatgggca gagagctgac agtcacggga ggctgcctac
tcccttgggg gaggctagag aggaagatgg gtccttgttc agggacagaa aatggaacta
 agtggccggc catggtggct cacgcctgta atcccagcac tttgggaggc cgaggtggc
agatcacatg aggtcaggag ttcgagacca gcctggccag catggtgaaa cctcatctct
actaaaaata caaaaattag ctggacatgg tggctcacat ctgtaatccc agctacttgg
gaggccgagg caggagattc gcttgaaccc aggggggcaga ggttgcagtg agccgagata
gtaccactgc actcggcgac aaagtgagac tccatctcaa aaaaataaat aaacaaataa
 aataaaaata aaaattatcg gccgggtgtg gtggctcacg cctgtaatcc cagtagtttg
ggaggctgag gtgggccgat cacaaggcca agagatcgag accagcctgg ccaacatggt
gaaacccccat ctcttctaaa aatacaaaaa ttagctgggc atggtggctc gtgcctgtag
tcccacctac ttggaaggct gaggcaggag aatcacttga acctgggagg cggaggttgc
agtgagccga gatcagacca ctgcactcca gcctggcgac agaatgagat tctgtctcaa
aaataaataa ataaataaat atcatccagg tgtggtgatg tacacctcta gtccagctac
tcagaagggt gaggcaggca gatggctgga gcccaggagg tcaaggctac agcaagctat
gactgcactc cagcctgggc aacagagcaa gaccctgtct caaaaaaaaa aaaaagtta
tcatgatgtt ctcatattat cgcaatctca atgttatcat aatgatgaaa ggtgaccttt
gtccaggtcc cagcaggtag attcagactc ccccaatcca gtagaccctg agcaacatta
ttggcttcat tttatgttag tgaagggcct tggccaattt cctcaaaact gtctgtttgg
gctcatttgt tacgcagcag atgcacgctg acatctgttt tgtaccagat acagcagtgt
cggtcctcat agggcttaca gcctccacga acaggtagaa aatgcccaag aatgggcact
gtggctcacg cctgtaatcc cagcactttc ggaggccaaa gcaggaggac catttgaggt
caggagttcg agaccaactt gggcaacata ttgagactcc atctctacaa aaagtttaaa
agttagccag gcatgatggt gtataccttg tagtcccagc tacttgggag gctgaggtgg
gaggatcact tgagcccgga gctggaagct gcagtgagcc atgattgcac cactgccctc
cagcctgggc aacataacaa gaccctgtat cttttttttt tttttaagac agatttcac
tcttgtcgcc caggggccag agtgcaatgg tgcgatcttg gctcactgca acctccacct
cccgggttca agcgattctc ctgcctcagc ctcccgagta gctgggatta caggcaccca
ccaccacacc cggctaattt ttgtattttt agtagagaca gggttttacc atgttggcca
ggctggtctc gaactcctga cctcaagtga tccaccacc tcagcctccc aaagtgctgg
gattataggc atgagccact gcacccagcc aagaccctgt atcttaataa taataaataa
ataaaaataa aataagttaa agaaaaaaaa gggaaaatgc ccaggctccc aaaaataagc
aaataacgcc cagtctccgt ctctcctcca caggtctgct ctggtctcag aagatcagga
aacaaggtgg gtgtgatgca gagtggtctt cgtgctgttt tcaaaatgtc cttcatggac
ctgtattagt cagggttctc tagaaggaca gaaaatcaaa ccagctgcca gcaaatataa
agcaggcagg gatcctaatc ccaggaaaac tgccccatga cttatcggga gtgggggata
```

Figure 11-18

```
cggcaccggg aaggcaggga ggtagtggtt cccttaacca gtcaggccgt ccttgcacaa
ctccaggggg gcaccattac ctagaccagg atgcaaatga ggccccagag ttatgcagtg
gagcggccct cagggaaaaa cccacacaga gccaagctcc ctgaagccca ggatatgata
ccacaaaagg gtagactgtc cacgctctgc ctccgattct ccacctggtt ctggatgcca
agaaaagcct ccctgtggcc gggcgcagcg tctcacgcct gtaatcccag cactttggga
ggccgaggca ggcggatcat ttgaggtcag gagttcaaga ccagcctggg caacatggca
agacccgtc cctaaaaaaa atacaaaaat tagccaggtg agccaagatc gtaccactgc
actccacagc ctgggcaata gggctagact ttgtctcaaa aaaagaaaaa aaaaaggaaa
gaaaagaaaa gcctccctgt gtgttgatgt ccaagggtat cctcaggcac aatggtttgc
cagaaggact cacagagctc agcaaagctg tcatactcac agttatggtt tatcacagtg
gcatggttta ttacagtaga agggtacagt taaaaatcag cagagttggg tgtggtggct
catgcctgta atcccagcac tttgggaggc cgaggcaggt ggatcacttg aaatcaggaa
ttcaagacca gcctggccaa tatggtgaaa ccccatctct actaaaaata taaaattagc
tgggtgtggt ggcacacacc tgtagtccca gctactcagg aggctgaggc aagagaattg
cttgaacctg ggaggcggag gttgcagtga gctgagattg caccattgca ttccagcctg
ggcaacagag caagactctg tttaaaaaaa aaaaacaaa aaaacaaaaa acttaacaaa
aggaagaggt gcatagggct ggatccagga gagatcgggt ggaagcctgc aagtgtcctc
tcccagtggg gttgtgtgga cagcctttat ttctcccagc agggatgtgt ggcaaaacac
acaaagtgct gccaactaga aagctgacc caagcctttc tagccagggt gtttatagag
agtcaactac atacacctgg ctgactgtct gcatggcttt tcttagcctc cagcccctgc
acagatcaag ctgatgccac gtgcccaag ttccaaccct aagtcacgtt gtgagtgtta
ttagtccatt ctcatgctgc tatgaagaaa tacccaagac cgggtaaatt ataaagaaaa
gaggtttaat tgactcacag ttctgcatgg ctggggaggc cccggaaatt ttataatcct
ggcggaagcc acctcttcac caggcagcag gagcgagaag tgctgagcaa agggggaaa
gcccttata aaaccatcag atctcgtgag aactcactac cacgagaaca gcatggaggt
agccgccccc atggttcagt tacctcccac tgagtaccgc ccacgacaag tggggttatg
ggaactacaa ttcaagatga gatttgggtg gggacacagc caaccatat cagttagcat
agactatctg gcatgaccca catagacact ccagccagga tgctccaaga gtttagaagt
taatcccagg agccagggaa ggaccaaact tttctttaga atgtgtggga tttatccttg
accacacagt ttttttgttt tgttttgttt ttgttgttgt tgttgttttt gagatggagt
ctcgctctgt cgcccaggct ggagtgcagt ggcatgatct tggctcactg caagctccgc
ctcccagggt cactccagtc tcttgcctca gcctcccaag tagctgggac tacaggcgtc
tgccaccaca cccagctaat tttttgtatt ttttagtaga cgggggttt caccatgtta
gccgggatgg tctcgatctc ctgacctcgt gatccacccg cttcggcctc ccaaagtgct
gagattacag gcgtgagcca ccatgcccag ctgaccacac agttttatac aaatctataa
gatggcctgg ccacatgcct tactacccat gtgacccagg aagctccaag ctaagaaata
aacatcaaaa atggccttag accagtgctg cttaaggggc actgagtaaa agttctcaat
gtatttctga aaagaccacc tcaacccaag ctctctggag atgagttcac atatacagac
agaaaacaca aggaaatcat ccaccatgag caaaagacag cagagacaac aaacagcaga
attagatctt gcctggagat ccttaggtgg ataagatata ataagcatgt tttaacaatt
aaaaacacaa aagaaggaat tgtaagaagc aatagatgaa tggatgaatg gataggtgga
taaatggatg gatggatgga tgagtggatg gatggaagga tgtttggatg atgggtggat
agatagatga atgaatgagt ggagggatgg gaggatagat ggatgatagg tggatggatg
gatggataaa tggatggatg gatggatggg tgaaggttnn nnnnnnnnn nnnnnnnnnn
nnnnnnnnnn nnnnnnnnnn nnnnnnnnnn nnnnnnnnnn nnnnnnnnnn nnnnnnnnnn
nnnnnnnnnn nnnnnnnnga gtgggtgggt ggatggatgg atggatggat ggatggatgg
atggacagat ggatgagtgg gtggatggat gggtgggcag atggatcaat ggataggtgg
gtggatggat ggatggatgg ttaatagat ggatgagtgg agggatggat ggatgaatgg
atggatgtgt gggtgggtgg atgggtggat ggacggatga gtgagtggct ggatgggtgg
gcagagggat gaatggatcc ctccattgag tgaatggatg ggtgagtgag tgtgtggatg
gatggatgga tggatggatg gatggatgga tgggtggatg gatagatgtg tgggtggttg
tatggttggt tagttggggg gtgggttgaa gcctcccctcc aggctgattg aggttgccag
tctccagggc ctgttctgct gaggcaccag gaaggaggcc ctcagagcca cacttagaaa
gtgggtggca ggagccgggc cctgaagggc atgtgccact cttgctgctg ggagttcacc
cacgctgggt gggatcattg ttttggatta catacatgta gaagcgcatt ttgcactttt
```

Figure 11-19

```
aacattaaca gcaataactt ggcctgtgtc tttccctccc tagcatgtcc tgaggcgacg
tgagcataac aaaggacatg gaagaagatt ccagatgcca gaaaacctct gtcagacgcc
 cactggcccc agatctcatc ctgcctcatc ctgagtccca atcttccaag ggtgccagcc
 cctccgttca tctctgaaac ccagcatcct tttcagctgc ttgaaaacat tgtattttt
 tttttaacg atgcagtatt tgtgcgttcc agaaaagggc ccagctctga gcccctcacc
 cttccacact cacgaactct cagccgagga aggcaagaag cgcaggggt ggcccgcgtg
 gcgtcggtgg cctccgctcc tgctcgcagc ctctgtggtc agagctggat acaagattca
 agacccttct cttgcttgtc acccgctcca ggttggagcc acagacaccc accgccaccc
 cggctgggtc tgcgtccttt cctgtgcctt tccctccaga atgcggcctc agacctagaa
 gctcaacccc cctatgaggg ccacgtcctg gggtagctcc tgacctccga ccttatgtcc
 aaatttcaca cccatggttt ttcatttgac ccgccccctt ctcgctcata atgacaccca
 gctcctttga gaggatcaga gcccattgca caagaagagc cgctgccaac catccttgtc
 ctccgattgc aaaatgacac cccagtaatc tagaacattc tcaagcccct ttaactcaga
 tgtcaagcca ccgggcaaac cccgtcaata cctcccacca aggaatgaga tatgtggacc
 tcactgctcc cccaacccag cgtcaggctg ggacacgcca acgctgttcc gggttggaac
 agcagaggct cagaaactgg ctctgaaata ggcagaccta gcaagaggaa gatacagggt
 atcgggcgtt tgagtgtttc agaagtcatt cgggaagata aatccagtgc gctggccgca
gccacctgca ttcaaagctt ggaccagcgg gttcttgttc gggaggcaaa tttccctagg
 aaaagaaga cagactttc taatgtggtc caaatgcgga tcactggtca gatggactct
 agaagcactg agctccctgt ctctggaagt atttaagaaa aggctgggcc aggcacgatg
 gctcacgcct gtaatccag actttgggag gccgaggcag gcggatcacc tgaggtgagg
 agtttgagaa cagcctggcc aacatggtga aacctcatct ctactaaaaa tacaaaaatt
 agccaggcgt ggtggcaggt gcctgtaatc ccagctactt gggaggctga ggcatgagaa
 tcacttaaac ctgagaggca gaggttacag tgagccaaga tcgtgccact gcattccagc
 ctgggcgaca gagcaagact ctgtctcaaa aaaaataaaa aataatcagg gcacagtggc
 tcatgcctgt aatcccagca ctctgggagg ctgaggtggg tggatcacct gaggtcagga
 gttcaagacc agcctggtga acatggcgaa accccgtctc taataaaaat acaaaaatta
 gccgggcatg gtggtgcatg cctgtaatcc cagctactcg ggaggctgag gcaggagaac
 tgcttgaacc caggaggcag aggttgcagt gatccaagat catgccactg cactccagcc
 tgggcaacaa gagcaaaact ccgtctcaaa ataaaaagaa aagaaaagaa tggacagtgt
 ttgcagagag ttgctcacga gtttccctct aatcctaaat gtcttcatgt ctatcagtct
 gagcagacgg tgagtagggc gggcacattc tccaggccct tcttcctagc tctgtggttg
 acctctcagc aagtgctatc caggctgggc caaccagacc cacaattaac tgagcctcag
 tgaaagcgtc cagtgcatct tgacctgaga cagcaaggaa ttgcatttgg ggttattcca
 acgatgatgg cagggaactg gtggtattta gtgctgaggg gcagtgatac agaaagattt
 gccctgtggg acaggtcct gcgcgagtcc catccccaaa agccagcagc tcctgccatg
aggaagacgg ggtttctgag caggcttatg cctgcaggtt cctgtggagc caccggctgt
 gacgggacac ctctgggtct cagcattgcc ctggggaggc tgggacattt agggacatgg
 tagggtttta acatttgttt cccaaatgtc aaatcccggg cacaggggca agaccctgtc
 ccgaattccc accccagtga atggtgtcgc tgccaaagcc aacacaagat gacaaagtg
 gctgggtacg gtggctcacg cctataatcc cagcactttg ggagaccgag acaggtggat
 cacctgaggt caggagttcg agaccaggct ggccaacatg gtgaacccc atctctacta
aaaatacaaa aattagctgg gtgtggtggc gcgcacctgt agtcccagct actcaggagg
 ctgaggtaga agaatagctg gaaccagga ggcagagatt gcagtcagcc gagattgcac
 cactgcactc cagcctggga gacagagcaa gactgactca aaagaaaaaa aatgacagaa
 gcctgattat cagactgccc ggaggagaca ggctccagca gatagatgcc agccaggccc
agctgccacg atttgtccca ggtgaccaaa ggcacgcagc tccagcatga atcgttctaa
 cccaacagtg acaagaactg ctgggcctta accgtcatgg aagactgggg ccgcttccaa
 gtcacagaca ggagacgggg acaggaaaga actcattcca cccaatcgga cacctaataa
 ttgagtgtct acagcagcaa tcaagtgaca agtgaggccc tacctgaccc agaaggtgcc
 tgccggctaa acattctgcc ccaccagaa actccagggg gtccgcccgt tatgccgtgg
 cccacccacg ccccttgga tcaccagcag tcacagacaa caggcaggcg aaactgaaga
 ccccaactca gccccagcgg accctccaga gcaaaagagg cccccggcga ggccacctgt
cggcaggcat gccgaggtca aacagccggg gccaccgttc ccagctgggc cacgacctgc
 accgtccaca gatgggcttt gagatggatt tgtatcaggg tgggggtgt ggtttggcca
```

Figure 11-20

```
aaatgcaatg gaccccgacc cctcctcgta aaaggatgtt gggtttccct ctggtgacac
atgggatgcg tcataaaccc tcccccaaag tcctggtcag cagcccatcc ttccaacgat
gagttttgcg gtttttcaga acagaaatga tcactacgat tgacgacggt cgtgatgtta
agacgtcgtc tccatgagct ttgggggggac ttttatgtgg aataaagaaa ctatcactg
```

METHODS FOR THE DETECTION OF VARIANT CAYMAN ATAXIA NUCLEIC ACIDS

This application claims priority to provisional patent applications serial No. 60/422,971, filed Nov. 1, 2002 and 60/424,973, filed Nov. 8, 2002, each of which is herein incorporated by reference in its entirety.

This invention was made in part with government support under Grant No. NS32130 awarded by the National Institutes of Health. The Government may have certain rights in the invention.

FIELD OF THE INVENTION

The present invention relates to ataxia, in particular to protein and nucleic acids encoding proteins associated with ataxia. The present invention provides assays for the detection of ataxia polymorphisms and mutations associated with disease or disease carrier states.

BACKGROUND OF THE INVENTION

Hereditary ataxia is a group of rare genetic neuromuscular disorders. It is characterized by degenerative changes in the brain and spinal cord. It can affect a person anytime between infancy through adulthood. Major symptoms include lack of coordination of the muscles used for voluntary movement. Many different hereditary ataxia's have been characterized, including Friedreich's Ataxia, Marie's Ataxia, Ataxia Telangiectasia, Vasomotor Ataxia, Vestibulocerebellar, Ataxiadynamia, Ataxiophemia, Olivopontocerebellar Atrophy, and Charcot-Marie-Tooth Disease.

Autosomal recessive Cayman cerebellar ataxia, or Cayman ataxia, was identified in a population isolate on Grand Cayman Island (Johnson et al., Neurology 28:352 [1978]). This disorder is characterized by marked psychomotor retardation and prominent nonprogressive cerebellar dysfunction including nystagmus, intention tremor, dysarthria, and wide-based ataxic gait. Hypotonia is present from early childhood. Retinal abnormalities are absent.

There is a need for identification of the molecular basis of ataxia, as well as for improved diagnostics and treatments for ataxia.

SUMMARY OF THE INVENTION

The present invention relates to ataxia, in particular to protein and nucleic acids encoding proteins associated with ataxia. The present invention provides assays for the detection of ataxia polymorphisms and mutations associated with disease or disease carrier states.

Accordingly, in some embodiments, the present invention provides a method for detection of a variant Cayman ataxia polypeptide or nucleic acid sequence in a subject, comprising providing a biological sample from a subject, wherein the biological sample comprises a Cayman ataxia polypeptide or nucleic acid; and detecting the presence or absence of a variant Cayman ataxia polypeptide or nucleic acid in the biological sample. In some embodiments, the variant Cayman ataxia polypeptide is a variant of SEQ ID NO:4 (e.g., SEQ ID NO:9). In some embodiments, the variant Cayman ataxia nucleic acid is a variant of SEQ ID NO:3 or SEQ ID NO:11 (e.g., SEQ ID NOs: 8 and 10). In certain embodiments, the presence of the variant Cayman ataxia polypeptide or nucleic acid is indicative of Caymans ataxia in the subject. In other embodiments, the presence of the variant Cayman ataxia polypeptide or nucleic acid is indicative of the subject being a carrier for Cayman ataxia. In still further embodiments, the presence of the variant Cayman ataxia polypeptide or nucleic acid is indicative of a disorder selected from the group consisting of ataxia, myoclonus, dystonia, epilepsy, and nystagmus in the subject. In some embodiments, the biological sample is selected from the group consisting of a blood sample, a tissue sample, a urine sample, a saliva sample, and an amniotic fluid sample. In some embodiments, the subject is selected from the group consisting of an embryo, a fetus, a newborn animal, a young animal, and an adult animal. In certain embodiments, the animal is a human (e.g., an adult female of child-bearing age). In some embodiments, the detecting comprises differential antibody binding. In other embodiments, the detection comprises a Western blot. In still further embodiments, the detection comprises a nucleic acid detection method selected from the group consisting of nucleic acid sequencing, polymerase chain reaction, hybridization, denaturing high pressure liquid chromatography, mass spectrometry, and enzymatic detection.

The present invention further provides a kit comprising a reagent for detecting the presence or absence of a variant Cayman ataxia nucleic acid or polypeptide in a biological sample. In some embodiments, the kit further comprises instruction for using the kit for the detecting the presence or absence of a variant Cayman ataxia nucleic acid or polypeptide in a biological sample. In some embodiments, the instructions comprise instructions required by the U.S. Food and Drug Agency for in vitro diagnostic kits. In some embodiments, the kit further comprises instructions for diagnosing Caymans ataxia or Cayman ataxia carrier status in the subject based on the presence or absence of the variant Cayman ataxia polypeptide. In other embodiments, the kit further comprises instructions for diagnosing a disorder selected from the group consisting of ataxia, myoclonus, dystonia, epilepsy, and nystagmus in the subject based on the presence or absence of the variant Cayman ataxia polypeptide. In some embodiments, the reagent is one or more antibodies. In other embodiments, the reagents comprise reagents for performing a nucleic acid detection assay selected from the group consisting of nucleic acid sequencing, polymerase chain reaction, hybridization, denaturing high pressure liquid chromatography, mass spectrometry, and enzymatic detection. In some embodiments, the variant Cayman ataxia polypeptide is a variant of SEQ ID NO:4 (e.g., SEQ ID NO:9). In some embodiments, the variant Cayman ataxia nucleic acid is a variant of SEQ ID NO: 3 or SEQ ID NO:11 (e.g., SEQ ID NOs: 8 and 10). In some embodiments, the biological sample is selected from the group consisting of a blood sample, a tissue sample, a saliva sample, a urine sample, and an amniotic fluid sample.

DESCRIPTION OF THE FIGURES

FIG. 1 shows the nucleic acid sequence of the mouse Jittery gene (SEQ ID NO:1).

FIG. 2 shows the amino acid sequence of the mouse Jittery protein (SEQ ID NO:2).

FIG. 3 shows the nucleic acid sequence of the human Cayman ataxia mRNA sequence (SEQ ID NO:3).

FIG. 4 shows the amino acid sequence of the human Cayman ataxia protein (SEQ ID NO:4).

FIG. 6 shows an alignment of human KIA1872 (SEQ ID NO:5), macaque (SEQ ID NO:6), mouse jittery (SEQ ID NO:7), human NIP2 (SEQ ID NO:26), and mouse NIP2 (SEQ ID NO:27) polypeptides.

FIG. 8 shows the nucleic acid sequence of SEQ ID NO:8 (Cayman Ataxia mutant).

FIG. 9 shows the amino acid sequence of SEQ ID NO:9 (Cayman Ataxia mutant of SEQ ID NO:8).

FIG. 10 shows the nucleic acid sequence of SEQ ID NO:10 (Cayman Ataxia splice site mutant).

FIG. 11 shows the nucleic acid sequence of the human Cayman ataxia genomic DNA (SEQ ID NO:11).

FIG. 12 shows a comparative map of human chromosome 19p13.3 and mouse chromosome 10 used in the development of some embodiments of the present invention.

FIG. 13 (SEQ ID NOS:14-21) shows a sequence alignment of predicted ATCAY protein sequences with related genes across species.

FIG. 14 shows recombinants in the region of atcay.

FIG. 15 shows Table 2, markers and primers used in mapping of atcay.

DEFINITIONS

Figure 5:
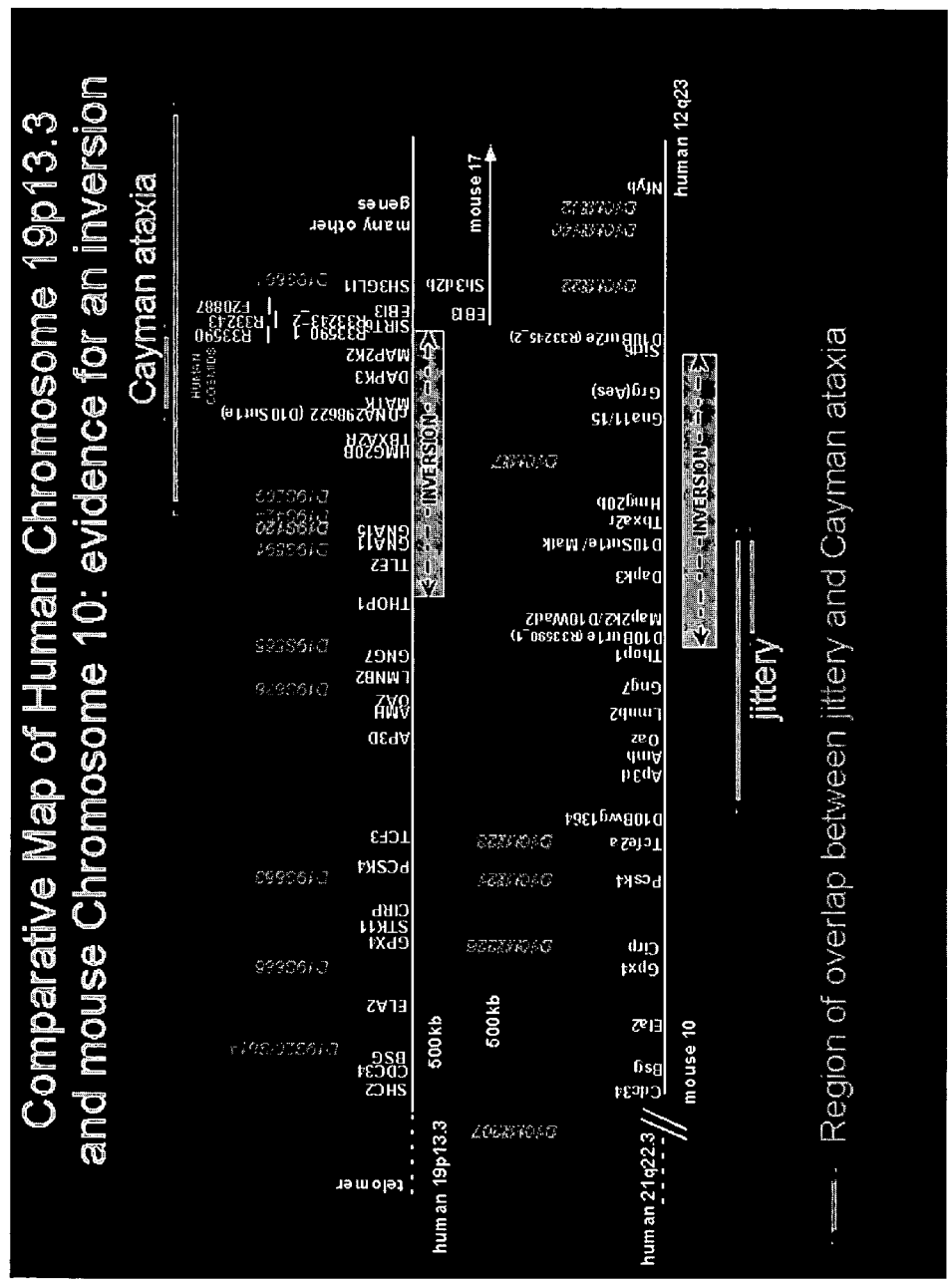
FIG. 5 shows a comparative map of human chromosome 19p13.3 and mouse chromosome 10 used in the development of some embodiments of the present invention.

To facilitate understanding of the invention, a number of terms are defined below.

As used herein, the term "Cayman ataxia" when used in reference to a protein or nucleic acid refers to a protein or nucleic acid encoding a protein that, in some mutant forms, is correlated with ataxia. The term Cayman ataxia encompasses both proteins that are identical to wild-type Cayman ataxia and those that are derived from wild type Cayman ataxia (e.g., variants of Cayman ataxia or chimeric genes constructed with portions of Cayman ataxia coding regions). In some embodiments, the "Cayman ataxia" is the wild type nucleic acid (SEQ ID NO: 3) or amino acid (SEQ ID NO:4) sequence. In other embodiments, the "Cayman ataxia" is a variant or mutant (e.g., including, but not limited to, variants resulting in disease).

As used herein, the term "instructions for using said kit for said detecting the presence or absence of a variant Cayman ataxia polypeptide in a said biological sample" includes instructions for using the reagents contained in the kit for the detection of variant and wild type Cayman ataxia polypeptides. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., Cayman ataxia). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "Cayman ataxia gene" refers to the full-length Cayman ataxia genomic sequence (e.g., contained in SEQ ID NO:11) or mRNA sequence (e.g., contained in SEQ ID NO:3). However, it is also intended that the term encompass fragments of the Cayman ataxia sequence, mutants as well as other domains within the full-length Cayman ataxia nucleotide sequence. Furthermore, the terms "Cayman ataxia nucleotide sequence" or "Cayman ataxia polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript.

These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-"A-G-T-3'," is complementary to the sequence 3'-"T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic, acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed. The present invention is not limited to the hybridization of probes of about 500 nucleotides in length. The present invention contemplates the use of probes between approximately 10 nucleotides up to several thousand (e.g., at least 5000) nucleotides in length.

One skilled in the relevant understands that stringency conditions may be altered for probes of other sizes (See e.g., Anderson and Young, Quantitative Filter Hybridization, in *Nucleic Acid Hybridization* [1985] and Sambrook et al., Molecular Cloning: A Laboratory Manual, Cold Spring Harbor Press, NY [1989]).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci. (U.S.A.)* 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., Cayman ataxia).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., the Cayman ataxia gene).

As used herein, the term "detection assay" refers to an assay for detecting the presence of absence of variant nucleic acid sequences (e.g., polymorphism or mutations) in a given allele of a particular gene (e.g., the Cayman ataxia gene). Examples of suitable detection assays include, but are not limited to, those described below in Section III B.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding Cayman ataxia includes, by way of example, such nucleic acid in cells ordinarily expressing Cayman ataxia where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5′ side by the nucleotide triplet "ATG" that encodes the initiator methionine and on the 3′ side by one of the three triplets, which specify stop codons (i.e., TAA, TAG, TGA).

As used herein, the term "purified" or "to purify" refers to the removal of contaminants from a sample. For example, antibodies to Cayman ataxia protein are purified by removal of contaminating non-immunoglobulin proteins; they are also purified by the removal of immunoglobulin that does not bind Cayman ataxia. The removal of non-immunoglobulin proteins and/or the removal of immunoglobulins that do not bind Cayman ataxia results in an increase in the percent of Cayman ataxia-reactive immunoglobulins in the sample. In another example, recombinant Cayman ataxia polypeptides are expressed in bacterial host cells and the polypeptides are purified by the removal of host cell proteins; the percent of recombinant Cayman ataxia polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced Cayman ataxia transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding Cayman ataxia (e.g., SEQ ID NOs:3 or 11) or fragments thereof may be employed as hybridization probes. In this case, the Cayman ataxia encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases (e.g., saliva, blood, urine, and tissue biopsies). Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "entering" as in "entering said genetic variation information into said computer" refers to transferring information to a "computer readable medium." Information may be transferred by any suitable method, including but not limited to, manually (e.g., by typing into a computer) or automated (e.g., transferred from another "computer readable medium" via a "processor").

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "computer implemented method" refers to a method utilizing a "CPU" and "computer readable medium."

DETAILED DESCRIPTION OF THE INVENTION

The present invention relates to ataxia, in particular to ataxia protein and nucleic acids encoding ataxia proteins. The present invention provides assays for the detection of ataxia and ataxia polymorphisms and mutations associated with disease states.

I. Cayman Ataxia Polynucleotides

The present invention provides a new gene associated with Caymans ataxia. Accordingly, the present invention provides nucleic acids encoding Cayman ataxia genes, homologs, variants (e.g., polymorphisms and mutants), including but not limited to, those described in SEQ ID NOs: 3, 11, 8, and 10. In some embodiments, the present invention provide polynucleotide sequences that are capable of hybridizing to SEQ ID NOs: 3, 11, 8, and 10 under conditions of low to high stringency as long as the polynucleotide sequence capable of hybridizing encodes a protein that retains a biological activity of the naturally occurring Cayman ataxia. In some embodiments, the protein that retains a biological activity of naturally occurring Cayman ataxia is 70% homologous to wild-type Cayman ataxia, preferably 80% homologous to wild-type Cayman ataxia, more preferably 90% homologous to wild-type Cayman ataxia, and most preferably 95% homologous to wild-type Cayman ataxia. In preferred embodiments, hybridization conditions are based on the melting temperature ($T_m$) of the nucleic acid binding complex and confer a defined "stringency" as explained above (See e.g., Wahl, et al., Meth. Enzymol., 152:399-407 [1987], incorporated herein by reference).

In other embodiments of the present invention, additional alleles of Cayman ataxia are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Examples of the alleles of the present invention include those encoded by SEQ ID NOs:3 and 11 (wild type) and disease alleles (SEQ ID NOs: 8 and 10; See Experimental Section below).

In still other embodiments of the present invention, the nucleotide sequences of the present invention may be engineered in order to alter an Cayman ataxia coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of Cayman ataxia may be extended utilizing the nucleotide sequence (e.g., SEQ ID NO: 3 or 11) in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318-22 [1993]). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055-60 [1991]). The PROMOTER-FINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed Cayman ataxia sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., Cayman ataxia function) for such purposes as altering the biological activity (e.g., prevention of disease). Such modified peptides are considered functional equivalents of peptides having an activity of Cayman ataxia as defined herein. A modified peptide can be produced in which the nucleotide sequence encoding the polypeptide has been altered, such as by substitution, deletion, or addition. In particularly preferred embodiments, these modifications do not significantly reduce the biological activity of the modified Cayman ataxia. In other words, construct "X" can be evaluated in order to determine whether it is a member of the genus of modified or variant Cayman ataxia's of the present invention as defined functionally, rather than structurally. In preferred embodiments, the activity of variant Cayman ataxia polypeptides is evaluated by methods described herein (e.g., the generation of transgenic animals).

Moreover, as described above, variant forms of Cayman ataxia are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of Cayman ataxia disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a Cayman ataxia coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

II. Cayman Ataxia Polypeptides

In other embodiments, the present invention provides Cayman ataxia polynucleotide sequences that encode Cayman ataxia polypeptide sequences. Cayman ataxia polypeptides (e.g., SEQ ID NOs: 4 and 9) are described in FIGS. 4 and 9. Other embodiments of the present invention provide fragments, fusion proteins or functional equivalents of these Cayman ataxia proteins. In some embodiments, the present invention provides truncation mutants of Cayman ataxia. In still other embodiment of the present invention, nucleic acid sequences corresponding to Cayman ataxia variants, homologs, and mutants may be used to generate recombinant DNA molecules that direct the expression of the Cayman ataxia variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NOs: 3, 11, 8, and 10 that encode substantially the same or a functionally equivalent amino acid sequence, may be used to clone and express Cayman ataxia. In general, such polynucleotide sequences hybridize to SEQ ID NOs: 3, 11, 8, and 10 under conditions of high to medium stringency as described above. As will be understood by those of skill in the art, it may be advantageous to produce Cayman ataxia-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of Cayman ataxia expression or to produce recombinant RNA transcripts having desirable properties, such as a longer half-life, than transcripts produced from naturally occurring sequence.

1. Vectors for Production of Cayman Ataxia

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOs: 3, 11, 8, and 10). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NO:3) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda PL and PR, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of Cayman Ataxia

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae,*

*Schizosaccharomycees pombe, Drosophila* S2 cells, Spodoptera Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of Cayman Ataxia

The present invention also provides methods for recovering and purifying Cayman ataxia from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having the coding sequence (e.g., SEQ ID NOs: 3, 11, 8, and 10) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of Cayman Ataxia

In addition, the present invention provides fragments of Cayman ataxia (i.e., truncation mutants). In some embodiments of the present invention, when expression of a portion of the Cayman ataxia protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751 [1987]) and *Salmonella typhimurium* and its in vitro activity has been demonstrated on recombinant proteins (Miller et al., Proc. Natl. Acad. Sci. USA 84:2718 [1990]). Therefore, removal of an N-terminal methionine, if desired, can be achieved either in vivo by expressing such recombinant polypeptides in a host which produces MAP (e.g., *E. coli* or CM89 or *S. cerivisiae*), or in vitro by use of purified MAP.

5. Fusion Proteins Containing Cayman Ataxia

The present invention also provides fusion proteins incorporating all or part of Cayman ataxia. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a Cayman ataxia protein. In some embodiments of the present invention, the VP6 capsid protein of rotavirus is used as an immunologic carrier protein for portions of the Cayman ataxia polypeptide, either in the monomeric form or in the form of a viral particle. In other embodiments of the present invention, the nucleic acid sequences corresponding to the portion of Cayman ataxia against which antibodies are to be raised can be incorporated into a fusion gene construct which includes coding sequences for a late vaccinia virus structural protein to produce a set of recombinant viruses expressing fusion proteins comprising a portion of Cayman ataxia as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of Cayman ataxia and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of Cayman ataxia is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the Cayman ataxia proteins can also be expressed and presented by bacterial cells.

In addition to utilizing fusion proteins to enhance immunogenicity, it is widely appreciated that fusion proteins can also facilitate the expression of proteins, such as the Cayman ataxia protein of the present invention. Accordingly, in some embodiments of the present invention, Cayman ataxia can be generated as a glutathione-S-transferase (i.e., GST fusion protein). It is contemplated that such GST fusion proteins will enable easy purification of Cayman ataxia, such as by the use of glutathione-derivatized matrices (See e.g., Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of Cayman ataxia, can allow purification of the expressed Cayman ataxia fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of Cayman Ataxia

Still other embodiments of the present invention provide mutant or variant forms of Cayman ataxia (i.e., muteins). It is possible to modify the structure of a peptide having an activity of Cayman ataxia for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject Cayman ataxia proteins as defined herein. A modified peptide can be produced in which the amino acid sequence has been altered, such as by amino acid substitution, deletion, or addition.

Moreover, as described above, variant forms (e.g., mutants or polymorphic sequences) of the subject Cayman ataxia proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present Cayman ataxia proteins, as well as truncation mutants, and is especially useful for identifying potential variant sequences (i.e., mutants or polymorphic sequences) that are involved in disease (e.g., ataxia or other movement diseases). The purpose of screening such combinatorial libraries is to generate, for example, novel Cayman ataxia variants that can act as either agonists or antagonists, or alternatively, possess novel activities all together.

Therefore, in some embodiments of the present invention, Cayman ataxia variants are engineered by the present method to provide altered (e.g., increased or decreased) biological activity. In other embodiments of the present invention, combinatorially-derived variants are generated which have a selective potency relative to a naturally occurring Cayman ataxia. Such proteins, when expressed from recombinant DNA constructs, can be used in gene therapy protocols.

Still other embodiments of the present invention provide Cayman ataxia variants that have intracellular half-lives dramatically different than the corresponding wild-type protein. For example, the altered protein can be rendered either more stable or less stable to proteolytic degradation or other cellular process that result in destruction of, or otherwise inactivate Cayman ataxia. Such variants, and the genes which encode them, can be utilized to alter the location of Cayman ataxia expression by modulating the half-life of the protein. For instance, a short half-life can give rise to more transient Cayman ataxia biological effects and, when part of an inducible expression system, can allow tighter control of Cayman ataxia levels within the cell. As above, such proteins, and particularly their recombinant nucleic acid constructs, can be used in gene therapy protocols.

In still other embodiments of the present invention, Cayman ataxia variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of Cayman ataxia homologs, variants or other related proteins are aligned, preferably to promote the highest homology possible. Such a population of variants can include, for example, Cayman ataxia homologs from one or more species, or Cayman ataxia variants from the same species but which differ due to mutation or polymorphisms. Amino acids that appear at each position of the aligned sequences are selected to create a degenerate set of combinatorial sequences.

In a preferred embodiment of the present invention, the combinatorial Cayman ataxia library is produced by way of a degenerate library of genes encoding a library of polypeptides which each include at least a portion of potential Cayman ataxia protein sequences. For example, a mixture of synthetic oligonucleotides can be enzymatically ligated into gene sequences such that the degenerate set of potential Cayman ataxia sequences are expressible as individual polypeptides, or alternatively, as a set of larger fusion proteins (e.g., for phage display) containing the set of Cayman ataxia sequences therein.

There are many ways by which the library of potential Cayman ataxia homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential Cayman ataxia sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules*, Elsevier, Amsterdam, pp 273-289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87: 6378 [1990]; each of which is herein incorporated by reference; as well as U.S. Pat. Nos. 5,223,409, 5,198,346, and 5,096,815; each of which is incorporated herein by reference).

It is contemplated that the Cayman ataxia nucleic acids (e.g., SEQ ID NO:3, and fragments and variants thereof) can be utilized as starting nucleic acids for directed evolution. These techniques can be utilized to develop Cayman ataxia variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1: 17-24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for Cayman ataxia activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]). Variants produced by directed evolution can be screened for Cayman ataxia activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of Cayman ataxia homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of Cayman Ataxia

In an alternate embodiment of the invention, the coding sequence of Cayman ataxia is synthesized, whole or in part, using chemical methods well known in the art (See e.g., Caruthers et al., Nucl. Acids Res. Symp. Ser., 7:215 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807 [1981]). In other embodiments of the present invention, the protein itself is produced using chemical methods to synthesize either an entire Cayman ataxia amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 [1995]) and automated synthesis may be achieved, for example, using ABI 431A Peptide Synthesizer (Perkin Elmer) in accordance with the instructions provided by the manufacturer. Additionally, the amino acid sequence of Cayman ataxia, or any part thereof, may be altered during direct synthesis and/or combined using chemical methods with other sequences to produce a variant polypeptide.

III. Detection of Cayman Ataxia Alleles

In some embodiments, the present invention provides methods of detecting the presence of wild or variant (e.g., mutant or polymorphic) Cayman ataxia nucleic acids or polypeptides. The detection of mutant Cayman ataxia polypeptides finds use in the diagnosis of disease (e.g., ataxia and other movement diseases).

A. Cayman Ataxia Alleles

In some embodiments, the present invention includes alleles of Cayman ataxia that increase a patient's susceptibility to Caymans ataxia and other movement diseases such as ataxia, dystonia or myoclonus (e.g., including, variants of SEQ ID NO:3 and 11 such as SEQ ID NOs 8 and 10; See e.g., the illustrative Examples below). However, the present invention is not limited to the mutations described herein. Any mutation that results in the undesired phenotype (e.g., ataxia) is within the scope of the present invention.

B. Detection of Cayman Ataxia Alleles

Accordingly, the present invention provides methods for determining whether a patient has an increased susceptibility to Caymans ataxia or other movement disorders by determining whether the individual has a variant Cayman ataxia allele. In other embodiments, the present invention provides methods for providing a prognosis of increased risk for ataxia to an individual based on the presence or absence of one or more variant alleles of Cayman ataxia. In some embodiments, diagnosis is prenatal diagnosis, allowing a couple to assess their risk of having a child with a mutant Cayman ataxia allele.

In other embodiments, the present invention provides methods of determining an individuals Cayman ataxia carrier status. The present invention is not limited to a particular mechanism. Indeed, an understanding of the mechanism is not necessary to practice the present invention. Nonetheless, it is contemplated that Cayman ataxia is often a recessive disorder. Thus, two mutant alleles are necessary for disease states. Accordingly, in some embodiments, couples contemplating starting a family are screened to determine both parents' carrier status. This allows for in utero testing (e.g., amniocentesis) only in cases where both parents are carriers.

A number of methods are available for analysis of variant (e.g., mutant or polymorphic) nucleic acid sequences. Assays for detection variants (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

1. Direct Sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, or automated sequencing. The results of the sequencing are displayed using any suitable method. The sequence is examined and the presence or absence of a given SNP or mutation is determined.

2. PCR Assay

In some embodiments of the present invention, variant sequences are detected using a PCR-based assay. In some embodiments, the PCR assay comprises the use of oligonucleotide primers that hybridize only to the variant or wild type allele of Cayman ataxia (e.g., to the region of polymorphism or mutation). Both sets of primers are used to amplify a sample of DNA. If only the mutant primers result in a PCR product, then the patient has the mutant Cayman ataxia allele. If only the wild-type primers result in a PCR product, then the patient has the wild type allele of Cayman ataxia.

3. Mutational Detection by dHPLC

In some embodiments of the present invention, variant sequences are detected using a PCR-based assay with consecutive detection of nucleotide variants by dHPLC (denaturing high performance liquid chromatography). Exemplary systems and Methods for dHPLC include, but are not limited to, WAVE (Transgenomic, Inc; Omaha, Nebr.) or VARIAN equipment (Palo Alto, Calif.).

4. Fragment Length Polymorphism Assays

In some embodiments of the present invention, variant sequences are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a SNP or a mutation will have a different banding pattern than wild type.

a. RFLP Assay

In some embodiments of the present invention, variant sequences are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assay

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

5. Hybridization Assays

In preferred embodiments of the present invention, variant sequences are detected a hybridization assay. In a hybridization assay, the presence of absence of a given SNP or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.), Current Protocols in Molecular Biology, John Wiley & Sons, NY [1991]). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics; Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or non-specifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

C. Enzymatic Detection of Hybridization

In some embodiments of the present invention, hybridization is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified genomic DNA. The isolated DNA sample is contacted with the first probe specific either for a SNP/mutation or wild type sequence and allowed to hybridize.

Then a secondary probe, specific to the first probe, and containing the fluorescein label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLI-TAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

6. Mass Spectroscopy Assay

In some embodiments, a MassARRAY system (Sequenom, San Diego, Calif.) is used to detect variant sequences (See e.g., U.S. Pat. Nos. 6,043,031; 5,777,324; and 5,605,798; each of which is herein incorporated by reference). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 second including repetitive data collection. The SpectroTYPER software then calculates, records, compares and reports the genotypes at the rate of three seconds per sample.

7. Detection of Variant Cayman Ataxia Proteins

In other embodiments, variant Cayman ataxia polypeptides are detected. Any suitable method may be used to detect truncated or mutant Cayman ataxia polypeptides including, but not limited to, those described below.

a) Cell Free Translation

For example, in some embodiments, cell-free translation methods from Ambergen, Inc. (Boston, Mass.) are utilized. Ambergen, Inc. has developed a method for the labeling, detection, quantitation, analysis and isolation of nascent proteins produced in a cell-free or cellular translation system without the use of radioactive amino acids or other radioactive labels. Markers are aminoacylated to tRNA molecules. Potential markers include native amino acids, non-native amino acids, amino acid analogs or derivatives, or chemical moieties. These markers are introduced into nascent proteins from the resulting misaminoacylated tRNAs during the translation process.

One application of Ambergen's protein labeling technology is the gel free truncation test (GFTT) assay (See e.g., U.S. Pat. No. 6,303,337, herein incorporated by reference). In some embodiments, this assay is used to screen for truncation mutations in a Cayman ataxia protein. In the GFTT assay, a marker (e.g., a fluorophore) is introduced to the nascent protein during translation near the N-terminus of the protein. A second and different marker (e.g., a fluorophore with a different emission wavelength) is introduced to the nascent protein near the C-terminus of the protein. The protein is then separated from the translation system and the signal from the markers is measured. A comparison of the measurements from the N and C terminal signals provides information on the fraction of the molecules with C-terminal truncation (i.e., if the normalized signal from the C-terminal marker is 50% of the signal from the N-terminal marker, 50% of the molecules have a C-terminal truncation).

b) Antibody Binding

In still further embodiments of the present invention, antibodies (See below for antibody production) are used to determine if an individual contains an allele encoding a variant Cayman ataxia gene. In preferred embodiments, antibodies are utilized that discriminate between variant (i.e., truncated proteins); and wild-type proteins (SEQ ID NOs:4). In some particularly preferred embodiments, the antibodies are directed to the C-terminus of Cayman ataxia. Proteins that are recognized by the N-terminal, but not the C-terminal antibody are truncated. In some embodiments, quantitative immunoassays are used to determine the ratios of C-terminal to N-terminal antibody binding. In other embodiments, antibodies that differentially bind to wild type or variant forms of Cayman ataxia.

Antibody binding is detected by techniques known in the art (e.g., radioimmunoassay, ELISA (enzyme-linked immunosorbent assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the result of the immunoassay is utilized.

In other embodiments, the immunoassay described in U.S. Pat. Nos. 5,599,677 and 5,672,480; each of which is herein incorporated by reference.

8. Kits for Analyzing Risk of Ataxia

The present invention also provides kits for determining whether an individual contains a wild-type or variant (e.g., mutant or polymorphic) allele of Cayman ataxia. In some embodiments, the kits are useful determining whether the subject is at risk of developing Cayman ataxia or other movement disease. The diagnostic kits are produced in a variety of ways. In some embodiments, the kits contain at least one reagent for specifically detecting a mutant Cayman ataxia allele or protein. In some embodiments, the reagent is a nucleic acid that hybridizes to nucleic acids containing the mutation and that does not bind to nucleic acids that do not contain the mutation. In other preferred embodiments, the reagents are primers for amplifying the region of DNA containing the mutation. In still other embodiments, the reagents are antibodies that preferentially bind either the wild-type or mutant Cayman ataxia proteins.

In some embodiments, the kit contains instructions for determining whether the subject is at risk for developing ataxia or other movement diseases. In preferred embodiments, the instructions specify that risk for developing ataxia is determined by detecting the presence or absence of a mutant Cayman ataxia allele in the subject, wherein subjects having an mutant allele are at greater risk for ataxia or for having offspring with Cayman ataxia (in the case of a parent who is a carrier).

The presence of absence of a disease-associated mutation in a Cayman ataxia gene can be used to may therapeutic or other medical decisions. For example, couples with a family history of hereditary ataxia may choose to conceive a child via in vitro fertilization and pre-implantation genetic screening. In this case, fertilized embryos are screened for mutant (e.g., disease associated) alleles of the Cayman ataxia gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a Cayman ataxia allele known to be associated with disease allows for early intervention (e.g., genetic or pharmaceutical therapies).

In some embodiments, the kits include ancillary reagents such as buffering agents, nucleic acid stabilizing reagents, protein stabilizing reagents, and signal producing systems (e.g., florescence generating systems as Fret systems). The test kit may be packages in any suitable manner, typically with the elements in a single container or various containers as necessary along with a sheet of instructions for carrying out the test. In some embodiments, the kits also preferably include a positive control sample.

9. Bioinformatics

In some embodiments, the present invention provides methods of determining an individual's risk of developing ataxia or related movement disorders based on the presence of one or more variant alleles of Cayman ataxia. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of contacting ataxia or related disorder associated with a given polymorphism, as well as the sequences). In some embodiments, one of the computers stores application programs (e.g., for analyzing the results of detection assays). Results are then delivered to the user (e.g., via one of the computers or via the internet.

For example, in some embodiments, a computer-based analysis program is used to translate the raw data generated by the detection assay (e.g., the presence, absence, or amount of a given Cayman ataxia allele or polypeptide) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant Cayman ataxia genes or polypeptides), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing ataxia or a diagnosis of ataxia) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

IV. Generation of Cayman Ataxia Antibodies

The present invention provides isolated antibodies or antibody fragments (e.g., FAB fragments). Antibodies can be generated to allow for the detection of Cayman ataxia protein. The antibodies may be prepared using various immunogens. In one embodiment, the immunogen is a human Cayman ataxia peptide to generate antibodies that recognize human Cayman ataxia. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against Cayman ataxia. For the production of antibody, various host animals can be immunized by injection with the peptide corresponding to the Cayman ataxia epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward Cayman ataxia, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., in *Monoclonal Antibodies and Cancer Therapy*, Alan R. Liss, pp. 77-96 [1985]).

In addition, it is contemplated that techniques described for the production of single chain antibodies (U.S. Pat. No. 4,946,778; herein incorporated by reference) will find use in producing Cayman ataxia specific single chain antibodies. An additional embodiment of the invention utilizes the techniques described for the construction of Fab expression libraries (Huse et al., Science 246:1275-1281 [1989]) to allow rapid and easy identification of monoclonal Fab fragments with the desired specificity for Cayman ataxia.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of Cayman ataxia (e.g., for Western blotting), measuring levels thereof in appropriate biological samples, etc. The antibodies can be used to detect Cayman ataxia in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human Cayman ataxia using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of Cayman ataxia detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of Cayman ataxia or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of Cayman ataxia. Such antibodies can also be used diagnostically to measure abnormal expression of Cayman ataxia, or the aberrant formation of protein complexes, which may be indicative of a disease state.

V. Gene Therapy Using Cayman Ataxia

The present invention also provides methods and compositions suitable for gene therapy to alter Cayman ataxia expression, production, or function. As described above, the present invention provides human Cayman ataxia genes and provides methods of obtaining Cayman ataxia genes from other species. Thus, the methods described below are generally applicable across many species. In some embodiments, it is contemplated that the gene therapy is performed by providing a subject with a wild-type allele of Cayman ataxia (i.e., an allele that does not contain a Cayman ataxia disease (e.g., free of disease causing polymorphisms or mutations). Subjects in need of such therapy are identified by the methods described above.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

VI. Transgenic Animals Expressing Exogenous Cayman Ataxia Genes and Homologs, Mutants, and Variants Thereof The present invention contemplates the generation of transgenic animals comprising an exogenous Cayman ataxia gene or homologs, mutants, or variants thereof. In preferred embodiments, the transgenic animal displays an altered phenotype as compared to wild-type animals. In some embodiments, the altered phenotype is the overexpression of mRNA for a Cayman ataxia gene as compared to wild-type levels of Cayman ataxia expression. In other embodiments, the altered phenotype is the decreased expression of mRNA for an endogenous Cayman ataxia gene as compared to wild-type levels of endogenous Cayman ataxia expression. In some preferred embodiments, the transgenic animals comprise mutant (e.g., truncated) alleles of Cayman ataxia. Methods for analyzing the presence or absence of such phenotypes include Northern blotting, mRNA protection assays, and RT-PCR. In other embodiments, the transgenic mice have a knock out mutation of the Cayman ataxia gene. In preferred embodiments, the transgenic animals display an ataxia disease phenotype.

Such animals find use in research applications (e.g., identifying signaling pathways that Cayman ataxia is involved in), as well as drug screening applications (e.g., to screen for drugs that prevent ataxia. For example, in some embodiments, test compounds (e.g., a drug that is suspected of being useful to treat ataxia) and control compounds (e.g., a placebo) are administered to the transgenic animals and the control animals and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Van der Putten, supra; Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the microinjection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., mutants in which the LRRs of Cayman ataxia are deleted). Methods for homologous recombination are described in U.S. Pat. No. 5,614,396, incorporated herein by reference.

VIII. Drug Screening Using Cayman Ataxia

As described herein, it is contemplated that Cayman ataxia is involved in hereditary movement disorders such as Caymans ataxia. Accordingly, in some embodiments, the isolated nucleic acid sequences of Cayman ataxia (e.g., SEQ ID NOs: 3, 11, 8, and 10) are used in drug screening applications for compounds that are useful in the treatment of ataxia and related disorders.

A. Identification of Binding Partners

In some embodiments, binding partners of Cayman ataxia amino acids are identified. In some embodiments, the Cayman ataxia nucleic acid sequences (e.g., SEQ ID NOs: 3, 11, 8, and 10) or fragments thereof are used in yeast two-hybrid screening assays. For example, in some embodiments, the nucleic acid sequences are subcloned into pGPT9 (Clontech, La Jolla, Calif.) to be used as a bait in a yeast-2-hybrid screen for protein-protein interaction of a human fetal kidney cDNA library (Fields and Song *Nature* 340:245-246, 1989; herein incorporated by reference). In other embodiments, phage display is used to identify binding partners (Parmley and Smith *Gene* 73 : 305-318, [1988]; herein incorporated by reference).

B. Drug Screening

The present invention provides methods and compositions for using Cayman ataxia as a target for screening drugs that can alter, for example, interaction between Cayman ataxia and Cayman ataxia binding partners (e.g., those identified using the above methods)

In one screening method, the two-hybrid system is used to screen for compounds (e.g., drug) capable of altering (e.g., inhibiting) Cayman ataxia function(s) (e.g., interaction with a binding partner) in vitro or in vivo. In one embodiment, a GAL4 binding site, linked to a reporter gene such as lacZ, is contacted in the presence and absence of a candidate compound with a GAL4 binding domain linked to a Cayman ataxia fragment and a GAL4 transactivation domain II linked to a binding partner fragment. Expression of the reporter gene is monitored and a decrease in the expression is an indication that the candidate compound inhibits the interaction of Cayman ataxia with the binding partner. Alternately, the effect of candidate compounds on the interaction of Cayman ataxia with other proteins (e.g., proteins known to interact directly or indirectly with the binding partner) can be tested in a similar manner.

In another screening method, candidate compounds are evaluated for their ability to alter Cayman ataxia signaling by contacting Cayman ataxia, binding partners, binding partner-associated proteins, or fragments thereof, with the candidate compound and determining binding of the candidate compound to the peptide. The protein or protein fragments is/are immobilized using methods known in the art such as binding a GST-Cayman ataxia fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., *E. coli* XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate Cayman ataxia physiological effects (e.g., ataxia).

In another screening method, one of the components of the Cayman ataxia/binding partner signaling system, is immobilized. Polypeptides can be immobilized using methods known in the art, such as adsorption onto a plastic microtiter plate or specific binding of a GST-fusion protein to a polymeric bead containing glutathione. For example, GST-Cayman ataxia is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of Cayman ataxia with the other peptide. A variation of this method allows for the screening of compounds that are capable of disrupting a previously-formed protein/protein complex. For example, in some embodiments a complex comprising Cayman ataxia or a Cayman ataxia fragment bound to another peptide is immobilized as described above and contacted with a candidate compound. The dissolution of the complex by the candidate compound correlates with the ability of the compound to disrupt or inhibit the interaction between Cayman ataxia and the other peptide.

Another technique for drug screening provides high throughput screening for compounds having suitable binding affinity to Cayman ataxia peptides and is described in detail in WO 84/03564, incorporated herein by reference. Briefly, large numbers of different small peptide test compounds are synthesized on a solid substrate, such as plastic pins or some other surface. The peptide test compounds are then reacted with Cayman ataxia peptides and washed. Bound Cayman ataxia peptides are then detected by methods well known in the art.

Another technique uses Cayman ataxia antibodies, generated as discussed above. Such antibodies capable of specifically binding to Cayman ataxia peptides compete with a test compound for binding to Cayman ataxia. In this manner, the antibodies can be used to detect the presence of any peptide that shares one or more antigenic determinants of the Cayman ataxia peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with Cayman ataxia and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding Cayman ataxia or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. In some embodiments, the reporter gene construct comprises the 5' regulatory region (e.g., promoters and/or enhancers) of a protein whose expression is controlled by Cayman ataxia in operable association with a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, calorimetric, or bioluminecent products of specific substrates (e.g., X-gal and luciferin). Comparisons between compounds of known and unknown activities may be conducted as described above.

Specifically, the present invention provides screening methods for identifying modulators, i.e., candidate or test compounds or agents (e.g., proteins, peptides, peptidomimetics, peptoids, small molecules or other drugs) which bind to Cayman ataxia of the present invention, have an inhibitory (or stimulatory) effect on, for example, Cayman ataxia expression or Cayman ataxia activity, or have a stimulatory or inhibitory effect on, for example, the expression or activity of a Cayman ataxia substrate. Compounds thus identified can be used to modulate the activity of target gene products (e.g., Cayman ataxia genes) either directly or indirectly in a therapeutic protocol, to elaborate the biological function of the target gene product, or to identify compounds that disrupt normal target gene interactions. Compounds that stimulate the activity of a variant Cayman ataxia or mimic the activity of a non-functional variant are particularly useful in the treatment of ataxia (e.g., Caymans ataxia).

In one embodiment, the invention provides assays for screening candidate or test compounds that are substrates of a Cayman ataxia protein or polypeptide or a biologically active portion thereof. In another embodiment, the invention provides assays for screening candidate or test compounds that bind to or modulate the activity of a Cayman ataxia protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

In one embodiment, an assay is a cell-based assay in which a cell that expresses a Cayman ataxia protein or biologically active portion thereof is contacted with a test compound, and the ability of the test compound to modulate Cayman ataxia's activity is determined. Determining the ability of the test compound to modulate Cayman ataxia activity can be accomplished by monitoring, for example, changes in enzymatic activity. The cell, for example, can be of mammalian origin.

The ability of the test compound to modulate Cayman ataxia binding to a compound, e.g., a Cayman ataxia substrate, can also be evaluated. This can be accomplished, for example, by coupling the compound, e.g., the substrate, with a radioisotope or enzymatic label such that binding of the compound, e.g., the substrate, to a Cayman ataxia can be determined by detecting the labeled compound, e.g., substrate, in a complex.

Alternatively, the Cayman ataxia is coupled with a radioisotope or enzymatic label to monitor the ability of a test compound to modulate Cayman ataxia binding to a Cayman ataxia substrate in a complex. For example, compounds (e.g., substrates) can be labeled with $^{125}I$, $^{35}S$ $^{14}C$ or $^3H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a Cayman ataxia substrate) to interact with a Cayman ataxia with or without the labeling of any of the interactants can be evaluated. For example, a microphysiometer can be used to detect the interaction of a compound with a Cayman ataxia without the labeling of either the compound or the Cayman ataxia (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and Cayman ataxia.

In yet another embodiment, a cell-free assay is provided in which a Cayman ataxia protein or biologically active portion thereof is contacted with a test compound and the ability of the test compound to bind to the Cayman ataxia protein or biologically active portion thereof is evaluated. Preferred biologically active portions of the Cayman ataxia proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 15 the assay should be maximal. An FRET binding event can be conveniently measured through standard fluorometric detection means well known in the art (e.g., using a fluorimeter).

In another embodiment, determining the ability of the Cayman ataxia protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize Cayman ataxia, an anti-Cayman ataxia antibody or its target molecule to facilitate separation of complexed from non-complexed forms of one or both of the proteins, as well as to accommodate automation of the assay. Binding of a test compound to a Cayman ataxia protein, or interaction of a Cayman ataxia protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase-Cayman ataxia fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or Cayman ataxia protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of Cayman ataxia binding or activity determined using standard techniques. Other techniques for immobilizing either Cayman ataxia protein or a target molecule on matrices include using conjugation of biotin and streptavidin. Biotinylated Cayman ataxia protein or target molecules can be prepared from biotin-NHS(N-hydroxysuccinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with Cayman ataxia protein or target molecules but which do not interfere with binding of the Cayman ataxia protein to its target molecule. Such antibodies can be derivatized to the wells of the plate, and unbound target or Cayman ataxia protein trapped in the wells by antibody conjugation.

Methods for detecting such complexes, in addition to those described above for the GST-immobilized complexes, include immunodetection of complexes using antibodies reactive with the Cayman ataxia protein or target molecule, as well as enzyme-linked assays which rely on detecting an enzymatic activity associated with the Cayman ataxia protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11: 141-8 [1998]; Hageand Tweed J. Chromatogr. Biomed. Sci. Appl 699:499-525 [1997]). Further, fluorescence energy transfer may also be conveniently utilized, as described herein, to detect binding without further purification of the complex from solution.

The assay can include contacting the Cayman ataxia protein or biologically active portion thereof with a known compound that binds the Cayman ataxia to form an assay mixture, contacting the assay mixture with a test compound, and determining the ability of the test compound to interact with a Cayman ataxia protein, wherein determining the ability of the test compound to interact with a Cayman ataxia protein includes determining the ability of the test compound to preferentially bind to Cayman ataxia or biologically active portion thereof, or to modulate the activity of a target molecule, as compared to the known compound.

To the extent that Cayman ataxia can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, Cayman ataxia protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with Cayman ataxia ("Cayman ataxia-binding proteins" or "Cayman ataxia-bp") and are involved in Cayman ataxia activity. Such Cayman ataxia-bps can be activators or inhibitors of signals by the Cayman ataxia proteins or targets as, for example, downstream elements of a Cayman ataxia-mediated signaling pathway.

Modulators of Cayman ataxia expression can also be identified. For example, a cell or cell free mixture is contacted with a candidate compound and the expression of Cayman ataxia mRNA or protein evaluated relative to the level of expression of Cayman ataxia mRNA or protein in the absence of the candidate compound. When expression of Cayman ataxia mRNA or protein is greater in the presence of the candidate compound than in its absence, the candidate compound is identified as a stimulator of Cayman ataxia mRNA or protein expression. Alternatively, when expression of Cayman ataxia mRNA or protein is less (i.e., statistically significantly less) in the presence of the candidate compound than in its absence, the candidate compound is identified as an inhibitor of Cayman ataxia mRNA or protein expression. The level of Cayman ataxia mRNA or protein expression can be determined by methods described herein for detecting Cayman ataxia mRNA or protein.

A modulating agent can be identified using a cell-based or a cell free assay, and the ability of the agent to modulate the activity of a Cayman ataxia protein can be confirmed in vivo, e.g., in an animal such as an animal model for a disease (e.g., an animal with ataxia).

C. Therapeutic Agents

This invention further pertains to novel agents identified by the above-described screening assays. Accordingly, it is within the scope of this invention to further use an agent identified as described herein (e.g., a Cayman ataxia modulating agent or mimetic, a Cayman ataxia specific antibody, or a Cayman ataxia-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments of ataxia (e.g., including, but not limited to, Caymans ataxia).

IX. Pharmaceutical Compositions Containing Cayman Ataxia Nucleic Acid, Peptides, and Analogs The present invention further provides pharmaceutical compositions which may comprise all or portions of Cayman ataxia polynucleotide sequences, Cayman ataxia polypeptides, inhibitors or antagonists of Cayman ataxia bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by mutant Cayman ataxia alleles (e.g., Cayman ataxia). Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, Cayman ataxia nucleotide and Cayman ataxia amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, Cayman ataxia polynucleotide sequences or Cayman ataxia amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of Cayman ataxia may be that amount that suppresses apoptosis. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of Cayman ataxia, conditions indicated on the label may include treatment of condition related to apoptosis.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts Cayman ataxia levels.

A therapeutically effective dose refers to that amount of Cayman ataxia that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for Cayman ataxia than for the inhibitors of Cayman ataxia. Administration to the bone marrow may necessitate delivery in a manner different from intravenous injections.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); U (units), mU (milliunits); min. (minutes); sec. (seconds); % (percent); kb (kilobase); bp (base pair); PCR (polymerase chain reaction); BSA (bovine serum albumin); Fisher (Fisher Scientific, Pittsburgh, Pa.); Sigma (Sigma Chemical Co., St. Louis, Mo.); Promega (Promega Corp., Madison, Wis.); Perkin-Elmer (Perkin-Elmer/Applied Biosystems, Foster City, Calif.); Boehringer Mannheim (Boehringer Mannheim, Corp., Indianapolis, Ind.); Clonetech (Clonetech, Palo Alto, Calif.); Qiagen (Qiagen, Santa Clarita, Calif.); Stratagene (Stratagene Inc., La Jolla, Calif.); National Biosciences (National Biosciences Inc, Plymouth Minn.) and NEB (New England Biolabs, Beverly, Mass.), wt (wild-type); Ab (antibody).

EXAMPLE 1

Genetic Mapping of Jittery/Hesitant

Both jittery and hesitant were genetically mapped in F2's, ji in a large (>3000 animals, >6000 meioses) intersubspecific cross with *Mus musculus* castaneus (strain CASA/Rk), hes in a small cross of (C3H-HeJ-hes×C57BL/6J) F2. After analyzing more than 6000 meioses (>3000 animals), the genetically defined ji interval was narrowed down to about 800 kb, much larger than was expected based on the number of mice. Tbxa2r and D10Bwg1364 were identified as the closest flanking (excluded) markers.

The physical mapping of this region of mouse Chromosome 10 was completed using pulsed field gel electrophoresis, showing conserved gene order and distances between mouse Chromosome 10 and human 19p13.3, but interrupted at the end by an 1000 kb inversion (FIG. 5).

A recessive form of ataxia prevalent on the Cayman islands has been mapped to human Chromosome 19p13.3 (Nystuen et al., Hum. Mol. Genet. 5:525 [1996]). Only a few clinical details have been described in abstracts (Brown et al., Neurology 34:273 [1984]; Johnson et al., Neurology 28:352 [1978]).

Comparison of the 19p13 map and the mouse Chromosome 10 map makes it clear that the nonrecombinant regions of jittery and Cayman ataxia overlap. While each region individually has been mapped to about 800-1000 kb, comparison of the human and mouse genome sequence shows that the region of overlap is about 250 kb. Given the variability of the different alleles of jittery and hesitant, there is clear similarity in phenotype.

Within the region of overlap, there were about 13 known or predicted genes—the precise number is unknown since different prediction programs sometimes disagree whether there are 2 genes or a single one and only after testing can these options be discriminated.

These genes were focused on as candidate genes, rather than the >100 in the genetic interval of jittery. Each gene was first screened by ordering an IMAGE cDNA clone, often two, one for the 3' region and one for the 5' region, isolated the inserts, and hybridized them to Southern blots prepared from DNA of different mutant alleles cleaved with a variety of enzymes. Table 1 lists the results of those genes tested. In a few cases (e.g. Mek2), Northern blots were prepared, each exon was sequenced, and the protein levels and sizes between mutants and controls were compared.

TABLE 1

Candidate gene testing performed in the nonrecombinant jittery/Cayman Ataxia region. Negative: no difference between mutant and wild type detected. Empty cells: not done.

| Gene | Southern | Northern | Sequence |
| --- | --- | --- | --- |
| D10Burle = chr10_7.293 | Negative | | |
| Map2k2 = mek2 = erk1 | Negative | Negative | Negative |
| Lrf | | | |
| Piasg | Negative | | |
| Eef2 | Negative | | |
| Dapk3 = zip kinase | Negative | Negative | Negative |
| chr10_7.297 —integrin related (is a different gene than below) | | | |
| chr10_7.297 KIAA1872 | Positive | ongoing | Changes |
| chr10_7.298 (zinc finger cont.) | Positive | Negative | negative |
| Matk | Negative | Negative | Negative |
| Mrp154 = D10Sutle = Sc32 | Negative | | |
| Apba3 | | | |
| Tjp3 | Negative | | |
| Pip5klc | Negative | | |

EXAMPLE 2

Identification of the Jittery Gene

After excluding many different candidate genes, a Southern blot change was detected in homozygous hesitant mice with a probe from the 5' end of a Zinc finger-containing gene. Comparing the restriction map of the region with the hybridization data from several enzymes lead to the conclusion that the actual difference is in a gene 5' to the Zinc-finger-containing gene. This jittery gene in the human databases is called KIAA1872, in mouse it is only part of a predicted gene called chr10_7.297. ESTs in IMAGE clones were available from mouse. Another probe was examined, this time for the mouse homologue of KIAA1872, and found with that probe, in addition to hesitant, there is also a Southern blot change in jittery. The products were then sequenced. It was determined that the hesitant allele is an insertion of an IAP element in intron 1 of the gene, whereas jittery is a small B1 element insertion in exon 4. Jittery is an old mutation and no appropriate control strain is available but the insertion predicts that after 65 (of a total of 372) amino acids, the protein will stop, and thus jittery is likely a null allele. In contrast, an insertion in an intron is likely often spliced across, so hesitant, which has a phenotype that is much milder, and is a viable allele, is likely to be a hypomorph with reduced expression due to the presence of a large intronic insertion. Because hesitant arose on a known strain, C3H/HeJ-Tyr<c-a> (Jackson Laboratory), the fragments were compared by PCR, and it was determined that C3H/HeJ (the strain on which hes is now maintained) and C3H/HeJ-Tyr<c-a> both do not have the insertion. Given the fact that two different changes were detected in two different alleles, one which arose on a known genetic background that does not carry the mutation, the identity of jittery/hesitant with the gene encoded by the mouse homologue of cDNA KIAA1872 was been established.

Figure 7:
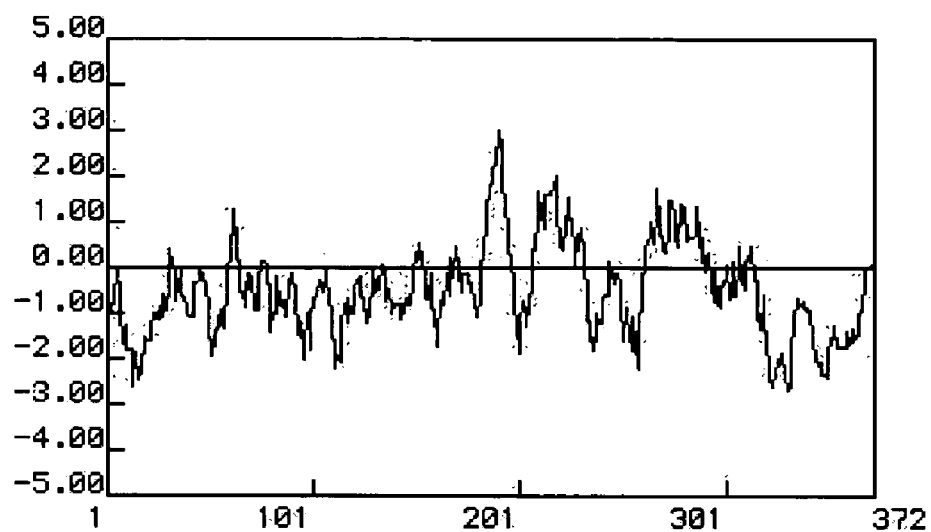
FIG. 7 shows a hydrophobicity plot of mouse jittery.

The jittery protein is predicted not to be secreted (no leader peptide), and is not likely to have a transmembrane region, since there is no extended region of hydrophobicity long enough to span the membrane (FIG. 7).

EXAMPLE 3

Identification of Cayman Ataxia Mutations

Genomic DNA of patients with Cayman ataxia was obtained. All coding exons and exon-intron junctions were sequenced and compared to control DNA sequences as well as to the databank sequence of KIAA1872. A point mutation that results in anon-conservative amino acid change in one exon (SEQ ID NO:8 (nucleic acid) and SEQ ID NO:9 (amino acid) and another point mutation at a splice junction (SEQ ID NO:10) were identified.

Given the genetic mapping data and the phenotypic similarities, it was concluded that the jittery gene is the Cayman ataxia gene. Because the different alleles of jittery have different phenotypes, other ataxia or dystonias in humans may also have mutations in the same gene.

EXAMPLE 4

Characterization of the "KIAA1872" Protein

The KIAA1872 (identified above as the Cayman ataxia protein) protein is a protein of unknown function. According to the predicted proteins found at various genome sites, it isn't even clear what the N-terminal amino acid, i.e. start of translation, of the protein is. The sequence of macaque, mouse and human of the predicted protein, and they are highly conserved. In contrast, the sequences of mouse and human protein just before the presumed translation start are not homologous (See below), indicating the MGTT is indeed the start of the protein.

PSSDAESAPASILFL LGSEGPGSVSDAQLHPGPARL-CLPVRRRGCLSCRGVIPASSQCLFPAPMGTTEAT (SEQ ID NO:24)

ASFHQAPRLGTIEKCPPLCPSDSAEAA-SATEIIFWVTRVSRPLLFPALMGTTEAT (SEQ ID NO:25)

The 5' sequence near this methionine has partial homology to the Kozak consensus sequence: CCAGCTCTCATGG (SEQ ID NO:22) matches 8/13 to GCCGCCACCAUGG (SEQ ID NO:23)—one of very few matches in the region of interest, and the first Methionine after an in-frame stop.

As shown in FIG. 6, the predicted protein is about 54% identical and highly homologous to the NIP2 (also called NIP21) protein of human and mouse. This protein has been initially identified as binding to Adenovirus E19 and to BCL-2, a known apoptosis inhibitor. Subsequently, NIP2 has been found to be downregulated by estrogen, and in-vitro transfection of NIP2 constructs result in cells undergoing apoptotic cell death, whereas co-transfection of NIP2 with BCL-2 constructs reduce the amount of NIP2-induced apoptotic cell death. In addition, several reports show that NIP2 mRNA is downregulated in response to estrogens (e.g., Brusadelli et al., Int J Dev Neurosci. 18:317 [2000]), which is known to act anti-apoptoticly. These authors postulate that NIP2 is an important mediator of the anti-apoptotic property of estrogens in neuronal cells (Maggi, 2000). Last, it was shown that the apoptotic activity of NIP2 acts via a caspase-dependent mitochondrial activation (Zhang et al., Circ. Res. 90:1251 [2002]) While only about a dozen papers have been published on NIP2, they all support the idea that NIP2 is an anti-apoptotic protein, binds BCL-2 and is negatively regulated by estrogen. The present invention is not limited to a particular mechanism. Indeed, an understanding of the mechanism is not necessary to practice the present invention. Nonetheless, it is contemplated that, given that KIAA1872/jittery protein is highly homologous, that these reports provide information on the function of the human Cayman ataxia/KIAA1872 protein. While many ataxias are presumably neurodegenerative, reduction in apoptosis has been proposed as a mechanism in one other recessive ataxia in humans, namely in Ataxia Telangiectasia (Lee and McKinnon, Apoptosis 5:523 [2000]).

The present invention is not limited to a particular mechanism. Indeed, an understanding of the mechanism is not necessary to practice the present invention. Nonetheless, it is contemplated that the identification of mutation in the Cayman ataxia gene and polypeptide disclosed herein find use in the diagnosis of ataxia or related disorders such as dystonia (characterized by involuntary muscle contractions that force a certain part(s) of the body into abnormal, sometimes painful, movements and positions), myoclonus (characterized by sudden, involuntary contractions of skeletal muscles) and nystagmus (characterized by involuntary, rapid movement of the eyeball).

EXAMPLE 5

Mutations in a Novel Gene Encoding a CRAL-TRIO Domain Cause Human Cayman Ataxia and Ataxia/Dystonia in the Jittery Mouse A. Materials and Methods Human DNA samples: Subjects (affected patients and family members) were recruited and gave consent several years ago, with approval by University of Miami IRB. DNA was extracted from blood and has previously been used to identify linkage and a region of homozygosity as described before (AN, VCS), approved by Iowa IRB (Nystuen et al., Hum. Mol. Genet. 5:525 [1996]). DNA was analyzed for mutations blind for affectation and family status, with approval by Michigan IRB. Complete concordance between genotypes and phenotypes was found.

Genomic control samples were genotyped from 20 Caucasian US men (anonymized controls), a panel of 90 US ethnically diverse samples (Coriell, Camden, N.J.), 84 British, 88 Jamaican, 185 Akan from Ghana and 96 Bamileke from Cameroon—the latter because the Cayman Islanders are of mixed, primarily British and Jamaican, ancestry (Drewett et al., in Prehistoric Settlements in the Caribbean 5-16 (Archetype Publications, London, UK, 2000), with Jamaicans originating primarily on the west coast of Africa. British genomic DNA samples were sent anonymized by Mike Owen's laboratory (Univ. of Wales). Genomic DNA from anonymous West Africans from Accra, Ghana (N=300) and Caribbeans from Kingston, Jamaica (N=200) were collected for population-based genetic studies on DNA variation in the African Diaspora and were used as control samples with IRB approval of Howard University.

Fine Mapping of Cayman Ataxia:

Previously a 2500 kb haplotype on 19p13.3 between GATA66B01 (now D19S1034) and D19S209, with D19S216 nonrecombinant, was reported in all Cayman Ataxia patients (Nystuen et al., supra). Novel polymorphic markers were developed by text word searches on sequence data for short tandem repeat polymorphisms (STRPs). Amplification of STRP markers was performed with 40 ng of DNA in an 8.3 µl PCR reaction mixture containing, 1.25 µl PCR buffer (100 mM Tris/HCl pH 8.8, 500 mM KCl, 15 mM MgCl$_2$, 0.01% w/v gelatin), 200 µM each dNTP, 2.5 pmol of each primer, and 0.25 U Taq polymerase. Samples were subjected to 40 cycles of 94° C. for 30 s, 55° C. for 30 s, and 72° C. for 30 s. Amplification products were denatured for 5 min at 95° C. and loaded onto a 6% denaturing polyacrylamide gel (7.7 M urea). Electrophoresis was carried out at 60 W for 2 hours. The polyacrylamide gels were visualized by silver staining. Single nucleotide polymorphisms (SNPs) were identified by non-denaturing SSCP gel electrophoresis (6% 49:1 acrylamide:bis-acrylamide containing 5% glycerol) of PCR products from various STSs known to map to the interval, ESTs, and gene sequencing.

Mice:

Originally, all mice were obtained from The Jackson Laboratory (Bar Harbor, Me.), and subsequently bred. The F2 cross was described previously (Kapfhamer et al., Genomics 35:533 [1996]). In addition to ji (jittery) and ji$^{hes}$ (hesitant), one additional allele was identified in 1999 by the Jackson Laboratory. This allele, sidewinder, ji$^{swd}$, is phenotypically very similar to jittery. Allelism was established by complementation tests.

Fine Genetic Mapping of Jittery:

A previously described cross was continued for a total of about 3000 offspring, or 6000 meioses. Resulting F2 animals were genotyped for the flanking microsatellite markers D10Mit140 and D10Mit207 as described (Kapfhamer et al., supra). When needed, progeny testing was performed with heterozygous recombinants (i.e. if the recombinant was between a CAST/Ei homozygous and a heterozygous genotype). Only recombinants between flanking markers were further analyzed. Recombinants were followed up by analysis with D10Mit21, D10Mit23, D10Mit226 and D10Mit7 and D10Mit22 using primers described previously (Dietrich et al., Genetics 131:423 [1992]), as well as Gna15 (see FIG. 12 for map positions). Gna15 was genotyped by amplification with primers CT222 and CT223 (GAGAACGTGATTGCCCTCATC (SEQ ID NO:12) and GGAGGTGTGAATCTTATCTTC (SEQ ID NO:13)) based on the sequence of the mouse cDNA. These primers span an intron that differs in length, resulting in amplified fragments 1.1 kb in size in CAST/Ei and 1.4 kb in most laboratory mouse strains. This cross identified D10Mit21/23 and Gna15 as the closest flanking genetic markers. D10Mit21 and D10Mit23 were never genetically separated, and D10Mit7 was nonrecombinant with ji. To further narrow the nonrecombinant region, Southern blots were tested for RFLPs in genes from the region, and RFLPs were used to type critical recombinants as described (Kapfhamer et al., supra). The following enzymes that showed RFLPs for previously described cDNA probes (Puttagunta etl al., Genome Res. 10:1369 [2000]) were used to map the genes relative to ji: Ap3d: HindIII; D10Bwg1364: HindIII; Tbxa2r: BglII; Matk: AccI; D10Sut1e: BglII and AccI. The results showed that D10Bwg1364 and Tbxa2r flank ji as the closest excluded genes. The interval identified is about 800 kb, much larger than expected from 6000 informative meioses: With the typical ratio of 1600-2000 kb/cM, it was expected that 6000 meioses would get a resolution of 25-33 kb, but this genetic interval recombines less often than expected. This nonrecombinant region contains over 100 genes. However, limiting the search to the region of overlap with Cayman Ataxia left only about 9 known or predicted genes, which were tested by Southern blots for mutations in jittery alleles.

Southern Blot:

Genomic DNA of all three jittery alleles was cleaved with 6 different restriction enzymes, AccI, MspI, Taq I, HindIII, PstI and PvuII, separated by 0.8% agarose gel electrophoresis, alkaline blotted to nylon membranes (Hybond N+, Amersham, Piscataway, N.J.) and hybridized to cDNA probes for the 5' and 3' ends of each of the 14 known or predicted genes as previously described (Reese et al., J. Comput. Biol. 4:311 [1997]. The cDNA probes were generated from IMAGE clones ordered from Research Genetics. Inserts were amplified by PCR with flanking primers, typically corresponding to the SP6, T7 or T3 sequences of the IMAGE clones.

Northern Blot:

10-30 µg poly (A)+ RNA was fractionated on a 1% agarose gel containing 1× Gel Prep/Gel Running Buffer and transferred to Hybond™-N+ (Amersham, Piscataway, N.J.) using the NorthernMax-Gly system (Ambion, Austin, Tex., USA) according to manufacturer's protocol, and using a commercial RNA size standard (0.363-9.488 Kb, USB, Cleveland, Ohio). Prehybridization and hybridization were carried out for 30 min and 1 hr respectively using Express Hyb (Clontech, Palo Alto, Calif.) hybridization solution at 68° C. Blots were washed four times with 2×SSC containing 0.05% SDS at room temperature for 10 min each, followed by two washes with 0.1×SSC containing 0.1% SDS at 50° for 20 min each cDNA probes were prepared from RT-PCR products or IMAGE clones by $P^{32}$ radioactively labeling using Random Primed DNA Labeling Kit (Roche Applied Science, Indianapolis, Ind.). Blots were exposed to BioMax MS film (Eastman Kodak Company, Rochester, N.Y., USA).

Genomic PCR:

Genomic PCR was performed on 50-100 ng template DNA (tail or spleen preparation from mouse, whole blood or lymphocyte DNA from human) using a PTC 100 thermal cycler (MJ Research, Watertown, Mass., USA). Primers were designed using the Web-based Primer 3 program (Burge et al., J. Mol. Biol. 268:78 [1997]), using the sequence surrounding KIAA1872 (NM_033064) from various publicly available Human Genome Internet servers. Products smaller than 1 Kb were amplified in a 20 µl reaction mix containing 4 mM dNTPs, 3 µM primers, 2 µl of 10× Optiprime Buffer (Stratagene, La Jolla, Calif., (see Table 2 (FIG. 15) for sequences of all primer sequences), and 2 U of Taq polymerase. Conditions used for PCR were 95° C. for 1 min, 40 cycles of 95° C. for 30 sec, 56°-61° C. for 1 min, 72° C. for 1 min, with final extension at 72° C. for Products larger than 1 kb were amplified in a 10 µl reaction mix containing 10 mM dNTPs, 3 µM primers, 1 µl Expand Long Template 10× Buffer (Hoffman LaRoche, Basel, Switzerland), and 0.75 U Expand Long Template Enzyme mix. PCR conditions were 94° C. for 2 min, 9 cycles of 94° C. for 10 sec, 56°-60° for 30 sec, 68° C cycles of 94° C. for 15 sec, 56°-60° C. for 30 sec, 68° C. for a start of 2 minutes incremented by 20 sec per cycle, and 7 min at 68° C. PCR products were separated by agarose gel electrophoresis and purified using QIAquick PCR Purification or QIAquick Gel Extraction Kits (Qiagen, Valencia, Calif., USA). Sequencing was performed by the University of Michigan's sequencing core, and was analyzed using Lasergene's Seqman analysis program.

Human Mutation Screen:

The C to G change at the $37^{th}$ base of ATCAY (KIAA1872) exon nine and a G to T change three bases after exon 9 are predicted to remove an Alu I and a TspRI site, respectively. Amplification with primers "exon 9 left" and "exon 9 right" (see Table 2) results in a PCR product 272 bp. In control, but not mutant samples this product is cleaved by Alu I into fragments of 174 and 98 bp. PCR amplification with primers "exon 9 left" and "exon 9 right (a)" Upon TspRI digestion, mutant samples result in fragments of 634, 559, 75, and 21 base pairs, whereas control samples result in fragments of 415, 340, 219, 75, and 21 base pairs. This complex pattern is due to partial cleavage at one of the TspRI restriction sites not related to Cayman Ataxia.

RT-PCR:

Total RNA was isolated from brain using TRIzol Reagent (Invitrogen Life Technologies, Carlsbad, Calif., USA) according to manufacturer's instructions. Poly (A)+ RNA was extracted from total RNA using PolyATtract (Promega, Madison, Wis., USA). cDNA was transcribed from 50-500 ng poly (A)+ RNA using Superscript II RNase H-Reverse Transcriptase according to manufacturer's protocol (Invitrogen life technologies, Carlsbad, Calif., USA). $ji^{hes}/ji^{hes}$ cDNA was transcribed using Superscript III RNAse H-Reverse Transcriptase with a gene specific primer (exon 3-8 right) and was incubated at 55° C. (Invitrogen life technologies, Carlsbad, Calif., USA). 50-100 ng of cDNA were used as a template under the PCR conditions listed above. RT-PCR products were separated on a 1% agarose gel, visualized with by Ethidium Bromide staining, purified using QIAquick PCR Purification or QIAquick Gel Extraction Kits (Qiagen, Valencia, Calif.), and sequenced at the University of Michigan Sequencing Core Facility. The partial mouse cDNA sequence of Atcay has genbank accession # AY349150, the jittery and hesitant mutations are #AY349151 (B1 insertion), AY349152 and AY349153 (two ends of the IAP element insertion).

Splice Prediction:

To evaluate whether the mutation in intron 9 of Cayman ataxia patients is likely to interfere with splicing, the sequence was analyzed. First, inspection of the splice site shows that the junction sequence is a typical: While (C/A) AG|gt(a/g)agt is the typical consensus of a splice donor, the exon 9/intron 9 boundary of ATCAY has the sequence: TGCA|gtgagt, whereas the mutant junction is TGCAgttagt. Nevertheless, this is the correct splice site based on numerous EST and RT-PCR sequences. To determine the consequence of the mutation, a splice donor prediction program based on neural networks was used (Herman et al., Endocrinology 127:2408 [1990], available for human genome on the world wide web site of fruitfly.org. This programidentified many potential donor sites in and around exon 9 and intron 9, including the correct splice donor site mentioned above. The score at the exon 9/intron 9 junction was 0.78, corresponding to about 78% chance this is a real splice donor. However, when the change found in Cayman Ataxia patients is tested, the program no longer predicts splicing at this site—in fact, the calculated score is 0.03. GenScan (Lin et al., Hum. Mol. Genet. 10:137 [2001]) is an exon prediction program that relies on consensus sequence, not coding frame, correctly predicts the 102 bp exon. However, when the Cayman mutant sequence is tested, a 133 bp exon is predicted which reads significantly into intron 9, with a predicted stop after 10 novel amino acids. Thus, two methods predict that the splice mutation severely interferes with splicing.

In-Situ Hybridization:

Fresh frozen brain tissues were sectioned at 15 microns on a Leica CM1900. Embryo sections, prepared from timed pregnancies and sectioned similarly, were purchased from the University of Michigan Morphology Core. Slides were fixed in 4% paraformaldehyde. Sections were washed for 1 hr in 2×SSC, acetylated for 10 min at room temperature with 0.25% acetic anhydride in 0.1 M triethanolamine (pH 8.0), and dehydrated through graded ethanol. Sections were then incubated overnight at 55° C. with ~1×10$^6$ dpm of probe in 30 µl of hybridization buffer (50% formamide, 3×SSC, 1× Denhardt's solution, 200 µg/ml tRNA, 50 mM sodium phosphate buffer pH 7.4, 10% dextran sulfate (70 kD average MW), and 10 mM DTT). The next day, slides were washed three times in 2×SSC, treated with RNase (200 µg/ml in 10 mM Tris/HCl, pH 8.0, 500 mM NaCl) for 1 hr at 37° C., washed in 0.1× SSC at 70° C. for 1 hr, and dehydrated through graded ethanol before exposure to BioMax MS film (Eastman Kodak Company, Rochester, N.Y., USA).

Emulsion Autoradiography and counterstaining was conducted to better interpret the exact location. Slides were dipped in Kodak NTB-2nuclear emulsion and exposed for one week. Slides were developed in D-19 (Eastman Kodak) for 3 minutes, and slightly counterstained with cresyl violet, dehydrated and coverslipped in Permount.

The probe for in-situ was prepared from clone UI-M-BHO-ajo-f-05-0-UI.sl, which contains exons 5-13 purchased from Research Genetics and sequence verified. Plasmid DNA was digested with Hind III for sense and Bgl I for antisense probe. After phenol extraction and ethanol precipitation, T3 (antisense) or T7 (sense) RNA polymerase reactions were performed on 1 µg linearized plasmid DNA template for 90 min. at 37° C. in transcription buffer, with 0.01 M DTT, S$^{35}$UTP, 0.5 mM each of ATP, GTP, CTP, and Rnasin. The reaction was stopped by the addition of RNAse free DNAse, and products purified by spin columns (Micro Bio-Spin 30, Biorad, Hercules, Calif.). After addition of DTT to 0.1 M, cpm were determined.

Histopathology:

Two jittery, two sidewinder, and five control littermate mice, aged 3 weeks +/−3 days were processed for histology. Mice were euthanized by decapitation, the brains extracted from the cranial vault and immersion fixed in 4% paraformaldehyde—0.1M phosphate buffer (pH 7.4). Brains were fixed for 24 to 48 hours and embedded in paraffin. Six-micron thick sections were cut on a rotary microtome in the horizontal plane, mounted on glass slides, and deparafinized and rehydrated. Sections were stained with 0.5% cresyl violet for routine histology. TUNEL labeling was assessed with an ApopTag Plus kit (Intergen Co., Purchase, N.Y.) according to the manufacturer's directions. Reactive gliosis was assessed with glial fibrillary acidic protein (GFAP) immunohistochemistry with a commercially available polyclonal antibody (1:250, Dako, Carpinteria, Calif.) and the ABC method using a commercially available kit (Vector, Carpinteria, Calif.).

B. Results

The Cayman ataxia locus, ATCAY, was previously mapped to a >2.0 Mb region on 19p13.3 (Nystuen et al., supra). Comparative mapping suggested that the mouse mutation jittery, which maps to the homologous region on mouse Chromosome 10 (Kapfhamer et al., supra), is the murine homologue of ATCAY. While hesitant animals show mild ataxia and dystonia but normal fertility and life expectancy, jittery mice have severe truncal and limb ataxia and die of dehydration and starvation by 3-4 weeks of age, but both are allelic (Kapfhamer et al., supra). Continuation of a previously described cross narrowed the critical interval to 800 kb (FIG. 12). Similarly, the Cayman Ataxia locus was narrowed further through additional obligate recombinants (FIG. 14). The critical intervals of Cayman Ataxia and jittery overlapped in a region spanning 150 kb in mouse and contained nine known or predicted genes (FIG. 5).

Because many spontaneous mouse mutations are caused by deletions or insertions (Kazazian et al., Nat. Genet. 19:19 [1998]), all genes from the critical region were screened by Southern blot hybridization. One probe for an unknown predicted gene showed DNA changes to controls with both jittery and hesitant alleles. In-silico restriction mapping predicted the locations of the mutations as intron 1 (hesitant) and exon 4 (jittery), respectively. Genomic PCRs showed larger products in each case. Sequence analysis of the aberrant PCR products showed an IAP element insertion in intron 1 causes hesitant, and a B1 element insertion in exon 4 in jittery. The mutation in a third allele, sidewinder, ji$^{swd}$, which is similar in phenotype to jittery and was identified at the Jackson Laboratory, was identified by exon sequencing as a two bp deletion in exon 5. The insertion in exon 4 of jittery is the first mouse mutation caused by Alu-related mutagenesis, although this mechanism is common in humans (Kazazian et al., supra).

The IAP insertion in hesitant results in aberrant, much larger transcripts and small amounts of normal transcript, explaining why hesitant is only mildly affected. Jittery shows reduced amounts of mRNA, with the predominant species about 190 bp larger due to B1 element insertion. The B1 element insertion predicts a truncated, not likely functional protein of only 62 (+21 missense) instead of the normal 372 amino acids. An additional rare smaller ji transcript is visible on Northern blots and by RT-PCR. Sequencing shows that the 222 bp exon 4 is skipped entirely in this minor product, which thus restores the open reading frame, with the predicted protein missing 74 amino acids. This process is likely due to nonsense-mediated altered splicing, as has been found in other mutations (Lui et al., Nat. Genet. 27:55 [2001]). The sidewinder ji$^{swd}$ allele is predicted to result in a shortened protein of 181 (+19 missense) amino acids.

In DNA from Cayman Ataxia patients, sequencing of exons and exon-intron boundaries identified two homozygous sequence variants: a G to C change in exon 9, predicting a serine to arginine substitution at amino acid 301, and a T to G substitution in the third base of intron 9. Both mutations completely segregated with the disorder/carrier status in over 40 family members that were genotyped blindly. None of over 1000 chromosomes from Caucasian, British, Jamaican, or African control samples showed either of the two mutations. These mutations are thus in complete linkage disequilibrium with each other. The serine that is changed to arginine is conserved between human, mouse and rat, but not across the different paralogues of the protein, and not predicted to interfere with the structure of the protein. In contrast, analysis of the splice mutation predicts aberrant splicing resulting in a truncated protein that would miss most of the most conserved domain of the protein, and is likely the disease-causing mutation. The present invention is not limited to a particular mechanism. Indeed, and understanding of the mechanism is not necessary to practice the present invention. Nonetheless, it is contemplated that, like in hesitant, some normal splicing may remain, and both mutations may contribute to the phenotype. These results strongly argue that the Cayman Ataxia gene ATCAY/Atcay, and the corresponding protein CAYTAXIN, have been identified.

Caytaxin is expressed exclusively in neuronal tissues. Northern blot analysis showed strong expression restricted to brain with tree main transcripts owing to different polyadenylation sites. In situ hybridization to adult mouse brain showed strong expression in virtually all parts of the brain, including cortex, cerebellum and olfactory bulbs. In the whole embryo, expression was also completely restricted to neuronal tissues, including brain, dorsal root ganglia and enteric nervous system. External brain morphology and brain weights of mutants were normal, and routine histology showed normal regional and cellular architecture. The present invention is not limited to a particular mechanism. Indeed, an understanding of the mechanism is not necessary to understand the present invention. Nonetheless, it is contemplated that, based on the above findings, that caytaxin does not effect normal brain development.

CAYTAXIN has sequence similarity to a protein called BNIP2 (See below and FIG. 13), which has been implicated in apoptosis (Boyd et al., Cell 79:341 [1994]). There was no evidence of reactive astrocytosis with GFAP immunohistochemistry or increased TUNEL staining. The present invention is not limited to a particular mechanism. Indeed, an understanding of the mechanism is not necessary to understand the present invention. Nonetheless, it is contemplated that increased apoptosis is unlikely to be responsible for the phenotype.

Sequence analysis of caytaxin showed similarities to two other proteins, BNIP2 and KIAA0367, as well as homology in the C-terminal end to a Sec14 domain with a CRAL-TRIO domain (FIG. 13). This domain, named after cellular retinal and the TRIO guanine exchange factor, binds small lipophilic molecules, such as retinal, vitamin E and squalene, a cholesterol precursor (Stocker et al., Structure (Camb) 10:1533 [2002], as well as inositol and related molecules (Sha et al., Nature 391:506 [1998]). Mutation of another protein containing a CRAL-TRIO domain, TTPA, which transports vitamin E, causes the rate Friedreich-like ataxia with selective vitamin E deficiency, which responds to large doses of vitamin E (Ouhchi et al., Nat Genet. 9:141 [1995]). Comparison of a three-dimensional model of caytaxin with that of TTPA suggests that the ligand-binding pocket of caytaxin is more polar than that of TTPA. In addition, feeding vitamin E (17 times the normal amount in food) to hesitant mice for one month did not improve the phenotype. The present invention is not limited to a particular mechanism. Indeed, an understanding of the mechanism is not necessary to practice the present invention. Nonetheless, it is contemplated that a ligand different from vitamin E binds to caytaxin.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

What is claimed is:

1. A method for detection of a variant Cayman ataxia nucleic acid sequence in a human subject, comprising:

a) providing a biological sample from a human subject, wherein said biological sample comprises a Cayman ataxia nucleic acid; and b) detecting the presence or absence of a variant Cayman ataxia nucleic acid in said biological sample, wherein said variant Cayman ataxia nucleic acid has a nucleic acid sequence selected from the group consisting of SEQ ID NOs: 8 and 10.

2. The method of claim 1, wherein the presence of said variant Cayman ataxia nucleic acid indicative of Caymans ataxia in said subject.

3. The method of claim 1, wherein the presence of said variant Cayman ataxia nucleic acid is indicative of said subject being a Cayman ataxia carrier.

4. The method of claim 1, wherein said biological sample is selected from the group consisting of a blood sample, a tissue sample, a urine sample, a saliva sample, and an amniotic fluid sample.

5. The method of claim 1, wherein said human is an adult female of child-bearing age.

6. The method of claim 1, wherein said detection comprises a nucleic acid detection method selected from the group consisting of nucleic acid sequencing, polymerase chain reaction, hybridization, denaturing high pressure liquid chromatography, mass spectrometry, and enzymatic detection.

* * * * *

SEQUENCE LISTING

<160> NUMBER OF SEQ ID NOS: 62

<210> SEQ ID NO 1
<211> LENGTH: 2166
<212> TYPE: DNA
<213> ORGANISM: Mus musculus

<400> SEQUENCE: 1

```
acacaaaagc agcttcctcc actatctgag ggaaagacag agcctcagcc atcagaaagg      60
gaaaagccag agccgcggca ggcctgggct gcgatggcag gggaaacagt gactaaaggg     120
ggacaggggt gctgctacta acccacggcg ccgccttcta cagttgggcc ggacaggtgt     180
gctgtggcca cgtcgccctg ggtgaccttc ctcagatgtg gacttggccc tgagcatcct     240
tccaccaggc ccctcgcctg ggtaccatcg agaaatgccc gcctttgtgt ccaagtgaca     300
gcgcagaggc agcttccgct accgagatca tcttctgggt cacccgagtt tccagaccac     360
ttctctttcc agctctcatg ggaaccacag aagctacact aaggatggaa aatgtggacg     420
tgagggatga atggcaggat gaggatctgc ccagaccgct cccagaagac accggggtgg     480
agcggctggg tggcgcagtg gaagactcct cctcacctcc ctccaccctg aacttgagcg     540
gagcacatcg aaagagaaag acgctggtgg ctccagagat caacatctcc ctggaccaaa     600
gcgagggctc tctgctgtcc gacgacttcc tcgacacacc tgatgacctg gacatcaatg     660
tggacgacat tgagacgcca gatgaaactg actctctgga gttcttggga aatggcaatg     720
aacttgagtg ggaagatgac accccagtgg ccaccgccaa aaacatgcct ggtgacagtg     780
cggacctgtt tggggacggc tctgcggaag acggcagtgc ggccaacggt cgtctgtggc     840
```

```
gaactgtcat cataggggag caagagcatc gcatcgacct gcatatgatc cggccctaca    900
tgaaggtggt cacccatgga ggatactacg gggaaggtct caacgccatc atcgtgtttg    960
cagcctgctt cctgccagat agcagctccc cagactatca ctacatcatg gagaatctct   1020
tcctgtacgt catcagcagc cttaaactgc tcgtggctga ggactacatg atcgtgtatc   1080
tgaacgcgc cacgccccgg aggaggatgc ctggcattgg ttggctgaag aagtgttacc   1140
acatgattga caggagactg aggaagaatc taaagtccct gatcatcgtc caccccctcct  1200
ggttcattcg cactgtgttg gccatctccc ggccattcat cagtgtcaag ttcatcagta   1260
aaattcagta cgtgcacagc ctggaagagc tggagcgact gattcccatg gaacacgtgc   1320
agctgccaga ctgtgtcctg caatatgaag agcagagact ccgagccaag agggagagca   1380
cacggccacc gcagccggag ttcctccttc ccaggtcaga agaaaagcca gagactgtgg   1440
aagaagagga cagggcagca gaggcaacag aggaccagga aactagcatg tcctgatcta   1500
cccagaacct agacatggac agagattatt cccaacatca tgtaaccctc atccgaagcc   1560
ctgggagccc cgccttcatc gagcctccac cgcctgagga tgcctggctc caccatgtcc   1620
cctgcacccg ggtcctctca ctgcttgagt ccatttcact gttttatttt gaagaaggcg   1680
gtatgagcac atctcggaat ggagcaggtt cttgacccctt tcacagtctg ggcttgtgga  1740
tgccaaaggt ggatgtgggc agtgccaccc acggttactc ttccaggcct tggcatcccc   1800
aagatgccct tctctgtccc agctaggata acacagatat gcattttggg ctgacccaat   1860
gagagaccct ttgctcggtt gccacctgtc cctagctgga gcctcagatg tctggtggcc   1920
ctggctgcag ctgcatctgc ttctctgtgg aatgtgaccc actgtcccct ctccctgcca   1980
cccccaggcag ggttgtgact gctgacctca catctccacc tgacatgcac tattctgcca  2040
tttgactgtc tttgggggcc ttcaagccca ttgcacatgt actgatcagc ctggtggtca   2100
acaaacccaa cattttgagc tcctttaaag tagatgtgac tccaaaaaaa aaaaaaaaa    2160
aaaaaa                                                              2166
```

<210> SEQ ID NO 2
<211> LENGTH: 372
<212> TYPE: PRT
<213> ORGANISM: Mus musculus

<400> SEQUENCE: 2

```
Met Gly Thr Thr Glu Ala Thr Leu Arg Met Glu Asn Val Asp Val Arg
1               5                   10                  15

Asp Glu Trp Gln Asp Glu Asp Leu Pro Arg Pro Leu Pro Glu Asp Thr
            20                  25                  30

Gly Val Glu Arg Leu Gly Gly Ala Val Glu Asp Ser Ser Ser Pro Pro
        35                  40                  45

Ser Thr Leu Asn Leu Ser Gly Ala His Arg Lys Arg Lys Thr Leu Val
    50                  55                  60

Ala Pro Glu Ile Asn Ile Ser Leu Asp Gln Ser Glu Gly Ser Leu Leu
65                  70                  75                  80

Ser Asp Asp Phe Leu Asp Thr Pro Asp Leu Asp Ile Asn Val Asp
                85                  90                  95

Asp Ile Glu Thr Pro Asp Glu Thr Asp Ser Leu Glu Phe Leu Gly Asn
            100                 105                 110

Gly Asn Glu Leu Glu Trp Glu Asp Asp Thr Pro Val Ala Thr Ala Lys
        115                 120                 125
```

```
Asn Met Pro Gly Asp Ser Ala Asp Leu Phe Gly Asp Gly Ser Ala Glu
            130                 135                 140

Asp Gly Ser Ala Ala Asn Gly Arg Leu Trp Arg Thr Val Ile Ile Gly
145                 150                 155                 160

Glu Gln Glu His Arg Ile Asp Leu His Met Ile Arg Pro Tyr Met Lys
                165                 170                 175

Val Val Thr His Gly Tyr Tyr Gly Glu Gly Leu Asn Ala Ile Ile
                180                 185                 190

Val Phe Ala Ala Cys Phe Leu Pro Asp Ser Ser Pro Asp Tyr His
                195                 200                 205

Tyr Ile Met Glu Asn Leu Phe Leu Tyr Val Ile Ser Ser Leu Glu Leu
    210                 215                 220

Leu Val Ala Glu Asp Tyr Met Ile Val Tyr Leu Asn Gly Ala Thr Pro
225                 230                 235                 240

Arg Arg Arg Met Pro Gly Ile Gly Trp Leu Lys Lys Cys Tyr His Met
                245                 250                 255

Ile Asp Arg Arg Leu Arg Lys Asn Leu Lys Ser Leu Ile Ile Val His
                260                 265                 270

Pro Ser Trp Phe Ile Arg Thr Val Leu Ala Ile Ser Arg Pro Phe Ile
            275                 280                 285

Ser Val Lys Phe Ile Ser Lys Ile Gln Tyr Val His Ser Leu Glu Glu
    290                 295                 300

Leu Glu Arg Leu Ile Pro Met Glu His Val Gln Leu Pro Asp Cys Val
305                 310                 315                 320

Leu Gln Tyr Glu Glu Gln Arg Leu Arg Ala Lys Arg Glu Ser Thr Arg
                325                 330                 335

Pro Pro Gln Pro Glu Phe Leu Leu Pro Arg Ser Glu Glu Lys Pro Glu
            340                 345                 350

Thr Val Glu Glu Glu Asp Arg Ala Ala Glu Ala Thr Glu Asp Gln Glu
    355                 360                 365

Thr Ser Met Ser
    370

<210> SEQ ID NO 3
<211> LENGTH: 2918
<212> TYPE: DNA
<213> ORGANISM: Homo sapiens

<400> SEQUENCE: 3
gccgagcctc tgccagccct gagctgggaa gaagcagcta cctcggaggc agggcgcgca      60
ggcgggcggc gatgagaggg ggcgcagccg cagccccgcg ctggggagcc accgctaac     120 cctgcacccc acccacccct gcacaaaaga gctggcgggc gctggccacg tcgccctggg     180
tgaccttcct cggatgcaga atccgcccct gcgagcatcc tcttcctcct aggctctgaa     240
ggcccgggga gcgtgagcga tgcccagctg caccgggcg gggctcgcct ttgtttgcca     300
gtaaggagga gaggctgtct cagctgcaga ggggtcatcc ctgcttcaag ccagtgcctc     360
ttcccagctc ccatggggac caccgaagcc acgctccgga tggaaaacgt ggacgtgaag     420
gaggaatggc aggacgaaga tcttcccagg ccactccag aagagacggg ggtggaactg     480
cttggcagcc cggtgaaga cacatcctct cctcccaaca cgctaaattt caacggagcg     540
catcgtaaga ggaagacgct ggtggcccca gagatcaaca tttctctgga tcagagtgag     600
gggtccctgc tgtccgatga cttcttggat acccctgatg acctggatat taacgtggat     660
gacatcgaga ccccgatga gaccgactcg ctggagttcc tggggaatgg caacgaactg     720
```

-continued

```
gagtgggaag acgacacccc cgtggccacc gccaagaaca tgcccgggga cagcgcggat    780
ctatttgggg acggcacgac ggaggacggc agcgccgcca acgggcgcct gtggcggaca    840
gtgatcatcg gggagcaaga gcaccgtata gacctgcaca tgatccggcc ttacatgaaa    900
gtggtcaccc acggagggta ctacggcgaa ggcctcaacg ccatcatcgt cttcgcagcc    960
tgcttccttc cagacagcag cctccccgac taccactaca tcatggagaa cctcttcctg   1020
tacgtcatca gcagcttaga gctcctggtg gctgaggact acatgatcgt gtacctgaac   1080
ggtgccacgc cccggcggag gatgcctgga atcggctggc tgaagaagtg ctaccagatg   1140
atcgaccgga ggttgcggaa aaacctgaag tccttgatca tcgtccaccc ctcgtggttc   1200
attcggactg tgctggccat ctctcgccct ttcatcagcg tcaagttcat caacaagatc   1260
cagtacgtgc acagcttgga agacctggag caactcatcc ctatggaaca cgtccagatc   1320
ccagactgcg tcctgcaata cgaagaggaa agactgaagg ccaggaggga gagcgcgagg   1380
ccccagccgg agtttgtgct gcccaggtct gaagagaagc cagaggtggc accagtggaa   1440
aacaggtctg ctctggtctc agaagatcag gaaacaagca tgtcctgagg cgacgtgagc   1500
ataacaaagg acatggaaga agattccaga tgccagaaaa cctctgtcag acgcccactg   1560
gccccagatc tcatcctgcc tcatcctgag tcccaatctt ccaagggtgc agcccctcc    1620
gttcatctct gaaacccagc atccttttca gctgcttgaa acattgtat tttttttttt    1680
taacgatgca gtatttgtgc gttccagaaa agggcccagc tctgagcccc tcacccttcc   1740
acactcacga actctcagcc gaggaaggca agaagcgcag ggggtggccc gcgtggcgtc   1800
ggtggcctcc gctcctgctc gcagcccctg tggtcagagc tggatacaag attcaagacc   1860
cttctcttgc ttgtcacccg ctccaggttg gagccacaga cacccaccgc caccccggct   1920
gggtctgcgt cctttcctgt gcctttccct ccagaatgcg gcctcagacc tagaagctca   1980
accccctat gagggccacg tcctggggta gctcctgacc tccgacctta tgtccaaatt    2040
tcacacccat ggttttcat ttgacccgcc cccttctcgc tcataatgac acccagctcc    2100
tttgagagga tcagagccca ttgcacaaga gagccgctg ccaaccatcc ttgtcctccg    2160
attgcaaaat gacaccccag taatctagaa cattctcaag ccccttaac tcagatgtca    2220
agccaccggg caaaccccgt caatacctcc caccaaggaa tgagatatgt ggacctcact   2280
gctcccccaa cccagcgtca ggctgggaca cgccaacgct gttccgggtt ggaacagcag   2340
aggctcagaa actggctctg aaataggcag acctagcaag aggaagatac agggtatcgg   2400
gcgtttgagt gtttcagaag tcattcggga agataaatcc agtgcgctgg ccgcagccac   2460
ctgcattcaa agcttggacc agcgggttct tgttcgggag gcaaatttcc ctaggaaaaa   2520
gaagacagac ttttctaatg tggtccaaat gcggatcact ggtcagatgg actctagaag   2580
cactgagctc cctgtctctg gaagtattta agaaaaggct gggccaggca cgatggctca   2640
cgcctgtaat cccagacttt gggaggccga ggcaggcgga tcacctgagg tgaggagttt   2700
gagaacagcc tggccaacat ggtgaaacct catctctact aaaaatacaa aaattagcca   2760
ggcgtggtgg caggtgcctg taatcccagc tacttgggag gctgaggcat gagaatcact   2820
taaacctgag aggcagaggt tacagtgagc caagatcgtg ccactgcatt ccagcctggg   2880
cgacagagca agactctgtc tcaaaaaaaa aaaaaaaa                          2918
```

<210> SEQ ID NO 4
<211> LENGTH: 371
<212> TYPE: PRT

<213> ORGANISM: Homo sapiens

<400> SEQUENCE: 4

```
Met Gly Thr Thr Glu Ala Thr Leu Arg Met Glu Asn Val Asp Val Lys
1               5                   10                  15
Glu Glu Trp Gln Asp Glu Asp Leu Pro Arg Pro Leu Pro Glu Glu Thr
            20                  25                  30
Gly Val Glu Leu Leu Gly Ser Pro Val Glu Asp Thr Ser Ser Pro Pro
        35                  40                  45
Asn Thr Leu Asn Phe Asn Gly Ala His Arg Lys Arg Lys Thr Leu Val
    50                  55                  60
Ala Pro Glu Ile Asn Ile Ser Leu Asp Gln Ser Gly Ser Leu Leu
65                  70                  75                  80
Ser Asp Asp Phe Leu Asp Thr Pro Asp Asp Leu Asp Ile Asn Val Asp
                85                  90                  95
Asp Ile Glu Thr Pro Asp Glu Thr Asp Ser Leu Glu Phe Leu Gly Asn
            100                 105                 110
Gly Asn Glu Leu Glu Trp Glu Asp Asp Thr Pro Val Ala Thr Ala Lys
        115                 120                 125
Asn Met Pro Gly Asp Ser Ala Asp Leu Phe Gly Asp Gly Thr Thr Glu
    130                 135                 140
Asp Gly Ser Ala Ala Asn Gly Arg Leu Trp Arg Thr Val Ile Ile Gly
145                 150                 155                 160
Glu Gln Glu His Arg Ile Asp Leu His Met Ile Arg Pro Tyr Met Lys
                165                 170                 175
Val Val Thr His Gly Gly Tyr Tyr Gly Glu Gly Leu Asn Ala Ile Ile
            180                 185                 190
Val Phe Ala Ala Cys Phe Leu Pro Asp Ser Ser Leu Pro Asp Tyr His
        195                 200                 205
Tyr Ile Met Glu Asn Leu Phe Leu Tyr Val Ile Ser Ser Leu Glu Leu
    210                 215                 220
Leu Val Ala Glu Asp Tyr Met Ile Val Tyr Leu Asn Gly Ala Thr Pro
225                 230                 235                 240
Arg Arg Arg Met Pro Gly Ile Gly Trp Leu Lys Lys Cys Tyr Gln Met
                245                 250                 255
Ile Asp Arg Arg Leu Arg Lys Asn Leu Lys Ser Leu Ile Ile Val His
            260                 265                 270
Pro Ser Trp Phe Ile Arg Thr Val Leu Ala Ile Ser Arg Pro Phe Ile
        275                 280                 285
Ser Val Lys Phe Ile Asn Lys Ile Gln Tyr Val His Ser Leu Glu Asp
    290                 295                 300
Leu Glu Gln Leu Ile Pro Met Glu His Val Gln Ile Pro Asp Cys Val
305                 310                 315                 320
Leu Gln Tyr Glu Glu Arg Leu Lys Ala Arg Arg Glu Ser Ala Arg
                325                 330                 335
Pro Gln Pro Glu Phe Val Leu Pro Arg Ser Glu Glu Lys Pro Glu Val
            340                 345                 350
Ala Pro Val Glu Asn Arg Ser Ala Leu Val Ser Glu Asp Gln Glu Thr
        355                 360                 365
Ser Met Ser
    370
```

<210> SEQ ID NO 5
<211> LENGTH: 371

```
<212> TYPE: PRT
<213> ORGANISM: Homo sapiens

<400> SEQUENCE: 5

Met Gly Thr Thr Glu Ala Thr Leu Arg Met Glu Asn Val Asp Val Lys
1               5                   10                  15

Glu Glu Trp Gln Asp Glu Asp Leu Pro Arg Pro Leu Pro Glu Glu Thr
            20                  25                  30

Gly Val Glu Leu Leu Gly Ser Pro Val Glu Asp Thr Ser Ser Pro Pro
        35                  40                  45

Asn Thr Leu Asn Phe Asn Gly Ala His Arg Lys Arg Lys Thr Leu Val
    50                  55                  60

Ala Pro Glu Ile Asn Ile Ser Leu Asp Gln Ser Glu Gly Ser Leu Leu
65                  70                  75                  80

Ser Asp Asp Phe Leu Asp Thr Pro Asp Leu Asp Ile Asn Val Asp
                85                  90                  95

Asp Ile Glu Thr Pro Asp Glu Thr Asp Ser Leu Glu Phe Leu Gly Asn
                100                 105                 110

Gly Asn Glu Leu Glu Trp Glu Asp Asp Thr Pro Val Ala Thr Ala Lys
            115                 120                 125

Asn Met Pro Gly Asp Ser Ala Asp Leu Phe Gly Asp Gly Thr Thr Glu
130                 135                 140

Asp Gly Ser Ala Ala Asn Gly Arg Leu Trp Arg Thr Val Ile Ile Gly
145                 150                 155                 160

Glu Gln Glu His Arg Ile Asp Leu His Met Ile Arg Pro Tyr Met Lys
                165                 170                 175

Val Val Thr His Gly Gly Tyr Tyr Gly Glu Gly Leu Asn Ala Ile Ile
            180                 185                 190

Val Phe Ala Ala Cys Phe Leu Pro Asp Ser Ser Leu Pro Asp Tyr His
        195                 200                 205

Tyr Ile Met Glu Asn Leu Phe Leu Tyr Val Ile Ser Ser Leu Glu Leu
    210                 215                 220

Leu Val Ala Glu Asp Tyr Met Ile Val Tyr Leu Asn Gly Ala Thr Pro
225                 230                 235                 240

Arg Arg Arg Met Pro Gly Ile Gly Trp Leu Lys Lys Cys Tyr Gln Met
                245                 250                 255

Ile Asp Arg Arg Leu Arg Lys Asn Leu Lys Ser Leu Ile Ile Val His
            260                 265                 270

Pro Ser Trp Phe Ile Arg Thr Val Leu Ala Ile Ser Arg Pro Phe Ile
        275                 280                 285

Ser Val Lys Phe Ile Asn Lys Ile Gln Tyr Val His Ser Leu Glu Asp
    290                 295                 300

Leu Glu Gln Leu Ile Pro Met Glu His Val Gln Ile Pro Asp Cys Val
305                 310                 315                 320

Leu Gln Tyr Glu Glu Arg Leu Lys Ala Arg Arg Glu Ser Ala Arg
                325                 330                 335

Pro Gln Pro Glu Phe Val Leu Pro Arg Ser Glu Glu Lys Pro Glu Val
            340                 345                 350

Ala Pro Val Glu Asn Arg Ser Ala Leu Val Ser Glu Asp Gln Glu Thr
        355                 360                 365

Ser Met Ser
    370

<210> SEQ ID NO 6
```

```
<211> LENGTH: 371
<212> TYPE: PRT
<213> ORGANISM: Macaca fascicularis

<400> SEQUENCE: 6

Met Gly Thr Thr Glu Ala Thr Leu Arg Met Glu Asn Val Asp Val Lys
1               5                   10                  15

Glu Glu Trp Gln Asp Glu Asp Leu Pro Arg Pro Leu Pro Glu Glu Thr
            20                  25                  30

Gly Val Glu Leu Leu Gly Ser Pro Val Glu Asp Thr Ser Ser Pro Pro
        35                  40                  45

Asn Thr Leu Asn Phe Asn Gly Ala His Arg Lys Arg Lys Thr Leu Val
    50                  55                  60

Ala Pro Asp Ile Asn Ile Ser Leu Asp Gln Ser Glu Gly Ser Leu Leu
65                  70                  75                  80

Ser Asp Asp Phe Leu Asp Thr Pro Asp Leu Asp Ile Asn Val Asp
                85                  90                  95

Asp Ile Glu Thr Pro Asp Glu Thr Asp Ser Leu Glu Phe Leu Gly Asn
                100                 105                 110

Gly Asn Glu Leu Glu Trp Gly Asp Asp Thr Pro Val Ala Thr Ala Lys
            115                 120                 125

Asn Met Pro Gly Asp Ser Ala Asp Leu Phe Gly Asp Gly Thr Thr Glu
130                 135                 140

Asp Gly Gly Ala Ala Asn Gly Arg Leu Trp Arg Thr Val Ile Ile Gly
145                 150                 155                 160

Glu Gln Glu His Arg Ile Asp Leu His Met Ile Arg Pro Tyr Met Lys
                165                 170                 175

Val Val Thr His Gly Gly Tyr Tyr Gly Glu Gly Leu Asn Ala Ile Ile
            180                 185                 190

Val Phe Ala Ala Cys Phe Leu Pro Asp Ser Ser Leu Pro Asp Tyr His
        195                 200                 205

Tyr Ile Met Glu Asn Leu Phe Leu Tyr Val Ile Ser Ser Leu Glu Leu
    210                 215                 220

Leu Val Ala Glu Asp Tyr Met Ile Val Tyr Leu Asn Gly Ala Thr Pro
225                 230                 235                 240

Arg Arg Arg Met Pro Gly Ile Gly Trp Leu Lys Lys Cys Tyr Gln Met
                245                 250                 255

Ile Asp Arg Arg Leu Arg Lys Asn Leu Lys Ser Leu Ile Ile Val His
            260                 265                 270

Pro Ser Trp Phe Ile Arg Thr Val Leu Ala Ile Ser Arg Pro Phe Ile
        275                 280                 285

Ser Val Lys Phe Ile Asn Lys Ile Gln Tyr Val His Ser Leu Glu Asp
    290                 295                 300

Leu Glu Gln Leu Ile Pro Met Glu His Val Gln Ile Pro Asp Cys Val
305                 310                 315                 320

Leu Gln Tyr Glu Glu Glu Arg Leu Lys Ala Arg Arg Glu Ser Ala Arg
                325                 330                 335

Pro Gln Pro Glu Phe Val Met Pro Arg Ser Glu Lys Pro Glu Val
            340                 345                 350

Ala Pro Val Glu Asn Arg Ser Ala Pro Val Thr Glu Asp Gln Glu Thr
        355                 360                 365

Ser Met Ser
    370
```

```
<210> SEQ ID NO 7
<211> LENGTH: 372
<212> TYPE: PRT
<213> ORGANISM: Mus musculus

<400> SEQUENCE: 7

Met Gly Thr Thr Glu Ala Thr Leu Arg Met Glu Asn Val Asp Val Arg
1               5                   10                  15

Asp Glu Trp Gln Asp Glu Asp Leu Pro Arg Pro Leu Pro Glu Asp Thr
            20                  25                  30

Gly Val Glu Arg Leu Gly Gly Ala Val Glu Asp Ser Ser Ser Pro Pro
        35                  40                  45

Ser Thr Leu Asn Leu Ser Gly Ala His Arg Lys Arg Lys Thr Leu Val
    50                  55                  60

Ala Pro Glu Ile Asn Ile Ser Leu Asp Gln Ser Gly Ser Leu Leu
65                  70                  75                  80

Ser Asp Asp Phe Leu Asp Thr Pro Asp Leu Asp Ile Asn Val Asp
                85                  90                  95

Asp Ile Glu Thr Pro Asp Glu Thr Asp Ser Leu Glu Phe Leu Gly Asn
                100                 105                 110

Gly Asn Glu Leu Glu Trp Glu Asp Asp Thr Pro Val Ala Thr Ala Lys
            115                 120                 125

Asn Met Pro Gly Asp Ser Ala Asp Leu Phe Gly Asp Gly Ser Ala Glu
    130                 135                 140

Asp Gly Ser Ala Ala Asn Gly Arg Leu Trp Arg Thr Val Ile Ile Gly
145                 150                 155                 160

Glu Gln Glu His Arg Ile Asp Leu His Met Ile Arg Pro Tyr Met Lys
                165                 170                 175

Val Val Thr His Gly Gly Tyr Tyr Gly Glu Gly Leu Asn Ala Ile Ile
            180                 185                 190

Val Phe Ala Ala Cys Phe Leu Pro Asp Ser Ser Pro Asp Tyr His
    195                 200                 205

Tyr Ile Met Glu Asn Leu Phe Leu Tyr Val Ile Ser Ser Leu Lys Leu
    210                 215                 220

Leu Val Ala Glu Asp Tyr Met Ile Val Tyr Leu Asn Gly Ala Thr Pro
225                 230                 235                 240

Arg Arg Arg Met Pro Gly Ile Gly Trp Leu Lys Lys Cys Tyr His Met
                245                 250                 255

Ile Asp Arg Arg Leu Arg Lys Asn Leu Lys Ser Leu Ile Ile Val His
            260                 265                 270

Pro Ser Trp Phe Ile Arg Thr Val Leu Ala Ile Ser Arg Pro Phe Ile
    275                 280                 285

Ser Val Lys Phe Ile Ser Lys Ile Gln Tyr Val His Ser Leu Glu Glu
    290                 295                 300

Leu Glu Arg Leu Ile Pro Met Glu His Val Gln Leu Pro Asp Cys Val
305                 310                 315                 320

Leu Gln Tyr Glu Glu Gln Arg Leu Arg Ala Lys Arg Glu Ser Thr Arg
                325                 330                 335

Pro Pro Gln Pro Glu Phe Leu Leu Pro Arg Ser Glu Glu Lys Pro Glu
            340                 345                 350

Thr Val Glu Glu Glu Asp Arg Ala Ala Glu Ala Thr Glu Asp Gln Glu
        355                 360                 365

Thr Ser Met Ser
    370
```

<210> SEQ ID NO 8
<211> LENGTH: 2918
<212> TYPE: DNA
<213> ORGANISM: Homo sapiens

<400> SEQUENCE: 8

```
gccgagcctc tgccagccct gagctgggaa gaagcagcta cctcggaggc agggcgcgca    60
ggcggcggc gatgagaggg ggcgcagccg cagccccgcg ctggggagcc caccgctaac    120
cctgcacccc acccacccct gcacaaaaga gctggcgggc gctggccacg tcgccctggg    180
tgaccttcct cggatgcaga atccgcccct gcgagcatcc tcttcctcct aggctctgaa    240
ggcccgggga gcgtgagcga tgcccagctg caccgggca gggctcgcct ttgtttgcca    300
gtaaggagga gaggctgtct cagctgcaga ggggtcatcc ctgcttcaag ccagtgcctc    360
ttcccagctc ccatggggac caccgaagcc acgctccgga tggaaaacgt ggacgtgaag    420
gaggaatggc aggacgaaga tcttcccagg ccactcccag aagagacggg ggtggaactg    480
cttggcagcc cggtggaaga cacatcctct cctcccaaca cgctaaattt caacggagcg    540
catcgtaaga ggaagacgct ggtggcccca gagatcaaca tttctctgga tcagagtgag    600
gggtccctgc tgtccgatga cttcttggat acccctgatg acctggatat aacgtggat    660
gacatcgaga cccccgatga gaccgactcg ctggagttcc tggggaatgg caacgaactg    720
gagtgggaag acgacacccc cgtggccacc gccaagaaca tgcccgggga cagcgcggat    780
ctatttgggg acggcacgac ggaggacggc agcgccgcca acgggcgcct gtggcggaca    840
gtgatcatcg gggagcaaga gcaccgtata gacctgcaca tgatccggcc ttacatgaaa    900
gtggtcaccc acgagggta ctacggcgaa ggcctcaacg ccatcatcgt cttcgcagcc    960
tgcttccttc cagacagcag cctccccgac taccactaca tcatggagaa cctcttcctg    1020
tacgtcatca gcagcttaga gctcctggtg gctgaggact acatgatcgt gtacctgaac    1080
ggtgccacgc cccggcggag gatgcctgga atcggctggc tgaagaagtg ctaccagatg    1140
atcgaccgga ggttgcggaa aaacctgaag tccttgatca tcgtccaccc ctcgtggttc    1200
attcggactg tgctggccat ctctcgccct ttcatcagcg tcaagttcat caacaagatc    1260
cagtacgtgc acaggttgga agacctggag caactcatcc ctatggaaca cgtccagatc    1320
ccagactgcg tcctgcaata cgaagaggaa agactgaagg ccaggaggga gagcgcgagg    1380
ccccagccgg agtttgtgct gcccaggtct gaagagaagc cagaggtggc accagtggaa    1440
aacaggtctg ctctggtctc agaagatcag gaaacaagca tgtcctgagg cgacgtgagc    1500
ataacaaagg acatgaagaa agattccaga tgccagaaaa cctctgtcag acgcccactg    1560
gccccagatc tcatcctgcc tcatcctgag tcccaatctt ccaagggtgc cagcccctcc    1620
gttcatctct gaaacccagc atccttttca gctgcttgaa acattgtat ttttttttt    1680
taacgatgca gtatttgtgc gttccagaaa agggcccagc tctgagcccc tcaccttcc    1740
acactcacga actctcagcc gaggaaggca agaagcgcag ggggtggccc gcgtggcgtc    1800
ggtggcctcc gctcctgctc gcagcccctg tggtcagagc tggatacaag attcaagacc    1860
cttctcttgc ttgtcacccg ctccaggttg gagccacaga cacccaccgc caccccggct    1920
gggtctgcgt cctttcctgt gccttttccct ccagaatgcg gcctcagacc tagaagctca    1980
accccctat gagggccacg tcctggggta gctcctgacc tccgacctta tgtccaaatt    2040
tcacacccat ggttttcat ttgacccgcc ccttctcgc tcataatgac acccagctcc    2100
tttgagagga tcagagccca ttgcacaaga agagccgctg ccaaccatcc ttgtcctccg    2160
```

-continued

```
attgcaaaat gacaccccag taatctagaa cattctcaag cccctttaac tcagatgtca      2220
agccaccggg caaaccccgt caatacctcc caccaaggaa tgagatatgt ggacctcact      2280
gctcccccaa cccagcgtca ggctgggaca cgccaacgct gttccgggtt ggaacagcag      2340
aggctcagaa actggctctg aaataggcag acctagcaag aggaagatac agggtatcgg      2400
gcgtttgagt gtttcagaag tcattcggga agataaatcc agtgcgctgg ccgcagccac      2460
ctgcattcaa agcttggacc agcgggttct tgttcgggag gcaaatttcc ctaggaaaaa      2520
gaagacagac ttttctaatg tggtccaaat gcggatcact ggtcagatgg actctagaag      2580
cactgagctc cctgtctctg aagtattta agaaaaggct gggccaggca cgatggctca      2640
cgcctgtaat cccagacttt gggaggccga ggcaggcgga tcacctgagg tgaggagttt      2700
gagaacagcc tggccaacat ggtgaaacct catctctact aaaaatacaa aaattagcca      2760
ggcgtggtgg caggtgcctg taatcccagc tacttgggag gctgaggcat gagaatcact      2820
taaacctgag aggcagaggt tacagtgagc caagatcgtg ccactgcatt ccagcctggg      2880
cgacagagca agactctgtc tcaaaaaaaa aaaaaaaa                             2918
```

<210> SEQ ID NO 9
<211> LENGTH: 371
<212> TYPE: PRT
<213> ORGANISM: Homo sapiens

<400> SEQUENCE: 9

```
Met Gly Thr Thr Glu Ala Thr Leu Arg Met Glu Asn Val Asp Val Lys
1               5                   10                  15

Glu Glu Trp Gln Asp Glu Asp Leu Pro Arg Pro Leu Pro Glu Glu Thr
            20                  25                  30

Gly Val Glu Leu Leu Gly Ser Pro Val Glu Asp Thr Ser Ser Pro Pro
        35                  40                  45

Asn Thr Leu Asn Phe Asn Gly Ala His Arg Lys Arg Lys Thr Leu Val
    50                  55                  60

Ala Pro Glu Ile Asn Ile Ser Leu Asp Gln Ser Glu Gly Ser Leu Leu
65                  70                  75                  80

Ser Asp Asp Phe Leu Asp Thr Pro Asp Leu Asp Ile Asn Val Asp
                85                  90                  95

Asp Ile Glu Thr Pro Asp Glu Thr Asp Ser Leu Glu Phe Leu Gly Asn
            100                 105                 110

Gly Asn Glu Leu Glu Trp Glu Asp Asp Thr Pro Val Ala Thr Ala Lys
        115                 120                 125

Asn Met Pro Gly Asp Ser Ala Asp Leu Phe Gly Asp Gly Thr Thr Glu
    130                 135                 140

Asp Gly Ser Ala Ala Asn Gly Arg Leu Trp Arg Thr Val Ile Ile Gly
145                 150                 155                 160

Glu Gln Glu His Arg Ile Asp Leu His Met Ile Arg Pro Tyr Met Lys
                165                 170                 175

Val Val Thr His Gly Gly Tyr Tyr Gly Glu Gly Leu Asn Ala Ile Ile
            180                 185                 190

Val Phe Ala Ala Cys Phe Leu Pro Asp Ser Ser Leu Pro Asp Tyr His
        195                 200                 205

Tyr Ile Met Glu Asn Leu Phe Leu Tyr Val Ile Ser Ser Leu Glu Leu
    210                 215                 220

Leu Val Ala Glu Asp Tyr Met Ile Val Tyr Leu Asn Gly Ala Thr Pro
225                 230                 235                 240
```

```
Arg Arg Arg Met Pro Gly Ile Gly Trp Leu Lys Lys Cys Tyr Gln Met
            245                 250                 255

Ile Asp Arg Arg Leu Arg Lys Asn Leu Lys Ser Leu Ile Ile Val His
        260                 265                 270

Pro Ser Trp Phe Ile Arg Thr Val Leu Ala Ile Ser Arg Pro Phe Ile
    275                 280                 285

Ser Val Lys Phe Ile Asn Lys Ile Gln Tyr Val His Arg Leu Glu Asp
290                 295                 300

Leu Glu Gln Leu Ile Pro Met Glu His Val Gln Ile Pro Asp Cys Val
305                 310                 315                 320

Leu Gln Tyr Glu Glu Glu Arg Leu Lys Ala Arg Arg Glu Ser Ala Arg
            325                 330                 335

Pro Gln Pro Glu Phe Val Leu Pro Arg Ser Glu Lys Pro Glu Val
            340                 345                 350

Ala Pro Val Glu Asn Arg Ser Ala Leu Val Ser Glu Asp Gln Glu Thr
            355                 360                 365

Ser Met Ser
    370

<210> SEQ ID NO 10
<211> LENGTH: 47219
<212> TYPE: DNA
<213> ORGANISM: Homo sapiens
<220> FEATURE:
<221> NAME/KEY: misc_feature
<222> LOCATION: (36437)..(36536)
<223> OTHER INFORMATION: n is a, c, g, or t
<220> FEATURE:
<221> NAME/KEY: misc_feature
<222> LOCATION: (42999)..(43098)
<223> OTHER INFORMATION: n is a, c, g, or t

<400> SEQUENCE: 10
ggaagccgag cctctgccag ccctgagctg ggaagaagca gctacctcgg aggcagggcg      60
cgcaggcggg cggcgatgag aggggggcgca gccgcagccc cgcgctgggg agcccaccgc    120
taaccctgca ccccacccac ccctgcacaa aagagctggc gggcgctggc cacgtcgccc    180
tgggtgacct tcctcggatg cagaatccgc ccctgcgagc atcctcttcc tcctaggctc    240
tgaaggcccg gggagcgtga gcgatgccca gctgcacccg ggcagggctc gcctttgttt    300
gccagtaagg aggagaggct gtctcagctg cagaggtgag tgcgcgcatc tccccttctc    360
ccaggataaa ccgtctccct ggaaggttta tccggcagcc tttgccgcct ctaaatccct    420
ttccagcaga tggggcgggt gggagcagag agccacggtc ttgtgactcc gtgaaggccc    480
tcacatccct gttcccggta ccaggaaaaa ccgttccctg agctgcgccc agcaacacag    540
tttaccttcc gcgcgcaccg ttcccctcta agtgcaccat tttcaggaca cgctgagagc    600
tcgggcggat gaaaacctca gcttctctct gggacgctga aatagaccca tcctagcccc    660
atgtatttcc tatttataac gctaggaagg ccaccagccg acgatttcgg gaaaaaaaaa    720
aaaaaaaaat ctaagtgtgt cgataaaggc tgtcctgtgg ggtggggagg aaggggggtgg    780 tttatggttt aagacacaga tgcctcctcc ttattggaac tcgtatgtga tttgttaata    840
atcagacatc agggctcaaa tgagcgcttc actcccgttc cttgatgtca ctgtcttctt    900
ttggccgtcc ccaaatgcga agccaggatc tgagtgcagg agtgtccggg gcccactgag    960
gacccacccc accccatcct tagaagactg tggagtcaac gcctgtggct gcagctggca   1020
gggggtgggg gtcgggggcg gggctggtgg gagtgttcct gggggctgag gtcacaccca   1080
```

```
gctcagtata aggaagggag aggcgaagac cccttcctcc ggagagcaaa tgcgtttcta    1140
ctgccgagga gaacttaccc tcgcgggaag ggcctggctg gctgctgcca ccgcccccc     1200
cccgacccca tagcatccag gagggatttt tttttttcc atgctgcgtg ttactgtccc     1260
tcctccaagc atgaatgacg acattgagga cagagaatcg agtgagaaac gctcaccctg    1320
tacgggggag ggtctagttt tagccgtccc ctccccccac ttcctcatct ggctgaggct    1380
gcctctgggt ccttccttgc taagccacag tccctgtcc ccgatgcaaa cccgatatct     1440
atgctggggg gctgcaggta acctactcca cagagaggca gcctggatgc catgagagtt    1500
gggggcctta gatgcttcat gtatttggtt ttttgagac agggtcttgc tatcttgccc     1560
gggctggtct aacctcctg tgctcaggcg atcctcgcaa agtgctggga ttacacgtgt     1620
gagccactgc ccccagccag atgctttatc ttttatttta ttttttgaag tagggtctct    1680
gttgctcagg ctggaaagca gtggcatgat catagctcac tgcagtctcg acctcctggt    1740
ctcaagcgat cctccaactt cagcctcctg aatagctggg acttcaggca ccaggcaccc    1800
atcaccatgt ttggttaatt tttgtatttt ttttttttta agagatgggg acttgctatg    1860
ttgcccaggc tggtcttgac cttccaggct caagcgatcc tcctatctca gcctcccaaa    1920
gtgctgggga ttacacgtgt gagccactgc ccccagccag atgccttatt ttatttatt    1980
ttattttctg aaatagaacc tcactctgtt gctcaggctg gaatgtggtg gcacaatcat    2040
acctcactgc agcctccacc tcctgggctc aggcaatcct cccacctcag cctcctgaac    2100
agctgtgact tcaggcaccc accaaattta attaattttt gtttttgttt ttgcttttcg    2160
tagagatggt gtcttgctat gttgcccagg ctggtcttga ccttctgggc tcaatcctcc    2220
cacctcagcc tctgaatag ctaagacctc aggcacccac cattgtgctt ggttagtttt    2280
tgtatttttt ttttgagaga tggggtcttg ctgtgttgcc caggctggtc tcgaacccct    2340
ggtctcaagt gatctgccca agtgctgga attccaggca tgcaccactg cacccagccc    2400
ctagacgctt taaaaagtgg atctagtggc ccggcagggt ggctcacacc tgtaatccca    2460
gcactttggg aggcaggtgg atcatgaggt caggagttcg agaccagcct ggccaatata    2520
gtgaaacccc atctctacta aaaatacaaa aattagctgg acgtggtggc acgcgcctgt    2580
agtccaagct actcaagagg tggaggttgc agtgagccga tcgcacca ctgcactcta     2640
gcctgggcga cagagcgaga ctctgtctca aaaaaaaat gacaacaaaa aaagtggatc    2700
tagctactcg gaagctgttg agagacagac agaggtaatg gaaggacaga gtgtacaata    2760
ctctataatg actgccggac acaggcctga aatccttcg caaacacggg aatgcacaca     2820
gaaatgacta ttgcctttaa gacaaggttt ctccaccttg gatctatgga tatttgggac    2880
ccagtcattc ttggtcatgg gcggccatcc tgggcactgt aaggtgctga gcagcacccc    2940
tggcctgccc aggggcact ccttcccctc agttgtgaca aaagtgcctc tagacaatgc      3000
caagtgtccc cttgcagcag ggaggcaga attgtccaca ggtgcaaagc actggtttca     3060
aagcccaaaa cagatgggt tggttgagtc ataagatgct ggtatgttat gtccaaaagg     3120
tatcttagag gtcatctcta attcaactct tttgtttaca gaaagggaaa ctgagaccca    3180
gagagggaga tggtctgaga gtctgccatg cccagagca gaccacaact cagtctcacc     3240
tggcagctct gatcctggcc cccacccaga ctgctccccc ctgccctgcc cctgcccctg    3300
cccccagtga gctcctcaga acaagaaaaa caaaactggt gtgggggtg ggcggcaca      3360
gtggctcaca cctgtaatcc cagcgctctg ggaggctgag gcaagaggat cacctgagcc    3420
```

-continued

```
cgaaagttca agaccagcct gggtgacata ccaagatcag agaaattagc caggcatgat     3480
ggcacacact cgtggtccca gatacttggg aggctgaggc aggaggatcg cttgagccca     3540
ggagttggag gctgtagtga gctgggatca caccactgca ctccagcctg gcgacagag      3600 caagaccccg tctctaaata aataaataaa taaataaagt ggcattttgt ggtagtaaag     3660
atgagggtct cctttctaac cccagtctct ttccacactg ccttagtgag ccctggagtc     3720
agaaagtcac taggacttgc ttgagggagg acagagaggg aggacaggtg gcctggtaca     3780
tatggcagat agcgatgggt tagagcctac tggattctct ttgaacttgg cattcccagc     3840
acggaagctg aagtatatca gccattcaca ctttagtatg aatgactgtt tggatttctt     3900
gctttctagt tgaggtccaa ggcacaagag ggagggtaag tctatctggg tcatggctca     3960
ccctggagaa ggtagatttc gaagtttcca agggagcagg acttgtatct gaaggctcag     4020
cctctcgccc acgttcaaac tctgaacccc actgtgcatc ctaagctctc tgtgcctctg     4080 tttctcatc tgtaaaacag gggaacctca tggggctcgg tgatggttca ataagaagtg      4140
ctggccgggc acagtggttt acccttgtaa tctcagcgct tagagaggcc gaggcaggag     4200
gattgcttga gcccaagagt ttgagaccac cctggccaac atagcaagac ccaatctctt     4260 aaaaaagat tttaaaaaat tacccaggca tgatggtaca cacctgtggt cacagctact      4320 ggtgggggc tgaggcagga ggattgctta agcccaggag ttcaaggctg ccatgagcca      4380
tgattgtgcc cctgcactcc agcccaggca acagagcaag atcatgtttt ttttttttaaa    4440 aaaaaaaaa aaaaaaaaaa aaacagccaa gctcagtggc tcacccctgt aatcccagca     4500
ctttgggagg ctgaggcggg tagaccgctt gagctcagga gtttgagacc agcctggcca    4560
acacagtgaa accccgtctc tattaaaaat acaaaaatta gccgggtgtg atggctcaag    4620
cctgtaatcc cagcactttg ggaggccaag gcaggaggat cacctgaggt caggagttcg    4680
agaccagcct ggccaacatg gcgaaaccct gtctctacta aaatacaag aattaaccag     4740 gcgtggtgat gggtgcctgt aaccccagct acttgggagg ctgaggcggg agaatcgctt    4800
gagcctggaa ggtggatgtt gcagtgagct gagatggcac cattgcacta cagcctgggc    4860
aacagagcaa gactccgtct caaaaaagaa gaagaagaag gagaaggaga gaggagagga     4920
gaaaggagag aggggggaggg gaaggggagg ggggagacgg aggggagtg ggaggggaa     4980 gagctgcatg gggtagacga ttgtcattag gactattgtc cagtaaaacc cattcctctg    5040
cggcttcctt tcaggggtca tccctgcttc aagccagtgc ctcttcccag ctcccatggg    5100
gaccaccgaa gccacgctcc ggatggaaaa cgtggacgtg aaggaggaat ggcaggacga    5160
agatcttccc aggtaggact tccacatccc tgagtcaacc gttgggggag caggtgtctc    5220
tcccaggtgg gacacaggag cggcccgggt ctctctctaa gtgggaaccg cccggggctg    5280
gcctggttcc atctccgcgt cctcctctcc cgcacactct gggaggcctg aggccctgtg    5340
tgcgagtctt ctctgtggcc tcacagtggg gtagtcctgg ccaggcacat aatgggtatt    5400
tgctcaatga tttaagattc atttctgtct tccctgcccc aaagctccaa aggaccccc    5460 accctacac cattttaaga gttcttaaca ttctggctgg gcgcggcggt tcacgcctgt     5520
aatcccagca ctttgggagg ccgaggtggg cggatcactt gaggtcagga gttcgagacc    5580
agcctggcca acatggcaaa accgcgtctc tactaaaact acaaaaatta gctgggcatg    5640
ccgggcgcag tgactcatgc ctgtaatccc agcactttgg gaggccgagg cgggcggatc    5700
atgaggtcag cagatggaaa ctatcctggc taacatggtg aaactccatc tctactaaaa    5760
atacaaaaat tagccgggtg tgtggcaggc gcctgtagtc ccagctactc gggaggctga    5820
```

```
ggcaggagaa tggcgtgaac ccaggaggcg gagcttgcag tgagccgaga tcgcgccact   5880
gcactccagc ctgggcgaca ggtgagactc catctcaaaa gaaaaaaaaa aaaattagct   5940
gggtatggtg tcatgcgcct ataattccag ctactcggga ggctgaggca ccatggtgat   6000
ttattagcag cctttaggag acacttacct cccctaacat gctgaacttt tttttttttt   6060
tttttgagtc tcactctgtc ccacaggctg gagtgcagtg gcacgatctc aggtcactgc   6120
aacctccagg tcctgggttc cagtgattct ccttcctcat gcccccgagt agcttggatt   6180
acaggcaccc gccaccacat ctggctgatt tttctatttt tagtagagac cggatttcac   6240
catgttggcc aggccagtct cgaactccga aagtgcttgg attccaggca agagccaccg   6300
cgcccggccc ctacgctgaa cattttgcag ggacatcttg tctacactct gtctccccac   6360
cacacggagc gccacaagag cagggtctt tgtttagctc actgctgtat cccaacctaa    6420
ggatagtgcc tggcatacag tcggcgctta acaaatattg ggtgacaggt gctgatcact   6480
ggtcagaata agaaatcaca ggggctgggc acggtggctc acgcctatga tcccagcact   6540
tacagaggct caggctgggg ggattgatag agctcaagag ttcgaaacca gcctgggcaa   6600
gatagtgaga ccccatttct accaaaaaaa aaaaaattag ctgggcatgg tggtgtgcac   6660
ctgcagtctt agctacttgg caggctgaga caggaggatc ccttgagccc agaaggcaga   6720
ggttgcagcg agccatgatt gcagccctgc actccagtct gggtgacaga gcgagactct   6780
gtctctattt tattttatt ttttattttt atttatttat ttatttttt ttgagacaga    6840 gtgtcgcttt gtcgcccagg ctggagtgca gtggcgcgat cttggctcac tgcaagctcc   6900
gcctcccggg ttcacgccat tctcctgcct cagcctcccg agtagctggg actacgggca   6960
cccgccacca cgcccggcta atttttgta ttttagtag agacgggtt tcaccatgtt     7020 agccaggatg gtctcgatcg tctgacctcg tgatccgccc acctcggcct cccaaagtgc   7080
tgggattaca ggcgtgagcc atcgcgccct accacctgtc tctatttaaa agagaggaa   7140 aaaaaaaaaa aaggccggtc gctgtggctc aggtgtgtgt aatcccagca ctttgggagg   7200
ccaaggtggg cagatcacaa ggtcaggaat ttgagaccag cctggccgac atagtgaaac   7260
cctgtctcta ctaaaaataa aaattaaaaa aaattagctg gcatggtgg tgcacgcctg    7320 taatccccag tactcgggag gctgaggcag gagaatccct tgaacccggg aggcagaggt   7380
tgcagtgagc cgagatgtgc caccgcactc cagcccgggt gacagtgtga gactccgtct   7440
caaaaaaaaa aaaatactac atggaaagga agctgtgcga atttgctgtt gagacgtgtg   7500
actctgattt gctggctaaa gatagctgct catccctctt ccctttcaga accaggaatt   7560
catccatccc ccaaacacaa tgcccaaggg tcagttatag aaactattgg gtgaggttca   7620
gtcaaaaaga ccaggtgtgt tccgcctgaa aaagagaatt ggaaaagaat ctccaggccg   7680
cgcacagtgg ctcacgtctg cagtcccaac agtttgggag gccgaggcgg gcaaatcact   7740
tgaggtcagg agttcgaggc cagcctggac aacatggtga aaccccgtct ctactaaaaa   7800
tacaaaaatt agtcgggcgt ggtggtgggc acctgtaatc ccagctactc aggaggctga   7860
ggcaggaaaa ctgctggaac tcgggaggcg aaggttgcag tgagccgaga tcgcgccact   7920
ggactccagc ccgggcagta gagtgagtga gagtgtctca aaaaacaga atctccagtt   7980 ccaggaaaat ttcaatctga gagggttccg gagggcagaa cgaggccaaa gaacgaact    8040 taaaagagaa tggggtttga aggagataca gaagaatgcc ttgaagtaat cggtctcctt   8100
caaaatgagt caggctggtg tgggaggccg agagcttcct tcccattcat gtccaggcag   8160
```

-continued

```
aaggaggact gttgaagacg gcatcttgat attcaagaac ttcagccctc tcctgaatcc    8220
agtcattgcc aggcctctaa ggcccatgca cctgtctgtg tttctttgca gcaggaggtc    8280
cctgttctca gaatagccga gaatcagaga atcacggctg ggagcggagg ctgatgtctg    8340
taatcccagc tctttgggag gccaaggcgg gaggatcgct tgagcccagg agtttgagat    8400
tagcctgggc aacatagcaa gacctcgtct cttaaaaaaa caaaaaacaa acaaaaactg    8460
gctgggccta gtggctcaca cctataatcc tagcactttg ggaagccaag gctggcagat    8520
cacctgaggt caggagtttg agaccagcct gaccaacatg gagaaacccc gtctctacta    8580
aaaatacaaa attagccggg cgtggtggcc catgcctgta ataccagcta ctcgggaagc    8640
tgaggaagga gaatcgcttg aacgcgggag gcggaggttg cagtgagcca agatcgcacc    8700
actgaactcc agcctgggcg acagagtgag actccgtctc aaaataaata aataaaaata    8760
aaaaataaaa aaaaattagt caggtatgct ggtgtgcacc tgtagtttca gctactcagg    8820
aggctgaggc aggaggattg tttgacttg ggacatcgca gcagtgagct atgatcacac    8880
caccgcactc cagcctggac aacagagcaa gactgcatat ctaagaaaaa taataataat    8940
tttaaaataa tgtcatttca agcagcacag cataaacaaa ggcgcataag ctttggaatc    9000
ggacgcccat ggttcaaatc ccaattcccc agcaggtttg ctctgccacc tgggctacct    9060
ctttgggcat ctcagtgcct ctgttttctg atctgtaaaa taggacaata atctctcgcg    9120
caccaggtgg tcatgaaatt ttgataaaac agccgagatg ggctgtgcaa atggcgaagg    9180
cagcacaaat aaataatcat ctccagcgtt attactatta ttagcttagc tccctttccc    9240
cctactgatt ttttttatt tctttacttt tcttttcttt tttttttttt gagacagagt    9300
ctcgctctgt cacccaggct ggggtgcagt ggcgccatct cagctcactg caacctccac    9360
ctcctgggtt caagtgattc tcctgcttca gcctcccaag tagctggatt acaggcatct    9420
gccaccacgc ccagctcatc tttgtatttt tagtagagac gaggtttcac cgtgttggcc    9480
aggctggtct cgaactctca acctcaggtg atctgcccac ctcccaaagt gctaggatta    9540
caggtgtgag ccattgggcc cagctccacc tataattttt tttttttttt tttttttttt    9600 ttttttttgca gacaaagtct cactctgtca cctaagctgg agtgcagtgg cgcgagttcg    9660
gctcactgca acctccacct cccgggttca agcaattctc ccacctcagc ctcccgagta    9720
gctgggatta caggcacaca ccaccacacc cagctaattt ttgtattttt ggtagagacg    9780
gggtttcacc atgttggcca ggctggtctc gaactcccaa cctcaagtga tccgcctacc    9840
tcggtctccc aaagtgctgg gattacaggc gcaagccacc acaccggcc tccaccgata    9900 atttttaaaag ctctcatctc acccaagcct tcttgagaca aaaccaagg ccgagcgcac    9960 ctgcaaatgc aagctggagg ccctttctgg aaggcgcgag gccagcggga gcgggaggag   10020
ggtgtgtttc tggtggattt cttacagctg caaggcttct cgcccacccg ctgcagcagc   10080
tttgtgtttg caggacagtg gcctcgctgt gccagcctgg cccccacgag ctacgccttt   10140
gccaacagga cacttcctcc acgaggcttc tgtcttcctc gtctctggaa gaactgagtc   10200
ggctcctcgg tgcaggtcca gctgcggcca cacataacca cctctgtctg ccgcaaaaca   10260
gctcacaatt ctgtttcttc cagcccagcc atcccctccc ctggggactg cagaagtggt   10320
ctttgtactg cccttaaggg tgtcagacag agccctgcat ggcctctgcc cttctagcac   10380
tttttttttt ttttttggag acagagtctc agtgtatcac ccaggctgga gtgcagtggt   10440
gcaacctcag ctcactgcaa cctccacttc ctggttcga gcaattctct tgcctcagcc   10500
tcccaagtag ctgggattac aggtacgcac caccatgcct ggctcatttt tgtattttcg   10560
```

```
ttagagacag ggtttcacca tgttggccag gctggtctcg aactcctaac ctcaagtgat  10620
tcgcctgcct cggcctccca aagtgctggg attacaggtg tgagccacgc gcccggcctc  10680
cttctagcat tttccttcac tctcacccct ctgcagccta ctacgagct agagctgaag  10740
gcagcccgga gattgctgcc tcaatttctc cattcattca ttctgatgct atgcgccaac  10800
tgtataccag tcccttatag cctcacaacc caatacaagg tggcagctgg gttcatggca  10860
cttctgacca ggccagggag ggaaggggag ctgtgattct tggctgtgaa gggtgaggag  10920
ggatgagccg gggaaggaag tggggtgtag gggccccaca ttccaagcag agagggcagc  10980
atgtgcaaag gctctgggct cagtggaagc aggttgaggg actggggaag gctgcgtggg  11040
gaaactgagg acttggggga ggagcttacc cagggcatcc tagccaagga gggtcagatg  11100
cagggtgagc tgcccatag ctccctctac tctcttcccc tcacagctga gtggctgcca  11160
gttttgtttg cttgcttgta acttttcctt tgtttgtttt gggttttctg gggggtttta  11220
tttatttatt tatttgaaac agagtctcgc tgcaacgccc aggctggaat gcaatgacgt  11280
gacctcggct cgctgcaacc tccacttccc aggttccagc aattctcctg cctcagcctc  11340
ccaaatagct gagtttacag gcgcccacca ccacgcccag ctaattttg tattttagc  11400
agagatgggg tttcaccata ttggtcaggc tggtctcgaa ctactgacct caagtgatcc  11460
acccgcctca gcttcccaaa gtgctgggat tacaggcgtg agccaccatg cccagctgct  11520
tgtaactttt taatttttt tttttttcca gacgggtct tgctctgtca cccaggctgg  11580
agtgcagtgg tgcgatcata gctcactaca gcctccacat cccaggctga ggcgatcctc  11640
ccactgcagc cccctgaata cctgggacca caggcatatg ccaccacacc cagctatgtt  11700
ttatttctg tagagacagg gtctcactgt gttgcccagg ttggtctcaa actcctgggt  11760
tcaaatgatc ctcccacctc agcctcccaa aatgctggga ttacaggcat gagccactgc  11820
gcctggccta tttgatatac ttccaaactt ggaaaaaaat tacaagaatg atataaagaa  11880
tatctgcata cctttagtag gattatacaa ttgttaacat tttgctcctt ttatatcaaa  11940
gtcagccctc agggctgggt gcggtgactc acatctgtaa tcccagcact ttgggaggcc  12000
aaggcaggtg gatcacctga ggtcgggagt tcaagaccag cctaggccaa catggtgaaa  12060
ccccgtctct actaaaaata caaaaatcaa ctgggtgtgg tggcgggcac ctgtaatccc  12120
agctactggg gaggctgaag caggagaatt gcttaaaccc aggaggcaga agttgcaatg  12180
agcccagatt gtgccgccac actctagcct gagcaacaca gcaagactct gtctccaaaa  12240
aaaaaatttt accctcaatt gtaccgataa tgtcccatgt ccctatttag ctaatgcccc  12300
tgccccaaac cctgggtcca agacccaatc tgggaccact cattgcatca ggttgagtat  12360
actgggttgt gtgtttactg gggtatgtgt ctcaccaggc actgggactt aaacttatct  12420
cttttagggg aacacgatcc aacccacctc agcaggacga agccacgctg tgcatcttgc  12480
atgtgggggg gaccccccact ttttttttt tttttttttg agacggagac ttgctctgtc  12540
gcccaggctg gagtgcagta gcatgatctc agctcactgc aacctccgcc tcctgggttc  12600
aagcgactct cctgcctcag cctcccaagt agctgtagct gggaccacag gcatgtgcca  12660
ccatgccagg ctaattttag tatttttagt agagacgggg tttcaccatg ttggccaggc  12720
tggtcttgat cgcttgacct tatgatccac ctgcctcggc ctcgcaaagt gctgggatta  12780
caggtgtgag ccaccatgcc cggctaggat ttccactttt tacctggatt gcccatcatg  12840
gactttgaga gccggctctg cagagggcta agtggatata ttataccca gggccacgga  12900
```

```
ggggatctcc aagtctggag agtctgcggt tctcctggag cttgcggaag taacaggatc  12960
tcacctgacc ttggaaactg cagctccatg aacaggcggg gagagcttgc tccacccatg  13020
ttccagagca gtgggtcttc cttcagggag cctggagccc tgccaggtcg gcttctccag  13080
ttctgcatga tcttaaacct ttcctgaaca tccactgcaa ctggcagctc agcctcagga  13140
cctcatccca tccccgaggc actgcctctc cctggccctc cctccctacc ctccatcctc  13200
caaccactcc ctcctccccc actgctctct ctgcgcagg caccctgagt ctgctttctg  13260
atctgccctt gaacttggca agcttattcc agtcccggag cctgggcctc tgcagtgcct  13320
tccatctgga gtgctcttgc ctggtctctg caggacgcca acatcatgct taaaagtcta  13380
cacttaaaag tcgcttccag ccaggcacag tggctcactc ctgtaatccc agcactctgg  13440
gaggccaagg cggaggatc acttgagccc aggagttcaa gaccagcctg caagacccca  13500
tctgcagaaa aatataaaaa ttagctgggt ggccgggcgc ggtggctcac gtctgtaatc  13560
ccagcacttt gggaggccga ggcgggcagg tcacgaggtc aggagatcga gaccatcctg  13620
gctaacacgg tgaaaccccg tctctactaa aaatacaaaa aattagctgg gcgtggtggc  13680
aggcgcctgt agtcccagct actcgggagg ctgaggcagg agaatggcgt gaacccggga  13740
ggcggagctt gcagtgacct gagatcgcgc cactgcactc cagcctgggt gacagagtga  13800
gactccgtct caaaaaaaaa aaaaaaaaaa aattagctgg acatagtagt gtgtgctggt  13860
agtcccagct acttgagagg ctgaggtagg aggattgctt gagcccaaga atttgagacc  13920
agcctgggca acatggcgag accctgtgtc tgcaaaaaaa aaaaaaaaaa aaaactgtaa  13980
aaacctgaaa aattaaccag gtgtggcagc tcactcctgt aatcccatca ctttaggaag  14040
ctgaggcagg agaattgctt gaaatgtgaa gttcaagacc agcctaggca ccacagtaag  14100
accctgtctc tacaaaaaat tttataatta gccgggtgtg gtggtgcaca cctagggtcc  14160
cagctactca gaagactgag acaggaggat cccttgagcc caggaatttg aggctgcagt  14220
gagctatgat ttcactactg tgctctaggc tgggcaacag agcaagaccc tgtctcaaaa  14280
aaaaaaaaaa aaaaaaaaag ctgcctcctc aatgaggcct tccctgacca ccccacagat  14340 tttttttctct ctctctcctc tccttttattt cattcatttt ctttgccgta agcatcacta  14400
tctgccttgt tcacttattt gcttattgtc ttcctttata tacatggtct caagccagga  14460
attgctttgc acaatcctgg gaaccaccaa gtccaaaatc cacagggcag gctggaaact  14520
gtcaggtaag agctaatgct gcagtttttg tttttgtttt tgagacggag tctcactctg  14580
tcgccaggct ggagtgcaat ggcacgatct cagctcactg caacctccgc ttcctgggtt  14640
caagccattc tcttgcctca gcctcctgag tagctgggt tacaggcatg caccaccaca  14700
cccagctaat ttttgtattt ttagtagaga tggggtttca ccacgttggc caggctggtc  14760
tcgaactcct gacctcaggt gatctgcccg cctcggcctc ccaaagtgct gggattacag  14820
gtgtgagcca ccgcgcctgg cccccatttt agtcatgagg aaaacagagg ctcagggagg  14880
agaaggcacc acccagactc gtagcgctgg atggagtggc agggctggga gttgtgctca  14940
gactctctga gactctctta ggcattccca ccctttctcc tgctttcctc actttcccag  15000
tatgtgcagc tgagatgctt tcttttttttc tttcttttct tttctttttt tttttttttt  15060
ttgatagact cttgctctgt tgctcaggcg ggagtgcagt ggtgccaatc acagctcact  15120
gcagcctcaa actcccggac tcaaacgatc ctcctgcctc agcctcctta gtagctggga  15180
ttacaagtgc atgccaccat gcctggctaa tatgttgtat tttttgtaga gatgggtct  15240 cactatgttg cccaggctag tctcgaactc ctagtctcaa gagatcctcc cacctcagcc  15300
```

-continued

```
tgctgagtag ctgggatcac aggcatgagc catcatgctg gctaatttt taaattttta    15360
gtagtgatgg ggtcttgctg tgtgggccag gcttgtcttc aactcttggg cttaagtgat    15420
cctccctcct cagcctccca aagtgctgtg attaccggca tgagccctg cgcccagtct     15480
gagatgcttt ctacagcttc acatttcagc tgcagcccag cagtggtcca cctagttcac    15540
agccaatgta gaatctgtgt ggaccatcca atgttgtgag gttgaatcac atccctttt    15600
tttttttttt ctcgagacag agtctcactc tgtcactcag gctggagtgc agtggcacgg    15660
tctcagctca ctgcaacctc cacctcccgg gttcaagcga ttctcttgcc tcagcctccc    15720
gagtagctga gattacaggc acgtgccacc acacccagct aattttgtgt ttttagtaga    15780
gacgggttt caccatgttg gccaggctgg tcttgaactc ttggcctcag atgatccacc     15840
tgcctcggcc tcccaaagtg ccgggattac aggcatgagc ccctgcgccc ggcctgagat    15900
gctttctaca gcttcatatt tcagctgcag cccagcaatg gtccactcag ttcacagcct    15960
acgtagagtc tgtgtggacc gtccaaggtt atgaggctaa atcacatctt gagaatcgaa    16020
ggcagtgccg gctgcaaagc aatgggggctt cctctggcg ggaggagatg gtggctggac    16080
agggaccctg gctgggcaag tggttgtttg tttgtttgtt ttgagacgga gtctcgctct    16140
gttgcccagg ctggagtgca gtgtcacgat ctcggctcac tgcaacctcc acctcccagg    16200
ttcaagcgat tctcctgcct cagcctcacc aatagctggg attacaggcg cccgccacca    16260
tgcccggcta atttttgtgt ttttattaga cagggttt tgccatgctg accaggctgg     16320
tctcgaactc ctgacctcag atgatccacc cgcctcagcc tcccaaagcg ctgggattac    16380
tgaggcatga gccaccacgc ccagccagaa atctagactt tttgcatctc ttcttcgaca    16440
gcaaatggaa aatgttttta aatgctgcat gggtgggaca taactaggct tggtgcatca    16500
gccatcagcc tgcaattttg cagcgctggt ttgggttaac cttctgaatg agcaggtcag    16560
ttcattcttc agtcctttct ttgaagtttg ctatatatat atatatatat agcaaaatct    16620
atatctatat ctatatctat atctatctat atcgcctcgc tctgtcatcc aggctggagt    16680
gcagtggctc gatcatggct cactgcagcc ttgacctcct gggctcagct gatcctccca    16740
ccttggcttc ccaaatagct gggactacag ggacacgcca ccatgcctgg cttttatt     16800
tttatagaga tggagtctcg ctgtgttgcc caggctgatc tcaaactcct gggctcaagg    16860
gatcctccca cctcagcctc ccaaagtgct gggattacaa gcgtgtgcca cctcatgccc    16920
agccaaagct tgcttttaa aaaattgagg tgaggcaag tacagtggct cacgcatgta     16980
atctcagcac tttgggaggc cgaggcaggt ggatcctg agctcaggag ttcgagacca     17040
gcctggccaa cgtggtgaaa ccccatctct actaaaaaca caaaaatcag ctgagcatgg    17100
tggtgggcgc ctataatcac agctactctg gaggctgagg cacaagaatc gcctaaaccc    17160
gggagatgga ggttgcagtg agccaagatt gtgccactgc actccagcct gggcaaaaga    17220
gtgaaactcc gtctcaaaaa ttaaataagt aaaataaaat ttaaaaaata taaaaaattg    17280
aggtggaatt ctcataacat gaattcatca ttttaaagtt catgattcag tgcagagtc     17340
cattcataat gttctgcaac cccacatcta tctaatttga agacattttc atcaccgtga    17400
gaggaaatcc tatctactaa gtcagcccca ttttcatccc tctcccccaa ccccagtgac    17460
cacacatcta cttcctgtga gaatttacgt gttctaaaca tctcttttt ttttcttttc    17520
ttttctgttt tgagcagggt gtcactcttt cacctaggct ggagtgcagt ggtgcaatca    17580
tagctcactg cagcctcgac ctcccaagtt agagcaatcc tcctgcctca gcctcctgag    17640
```

```
tacttggaac tagacgtgta ccaccacacc cagctaattg ttttgtatttt ttagtagaga    17700 cgggctttcg ccatgttgcc ccgactggtc ttgaactcct gggctcaatg aacccgcccg    17760
catcagcctt tcaaagtgct gggattacag gcataagcca ccacactcag ccaacatttc    17820
atgtaattgg aatcacacac tgtgtggcct tttgtgtctg gcatctctca ctgagcatga    17880
tgtcctcaag gtgcatccat gctgtggtct gtgtcagagc cctgttcctt ttcagggcta    17940
aatagtattc cattgaatgg atataccaca tttgttgatc cagtcagctg ttaatggact    18000
ggtgttgttt gtttgtttgt ttgttttttga gacagagtct cactctgtcc ccaggctgga    18060
gtgtagtggc gtgacttcag ctcactgcaa cttccacctc ccaggttcaa gtgatcctct    18120
tgcctcagcc tcccaagtag ctaggattat aggcatgcgc caccatgtcc agctaatttt    18180 tgtatttta gtacagacag ggtttcatcg tgttggccag gatggtctca atctcttggc    18240
ctcatgatgt gccctcctcg gcctcccaaa gtgccaggat gacaggcgtg agccaccgcg    18300
cctggccgtc aatggactct tgaattgttt ccacttttg gttttatga attatgttca    18360 ttcaagtatg agttttcgtg tgaacagatg ttttcatttc ctttgggaat ccgctccatt    18420
ttgatctttg ccatgaacag gaggagggtg acatctgatt cctcctttac ctccaagccc    18480
catagatgca ctggagacgc agtggttacg caaaaacatt tgatgaatag agaaagaga    18540 gggagggaaa gggagaggga aaagcataa atagattccg ccccaaaaag gttaacagct    18600
catgccctaa gtgaacaga aatgagggaa taaatctttt tttttttttt tttttttttg    18660
agagagagtc tcactttgtt gcccaggctg gagtgcaatg gcacgatctc ggctcaccgc    18720
aacctccgcc tccagggttc aagtgattct cctgcctcag cctccccagt agctgagact    18780
gcaagcacgc accaccacgc ccagataatt tttgtatttt tcagtagaga ctgggtttca    18840 ccatttttggc caggctagtc ttgaactcct gacctcaggt gatccgcccg cctcggcctc    18900
cctaagtgcc aggattacag gcatgagcca ccacgcccgg ccaataaatc attttttaa    18960 aggaaaggaa catgcattcc accgcccttc catctaaaca gcttgccttg cagctgagcc    19020
aggaatgctg agttacagag acgaattaag ctgtagcctg gctttccgga gtcagcacgc    19080
cctgccgcta ggacctctgg cagccccgtg caaaatgttc tgcccggaat ggaatatttc    19140
ccagggtagc caaggagcca gtgctcctgg gtcaaactcg ggcagcacgg gctgcggctt    19200
caagaagtga tctgggccgg ggtgcggtgg ctcatgctgt aattccagca tttctgtctc    19260
aaaaagaaag aaaaagttgc aaagttagta cagataattc ctgtagactg ggaacctagt    19320
ttctcccata attaacatct tatattagct gtgtatatttt tatatttgtc acaattgatg    19380
aatcaatatt gatactattg gttattgata atcaacattg atcaataaca atattgatca    19440
atattggtta ttagttacca aagtccatgc tttttagat tttcaaagtt tttcctaatg    19500
tcctcttttt ttttcttttc tctctttttt ttttaagag acagggtctc actctgtcat    19560
ccaggctggg gtgcagtggt gccatcatac ctcactgcag cctccgcctc ccaggctcaa    19620
gcagtcctcc cacctcagcc tccagagtag ctgggactac aggcaccacc acgtccagct    19680
aatctttgta attttttgtag agacagagtt acgccatgtt gcccaggctg gcctaatgtc    19740
cttttccttc tgccccacaa ccccatccag gatcccagat gacatttagt tatcacatct    19800
cctgacactc ctctggactg tggcagtctc cctgtctttc ttgttttgat gcccttgata    19860
gttttgtttg tttgtttgtt ttgagatgga gtctcactct gtcacccagg ctggagagca    19920
gtggcacgat ctcggctcac tgcaacctcc gcctcccggg ttcaagcgat tctcctgcct    19980
cagcctcctg atagctggga ttacaggtgt cctccaccat gcctgcctaa ttttttgtatt    20040
```

```
tttagtagag atggcgtttc accatgttgt ccaggctggt ctcgaattcc tgagctcaag   20100
tgatcctcct gcctcagcct cccaaagtgc tgggattaca ggcgtgagct gctgcgcctg   20160
gcccatcctg tattttttgg aatgacatca ctatacacag cctacacaga gttatccttc   20220
atcttttttt tttttttttt tttttttgag acagagtctt gctctgtggc ccaggctgga   20280
gtgcagtggc acgatctcgg ctcactgcaa gctccgcctc ctgggttcat gccattctcc   20340
tgcctcagcc tcctgagtag ctgggactac aggcacctgc caccacgccc cgctattttt   20400
tttgtacttt tagtagagac ggggtttcac catgttagcc aggatggtct cgatctcctg   20460
acctcgtgat ccgcacgcct cggcctccca agtgctggg  attacaggcg tgagccaccg   20520
cacccggcct atccttcatc ttcttgaggg cagaactgta cataaactat ttccaattct   20580
tctgcacaag aaatgtgtct cttctctcct gtttatttgt tcagtgactt atttatatcc   20640
gtatggactc atagacattt attttacatc ttgggttata attcaatatt tcattattta   20700
tttggttgca caaactgttc cagcattgac atagagatct cttctggttg actcaggttt   20760
ttgtgggggt tttatctatt tatttatttt taatactttt tgctgcattt gagagtcaac   20820
aactcatcag agaccaaatc ccacagggtc gccctagaga gaattcaact tactaactta   20880
tttcaaagtt tttgaagtca tgtgatgctg gggaaaaacc ttcattctcc tcaagccgtg   20940
caaaaatctc caaaaggctt aatataaatt tgattatcta aaagaagccc ttcagccctg   21000
atgcgttata attttcttcc tctgctaaag aaaaaacatg ctgggcgggc gcggtggctc   21060
atgcctgtaa tcccagcact tgagaggcc  gaggtgggca gatcacaagg tcaggagttc   21120
cagaccagcc tggccaatat ggtgaaaccc cgtctctact aaaaatacaa aaattagccg   21180
ggcatggtag cgggcacctg tagtcccagt ttacttagga ggctgaggca gaagaatggc   21240
ctgaacccgg gaggcggagg ttgccgtgag ccgagatcat gccactctac tccatccagc   21300
ctgggcgaca gagcgagact ctgtctcaaa agaaaaaaat aaaagaaaaa gaaaaaacat   21360
gcgcttgtgg tggctcacgc ccgtaatccc aacactttgg gaggctgagg tgggaagatg   21420
gcttgagccc aggagttcaa gagcaacctg gcaacatag  tgagacccca tctctacaaa   21480
aaaccaaaaa actacaaaaa ttagccagcc gtggtggtgt gcacctgtag tcccagctac   21540
tcaggaggct gaggcaggag gatctcttga gcccaggagg ttgaggctgc agtgagccat   21600
gatcacgcta ctgcactcca gcctgggcga tacagtgagg ctctgtctcc aaaaaaatgt   21660
atatatttag gtccagtgat tctccagaac taaatgtgtt ttgcttttgt tcttgtctga   21720
ctcgcctggc tggacctgtc tgggccactc cactgtcctc tgcctgaatc tctggtgccc   21780
ggcgactgat gcctgttcct ggatgggtcc gcaggccact cccagaagag acggggtgg   21840 aactgcttgg cagcccggtg gaagacacat cctgtaagtt tccacgtcca cagaagggcg   21900
gaaacaggct cagtgtttcc gggtttcagc cctgcctggg gctgtaactg tagaaatgtc   21960
agaggccaca caccgtgggt agaatgttct gtcctgggt  ctatggtgga agtggccgtg   22020
gtgggtgaga gacacaatgg atgatggcgc tctcatgaag ccagcacgct gtgttgctgt   22080
gtgtccctgt gctagtcact cagcctctct gtgcccccaat gcctcatcta ctaaatgtag   22140
gtagcgagct tctcgcagag ggggcatgta aggattaaat gaggtgatgc caaatgccct   22200
ggaggcacaa agtcagcaca gccaagggtg cactgggagg ctctgctatc tggagctcta   22260
aacatataca ttttaatgtg taataccttta tattagaccc aaatatatac atttttgggg  22320
agaccgggtc acactctgtc atccaggctg gagtgcagtg gcgtgatcat ggctcactgc   22380
```

-continued

```
agcctcaacc tccagggctc aagagatcct cctgcctcag ccttctgagt agctgggact    22440
acaggtgcac accaccatgg ctggctaatt ttggtagttt ttgtagaaat gggatctagc    22500
tatgttgccc aggctgctct tgaactcctg ggctcaagcc atcttcttgc ctcagcctcc    22560
caaagtgctg ggattacggg cgtgagccac cacgcctggc atgttttttc ttcagcagag    22620
gaaaaaaatc ataatgtatc aggctctgaa gccccagatc ccggggatgg gagtcctggg    22680
cggccagagg agagttttag ccgtaacctg gcgattgcaa cgtgcctccg gaggcaggga    22740
aagggcccag gttggcaccg tggggagagg tggggtctgg ggaggacctg gcagccagcc    22800
ccacttaacg acattcagtt aagcagaata tggaaaataa acctgtgagg gccaaacaaa    22860
attttttttgg agacagagcc tcactgtatc gcccaggctg gagtgcagta gcgtgatcat    22920
ggctcactgc agcctcaacc tcctgggctc aagagatcct cctgcctcag cctcctgagt    22980
agctgggact acaggtacac accaccatgg ctggttaatt tttgtagttt tttgtagaga    23040
tggggtctca ctatgttgcc caggctgctc ttgaactcct gggctcaagc catcttccca    23100
ccttggcctc ccaaagtgtt gggattacgg gcgtgagcca ctgcacccgg ccgcctgtct    23160
ctatttaaaa agaaaaaaaa aaaaggcagg tcaccgtggc tcacgcctgt aatcccagca    23220
cttttgggagg ccgaggcggg cagatcacga ggtcaggagt ttgagaccaa cctggccaac    23280
atggtgaagc cccgtctcta ctaaagatac aaaaaaaaaa aaaaaaaaaa attagccggg    23340
cattgtggca cttgcctgta atcccagtca ctcaggaggc tgaggcatga ggatcgcttg    23400
aacccaggag acgaggttgc agcaagctg agattgtgcc attgcactcc agcctgggtg    23460
acaaggcgag actctgtcta aacaaaacaa aacaaaaaaa gattagtcgg gcttggtggc    23520
gcatgcctgt aatcccagct acttgggagg ctgaggtggg agaatcactt gaacctggga    23580
ggcggaggtt gcagtgagct gagatcctac cattgtactc cagcctgggt aacggagtga    23640
gactccatct caaaaaaata aatacataaa taaacaaaa taaattagca gactttggat    23700
taaagcaggc agccatctgt gatgtgggtg ggcctcatct aatcagttga aggttttaag    23760
agaaacagac tgaggttccc ccaggcagag acaattctgc ctgcggacgg ttttgcaaca    23820
tcaactcttc cctaggcgtc ccgcctgctg gcctgccctg ccgattgagg acttgtcagt    23880
ctctgtgatc acgcagcta attccttaaa ataaatttct ccctctctct ttttttccat    23940
acatatagga aaaaatatg tatacacaca cacacacaca cacacgtc ctattggatt    24000
tgtttccctg gagcactctg attaaaatag gagactatcc tggatcctgt attatccagg    24060
tggcctgaca tcgttacagg atcctcatga gtggagacag gagggtgaga gtcagagaaa    24120
gcctagaaga agatgggctg ctttcacaat ttgtctgcac aagagatatg tctcttctcc    24180
tttattatt tatttattta tttttgagat agagtttcac tctgtcaccc aggctggagt    24240
gcaatggtac gatcttggct cactgtaacc tccgcctcct gggctcaagt gattctcctg    24300
cctcagactc ccaagcagct gggattacag gcgccaccg tgtgcccggc taattttat    24360
attttttagta gagatggggt ttcgccatgt tggccaggct ggtctcgaac tcctgacctc    24420
aggtgatctg cccgcctcgg cctccaaagt gctgggatta caggcgtgag ccaccgcacc    24480
cggcccaaag tcaggctttg aactcatgtc tgcccaatgt ccaagcatcc atcccttaa    24540
tctctgaggc ttgcccacag gacagaggtt ataacattca ccctgtcag gatgatgtcg    24600
gtttaattct gcccacccc gccaatggca tggatacaga agggagccca ccctctcttc    24660
ccattcctgc atgatgaaac agcttccacc aggtaggaaa atggggggaa ggtaaaagag    24720
agaaagcaaa gatgttttcc atttttctca tttccctgca gctcctccca acacgctaaa    24780
```

```
tttcaacgga gcgcatcgta agaggaagac gctggtggcc ccagagatca acatttctct   24840
ggatcagagt gagggggtccc tgctgtccga tgacttcttg gataccccctg atgacctgga   24900
tattaacgtg gatgacatcg agaccccccga tgagaccgac tcgctggagt tcctggggaa   24960
tggcaacgaa ctggagtggg aaggtaaagt tcagggtctc tctggggcct gctggagccc   25020
acccccccca ccccacctttt ccgtctctgg attcccatag gctcagagag tcacaagtgg   25080
ggcagggggct ctaagcagtc tagccttaaa cccaggagat caagactgca gtgagacgtg   25140
atcatgccac tgcactccag cctggacaac agagtgagac cctgtctcaa aaataaaatt   25200
tttaaaaaag agagaggtgg ctgggcgcag tggctcatgc ctgtaatcct agcactttgg   25260
gaggccgagg cgggcagatc acgaggtcag gagatcgaga ccatcctggc tgacacagtg   25320
aaaccccgtc tctactaaaa tacaaaaaat tagccaggca tggtggcggg cacctgaagt   25380
cccagctact caggaggctg aggcaggaga acggtgtgaa cccaggaggc cgagcttgcg   25440
gtgagccaag attgtgccac tgcactccag cctgggcgac agagcgagac tccgtctcaa   25500
aaaaaaaaaa aaagagagag agaggttggt gaatgggtac caacatacag ttagacagaa   25560
ggaataagtt ctattgttcg atagcagaat aggagggggtg ccaggaggag ggtccatccg   25620
ctcctgcgac tgtttttttt ttttttttga gacagagtct cactctgttg cccaggctgg   25680
agtgcagtgg tgtgatctca gctcactgca tcctccacct cccggggttca agcgattctt   25740
ttgcctcagc ctcccgagta gctgggatta caggcatgca ctaccacttc cggctgatgt   25800
ttatattttt agtagagatg gggtttttccc atgttgccca ggctggtctc aaactcctga   25860
cttcaagtga tacacccacc tcggcctccc aaagtgctgg gatcacaggt gtgagccacg   25920
gcgcccagcc tgccctgca atttgatgca tattttttctt gtgggcttgt gaattttttct   25980
gcagaacgtg gctttcatca gaatctcaaa ggcgaccaag atcccaacaa actgccctcg   26040
atgtatgcaa caaatacttt ttgaccattt actccagggc aagtcctgat tcaggcgtgg   26100
ggtatatggc agggctatga taagaagaga tggtcctggt ccctacctgc acacacagat   26160
catcagaaag acagaccacg aaaggccagg cgcagtgact cacgcctgta atcccagcac   26220
tttgggaggc tgaggtgggc agatcacctg aggtcaggag tttgagacca gcctggccaa   26280
catggtgaag ctccatctct actaaaaata cagaaattag ccgggcatgg tggcgtgcgt   26340
agtcccagct actcgggagg ctgaggcagg agaatcgctt gaactctgga ggcagaggct   26400
gcagtgagca gagatcgcac cactccactc cagcctgggc gatggaacaa gactctctca   26460
aaaaaaaaaa agaaagaaaa aaaaaaatta aggacaatgt agtggctcat tcctgtaatc   26520
ccagagcttc ggggaggccag ggtaggagga tcgcttaagg ccaggagttt gagaccagcc   26580
tgggcaacat attgaaaccc catctctaca aaatataaa aattagctgg gtgtggtggt   26640
gcacaactgt agtcccaggt atctgggagg ctgaggcagg aggactgctc tctgtgtgcc   26700
aggctcctgg gagagtaaaa accaagcatg catgccccga gtatcctcgt ggtttgatga   26760
agcagatgca ttcaccagct ctgagaagct ccaggacaca ggtccttaac caacagagtg   26820
ccctgggagg ccagcaaagg gaatgtccag aaaggcttcc tggaggaggc ggcatttgag   26880
ccaggccttg aaaggggagt aggagaggaa aatgggtcag cagggcagcc aggtggggag   26940
aagcgaagga cttgtgggtc ccggcagcga gggaggtggg agagggaag gaaggctgag   27000
caggagggca ggagatatcc ggactctggc gtccatgcga ctctccgcca cctgcttcta   27060
gacgacaccc ccgtggccac cgccaagaac atgcccgggg acagcgcgga tctatttggg   27120
```

```
gacggcacga cggaggacgg cagcgccgcc aacgggcgcc tgtggcggac agtgatcatc    27180
ggggagcaag agcaccgtat agacctgcac atgatccggc cttacatgaa agtggtcacc    27240
cacggaggtg agacccgccc cccggtgccc ccttggggct ccagcccggc ccactgggca    27300 acaggggtt cgtcagtgcc cctctctgat gcacgggat gttaagccgt caactcgctt     27360
cgggtggacg gactgtgggc aaggcgtgca tggtcaggga ggcgcactgg gggccctga     27420 tggtcgctgt cactcctcag cgaaggcaga gactggctaa ggggtcgccg gctgctgtgg    27480
ctcggagcca tgccctcccg agcgtgtggg caccgggacg tggtgggtgg tgcgcgggag    27540
gcagctcagg gctgggagag gactctgacg ttgccgatcg gctgcctctc tcagggtac    27600 tacggcgaag gcctcaacgc catcatcgtc ttcgcagcct gcttccttcc agacagcagc    27660
ctccccgact accactacat catggagaac ctcttcctgt gagtcccgc ccgcggcgag    27720 cagcctcggg ccagctctga tgcctccctg gccacagggg caccaggctg caaggattgc    27780
attgtggccc taggaagcct gcctggcacc agggaagggc gtggtggcca cagaccttga    27840
tctgagtccc tgctggccct gaggctcaca gtggccttcc ctctgggcca ccctgttctc    27900
ctccccgtcc tcctcctcct cctcttcctc ctccttcccc tcctcctcac tgtcctcctc    27960
ctcctcccct tcttcctccc ccttcccctt tcttctcctc cttctcctcc ccttcttcct    28020
cccccctcct cctcccttt ctcctcctcc tccccttccc tctcctcctc ccctctccc    28080 ccttccctct cctcctcccc cctcttcctt ctcctcctct tcctcccctt tctccacctc    28140
atcctctttc tcttcctccc ctttctcccc ccttcctcct ccttctcctc cttccctcat    28200
cttcctctcc ttccctctcc tccccctccc catcctcctc ctccccatcc tcttccctt    28260 cctcctcctc ttcccgctct gagatggcac cactgcactc cagcctgggt gacagagtga    28320
gaacctgtct caaaaaaaaa aaaaaaaaa aaaagcaagg cctagagacc agcctggcca    28380
acatagtgaa atcctgcctc tactaaaact acaatttagc tgggctcggt ggcaggcgcc    28440
tgtaatccca gctactaggg aggctgtggc aggagaatgg cgtgaacctg ggaggcggag    28500
cttgcagtga gccgagatcg caccactgca ctctagcctg gcaacagag cgagattccg    28560 tctcaaaaaa aaaaaacgac tcaataaaag agtaactgcc ctatgaggat gcccgctgac    28620
actcatgtgg agtgtgctgg gatcatccac gtcctctccc accctgcagt ccgccaggac    28680
agcagacaac acctggacca gtggggctga cccagccagc ggcaggagtg gaggcaggca    28740
gggtcggcac cgcaggtgtc ctgaccctgg accctccat gttgggtccc tgccttctgt     28800
gccccgtgag caggtacgtc atcagcagct tagagctcct ggtggctgag gactacatga    28860
tcgtgtacct gaacggtgcc acgccccggc ggaggatgcc tggaatcggc tggctgaaga    28920
agtgctacca gatgatcgac cggaggtgag gtggggatgc ctcaggaagc acagtggggg    28980
catgaaaatc acacaggggg ctggacatgg tggctcacac ctggaatccc agcacttcgg    29040
gaggctgagg tgggaaggtc ccttgagccc aggagtttga ccagcctg ggcaacgcag     29100 caagacgctg tctctacaga aaacttttta ggccgggcaa gggggctcac acctctaatc    29160
ccagcacttt gggaggccaa ggtgggtgga tcacctgagg tcaggagttc aagaccagcc    29220
cggccaacat atagtgaaac cccatctcta ctaaaaaat tcaaaaatta gctgggcgtg    29280
gtggcgcatg cctgtagtcc cagctacttg ggaagctgag gcaggagaat cacttgaacc    29340
caggaggtgg aggttgcagt gagccgagat catgccactg cacttcagcc tgggcaacag    29400
agcgagactc tgtccccatg aaacactcac tccctattcc ttctccccag gctccggcac    29460
cccccatcct actttctgtc tctgtaaatc tgatgactct agggacctcc taggactgga    29520
```

```
atcacacagg atttgtcctt ttgtgtctgg ctttcctcac tgagtgtgat gtcctcaggg   29580
tgcatccaca ttgtagcctg tgtcagagcc tccttccttt tcatggctgc ataatattcc   29640
actgtatgga cataccacat ttggtttgtc cattccattc atctcttgat ggacatgggt   29700
tgcttccacc cctgagttat tgtaaatagc ctcagagtga cattaaaatt gagccagcca   29760
atccatcctt gcacccaggt tagtggaggg aggctccaag gacaggctgg tccctcctag   29820
ggcattaggt ggtgaaaata caatcttggc tgctcaaata actaccaacc tggttcacct   29880
gctctgcacc atgggtctc tacctacctc atccacctga gggtcttagg gactcaaagg   29940
gtgtgtcttt atcccaccat aggaccccca tgtcttggat gggggcaggg atttgacagg   30000
tacctggaga ccacacgtgg aatgagcaga gtgacgaatg cttgcttgtg gctctcccgt   30060
cccacccagc tcctccctcc ccagggctcg ccccaggagc ccatcttgct tcctttgcgg   30120
ccccacacag gttgcggaaa aacctgaagt ccttgatcat cgtccacccc tcgtggttca   30180
ttcggactgt gctggccatc tctcgccctt tcatcaggtg agacggggag gctgcaaccc   30240
aagtccagtg gcctcagtgt gcgtgtgtgc gtgtgtgtat gcatgcattt gtgtgtgcat   30300
gtgtgcacgt gtgtgcgtgt gtgcatctgt gtgtgtgtgc atccatgtgt gtgtttgatg   30360
tgcatgttcc agcttctcta tgatgaatac atattattgc tttaaacagt tttaaattgc   30420
acacagccag gcacagtggc tgacacctgt aatcccagct actcagaagg ctgaggtggg   30480
aggatcgttt gaggccagcc tgagcaacat agcaaaaccc ccatctctac aaaaaataca   30540
aaaattagca ggacgtggtg gtgcacacct gtagtttcag ctacttggga ggctcacgtg   30600
ggaggatggc ttgagcccag gagatcaagg ctgcaatgag ccgtgatcga gccactgtac   30660
tccagcctgg atgacagagt gagaccctgt ctcaaaagaa aatcagtcat gcatggcatc   30720
acatgcctgt agtcccagct actcaggagg ctgaggcagg aggatcactt gagcccagga   30780
ggtagaggct gcagtgagct atgatcactc cactgcactc cagcctggga gacagagcaa   30840
aacaaccctg tctctaaaaa taaaatatat atatatgtat gtataaataa ataaataata   30900
tgactaataa atttaaaatt taaaactaca tatattctat aatgtatatc atatatagtt   30960
actatattaa acatatagta aaacagatca agtgaaataa aattaggcat gttaaatgcc   31020
ctattcaatc caataaaatg tcatgcaaat ttaatttaat ctaatgcaaa acattgaatt   31080
gaataaagat tcctaatgtt cacgttccca gttacaaatc tgggatgagc gaaagagacg   31140
agggcttcac tttcccttga acaacaggac acattcacag caggcccgat tttcaaggaa   31200
gactctttaa acatgctgtt ttcaaggact gctaagtacc ctgaaggggc ttatttgcat   31260
attagcgaaa tgagatgagg aatacactaa ttatggatca ttttagctaa taatgaatca   31320
acaggcaaaa cggtaaacac gcatttcagt ctaagataat tgcatttgct cctctatatt   31380
ccagaattca gtaacataga ctacctttgc ctttaatgta gatattagga tggtgcaaaa   31440
ataattgagg ttcttgccat attttcatta caaaaactgc aatcactctt gcacgaaccc   31500
aataattctg tcactcttca ccggtcgcca tggctcacac ctgtaatccc aacactttgg   31560
aaggtcgaga tgagaggatc gcttgagccc gggagttcga gaccagcctg ggtgacatag   31620
cgagaccctg tctctacaaa aaaaaatttt tttttttttc agacggagtc tcactctgtc   31680
gcccaggctg gagtgcagtg gcgcgatctc agctcactgc aagctccgcc tcccgggttc   31740
acgctattct gcctcagcct cccgagcagc tgggactaca ggcgcccgcc accaggccca   31800
gctaactttt tgtattttta gtagagatgg ggtttcatcg tgttagccag gatggtctcg   31860
```

```
atctcctgac ttcgtgatcc gcctgccttg gcctcccaaa gtgaaaaaaa ttttttttta    31920
aatacggcca ggtgtggtga cccaggcttg taatcccagc actttgggag accgaggcag    31980
gaggatcgct tgaggccagg agttgaagac cagtctgggc aacatagcaa gacctccatc    32040
tctacaaaaa aaaattttt ttaattagcc aggcctggtg gcgcgcacct gtgatcccag     32100
ctactcagag gctgagggag gaggatcact tgagcccagg aggtcgaggc tgtagtgagc    32160
catgattaca ccactgcact ccagcctggg tgacagagtg agactctgtc tcttaaaaaa    32220
aaaataccat gaagtgctgg tgatgaaaca ccacatggta tcagatggcc agaattcagg    32280
attggaaggg aaagaaggga aagaaccatt catccctgaa aaacagagaa ttgggccagg    32340
cagggtagct catgactgta atcccagcac tttgggagtt agaggcaggc agatcacatg    32400
aggtcaggag ttggagacta gcctggccaa catgatgaaa ccccatctcc attaaaaata    32460
caaaattagc cgagagtggt ggtgcatgcc tgtagtccca gctactcggg aggctgaggc    32520
agggaaaatc gcttgaaccg gggaggcgga ggtggcagtg agccgagatc acaccactgc    32580
actccagcct gggtgaagag caagactctg tgtcaaaaaa taacaataac agagaatcaa    32640
tgggcagccc cgtgtgcccc cttcttgtgc ccagctgagt gttggctgtg ccgtcctgtg    32700
cggtgacatg gagagaaagc atccctggga aaaattaaca cagaggagca acttttagag    32760
atgatgggaa aacagcctgt agagtctaag acaatctccc cacctcctga cttccttcca    32820
acaagatcct cattgcaggg acccatgtca ggtgcatggc cctgcttgca agggcctcgg    32880
cgcagacccg gggtctccac tccatgcatg gggtgcaaga taattaaggc tgtcatcggg    32940
cgggagggag gtgtcgtcgt ctgcactggg gcatcctgga gtggggtcct gtggggatcc    33000
ctgtcgccat ggctctgtct ggacctaggt aaccccacc ccatgggttg catttcagac     33060
ctctccctcc ttctccccc gccagcgtca agttcatcaa caagatccag tacgtgcaca    33120
gcttggaaga cctggagcaa ctcatcccta tggaacacgt ccagatccca gactgcgtcc    33180
tgcagttagt ggccccacag tccacccgc cgtattagtc tgttttcgtg ctgctgataa     33240
agacacacct gagacagggc aatttacaaa agaggtttaa ggggccgggc gcggtggctc    33300
ctgcctgtaa tcccagcact tgggaggct gaggcgggcg gatcacgagg tcaggggatc     33360
gagaccatcc tggctaacat ggtgaaaccc cgtctctact aaaaatacaa aaaattagcc    33420
gggcgtggtg gcgggcgcct gtagtcccag ctactcagga ggctgaggca ggagaatggc    33480
gtgaaccccg gaggcggagg ttgcagtaag ctgagatcgc gccactgcac tccagcctgg    33540
gccacagagc gagactccat cgcaaaaaaa aaaaaaaagg ctaacggac tcacaattcc     33600 atgtggctgg caacgcctcc caatcacggt ggaaggcaaa aggcacgtct cccatgcgg     33660 cagagaagag aaggaaattt gtacaggcaa attcccttt ataaaaccat cagatctcat     33720
gagacttact cactgtcgcg agaatagcac aggaaagacc tgcccccatg attcagtgac    33780
ctcccaccag gtcactccca caacaggagg gaattatggg agctacaatt caagatgaga    33840
tttgggtgaa gagaccaggc aaggtggctc acacctataa tcccagcact gtaatcccag    33900 catttgaga ggctgagaca ggcagatcac ttgaggtcag gagttcgaga ctagcctggc     33960
caagatggtg aaaccctgtc tcctaaaa atacaaaaat tagccaggtg tggtggtgca     34020
tgcctgtaat cccagatact gaggaggctg aggcaggaga atcgcttgaa cctgggaggc    34080
agaggttgtg gtgagccgag atcgcaccac tgcactccag cctgggcaac aagagtgaaa    34140
ctccgtctca agaaaaaaaa aaaaagattt ggtggagat acagtcaaac cctgtcaccc    34200
ccaacacccc cccaccgggt cccctggct accaggagcc agcaatgagg ggaaacgcag     34260
```

```
acttggaagg gaggaactag aacccaccca ttttatttcc tggagcccct cagggacccc   34320
ccggagcttg gggaagggat gggcagcttc aagtcctgtt gtttttcact gaatgtcata   34380
tcatcggcac ctcccctagg ttcatgctgc aaaaatctcc ttaaacgtac attttttttat  34440 tgtggtaaaa tacacgtaac atagaacttc ccatcttagc cattccttttt ttaattttat  34500 ttatttattt attttttgag aaggagtttc actcttgttg cccaggctgg agtgcaatgg   34560
cgccatctcg gctcaccaca acctccgcct cccgggttca agcgattctc ctgcctcagc   34620
ctcccaacta gctgggatta caggcatgag ccgccatgcc tggctaattt tttttttttt   34680
ttttgtattt ttagtagaga cagggtttct ccatgttcgt caagctggtc tcaaacccct   34740
gacctcagat gatctaccgg cctcggcctc ccaaagtgct gggattacag gcgtgagcca   34800
ctgcgcccgg cctatcttag ccatttctaa aagcacattc gcatatttgt gcagccatca   34860
ccaccatcct ctccagacct ttctttttttt ttttttgag atggagtctt gctctgttgc   34920
ccaggctgga gtgcagtggc acgatctcgg gtcactgcaa cctccacctc ctgggttcaa   34980
gtgattctcc tgcctcagcc tcccagtag ctgggattaa ggcacccacc accatgccca   35040 gctaatttt tttttttttt ttttgagat ggagtttaac tcttgttgcc caggctggtc   35100
tcgaactccc gacctcaggt gatccgccca cctcagcctc ccaaagtgct gggattacag   35160
gcgtgagcca ccacgcctgg ccgattttg tattttagt agagacggag ttttgtcatg   35220
ttggccaggc tggtcttgaa ctcctgacct cagttgatct gcctggctcg gcctcacaaa   35280
gtgctgggat tacaggcatg agccactgca cccggccctc tccagaacgt tctcatcttc   35340
ccaaactgaa actctgtctc catgaaacac tcactcccca ttccacatcc caaccctgg   35400 cagccccat cctactttct gtctctggga gtctgacgac tctagggacc tcctaggaat   35460
ggatccacac aggatttgtc cttttgtgtc tgacgtctct cactgagcgt gacatcctca   35520
aggtgcatcc acattgtagc ctgtgtcaga atgtccttcc ttttcatggc tgaataatat   35580
tccattgcgt gaatggacca cattttgtca atccatttgt ccatcaatgg acaattgggt   35640
tgtttccacc ttttggctct tgtgaatagt catgttattt atatgctact cacctatgac   35700
cgtagatgta caaatatctc tgtaagaccc tactttcaat tctaatgagt atatacccaa   35760
aagtggaatt gctgataatt ctgtttttttt gaggaaccac catactgttt tgttttgttt   35820
tgctttgctt tgcttttttg agacggagtc tcactctgtc acccaggctg gagtgcagtg   35880
gcgctatctt ggctcgctgc aacctccacc tcccgggttc aagcaactct cctgcctcag   35940
cctcccgagt agctgggact acaggcgccc accaccacac ccagataatt ttttttgtatt  36000 tttagtagag atgggttttc accatgttgg cctggctggt ctcaaactcc cacctcagc   36060 ctcccaaagt gctgggatta caggcgtgag ccatcgcacc cagcctgttt tttgttgttg   36120
ttgttttgtt gggttttttc tggtttttttt ttttagacag agtctcactc tgttgcctac   36180
gctggaacgc aatggcgcaa tctcggctca ccatatcctc cagcttctac gttcaaggga   36240
ttctcgtgcc tcagcctccc gaatagctgg gattacaggc acctgccacc acgcccagct   36300 aattttttgta ttttttagtag atatagggtt tcaccatgtt ggccaggatg gtctcagtct   36360
cctgaactca gtgatctgcc cgcctcggcc tcccaaagtt ctgggattat aggcgtgagc   36420
caccgtgctc agccaannnn nnnnnnnnnn nnnnnnnnnn nnnnnnnnnn nnnnnnnnnn   36480
nnnnnnnnnn nnnnnnnnnn nnnnnnnnnn nnnnnnnnnn nnnnnnnnnn nnnnnaaaa    36540 tgcatctatg ggccaggtgt ggtggctcat gcctgtaatc ccagcacttt gggaggctga   36600
```

-continued

```
ggccagagga tcgcttgagc ccaggagttg gaggctacaa gtgagttcat gccactgcac    36660
tccagtctgg gctatgacag aatgagaacc tgtctaaaaa aaagagaaga ggccgggcgc    36720
ggtggttcgc gcctgtaatc ccagcacttt gggaggccga ggtgggtgga tcatgaggtc    36780
aggagtttga gaccagccag gccaacatag ggaaaccccg tctgtactaa aaatacaaaa    36840
aattagctgg gcgtggtagc aggtgcctgt aagtcccagc tactccggag gctgaggcag    36900
cagaatcact caaaccgggg aggtggaggt tgcagtgagc caagatcgca ccactgcact    36960
ccagcttggg cgacagtgca agactccatc tcaaaaaaaa aaaaaaaaaa aaaaaaagg    37020 aagaagaaga agaagaaaag aaagaaaaaa gagagcttgt ttctctgctt gaaaggaaa    37080 gggatttccc caaaaagtat atctcagggg aaaggaaggt tgtgtctgac atcttttttct    37140 ttctttcaga tacgaagagg aaagactgaa ggccaggagg gagaggtgtg tgcagagtgg    37200
tttctgctgg ggctgggtcg gggcagcggg gggctgagct gaactctcag ttagggcaac    37260
ccggtgactt ctgggcagca gggaccattg tcctgtgcag ggctcaagac gctgcccttc    37320
tggcaaggac tttaaactca gacctgggtt caaatactgg ctcccgcatt gagctgcaag    37380
gtaacattaa gcaaataaaa agctaacaac caccttggag gttattgtgc aagatgaggc    37440
acccttggca aaaaggttg agcacagact tcacgctcca taaagcataa aagtcaagac    37500
gggcgcggtg gctcacccag cactttgaga ggctgtaatc ccagcacttt gggaggctga    37560
ggcaggagga ttgtgtgagg tcaggagttg gagaacaacc tggacaacat ggcgtaactc    37620
cgtctctacc aaaaatacaa aaattagcca ggcgtggtgg tgcgtgcctg taatcccagc    37680
tacttgggag gctgagccag gagaatcact tgaacctggg aggcggaggt tgcagtgagc    37740
cgagatcatg ccactgcact ccagcgtggg tgacagagca agactctgtc tcaaaaaaa    37800 aaaaaataa attagccagg tgtggtggca tgcgcctgta gttcagctac ttgcagggag    37860
actgaatcgg gacgactgct tgagcccagg aagttgaggc tgcagtgagc catgattgta    37920
ccattgcact ccagcctggg caacagagca agatcctgtc tcaaaaaaaa aaacaaaaaa    37980
aaacagcctt tatcatgcca ggtccaatgc cagctttgag ggaaacagag gcaaataaga    38040
cagagtcttg gtcccagaag tttctcaaa tagcaaaggc agggaacatc tcactggttt     38100
ggaaaacagg tcccagggga caggaaaacc agagaggcca gtactagctg agagcccacc    38160
ccttggcctg gctgggctag tcacccttgt cacctcgttc tctctgtcca cagcgcgagg    38220
ccccagccgg agtttgtgct gcccaggtct gaagagaagc cagaggtggc accagtggaa    38280
aacaggtagg tgtgcagggg accatgggca gagagctgac agtcacggga ggctgcctac    38340
tcccttgggg gaggctagag aggaagatgg gtccttgttc agggacagaa aatggaacta    38400
agtggccggc catggtggct cacgcctgta atcccagcac tttgggaggc cgaggtgggc    38460
agatcacatg aggtcaggag ttcgagacca gcctggccag catggtgaaa cctcatctct    38520
actaaaaata caaaaattag ctggacatgg tggctcacat ctgtaatccc agctacttgg    38580
gaggccgagg caggagattc gcttgaaccc aggggggcaga ggttgcagtg agccgagata    38640
gtaccactgc actcggcgac aaagtgagac tccatctcaa aaaataaat aaacaaataa    38700 aataaaaata aaaattatcg gccgggtgtg gtggctcacg cctgtaatcc cagtagtttg    38760
ggaggctgag gtgggccgat cacaaggcca agagatcgag accagcctgg ccaacatggt    38820
gaaaccccat ctcttctaaa aatacaaaaa ttagctgggc atggtggctc gtgcctgtag    38880
tcccacctac ttgaaggct gaggcaggag aatcacttga acctgggagg cggaggttgc    38940
agtgagccga gatcagacca ctgcactcca gcctggcgac agaatgagat tctgtctcaa    39000
```

```
aaataaataa ataaataaat atcatccagg tgtggtgatg tacacctcta gtccagctac    39060
tcagaagggt gaggcaggca gatggctgga gcccaggagg tcaaggctac agcaagctat    39120
gactgcactc cagcctgggc aacagagcaa gaccctgtct caaaaaaaaa aaaaaagtta    39180
tcatgatgtt ctcatattat cgcaatctca atgttatcat aatgatgaaa ggtgaccttt    39240
gtccaggtcc cagcaggtag attcagactc ccccaatcca gtagccctg agcaacatta     39300 ttggcttcat tttatgttag tgaagggcct tggccaattt cctcaaaact gtctgtttgg    39360
gctcatttgt tacgcagcag atgcacgctg acatctgttt tgtaccagat acagcagtgt    39420
cggtcctcat agggcttaca gcctccacga acaggtagaa aatgcccaag aatgggcact    39480
gtggctcacg cctgtaatcc cagcactttc ggaggccaaa gcaggaggac catttgaggt    39540
caggagttcg agaccaactt gggcaacata ttgagactcc atctctacaa aaagtttaaa    39600
agttagccag gcatgatggt gtataccttg tagtcccagc tacttgggag gctgaggtgg    39660
gaggatcact tgagcccgga gctggaagct gcagtgagcc atgattgcac cactgccctc    39720
cagcctgggc aacataacaa gaccctgtat cttttttttt tttttaagac agattttcac    39780
tcttgtcgcc caggggccag agtgcaatgg tgcgatcttg gctcactgca acctccacct    39840
cccgggttca gcgattctc ctgcctcagc ctcccgagta gctgggatta caggcaccca     39900
ccaccacacc cggctaattt ttgtattttt agtagagaca gggttttacc atgttggcca    39960
ggctggtctc gaactcctga cctcaagtga tccaccccacc tcagcctccc aaagtgctgg   40020
gattataggc atgagccact gcacccagcc aagaccctgt atcttaataa taataaataa    40080
ataaaaataa aataagttaa agaaaaaaaa gggaaaatgc ccaggctccc aaaaataagc    40140
aaataacgcc cagtctccgt ctctcctcca caggtctgct ctggtctcag aagatcagga    40200
aacaaggtgg gtgtgatgca gagtggtctt cgtgctgttt tcaaaatgtc cttcatggac    40260
ctgtattagt cagggttctc tagaaggaca gaaaatcaaa ccagctgcca gcaaatataa    40320
agcaggcagg gatcctaatc ccaggaaaac tgccccatga cttatcggga gtgggggata    40380
cggcaccggg aaggcaggga ggtagtggtt cccttaacca gtcaggccgt ccttgcacaa    40440
ctccaggggg gcaccattac ctagaccagg atgcaaatga ggccccagag ttatgcagtg    40500
gagcggccct cagggaaaaa cccacacaga gccaagctcc ctgaagccca ggatatgata    40560
ccacaaaagg gtagactgtc cacgctctgc ctccgattct ccacctggtt ctggatgcca    40620
agaaaagcct ccctgtggcc gggcgcagcg tctcacgcct gtaatcccag cactttggga   40680
ggccgaggca ggcggatcat ttgaggtcag gagttcaaga ccagcctggg caacatggca    40740
agaccccgtc cctaaaaaaa atacaaaaat tagccaggtg agccaagatc gtaccactgc    40800
actccacagc ctgggcaata ggctagact ttgtctcaaa aaagaaaaa aaaaaggaaa      40860 gaaaagaaaa gcctccctgt gtgttgatgt ccaagggtat cctcaggcac aatggtttgc    40920
cagaaggact cacagagctc agcaaagctg tcatactcac agttatggtt tatcacagtg    40980
gcatggttta ttacagtaga agggtacagt taaaaatcag cagagttggg tgtggtggct    41040
catgcctgta atcccagcac tttgggaggc cgaggcaggt ggatcacttg aaatcaggaa    41100
ttcaagacca gcctggccaa tatggtgaaa ccccatctct actaaaaata taaaattagc    41160
tgggtgtggt ggcacacacc tgtagtccca gctactcagg aggctgaggc aagagaattg    41220
cttgaacctg ggaggcggag gttgcagtga gctgagattg caccattgca ttccagcctg    41280
ggcaacagag caagactctg tttaaaaaaa aaaaacaaaa aaaacaaaaa acttaacaaa    41340
```

```
aggaagaggt gcatagggct ggatccagga gagatcggt ggaagcctgc aagtgtcctc    41400
tcccagtggg gttgtgtgga cagcctttat ttctcccagc agggatgtgt ggcaaaacac    41460
acaaagtgct gccaactaga gaagctgacc caagcctttc tagccagggt gtttatagag    41520
agtcaactac atacacctgg ctgactgtct gcatggcttt tcttagcctc cagcccctgc    41580
acagatcaag ctgatgccac gtggcccaag ttccaaccct aagtcacgtt gtgagtgtta    41640
ttagtccatt ctcatgctgc tatgaagaaa tacccaagac cgggtaaatt ataaagaaaa    41700
gaggtttaat tgactcacag ttctgcatgg ctggggaggc cccgggaaat ttataatcct    41760
ggcggaagcc acctcttcac caggcagcag gagcgagaag tgctgagcaa agggggggaaa    41820 gccccttata aaccatcag atctcgtgag aactcactac cacgagaaca gcatggaggt    41880
agccgccccc atggttcagt tacctcccac tgagtaccgc ccacgacaag tggggttatg    41940
ggaactacaa ttcaagatga gatttgggtg gggacacagc ccaaccatat cagttagcat    42000
agactatctg gcatgaccca catagacact ccagccagga tgctccaaga gtttagaagt    42060
taatcccagg agccagggaa ggaccaaaact tttctttaga atgtgtggga tttatccttg    42120
accacacagt ttttttgttt tgttttgttt ttgttgttgt tgttgttttt gagatggagt    42180
ctcgctctgt cgcccaggct ggagtgcagt ggcatgatct tggctcactg caagctccgc    42240
ctcccagggt cactccagtc tcttgcctca gcctcccaag tagctgggac tacaggcgtc    42300
tgccaccaca cccagctaat ttttgtatt ttttagtaga cggggtttt caccatgtta    42360 gccgggatgg tctcgatctc ctgacctcgt gatccacccg cttcggcctc ccaaagtgct    42420
gagattacag gcgtgagcca ccatgcccag ctgaccacac agttttatac aaatctataa    42480
gatggcctgg ccacatgcct tactacccat gtgacccagg aagctccaag ctaagaaata    42540
aacatcaaaa atggccttag accagtgctg cttaaggggc actgagtaaa agttctcaat    42600
gtatttctga aaagaccacc tcaacccaag ctctctggag atgagttcac atatacagac    42660
agaaaacaca aggaaatcat ccaccatgag caaaagacag cagagacaac aaacagcaga    42720
attagatctt gcctggagat ccttaggtgg ataagatata ataagcatgt tttaacaatt    42780
aaaaacacaa aagaaggaat tgtaagaagc aatagatgaa tggatgaatg gataggtgga    42840
taaatggatg gatggatgga tgagtggatg gatggaagga tgtttggatg atgggtggat    42900
agatagatga atgaatgagt ggagggatgg gaggatagat ggatgatagg tggatggatg    42960
gatggataaa tggatggatg gatggatggg tgaaggttnn nnnnnnnnnn nnnnnnnnnn    43020
nnnnnnnnnn nnnnnnnnnn nnnnnnnnnn nnnnnnnnnn nnnnnnnnnn nnnnnnnnnn    43080
nnnnnnnnnn nnnnnnnnga gtgggtgggt ggatggatgg atggatggat ggatggatgg    43140
atggacagat ggatgagtgg gtggatggat gggtgggcag atggatcaat ggataggtgg    43200
gtggatggat ggatggatgg ttgaatagat ggatgagtgg agggatggat ggatgaatgg    43260
atggatgtgt ggtgggtgg atgggtggat ggacggatga gtgagtggct ggatgggtgg    43320
gcagagggat gaatggatcc ctccattgag tgaatggatg ggtgagtgag tgtgtggatg    43380 gatgatgga tggatggatg gatgatgga tgggtggatg gatagatgtg tgggtggttg    43440
tatggttggt tagttggggg gtgggttgaa gcctccctcc aggctgattg aggttgccag    43500
tctccagggc ctgttctgct gaggcaccag gaaggaggcc ctcagagcca cattagaaa    43560 gtgggtggca ggagccgggc cctgaagggc atgtgccact cttgctgctg ggagttcacc    43620
cacgctgggt gggatcattg ttttggatta catacatgta gaagcgcatt ttgcactttt    43680
aacattaaca gcaataactt ggcctgtgtc tttccctccc tagcatgtcc tgaggcgacg    43740
```

-continued

```
tgagcataac aaaggacatg gaagaagatt ccagatgcca gaaaacctct gtcagacgcc    43800
cactggcccc agatctcatc ctgcctcatc ctgagtccca atcttccaag ggtgccagcc    43860
cctccgttca tctctgaaac ccagcatcct tttcagctgc ttgaaaacat tgtattttt    43920 tttttaacg atgcagtatt tgtgcgttcc agaaaagggc ccagctctga gcccctcacc    43980
cttccacact cacgaactct cagccgagga aggcaagaag cgcaggggt ggcccgcgtg    44040 gcgtcggtgg cctccgctcc tgctcgcagc ctctgtggtc agagctggat acaagattca    44100
agacccttct cttgcttgtc acccgctcca ggttggagcc acagacaccc accgccaccc    44160
cggctgggtc tgcgtccttt cctgtgcctt tccctccaga atgcggcctc agacctagaa    44220
gctcaacccc cctatgaggg ccacgtcctg gggtagctcc tgacctccga ccttatgtcc    44280
aaatttcaca cccatggttt ttcatttgac ccgccccctt ctcgctcata atgacaccca    44340
gctcctttga gaggatcaga gcccattgca caagaagagc cgctgccaac catccttgtc    44400
ctccgattgc aaaatgacac cccagtaatc tagaacattc tcaagcccct ttaactcaga    44460
tgtcaagcca ccgggcaaac cccgtcaata cctcccacca aggaatgaga tatgtggacc    44520
tcactgctcc cccaacccag cgtcaggctg ggacacgcca acgctgttcc gggttggaac    44580
agcagaggct cagaaactgg ctctgaaata ggcagaccta gcaagaggaa gatacagggt    44640 atcggcgtt tgagtgtttc agaagtcatt cgggaagata aatccagtgc gctggccgca    44700
gccacctgca ttcaaagctt ggaccagcgg gttcttgttc gggaggcaaa tttccctagg    44760
aaaaagaaga cagacttttc taatgtggtc caaatgcgga tcactggtca gatggactct    44820
agaagcactg agctccctgt ctctggaagt atttaagaaa aggctgggcc aggcacgatg    44880
gctcacgcct gtaatcccag actttgggag gccgaggcag gcggatcacc tgaggtgagg    44940
agtttgagaa cagcctggcc aacatggtga aacctcatct ctactaaaaa tacaaaaatt    45000
agccaggcgt ggtggcaggt gcctgtaatc ccagctactt gggaggctga ggcatgagaa    45060
tcacttaaac ctgagaggca gaggttacag tgagccaaga tcgtgccact gcattccagc    45120
ctgggcgaca gagcaagact ctgtctcaaa aaaataaaa aataatcagg gcacagtggc    45180
tcatgcctgt aatcccagca ctctgggagg ctgaggtggg tggatcacct gaggtcagga    45240
gttcaagacc agcctggtga acatggcgaa acccgtctc taataaaaat acaaaaatta    45300
gccgggcatg gtggtgcatg cctgtaatcc cagctactcg ggaggctgag gcaggagaac    45360
tgcttgaacc caggaggcag aggttgcagt gatccaagat catgccactg cactccagcc    45420
tgggcaacaa gagcaaaact ccgtctcaaa ataaaagaa aagaaaagaa tggacagtgt    45480
ttgcagagag ttgctcacga gtttccctct aatcctaaat gtcttcatgt ctatcagtct    45540
gagcagacgg tgagtagggc gggcacattc tccaggccct tcttcctagc tctgtggttg    45600
acctctcagc aagtgctatc caggctgggc caaccagacc cacaattaac tgagcctcag    45660
tgaaagcgtc cagtgcatct tgacctgaga cagcaaggaa ttgcatttgg ggttattcca    45720
acgatgatgg cagggaactg gtggtattta gtgctgaggg gcagtgatac agaaagattt    45780
gccctgtggg acagggtcct gcgcgagtcc catccccaaa agccagcagc tcctgccatg    45840
aggaagacgg ggtttctgag caggcttatg cctgcaggtt cctgtggagc caccggctgt    45900
gacgggacac ctctgggtct cagcattgcc ctggggaggc tgggacattt agggacatgg    45960
tagggtttta acatttgttt cccaaatgtc aaatcccggg cacaggggca agaccctgtc    46020
ccgaattccc accccagtga atggtgtcgc tgccaaagcc aacacaagat gacaaaagtg    46080
```

```
gctgggtacg gtggctcacg cctataatcc cagcactttg ggagaccgag acaggtggat    46140
cacctgaggt caggagttcg agaccaggct ggccaacatg gtgaaacccc atctctacta    46200
aaaatacaaa aattagctgg gtgtggtggc gcgcacctgt agtcccagct actcaggagg    46260
ctgaggtaga agaatagctg gaacccagga ggcagagatt gcagtcagcc gagattgcac    46320
cactgcactc cagcctggga gacagagcaa gactgactca aaagaaaaaa aatgacagaa    46380
gcctgattat cagactgccc ggaggagaca ggctccagca gatagatgcc agccaggccc    46440
agctgccacg atttgtccca ggtgaccaaa ggcacgcagc tccagcatga atcgttctaa    46500
cccaacagtg acaagaactg ctgggcctta accgtcatgg aagactgggg ccgcttccaa    46560
gtcacagaca ggagacgggg acaggaaaga actcattcca cccaatcgga cacctaataa    46620
ttgagtgtct acagcagcaa tcaagtgaca agtgaggccc tacctgaccc agaaggtgcc    46680
tgccggctaa acattctgcc cccaccagaa actccagggg gtccgcccgt tatgccgtgg    46740
cccacccacg cccctttgga tcaccagcag tcacagacaa caggcaggcg aaactgaaga    46800
ccccaactca gccccagcgg accctccaga gcaaagagg ccccggcga ggccacctgt     46860 cggcaggcat gccgaggtca aacagccggg gccaccgttc ccagctgggc cacgacctgc    46920
accgtccaca gatgggcttt gagatggatt tgtatcaggg tgggggtgt ggtttggcca     46980 aaatgcaatg gaccccgacc cctcctcgta aaaggatgtt gggtttccct ctggtgacac    47040
atgggatgcg tcataaaccc tcccccaaag tcctggtcag cagcccatcc ttccaacgat    47100
gagttttgcg gttttcaga acagaaatga tcactacgat tgacgacggt cgtgatgtta     47160
agacgtcgtc tccatgagct ttgggggggac ttttatgtgg aataaagaaa ctatcactg    47219
```

<210> SEQ ID NO 11
<211> LENGTH: 59884
<212> TYPE: DNA
<213> ORGANISM: Homo sapiens
<220> FEATURE:
<221> NAME/KEY: misc_feature
<222> LOCATION: (49102)..(49201)
<223> OTHER INFORMATION: n is a, c, g, or t
<220> FEATURE:
<221> NAME/KEY: misc_feature
<222> LOCATION: (55664)..(55763)
<223> OTHER INFORMATION: n is a, c, g, or t

<400> SEQUENCE: 11

```
cccaccatca ggggtcagtg ccctccacac tcgaatgttg ctgcccctg cccagtcggg       60 aaacttccca ggtctctgcc ttctcctcct ccagcaatcg gggattaacg cccctctgcc     120
cttcccctcc tcctgcccag ccagacaccc tcccaggtct gaattctctc cccctaccag     180
caatcggggt cagctccgct ctagctctcc ccctgtccag ccagacaccc tcccaggttt     240
ctgtcttctc tcttaccccc atcaggggcc aattcctcac ccctcgactg tggcttcctc     300
ctgcccagcc aggaaccctc gctgatctct gtttttctcct cccctacaag taatcggggg    360
tcagctaccc tctgtccatc cccctgcccg gccaggcacc ctcccaggtc tgtgtcttct    420 cctcccccg caatcggggg tcaatgcccc tctgcccttc cctcctcct gcccagccag       480 acaccctcct aggtctgtgt cttctcttcc cctaccagca atcagggtc agctcccctc     540 tgcccatccc cacccactcc ccggccaggc acctccaggg tctcctccct gcattgggtc    600
agttccgtcc cctcccctcc tcggtcagac cacccacccc ccgccgggt ctgtccctc      660 tcgctgccct cctcgtggcg ccccatcag gggctgaccc cccgacccc gcacaggccc      720 aggcccaaac ccaggccccc tcccacttca ggagcccct cccgctcccg ccgacagaca     780
```

-continued

```
ccgttggctg cagagacgtc tcagccggag ccccggagcc cgcatcccgc ccggtgccta    840
acctgaggcc gccccgcctg cttctcccgg cgccgcggct tccctcaggc cggggttcca    900
ggttggggct gggactgggg ccgggccggg cgcacgcggc gggagaaggg gtaggcgggg    960
tcccggccag gctgcagggg ccgggactgg cgggggctgg cgcggcgggg cagttacctg   1020
tactgcgggc cgccgccctg cgcgaagtcg aaatactgac tcgtcgccat cttggcgtct   1080
tccccgagcc tggcggaccc gcgacgtcac ccgccccgcc cccgagccgc gtgccgctcg   1140
cgcctggcca cgcgccccaa gctccgcccc ctgcgcgaag ccctcacctt ctcgcttcct   1200
tctcttaggc tagggagaca ccgccccgcg accacacctg ccccgaggcc cgcctccta   1260
cgcagagccc cgccctcctc ttaaccactc aaatgtggag gtctctgctc aagccccgcc   1320
catgctagaa gccctgcctc tttctcggag ccccacattc cctttaacca ctcagatgtg   1380
gtggtatctg atcaagtccc gcccatgcta caagccccgc ctcttactca gagccctgcc   1440
ttccctttac ccactcagat gtgatctctg ctcaaccccc acccatgcca caagccccgc   1500
cttttttggg aaccgtacct tcccctttaac cattcaggtg tggaggtctc tgctcaagcc   1560
ccacccatgc cacaagcccc gcctctttct cggagccccg ccttcccttt acctgctcag   1620
atatggtctc tgcacaagcc ctacctctgt ctccgagccc caccttctct ttaaccactc   1680
agatgtggag gtctctgctc aagccccacc accaccacag ccagctaatt tttaaatttt   1740
ttgtagagac agtgtcttgc tatgttgccc aggctgatgt tgaactcctg gcctcaaata   1800
atcttgcctt ggcctccaaa agtgctggga ttacagacgt gagccactgc atctagcctc   1860
agaatgactc ttcagaaggc ccccatggtc tctgcctcct gtgttcacaa cgtgatataa   1920
ataaatgata ggccgggcac agtggctcac gtctgtaatc ccaacatttt gagaggcgga   1980
ggcaggagga tcttgagccc taggactttg agactagcct gggcaacata gcaagaccct   2040
gtttctacaa ttttttttta attagctggt catggtggta catgcctgtg gtcccagcta   2100
ctcaggaggc taaggtggga ggatcacttg agcctgggct gtcaaggctg cagtgatctg   2160
tgactgtacc actgcactcc agagtgagac cctgtctcaa aaagagaaa agaaagaaag   2220
ggctgggcgt ggtggctcac gcctgtaatc ccagcacttt gggaaggcga ggtgggcagc   2280
tcacccaagg tcaggagttc aagagcagcc tagccaacat ggcaaaaccc tgtctctact   2340
aaaaatacaa aaaaaaaat tagccaggcg tggtggggca cacctgtaat cccagctact   2400
cgggaggctg aggcaggaga attacctaac ccaggaggtg gaggatgcag cgagccgaga   2460
tcacaccact gtactccagc ctgggcaaca gagcaataca ccgtctcaaa aaataaaaa   2520
aataaaaaat aaaaaaataa ataaataaat aataaaagag gagagggaga ggagcaggga   2580
gggagggaag ggaaggaaag aagagagaga gagagagaga gagaaagaat tgaatgaata   2640
aacaaataaa tggaggcaaa cagacaaatc tcttatgcag aagaattcct aatttgtgta   2700
gctacactgc gcttaaggag atagagagta actctacacc tcttgagtgt gggttgtgca   2760
tagtgacttc cttcccaaga ctgcagcctg aaggagggg gagggagagt cacttgacag   2820
tattgaaacc tgacaagcag cagcgtgttt ggcggtcccg cggatccgtc tcttgcttcc   2880
acagtgtttg gatggaacag atccgggaac tcacttccag cctccgacca cccgctgatt   2940
tcctctcttc ttgcaacctc caggagcatc ggctcagcca tctcctgctt ctcggaccaa   3000
ccaacgccgt ttttttggtt agctccttct tgccgaccaa ccatgagctc ccagattcgt   3060
cagaattatt ccaccgcggt ggaggcagcc gtcaaccgcc tggtcagttt gcacctgcgg   3120
```

```
gcctcctaca cctcctccct ctgcgggttt tttttttttt tttttttgctt gtttttttttt    3180
tgagacggag tctggctctg tcgcccaggc tggagtgcag tggtgcgatc tctgctcact      3240
gcaagctccg cctcctaggt tcacgccatt ctcccgcctc agcctcccga gtagctggga      3300
ctacaggcgc ccaccaccac gcctggctaa ttttttttgta ttttttagtag agacggggtt   3360
tcaccgtgtt agccaggatg gtctcgatct cccgacctca tgatccgcct gcctcggcct     3420
cccaaagtgc tgggattaca ggcgtgagcc atcgtctgcg cttctatttc gatcaccaag     3480
atgtggctcc ggaatgcggg gcttacttct tccatgaatt ggccaaggag aagcgcaagg     3540
gtgttgagcg tctcctgaag atgcaaaacc agcgtggtgg ccctgctgtc ttccaggaca    3600
tcctgaagcc aggtcaagat gagtgggggta aaccctggaa agccatggaa gccgccatgg   3660
cccccgggaa aaatctcaac cagagtcttt tggatcttca tgcactgggt tccgccccta    3720
cagaccccca tctctgtgac ttcctggaga gtcacttccg agatgaggaa gtgggctgca    3780
cgcggtggct cacacctgta atccctgcac tttgggagac cgaggcaggc agatcacctg    3840
aggtcaggag tttgagacca gcctggccaa catggcgaaa ctccagttct tctaaaaata    3900
caaaaattag ccgggcgtgg tgagctactc aagaggctga ggcatgagaa tcgcttgaac    3960
ccaagaggca ggggatgcag tgagccgaga tcacgctact gcactccagc ctgggaata    4020
gagtgaggct ctccaaaaaa aaagaagaa gaagatgggt gaccacctga ccaacctcca    4080
caggctggcc ggcccggaag ctgggggggcc cagaggctgg gctgcatgag tatctcttag  4140
aaaagccgac tctcaaacac ggctaggaac ctactgagcc cagcgacttc tgaagggccc    4200
cacgtaaagt aacggggctt ctgcctaagc cttttcctcc attcactagg cagctttttt    4260
gtttatttgt ttgttggttt gttttgtttt gttttgagaa ggaatctcgc tctgtcgctg    4320
gagtgcaata gcacaatttc agctcactgc aacctccgcc tccaggcttt tggcgatcct   4380
ccaacctcag cctcccgagt agctgggatt actggcatgc gccaccacac ccggctaatt   4440
tttgtatttt tagtagagac ggggtttcac catgttggcc aggctggtat caaactcctg    4500
agctcaggtg atccacccgc ctcggtctcc caaagtgctg ggattatagg cgtgagccac   4560
tgcgcctggc tttgttatag caccctgaac agactaagac gcccactttg aacactagat    4620
tccaaaaagc atcatagaag tcttgggctt ctgttagata ggcatggtgg caggtgcctg    4680
tggtcccagc tactcaggag gctgaggcgg gaggatcact tgagcccagg aggcagaggt   4740
tacagtgagc caagatctca ccactgcact ccagcctggg tgacagagcc agaccccgt     4800
ctcaaaacaa acaaacaaac aaaaaacata aaggggcct ggcgcagtgg ctcatgcctg    4860
taatcccagc actttgggag gctgaggcgg gcggatcacc tgaggtcacg agttcaagac    4920
gagcctggtc aacatggtga aaccctgtct ctactaaaaa atacaaaaat tagccaggca    4980
aggtggcggg tgactgtagt cccagctact cgggaggcca aggcaggaga attgcttgaa   5040
cctgggaggc agatgttgca gtgagccgag atcgcgccac tgcactccag cccaggtgac   5100
ggagtgagac tcagtctcaa aacaaaacaa acaaacaaa aaggaagtc ttgggtcttg     5160
ggcatctatg aacttttgct ttgctgaagt ctttcaaatc agttggcttt ttgacaatgg    5220
agtattacga gagcattaaa gtaagaagtg cattcagcag atacagggct actaattctt    5280
ggacaggctc catggagagc ccagggtgct gagggaagcc acatttggtg atttagcgga    5340
tggcactctt ccatctgtaa ctccatgacc atgtgtggcc accaggaatg gtctggtggg    5400
tctggccagt gcagctctcc ctgccatgcc ctggctaaag tccaacaagg taattaattg    5460
cacacggcct ctctccaagt ccctgccgtt ctaattaggt aatgaaggct gtgtctcttt    5520
```

```
acaaaggatc tgttgtagtg ttttctctgg gttgcatttt ttctattatt tactgcaagg    5580
attgtgctaa atgctttaca tgcaaaatgt gatctagttc ccacaacagc cttcagaagg    5640
ccgggcatgg tggcttacac ctgtaatccc agcactttgg gaggccgagg ttgggagttc    5700
aagaccagcc tggctaacat agtgaaaccc tgtctctatt aaaaatacaa aaaattagc     5760 tgggcgtggt ggtagttgcc tataatccca gctactcagg aggctgaggc aggagaactg    5820
cttgaacctg gagggcagag gttgcagtga gttgagatca caccactgca ctccagcctg    5880
ggtgaaagag tgaaactctg tctcaaaaca aaaaaaaac caaaaaaaaa aaaacagcc      5940 ttcagaagta gaaacaggca tagtggctca taccagtaac cccagctact cggaggcca    6000 aggcaggagg attgcttgag cccaggagtt tgagaccagt ctgggcaaca tagggagacc   6060
ccatctctac aaaatacaaa aattagctgg atgtggttgt gtgtgcctgt agtcctagcc    6120
acttaggagg ctgaggtggg aggatcgctt gagcccagga ggtggaggct gcagtgagcc    6180
ataagtgtac cactgcattc cagtctgggt gacacagcaa gacccagtct aaaaaaaaag    6240
aaagaaagaa aagaaaagaa aaagagggcc aggcgtggtg gctcacacct ataatcccag    6300
cactttggga ggccaaggca ggcagatcat gaggtcagga gatggagacc atcctggcta    6360
acacagtgaa accccgtctc tactaaaaat acaaaaaaat tagcaaggca tggtggcacc    6420
tgtagtccca gctactcggg aggctgaggc agaagaatgg catgaacccg ggaggcggag    6480
cttgcagtga gccgagattg caccactgca ctccagcctg gcgacacag caagactccg    6540 tcccccaaaa aaaaaaaaa aagaagtaga cacagtcgat tctcattaat tctgttctct    6600
aaagtcaata ccaagctcac taatactgac catcgctcct aagagaaaca cgaggttgag    6660
ttcctgtgag cctctagtca cagtgtttgc atcaaccatc aatacacgac ctcggccagt    6720
gcagtggctc acgcctgtaa tcccagcact ttgagaggat gaggagggcg gatcaactga    6780
ggtcaggagt tcgagacccg cctgaccaac atctctacta aaaatacaaa attgccagg    6840 agtggtggtg catgcctgta atctcagcta ctcaggaggc tgaggcagga gaatcacttt    6900
aacccaggac gtggaggttg cagtgagctg agattgcgtc attgcactcc aacctgggca    6960
ataagagcga aactccgtct caaaaaaaaa aaaaagaaa aaaagaaag ttcaaatgtc    7020 tagccaaccg ggattagttc agattgtgtg acccgacccc ggccaatggg gaagggcac    7080 aggggcagga cttgcctcag gaataaaggc tctcatgccc ctttgttcag gtgcgctctc    7140
atgacgactg gacaaagaaa aacacctctc tgcgcagaag taaaattgct ttgctaaaat    7200 cccttttgttt gtgtattcaa tcttcttagg attttgagcg ttattcccaa caaatagaca    7260
tggttgattc attcacattg aactcatagc acttttactc atatctgaag ttctctaaca    7320
cactgctttt cttcttggag cttctttttt tttttttttt gagatggagt cttgctctgt    7380
tgcccaggcc agactgaagt ggcgcgatct tggctcactg caagctccgc ctcccgggtt    7440
cacgccattc tcctgcctca gcctcccgag tagctgggac cacaggcgcc cgccaccacg    7500
cccggctaat ttttttgtatt tttagtagag acggggtatt gccgtgttag ccaggctggt    7560
ctcgatgtcc tgaccttgtg atccgcccac ctcagcctcc caaagtgctg ggattacagg    7620
cgtgagccac cgcgcccggc ctctccttgg agctttcttg cacttaggaa gactagacag    7680
tgcttcagca tgaagcttgg aagtcatttt attttatgga tttatttatt tattttgag    7740 acagagtctt gctctttcac ccaggctgga gtgcagtggc gcagtctcag ctcactgcaa    7800
cctccgcctc cctggttcaa gcaattctcc tgcctcagcc tctgaatag ctgggattgc    7860
```

-continued

```
aggcgcgtgc caccacgccc ggctaatttt tgtatttta gtacagacgg ggtttcacca    7920
tgttggccag gctggtcttg aacttctgac ctcctgacca cccactttgg cctcccaaag    7980
tgctgggatt atacgcgtga gccacattgc ctggcctgta tcaagcattc ttttagggca    8040
gaatttttct tgctcagtac cgtggacatt gggaccagat tattctctgg ggcggagcca    8100
tcctgggcac tgcagggtgc tgagcagcgt ccctggcccc catccactcc ataacaggag    8160
tatcccccag tcgcaacaaa cacaagtgtc cccagaaatc gtccggtgtc cgctgcgggc    8220
aggatcacca ccccccagg tgacagccac tggtgtaggg gttaaagata cagggtgaca    8280
ggccgggatt acacctgtaa tcccagcact gagcccagca ctcctggcct caagtgatcc    8340
acccgcctca gactcccaaa gtgctgggat tacaggtgtg agccactgca cccagcccac    8400
aagaaatt tctacaagct caccttcaga aagtttcaa gatcctacaa aatctagccc    8460
ttttgtgcat ttccaaacga attcctcagg gatggccggc agaataatgg cccctaaaga    8520
tatccacacc cactgggtgt ggtatgtttg cctgggaaaa atagtgagac cccatctcta    8580
caaaaaattg tcaaattaac caagtgtgat ggcatacacc tgtagtccca gctgccaggg    8640
aggctgagat aggaggatca cttgagccca ggaggttgag gctgcagtga gccatgatca    8700
cacccccgca ctccagcctg ggctacagag caagaacctg tctcaaaaa attaaattaa    8760
attaaatttt ttccatttta aaattaaaat aaaacgaaat gaaaacagac agaggccagc    8820
tgcagtggct cacacctgtg atcacagcac tttgggaggc caaggtaagc ggatcacctg    8880
aggtcaggag tttgagacca gcctggccaa catggtgaaa ccccgtctct actaaaaata    8940
caaaaattag cctggcgtgg tggtgggtgc ctgtaatccc agctactcgg gaggctgagg    9000
cagaaaaatc gcctgaacct gggaggtaga ggttgcagtg agccgagatc gcaccagcct    9060
gggtgacaga gcaagcctct gtctcaaagg gaaaaaaaaa cagggaacca agcttaggtc    9120
acacgctgtg gctcctcggt ggtggctgta gcaccatgga cagctcccag gctttggtgg    9180
actggggaga agctgttgct ctttaaatgc cagtctgggc aggcctgtct gtccagaata    9240
tgccttcctc cctctttttt attcatctaa ctccactcac tcctcagggg tctcactcat    9300
gcagtcgcca cctctgtgcc ccaccaggaa acctccccaa cggtccccca acctgcacca    9360
ctccaaagat gtctctagat cagcccgac tctgttgtcc acctgtttct ctcaactgaa    9420
tgggaattat ttatttttt ttttttgag atggagtctc actctgtcac cccacctgga    9480
atgcagtggc tcaatctggg ctcactgcaa cctccacctc ccgggttcaa gcgattctcc    9540
tgcctcagtc tcccgagtag ctggaattac aggcgcccac cgccacgtct gaccaattt    9600
tgtattttta gtagaggcgg ggtttcacca tgttgtccag gctggtctca acccccaac    9660
ctcaagttat ctgcccgcct cagcctccca agtgctgag attacaggtg tgagcggcct    9720
cccaaagtgc tgggattaca tgcctggcct caactgaatg gtcattctaa gagaattccc    9780
aatcctgcac acaaaacag cataaattaa ctgaattagg gaagcacgc ctctgccagc    9840
cgtgagctgg gaagaagcag atacctcaga ggcagggagc gcaggcgggt gatgatgaga    9900
ggggccacag ccgcagcccc acgcagggga gcccaccact aaccctgcac ccccacccct    9960
gcacaaaaga gctggtgggc actagccata tcgccttgca accttcctcg gatgcagaat   10020
ccactccttc aggcatcctc ttcctccaat gctctgaagg cctggggagc ctgagagatg   10080
cccgctgcac ccaggcaggg ctcgcctttg tttgccagta atgggaatta ctcatatctt   10140
gtgcccagtg cccagcacag ggactcatcg aatccacccc tcagttaaca caagtgtctc   10200
ttacaagacc tccattttct ccagccagga gatgggaagt cccaaccttg tgctaaagtc   10260
```

```
tctgggcct  ctgcttcccc  atcagggctt  tctgcctctg  ctgtgggcag  gttacccttta  10320 tgcctcggaa  gagtgcagac  ctccatgcag  cgggtgaggc  tgccagccta  ggtggggtgt  10380
cattgaatgt  catgaaggga  gccagccttc  atgcactctg  cctgcgtctc  ctgaacagct  10440
ttggaccagg  agttgctacc  ttgtgcggag  aacgtgtggt  gcataagaac  aaccgagcct  10500
ctgctcttcg  aaaatgtata  ttctggccag  gtgcggtggc  tcacgcctgt  aatcccaaca  10560
ctttgggagg  ccaaggtggg  caggttgcct  gaggtcagga  gtttaagacc  agcctggcca  10620
acatggtgaa  accccgtttc  taccaaaaat  aaaaaaaata  gctgggtgtg  gtggtgcatg  10680
cctgtagtcc  cagatgcttg  ggaggctgag  gcatgagaat  cgcttgaacc  tgagaggagg  10740
aggaggttgc  ggtgagctga  gatcacacca  ctgcactcca  gcctgggaaa  cagagcaagt  10800
ctctgtctca  aaacaaaaca  aaacaaaaca  aacccagta   tattctaata  aggaggagca  10860
gagaatcaac  aacaacaaca  aaaagtgta   aataatttca  attaatagta  agtgctgtgg  10920
gtcaggcacg  gtggctcaca  cctataatcc  caacatttt   cgaggctgag  atgagaggct  10980
cacttgagcc  caagaattca  agaccagcct  gggcaataga  gagatacct   atttctacaa  11040 aaattacaca  gattagcagg  gcgtggtggt  aggagcctgt  agtctcaacc  actggagaga  11100
aagaggtgta  aggatcacct  gagcccggga  gttcaagact  gcagcgagct  gtgattgtgc  11160
cattgcactc  cagcctggat  gacagggaaa  actcctgttt  cttaaaaaaa  taagtaaata  11220
aaataaacat  taaaaacagc  aatagcaaga  aatacatata  ggccgagcac  agtgattcgc  11280
acctctaatc  ccagcacttt  gggaggccaa  ggtgggcgga  tcacctgaag  tcaggagttc  11340
gagaccagcc  tggccaacat  gttgaaaccc  cgcctctact  aaaaatacaa  aaaaaaatt   11400 agccaggtgt  ggtggtgtgt  gcctgtaatc  ccagctactt  gggaggctga  gggaggagaa  11460
ccacttgaac  ctgggagtcg  gaggttgcag  tgagccaaga  tcgcaccact  gtactccagc  11520
ctggcaacag  agcgagactc  cacctaaaaa  aaaaaaaaa   agaaagaaag  aaagaaagaa  11580
agaaagaaag  aaagaaagaa  agaaagaaag  aaagaaagag  aaagaaacac  atagggagct  11640
tttcttgtgc  cccagcactg  tgtttagtgc  tgtctatgca  ttatctcata  atgtggaaaa  11700
gccatagcgg  ctccatttca  cagatgagaa  aaactgaggc  ccgcaggtga  gatcactcat  11760
gcccactggt  ctgccagctg  gggagtggct  gggctagagt  tcaaacccac  ttccagtccg  11820
actgcacggc  ctgcactctc  caccctacca  tcttccacag  tctccttgaa  ttcctccagg  11880
gcgaggccac  gccagcgcac  aactgcaggg  ggcgccgttc  ccacagcagc  cctgcaaagt  11940
gagtgtgcct  gagaaacttc  cgcctcccct  gcacccagcc  ctgtttaggg  cacgaggctg  12000
aatcaatggt  aagtgaccat  ctaatggacc  cacaacacgg  tgacctgggg  acagtcattt  12060
cttctttttt  tttttttttt  ctttgagaca  gagtctccct  ctgccgccca  ggctgcagtg  12120
cagtggcgcc  atctcggctc  actgcaacct  ccgcctccca  ggttcaagcg  attcctctgc  12180
ctcagcctcc  cgagtagctg  ggattacagg  cgcacgccac  cacgcctggc  taattttgt   12240 attttcagta  gaaacggggt  ttcaccatgt  tggccaggct  ggtatcgaac  tcctgacttc  12300
aggtgatcct  ccctcctcgg  cctccgaaag  tgctgggatt  acaggcgtga  gccatggcat  12360
ccgacctggg  gacagtcatt  tctttgcctg  cacagacttt  tgggggatg   ccaccccctca 12420 cccctgctcc  ctttgcaagg  agaagtgcca  agaagacctt  tcccaactcc  cccacccccc  12480
attctctaag  gaatgaggcc  atcttgccat  ttatttattt  atttgtccgt  tgttttgttt  12540
ttaaatctct  gatgcgccat  cagaaaatta  tttctgcctc  tgccctggc   gtggctttcg  12600
```

```
gagatgcttg tctgtcagcc aatggggagg atcggattct ggcagggggc tgtgcttttc    12660
cgtcaggccg ccaccccca cccctcctc cctgcacaca aaagcagcat aaattaaccg      12720
tcttcgggaa gccgagcctc tgccagccct gagctgggaa gaagcagcta cctcggaggc    12780
agggcgcgca ggcgggcggc gatgagaggg ggcgcagccg cagcccgcg ctggggagcc     12840 caccgctaac cctgcacccc acccacccct gcacaaaaga gctggcgggc gctggccacg    12900
tcgccctggg tgaccttcct cggatgcaga atccgcccct gcgagcatcc tcttcctcct    12960
aggctctgaa ggcccgggga gcgtgagcga tgcccagctg cacccgggca gggctcgcct    13020
ttgtttgcca gtaaggagga gaggctgtct cagctgcaga ggtgagtgcg cgcatctccc    13080
cttctcccag gataaaccgt ctccctggaa ggtttatccg gcagccttg ccgcctctaa     13140 atccctttcc agcagatggg gcgggtggga gcagagagcc acggtcttgt gactccgtga    13200
aggccctcac atccctgttc ccggtaccag ggaaaaccgt tccctgagct gcgcccagca    13260
acacagttta ccttccgcgc gcaccgttcc cctctaagtg caccattttc aggacacgct    13320
gagagctcgg gcggatgaaa acctcagctt ctctctggga cgctgaaata gacccatcct    13380
agccctatgt atttcctatt tataacgcta ggaaggccac cagccgacga tttcgggaaa    13440
aaaaaaaaaa aaaatctaa gtgtgtcgat aaaggctgtc ctgtggggtg gggaggaagg     13500
gggtggttta tggtttaaga cacagatgcc tcctccttat tggaactcgt atgtgatttg    13560
ttaataatca gacatcaggg ctcaaatgag cgcttcactc ccgttccttg atgtcactgt    13620
cttcttttgg ccgtccccaa atgcgaagcc aggatctgag tgcaggagtg tccgggccc    13680 actgaggacc caccccaccc catccttaga agactgtgga gtcaacgcct gtggctgcag    13740
ctggcagggg gtggggtcg gggcggggc tggtgggagt gttcctgggg gctgaggtca      13800
cacccagctc agtataagga agggagaggc gaagaccct tcctccggag agcaaatgcg     13860
tttctactgc cgaggagaac ttaccctcgc gggaagggcc tggctggctg ctgccaccgc    13920
cccccccccg accccatagc atccaggagg gattttttt ttttccatgc tgcgtgttac     13980
tgtccctcct ccaagcatga atgacgcat tgaggacaga gaatcgagtg agaaacgctc     14040
accctgtacg ggggagggtc tagttttagc cgtcccctcc ccccacttcc tcatctggct    14100
gaggctgcct ctgggtcctt ccttgctaag ccacagtccc ctgtccccga tgcaaacccg    14160
atatctatgc tgggggctg caggtaacct actccacaga gaggcagcct ggatgccatg     14220
agagttgggg gccttagatg cttcatgtat ttggtttttt tgagacaggg tcttgctatc    14280
ttgcccgggc tggtcttaac ctcctgtgct caggcgatcc tcgcaaagtg ctgggattac    14340
acgtgtgagc cactgccccc agccagatgc tttatctttt atttatttt ttgaagtagg     14400 gtctctgttg ctcaggctgg aaagcagtgg catgatcata gctcactgca gtctcgacct    14460
cctggtctca gcgatcctc caacttcagc ctcctgaata gctgggactt caggcaccag    14520
gcacccatca ccatgtttgg ttaatttttg tattttttt tttttaagag atggggactt     14580
gctatgttgc ccaggctggt cttgaccttc caggctcaag cgatcctcct atctcagcct    14640
cccaaagtgc tgggattac acgtgtgagc cactgccccc agccagatgc cttatttat     14700 tttattttat tttctgaaat agaacctcac tctgttgctc aggctggaat gtggtggcac    14760
aatcatacct cactgcagcc tccacctcct gggctcaggc aatcctccca cctcagcctc    14820
ctgaacagct gtgacttcag gcacccacca aatttaatta attttttgttt ttgttttttgc 14880 ttttcgtaga gatggtgtct tgctatgttg cccaggctgg tcttgacctt ctgggctcaa    14940
tcctcccacc tcagcctcct gaatagctaa gacctcaggc acccaccatt gtgcttggtt    15000
```

```
agtttttgta ttttttttttt gagagatggg gtcttgctgt gttgcccagg ctggtctcga    15060
acccctggtc tcaagtgatc tgcccaaagt gctggaattc caggcatgca ccactgcacc    15120
cagcccctag acgctttaaa aagtggatct agtggcccgg cagggtggct cacacctgta    15180
atcccagcac tttgggaggc aggtggatca tgaggtcagg agttcgagac cagcctggcc    15240
aatatagtga aacccatct ctactaaaaa tacaaaaatt agctgacgt ggtggcacgc      15300 gcctgtagtc caagctactc aagaggtgga ggttgcagtg agccgagatc gcaccactgc    15360
actctagcct gggcgacaga gcgagactct gtctcaaaaa aaaatgaca acaaaaaaag     15420 tggatctagc tactcggaag ctgttgagag acagacagag gtaatggaag acagagtgt    15480 acaatactct ataatgactg ccggacacag gcctgaaatc ctttcgcaaa cacgggaatg    15540
cacacagaaa tgactattgc ctttaagaca aggtttctcc accttggatc tatggatatt    15600
tgggacccag tcattcttgg tcatgggcgg ccatcctggg cactgtaagg tgctgagcag    15660 caccctggc ctgcccaggg ggcactcctt cccctcagtt gtgacaaaag tgcctctaga    15720
caatgccaag tgtccccttg cagcagggga ggcagaattg tccacaggtg caaagcactg    15780
gtttcaaagc ccaaaacaga tggggttggt tgagtcataa gatgctggta tgttatgtcc    15840
aaaaggtatc ttagaggtca tctctaattc aactcttttg tttacagaaa gggaaactga    15900
gacccagaga gggagatggt ctgagagtct gccatgcccc agagcagacc acaactcagt    15960
ctcacctggc agctctgatc ctggccccca cccagactgc tccccctgc cctgcccctg     16020 cccctgcccc cagtgagctc ctcagaacaa gaaaaacaaa actggtgtgg ggggtggggc    16080
ggcacagtgg ctcacacctg taatcccagc gctctgggag gctgaggcaa gaggatcacc    16140
tgagcccgaa agttcaagac cagcctgggt gacataccaa gatcagagaa attagccagg    16200
catgatggca cacactcgtg gtcccagata cttgggaggc tgaggcagga ggatcgcttg    16260
agcccaggag ttggaggctg tagtgagctg ggatcacacc actgcactcc agcctgggcg    16320
acagagcaag accccgtctc taaataaata aataaataaa taaagtggca ttttgtggta    16380
gtaaagatga gggtctcctt tctaaccccca gtctctttcc acactgcctt agtgagccct    16440
ggagtcagaa agtcactagg acttgcttga gggaggacag agaggcagga caggtggcct    16500
ggtacatatg gcagatagcg atgggttaga gcctactgga ttctctttga acttggcatt    16560
cccagcacgg aagctgaagt atatcagcca ttcacacttt agtatgaatg actgtttgga    16620
tttcttgctt tctagttgag gtccaaggca caagagggag ggtaagtcta tctgggtcat    16680
ggctcaccct ggagaaggta gatttcgaag tttccaaggg agcaggactt gtatctgaag    16740
gctcagcctc tcgcccacgt tcaaactctg aaccccactg tgcatcctaa gctctctgtg    16800
cctctgtttt ctcatctgta aaacagggga acctcatggg gctcggtgat ggttcaataa    16860
gaagtgctgg ccgggcacag tggtttaccc ttgtaatctc agcgcttaga gaggccgagg    16920
caggaggatt gcttgagccc aagagtttga gaccaccctg gccaacatag caagacccaa    16980
tctcttaaaa aaagatttta aaaaattacc caggcatgat ggtacacacc tgtggtcaca    17040
gctactggtg gggggctgag gcaggaggat tgcttaagcc caggagttca aggctgccat    17100
gagccatgat tgtgccctg cactccagcc caggcaacag agcaagatca tgttttttt     17160 tttaaaaaaa aaaaaaaaaa aaaaaaaaac agccaagctc agtggctcac ccctgtaatc    17220
ccagcacttt gggaggctga ggcgggtaga ccgcttgagc tcaggagttt gagaccagcc    17280
tggccaacac agtgaaaccc cgtctctatt aaaaatacaa aaattagccg ggtgtgatgg    17340
```

```
ctcaagcctg taatcccagc actttgggag gccaaggcag gaggatcacc tgaggtcagg    17400
agttcgagac cagcctggcc aacatggcga aaccctgtct ctactaaaaa tacaagaatt    17460
aaccaggcgt ggtgatgggt gcctgtaacc ccagctactt gggaggctga ggcgggagaa    17520
tcgcttgagc ctggaaggtg gatgttgcag tgagctgaga tggcaccatt gcactacagc    17580
ctgggcaaca gagcaagact ccgtctcaaa aagaagaag aagaaggaga aggagagagg     17640
agaggagaaa ggagagaggg ggaggggaag ggggaggggg agacggaggg ggagtgggag    17700
ggggaagagc tgcatggggt agacgattgt cattaggact attgtccagt aaaacccatt    17760
cctctgcggc ttcctttcag gggtcatccc tgcttcaagc cagtgcctct tcccagctcc    17820
catggggacc accgaagcca cgctccggat ggaaaacgtg gacgtgaagg aggaatggca    17880
ggacgaagat cttcccaggt aggacttcca catccctgag tcaaccgttg ggggagcagg    17940
tgtctctccc aggtgggaca caggagcggc ccgggtctct ctctaagtgg gaaccgcccg    18000
gggctggcct ggttccatct ccgcgtcctc ctctcccgca cactctggga ggcctgaggc    18060
cctgtgtgcg agtcttctct gtggcctcac agtggggtag tcctggccag gcacataatg    18120
ggtatttgct caatgattta agattcattt ctgtcttccc tgccccaaag ctccaaagga    18180
ccccccaccc ctacaccatt ttaagagttc ttaacattct ggctgggcgc ggcggttcac    18240
gcctgtaatc ccagcacttt gggaggccga ggtgggcgga tcacttgagg tcaggagttc    18300
gagaccagcc tggccaacat ggcaaaaccg cgtctctact aaaactacaa aaattagctg    18360
ggcatgccgg gcgcagtgac tcatgcctgt aatcccagca ctttgggagg ccgaggcggg    18420
cggatcatga ggtcagcaga tggaaactat cctggctaac atggtgaaac tccatctcta    18480
ctaaaaatac aaaaattagc cgggtgtgtg gcaggcgcct gtagtcccag ctactcggga    18540
ggctgaggca ggagaatggc gtgaacccag gaggcggagc ttgcagtgag ccgagatcgc    18600
gccactgcac tccagcctgg gcgacaggtg agactccatc tcaaaagaaa aaaaaaaaa     18660 ttagctgggt atggtgtcat gcgcctataa ttccagctac tcgggaggct gaggcaccat    18720
ggtgatttat tagcagcctt taggagacac ttacctcccc taacatgctg aactttttt     18780 tttttttttt tgagtctcac tctgtcccac aggctggagt gcagtggcac gatctcaggt    18840
cactgcaacc tccaggtcct gggttccagt gattctcctt cctcatgccc ccgagtagct    18900
tggattacag gcacccgcca ccacatctgg ctgattttc tattttagt agagaccgga     18960 tttcaccatg ttggccaggc cagtctcgaa ctccgaaagt gcttggattc caggcaagag    19020
ccaccgcgcc cggcccctac gctgaacatt ttgcaggac atcttgtcta cactctgtct     19080
ccccaccaca cggagcgcca caagagcagg ggtctttgtt tagctcactg ctgtatccca    19140
acctaaggat agtgcctggc atacagtcgg cgcttaacaa atattgggtg acaggtgctg    19200
atcactggtc agaataagaa atcacagggg ctgggcacgg tggctcacgc ctatgatccc    19260
agcacttaca gaggctcagg ctggggggat tgatagagct caagagttcg aaaccagcct    19320
gggcaagata gtgagacccc atttctacca aaaaaaaaa aattagctgg gcatggtggt    19380
gtgcacctgc agtcttagct acttggcagg ctgagacagg aggatccctt gagcccagaa    19440
ggcagaggtt gcagcgagcc atgattgcag ccctgcactc cagtctgggt gacagagcga    19500
gactctgtct ctattttatt ttatttttt tattttattt atttatttat ttattttga    19560 gacagagtgt cgctttgtcg cccaggctgg agtgcagtgg cgcgatcttg gctcactgca    19620
agctccgcct cccgggttca cgccattctc ctgcctcagc ctcccgagta gctgggacta    19680
cgggcacccg ccaccacgcc cggctaattt tttgtatttt tagtagagac ggggtttcac    19740
```

```
catgttagcc aggatggtct cgatcgtctg acctcgtgat ccgcccacct cggcctccca   19800
aagtgctggg attacaggcg tgagccatcg cgccctacca cctgtctcta tttaaaaaga   19860
gaggaaaaaa aaaaaaaagg ccggtcgctg tggctcaggt gtgtgtaatc ccagcacttt   19920
gggaggccaa ggtgggcaga tcacaaggtc aggaatttga ccagcctg ccgacatag    19980 tgaaaccctg tctctactaa aaataaaaat taaaaaaat tagctgggca tggtggtgca   20040
cgcctgtaat ccccagtact cgggaggctg aggcaggaga atcccttgaa cccgggaggc   20100
agaggttgca gtgagccgag atgtgccacc gcactccagc ccgggtgaca gtgtgagact   20160
ccgtctcaaa aaaaaaaaa tactacatgg aaaggaagct gtgcgaattt gctgttgaga   20220
cgtgtgactc tgatttgctg gctaaagata gctgctcatc cctcttccct ttcagaacca   20280
ggaattcatc catcccccaa acacaatgcc caagggtcag ttatagaaac tattgggtga   20340
ggttcagtca aaaagaccag gtgtgttccg cctgaaaaag agaattggaa agaatctcc   20400 aggccgcgca cagtggctca cgtctgcagt cccaacagtt gggaggccg aggcgggcaa    20460 atcacttgag gtcaggagtt cgaggccagc ctggacaaca tggtgaaacc ccgtctctac   20520
taaaaataca aaattagtc gggcgtggtg gtgggcacct gtaatcccag ctactcagga   20580
ggctgaggca ggaaaactgc tggaactcgg gaggcgaagg ttgcagtgag ccgagatcgc   20640
gccactggac tccagcccgg gcagtagagt gagtgagagt gtctcaaaaa aacagaatct   20700
ccagttccag gaaatttca atctgagagg gttccggagg gcagaacgag gccaaaagaa   20760
cgaacttaaa agagaatggg gtttgaagga gatacagaag aatgccttga agtaatcggt   20820
ctccttcaaa atgagtcagg ctggtgtggg aggccgagag cttccttccc attcatgtcc   20880
aggcagaagg aggactgttg aagacggcat cttgatattc aagaacttca gccctctcct   20940
gaatccagtc attgccaggc ctctaaggcc catgcacctg tctgtgtttc tttgcagcag   21000
gaggtccctg ttctcagaat agccgagaat cagagaatca cggctgggag cggaggctga   21060
tgtctgtaat cccagctctt tgggaggcca aggcgggagg atcgcttgag cccaggagtt   21120
tgagattagc ctgggcaaca tagcaagacc tcgtctctta aaaaacaaa aaacaaacaa   21180 aaactggctg ggcctagtgg ctcacaccta taatcctagc actttgggaa gccaaggctg   21240
gcagatcacc tgaggtcagg agtttgagac cagcctgacc aacatggaga acccccgtct   21300
ctactaaaaa tacaaaatta gccgggcgtg gtggcccatg cctgtaatac cagctactcg   21360
ggaagctgag gaaggagaat cgcttgaacg cgggaggcgg aggttgcagt gagccaagat   21420
cgcaccactg aactccagcc tgggcgacag agtgagactc cgtctcaaaa taaataaata   21480 aaataaaaa ataaaaaaaa attagtcagg tatgctggtg tgcacctgta gtttcagcta    21540
ctcaggaggc tgaggcagga ggattgtttg gacttggac atcgcagcag tgagctatga   21600
tcacaccacc gcactccagc ctggacaaca gagcaagact gcatatctaa gaaaaataat   21660
aataatttta aaataatgtc atttcaagca gcacagcata aacaaaggcg cataagcttt   21720
ggaatcggac gcccatggtt caaatcccaa ttccccagca ggtttgctct gccacctggg   21780
ctacctcttt gggcatctca gtgcctctgt tttctgatct gtaaaatagg acaataatct   21840
ctcgcgcacc aggtggtcat gaatttttga taaaacagcc gagatgggct gtgcaaatgg   21900
cgaaggcagc acaaataaat aatcatctcc agcgttatta ctattattag cttagctccc   21960
tttcccccta ctgatttttt ttatttctt tactttctt ttctttttt tttttgaga    22020 cagagtctcg ctctgtcacc caggctgggg tgcagtggcg ccatctcagc tcactgcaac   22080
```

```
ctccacctcc tgggttcaag tgattctcct gcttcagcct cccaagtagc tggattacag    22140
gcatctgcca ccacgcccag ctcatctttg tatttttagt agagacgagg tttcaccgtg    22200
ttggccaggc tggtctcgaa ctctcaacct caggtgatct gcccacctcc caaagtgcta    22260
ggattacagg tgtgagccat tgggcccagc tccacctata attttttttt tttttttttt    22320
tttttttttt tttgcagaca aagtctcact ctgtcaccta agctggagtg cagtggcgcg    22380
agttcggctc actgcaacct ccacctcccg ggttcaagca attctcccac ctcagcctcc    22440
cgagtagctg ggattacagg cacacaccac cacacccagc taattttttgt attttttggta   22500 gagacggggt ttcaccatgt tggccaggct ggtctcgaac tcccaacctc aagtgatccg    22560
cctacctcgg tctcccaaag tgctgggatt acaggcgcaa gccaccacac ccggcctcca    22620
ccgataattt aaaagctctc catctcaccc aagccttctt gagacaaaaa ccaaggccga    22680
gcgcacctgc aaatgcaagc tggaggccct ttctggaagg cgcgaggcca gcgggagcgg    22740
gaggagggtg tgtttctggt ggatttctta cagctgcaag gcttctcgcc cacccgctgc    22800
agcagctttg tgtttgcagg acagtggcct cgctgtgcca gcctggcccc cacgagctac    22860
gcctttgcca acaggacact tcctccacga ggcttctgtc ttcctcgtct ctggaagaac    22920
tgagtcggct cctcggtgca ggtccagctg cggccacaca taaccacctc tgtctgccgc    22980
aaaacagctc acaattctgt ttcttccagc ccagccatcc cctcccctgg ggactgcaga    23040
agtggtcttt gtactgccct taagggtgtc agacagagcc ctgcatggcc tctgcccttc    23100
tagcactttt tttttttttt ttggagacag agtctcagtg tatcacccag gctggagtgc    23160
agtggtgcaa cctcagctca ctgcaacctc cacttcctgg tttcgagcaa ttctcttgcc    23220
tcagcctccc aagtagctgg gattacaggt acgcaccacc atgcctggct cattttttgta   23280 ttttcgttag agacagggtt tcaccatgtt ggccaggctg gtctcgaact cctaacctca    23340
agtgattcgc ctgcctcggc ctcccaaagt gctgggatta caggtgtgag ccacgcgccc    23400
ggcctccttc tagcattttc cttcactctc acccttctgc agcctactac ggagctagag    23460
ctgaaggcag cccggagatt gctgcctcaa tttctccatt cattcattct gatgctatgc    23520
gccaactgta taccagtccc ttatagcctc acaacccaat acaaggtggc agctgggttc    23580
atggcacttc tgaccaggcc agggagggaa ggggagctgt gattcttggc tgtgaagggt    23640
gaggagggat gagccgggga aggaagtggg gtgtaggggc cccacattcc aagcagagag    23700
ggcagcatgt gcaaaggctc tgggctcagt ggaagcaggt tgaggactg gggaaggctg    23760 cgtgggaaa ctgaggactt gggggaggag cttacccagg gcatcctagc caaggagggt    23820
cagatgcagg gtgagctgcc ccatagctcc ctctactctc ttcccctcac agctgagtgg    23880
ctgccagttt tgtttgcttg cttgtaactt tttctttgtt tgttttgggt tttctggggg    23940 gtttttattta tttatttatt tgaaacagag tctcgctgca acgcccaggc tggaatgcaa    24000
tgacgtgacc tcggctcgct gcaacctcca cttcccaggt tccagcaatt ctcctgcctc    24060
agcctcccaa atagctgagt ttacaggcgc ccaccaccac gcccagctaa tttttgtatt    24120
tttagcagag atggggtttc accatattgg tcaggctggt ctcgaactac tgacctcaag    24180
tgatccaccc gcctcagctt cccaaagtgc tgggattaca ggcgtgagcc accatgccca    24240
gctgcttgta acttttttaat ttttttttttt tttccgacg gggtcttgct ctgtcaccca    24300
ggctggagtg cagtggtgcg atcatagctc actacagcct ccacatccca ggctgaggcg    24360
atcctcccac tgcagccccc tgaatacctg ggaccacagg catatgccac cacacccagc    24420
tatgttttat tttctgtaga gacagggtct cactgtgttg cccaggttgg tctcaaactc    24480
```

-continued

```
ctgggttcaa atgatcctcc cacctcagcc tcccaaaatg ctgggattac aggcatgagc    24540
cactgcgcct ggcctatttg atatacttcc aaacttggaa aaaaattaca agaatgatat    24600
aaagaatatc tgcatacctt tagtaggatt atacaattgt taacattttg ctccttttat    24660
atcaaagtca gccctcaggg ctgggtgcgg tgactcacat ctgtaatccc agcactttgg    24720
gaggccaagg caggtggatc acctgaggtc gggagttcaa gaccagccta ggccaacatg    24780
gtgaaacccc gtctctacta aaatacaaa aatcaactgg gtgtggtggc gggcacctgt    24840
aatcccagct actggggagg ctgaagcagg agaattgctt aaacccagga ggcagaagtt    24900
gcaatgagcc cagattgtgc cgccacactc tagcctgagc aacacagcaa gactctgtct    24960
ccaaaaaaaa aaatttaccc tcaattgtac cgataatgtc ccatgtccct atttagctaa    25020
tgcccctgcc ccaaaccctg gtccaagac ccaatctggg accactcatt gcatcaggtt     25080
gagtatactg ggttgtgtgt ttactggggt atgtgtctca ccaggcactg ggacttaaac    25140
ttatctcttt taggggaaca cgatccaacc cacctcagca ggacgaagcc acgctgtgca    25200
tcttgcatgt gggggggacc cccactttt tttttttttt tttttgagac ggagacttgc     25260
tctgtcgccc aggctggagt gcagtagcat gatctcagct cactgcaacc tccgcctcct    25320
gggttcaagc gactctcctg cctcagcctc ccaagtagct gtagctggga ccacaggcat    25380
gtgccaccat gccaggctaa ttttagtatt tttagtagag acgggtttc accatgttgg     25440 ccaggctggt cttgatcgct tgaccttatg atccacctgc ctcggcctcg caaagtgctg    25500
ggattacagg tgtgagccac catgcccggc taggatttcc acttttttacc tggattgccc    25560 atcatggact ttgagagccg gctctgcaga gggctaagtg gatatattat accccagggc    25620
cacggagggg atctccaagt ctggagagtc tgcggttctc ctggagcttg cggaagtaac    25680
aggatctcac ctgaccttgg aaactgcagc tccatgaaca ggcggggaga gcttgctcca    25740
cccatgttcc agagcagtgg gtcttccttc agggagcctg gagccctgcc aggtcggctt    25800
ctccagttct gcatgatctt aaaccttttcc tgaacatcca ctgcaactgg cagctcagcc    25860
tcaggaccct atcccatccc cgaggcactg cctctccctg ccctccctc cctaccctcc     25920 atcctccaac cactccctcc tccccactg ctctctctgc gccaggcacc ctgagtctgc     25980
tttctgatct gcccttgaac ttggcaagct tattccagtc ccggagcctg ggcctctgca    26040
gtgccttcca tctggagtgc tcttgcctgg tctctgcagg acgccaacat catgcttaaa    26100
agtctacact aaaagtcgc ttccagccag gcacagtggc tcactcctgt aatcccagca     26160
ctctgggagg ccaaggcggg aggatcactt gagcccagga gttcaagacc agcctgcaag    26220 acccatctg cagaaaaata taaaaattag ctgggtggcc gggcgcggtg gctcacgtct      26280
gtaatcccag cactttggga ggccgaggcg ggcaggtcac gaggtcagga gatcgagacc    26340
atcctggcta acacggtgaa accccgtctc tactaaaaat acaaaaaatt agctgggcgt    26400
ggtggcaggc gcctgtagtc ccagctactc gggaggctga ggcaggagaa tggcgtgaac    26460
ccgggaggcg gagcttgcag tgacctgaga tcgcgccact gcactccagc ctgggtgaca    26520
gagtgagact ccgtctcaaa aaaaaaaaa aaaaaaatt agctggacat agtagtgtgt       26580
gctggtagtc ccagctactt gagaggctga ggtaggagga ttgcttgagc ccaagaattt    26640
gagaccagcc tgggcaacat ggcgagaccc tgtgtctgca aaaaaaaaa aaaaaaaaa      26700 ctgtaaaaac ctgaaaaatt aaccaggtgt ggcagctcac tcctgtaatc ccatcacttt    26760
aggaagctga ggcaggagaa ttgcttgaaa tgtgaagttc aagaccagcc taggcaccac    26820
```

```
agtaagaccc tgtctctaca aaaaatttta taattagccg ggtgtggtgg tgcacaccta    26880
gggtcccagc tactcagaag actgagacag gaggatccct tgagcccagg aatttgaggc    26940
tgcagtgagc tatgatttca ctactgtgct ctaggctggg caacagagca agaccctgtc    27000
tcaaaaaaaa aaaaaaaaaa aaaaagctgc ctcctcaatg aggccttccc tgaccacccc    27060
acagattttt ttctctctct ctcctctcct ttatttcatt cattttcttt gccgtaagca    27120
tcactatctg ccttgttcac ttatttgctt attgtcttcc tttatataca tggtctcaag    27180
ccaggaattg ctttgcacaa tcctgggaac caccaagtcc aaaatccaca gggcaggctg    27240
gaaactgtca ggtaagagct aatgctgcag ttttttgtttt tgttttttgag acggagtctc    27300 actctgtcgc caggctggag tgcaatggca cgatctcagc tcactgcaac ctccgcttcc    27360
tgggttcaag ccattctctt gcctcagcct cctgagtagc tggggttaca ggcatgcacc    27420
accacaccca gctaattttt gtattttttag tagagatggg gtttcaccac gttggccagg    27480
ctggtctcga actcctgacc tcaggtgatc tgcccgcctc ggcctcccaa agtgctggga    27540
ttacaggtgt gagccaccgc gcctggcccc cattttagtc atgaggaaaa cagaggctca    27600
gggaggagaa ggcaccaccc agactcgtag cgctggatgg agtggcaggg ctgggagttg    27660
tgctcagact ctctgagact ctcttaggca ttcccaccct ttctcctgct ttcctcactt    27720
tcccagtatg tgcagctgag atgctttctt ttttcttttc ttttcttttc tttttttttt    27780
ttttttttga tagactcttg ctctgttgct caggcgggag tgcagtggtg ccaatcacag    27840
ctcactgcag cctcaaactc ccggactcaa acgatcctcc tgcctcagcc tccttagtag    27900
ctgggattac aagtgcatgc caccatgcct ggctaatatg ttgtattttt tgtagagatg    27960
gggtctcact atgttgccca ggctagtctc gaactcctag tctcaagaga tcctcccacc    28020
tcagcctgct gagtagctgg gatcacaggc atgagccatc atgctgggct aattttttaaa    28080 tttttagtag tgatggggtc ttgctgtgtg ggccaggctt gtcttcaact cttgggctta    28140
agtgatcctc cctcctcagc ctcccaaagt gctgtgatta ccggcatgag cccctgcgcc    28200
cagtctgaga tgctttctac agcttcacat ttcagctgca gcccagcagt ggtccaccta    28260
gttcacagcc aatgtagaat ctgtgtggac catccaatgt tgtgaggttg aatcacatcc    28320 ctttttttttt tttttttctcg agacagagtc tcactctgtc actcaggctg gagtgcagtg    28380
gcacggtctc agctcactgc aacctccacc tcccgggttc aagcgattct cttgcctcag    28440
cctcccgagt agctgagatt acaggcacgt gccaccacac ccagctaatt ttgtgttttt    28500
agtagagacg gggtttcacc atgttggcca ggctggtctt gaactcttgg cctcagatga    28560
tccacctgcc tcggcctccc aaagtgccgg gattacaggc atgagcccct gcgcccggcc    28620
tgagatgctt tctacagctt catatttcag ctgcagccca gcaatggtcc actcagttca    28680
cagcctacgt agagtctgtg tggaccgtcc aaggttatga ggctaaatca catcttgaga    28740
atcgaaggca gtgccggctg caaagcaatg gggctttcct ctggcgggag gagatggtgg    28800
ctggacaggg accctggctg ggcaagtggt tgtttgtttg tttgttttga cacggagtct    28860
cgctctgttg cccaggctgg agtgcagtgt cacgatctcg gctcactgca acctccacct    28920
cccaggttca agcgattctc ctgcctcagc ctcaccaata gctgggatta caggcgcccg    28980
ccaccatgcc cggctaattt ttgtgttttt attagagaca gggttttgcc atgctgacca    29040
ggctggtctc gaactcctga cctcagatga tccacccgcc tcagcctccc aaagcgctgg    29100
gattactgag gcatgagcca ccacgcccag ccagaaatct agacttttttg catctcttct    29160 tcgacagcaa atggaaaatg tttttaaatg ctgcatgggt gggacataac taggcttggt    29220
```

```
gcatcagcca tcagcctgca attttgcagc gctggtttgg gttaaccttc tgaatgagca    29280
ggtcagttca ttcttcagtc ctttctttga gtttgctat atatatatat atatatagca    29340
aaatctatat ctatatctat atctatatct atctatatcg cctcgctctg tcatccaggc    29400
tggagtgcag tggctcgatc atggctcact gcagccttga cctcctgggc tcagctgatc    29460
ctcccacctt ggcttcccaa atagctggga ctacagggac acgccaccat gcctggcttt    29520
ttatttttta tagagatgga gtctcgctgt gttgcccagg ctgatctcaa actcctgggc    29580
tcaagggatc ctcccacctc agcctcccaa agtgctggga ttacaagcgt gtgccacctc    29640
atgcccagcc aaagcttgct ttttaaaaaa ttgaggtgag gccaagtaca gtggctcacg    29700
catgtaatct cagcactttg ggaggccgag gcaggtggat ctcctgagct caggagttcg    29760
agaccagcct ggccaacgtg gtgaaacccc atctctacta aaaacacaaa aatcagctga    29820
gcatggtggt gggcgcctat aatcacagct actctggagg ctgaggcaca gaatcgcct    29880 aaacccggga gatggaggtt gcagtgagcc aagattgtgc cactgcactc cagcctgggc    29940
aaaagagtga aactccgtct caaaaattaa ataagtaaaa taaatttaa aaatataaa    30000 aaattgaggt ggaattctca taacatgaat tcatcatttt aaagttcatg attcagtggc    30060
agagtccatt cataatgttc tgcaacccca catctatcta atttgaagac attttcatca    30120
ccgtgagagg aaatcctatc tactaagtca gcccattt catccctctc ccccaacccc    30180
agtgaccaca catctacttc ctgtgagaat ttacgtgttc taaacatctc ttttttttt    30240 cttttctttt ctgttttgag cagggtgtca ctctttcacc taggctggag tgcagtggtg    30300
caatcatagc tcactgcagc ctcgacctcc caagttagag caatcctcct gcctcagcct    30360
cctgagtact tggaactaga cgtgtaccac cacacccagc taattgtttt gtatttttag    30420
tagagacggg ctttcgccat gttgccccga ctggtcttga actcctgggc tcaatgaacc    30480
cgcccgcatc agcctttcaa agtgctggga ttacaggcat aagccaccac actcagccaa    30540
catttcatgt aattggaatc acacactgtg tggcctttttg tgtctggcat ctctcactga    30600
gcatgatgtc ctcaaggtgc atccatgctg tggtctgtgt cagagccctg ttccttttca    30660
gggctaaata gtattccatt gaatggatat accacatttg ttgatccagt cagctgttaa    30720
tggactggtg ttgtttgttt ttgtttgt ttttgagaca gagtctcact ctgtccccag    30780
gctggagtgt agtggcgtga cttcagctca ctgcaacttc cacctcccag gttcaagtga    30840
tcctcttgcc tcagcctccc aagtagctag gattataggc atgcgccacc atgtccagct    30900
aatttttgta ttttttagtac agacagggtt tcatcgtgtt ggccaggatg gtctcaatct    30960
cttggcctca tgatgtgccc tcctcggcct cccaaagtgc caggatgaca ggcgtgagcc    31020
accgcgcctg gccgtcaatg gactcttgaa ttgtttccac ttttttggttt ttatgaatta    31080 tgttcattca agtatgagtt ttcgtgtgaa cagatgttt catttccttt gggaatccgc    31140
tccattttga tctttgccat gaacaggagg agggtgacat ctgattcctc ctttacctcc    31200 aagcccata gatgcactgg agacgcagtg gttacgcaaa acatttgat gaatagagaa    31260 aagagaggga gggaaaggga gagggaaaaa gcataaatag attccgcccc aaaaaggtta    31320
acagctcatg ccctaagtgg aacagaaatg agggaataaa tctttttttt tttttttttt    31380 ttttgagag agagtctcac tttgttgccc aggctggagt gcaatggcac gatctcggct    31440
caccgcaacc tccgcctcca gggttcaagt gattctcctg cctcagcctc cccagtagct    31500
gagactgcaa gcacgcacca ccacgcccag ataattttg tattttttcag tagagactgg    31560
```

-continued

```
gttttcaccat tttggccagg ctagtcttga actcctgacc tcaggtgatc cgcccgcctc   31620
ggcctcccta agtgccagga ttacaggcat gagccaccac gcccggccaa taaatcattt   31680
ttttaaagga aaggaacatg cattccaccg cccttccatc taaacagctt gccttgcagc   31740
tgagccagga atgctgagtt acagagacga attaagctgt agcctggctt tccggagtca   31800
gcacgccctg ccgctaggac ctctggcagc cccgtgcaaa atgttctgcc cggaatggaa   31860
tatttcccag ggtagccaag gagccagtgc tcctgggtca aactcgggca gcacgggctg   31920
cggcttcaag aagtgatctg gggccgggtg cggtggctca tgctgtaatt ccagcatttc   31980
tgtctcaaaa agaaagaaaa agttgcaaag ttagtacaga taattcctgt agactgggaa   32040
cctagtttct cccataatta acatcttata ttagctgtgt atattttata tttgtcacaa   32100
ttgatgaatc aatattgata ctattggtta ttgataatca acattgatca ataacaatat   32160
tgatcaatat tggttattag ttaccaaagt ccatgctttt ttagattttc aaagttttc   32220
ctaatgtcct ctttttttt cttttctctc tttttttttt taagagacag ggtctcactc   32280
tgtcatccag gctggggtgc agtggtgcca tcatacctca ctgcagcctc cgcctcccag   32340
gctcaagcag tcctcccacc tcagcctcca gagtagctgg gactacaggc accaccacgt   32400
ccagctaatc tttgtaattt ttgtagagac agagttacgc catgttgccc aggctggcct   32460
aatgtccttt tccttctgcc ccacaacccc atccaggatc ccagatgaca tttagttatc   32520
acatctcctg acactcctct ggactgtggc agtctccctg tctttcttgt tttgatgccc   32580
ttgatagttt tgtttgtttg tttgttttga gatggagtct cactctgtca cccaggctgg   32640
agagcagtgg cacgatctcg gctcactgca acctccgcct cccgggttca gcgattctc   32700
ctgcctcagc ctcctgatag ctgggattac aggtgtcctc caccatgcct gcctaatttt   32760
tgtatttta gtagagatgg cgtttcacca tgttgtccag gctggtctcg aattcctgag   32820
ctcaagtgat cctcctgcct cagcctccca aagtgctggg attacaggcg tgagctgctg   32880
cgcctggccc atcctgtatt ttttggaatg acatcactat acacagccta cacagagtta   32940
tccttcatct ttttttttt tttttttttt tttgagacag agtcttgctc tgtggcccag   33000
gctggagtgc agtggcacga tctcggctca ctgcaagctc cgcctcctgg gttcatgcca   33060
ttctcctgcc tcagcctcct gagtagctgg gactacaggc acctgccacc acgcccgct   33120
atttttttg tactttagt agagacggg tttcaccatg ttagccagga tggtctcgat   33180
ctcctgacct cgtgatccgc acgcctcggc ctcccaaagt gctgggatta caggcgtgag   33240
ccaccgcacc cggcctatcc ttcatcttct tgagggcaga actgtacata aactatttcc   33300
aattcttctg cacaagaaat gtgtctcttc tcctgttt atttgttcag tgacttattt   33360
atatccgtat ggactcatag acatttattt tacatcttgg gttataattc aatatttcat   33420
tatttatttg gttgcacaaa ctgttccagc attgacatag agatctcttc tggttgactc   33480
aggttttgt gggggtttta tctatttatt tattttaat acttttgct gcatttgaga   33540
gtcaacaact catcagagac caaatcccac agggtcgccc tagagagaat tcaacttact   33600
aacttatttc aaagttttg aagtcatgtg atgctgggga aaaaccttca ttctcctcaa   33660
gccgtgcaaa atctccaaa aggcttaata taaatttgat tatctaaaag aagcccttca   33720
gccctgatgc gttataattt tcttcctctg ctaaagaaaa aacatgctgg gcgggcgcgg   33780
tggctcatgc ctgtaatccc agcactttga gaggccgagg tgggcagatc acaaggtcag   33840
gagttccaga ccagcctggc caatatggtg aaaccccgtc tctactaaaa atacaaaaat   33900
tagccgggca tggtagcggg cacctgtagt cccagtttac ttaggaggct gaggcagaag   33960
```

-continued

```
aatggcctga acccgggagg cggaggttgc cgtgagccga gatcatgcca ctctactcca    34020
tccagcctgg gcgacagagc gagactctgt ctcaaaagaa aaaataaaa gaaaagaaa      34080 aaacatgcgc ttgtggtggc tcacgcccgt aatcccaaca cttttgggagg ctgaggtggg   34140 aagatggctt gagcccagga gttcaagagc aacctgggca acatagtgag accccatctc   34200
tacaaaaaac caaaaaacta caaaaattag ccagccgtgg tggtgtgcac ctgtagtccc   34260
agctactcag gaggctgagg caggaggatc tcttgagccc aggaggttga ggctgcagtg   34320
agccatgatc acgctactgc actccagcct gggcgataca gtgaggctct gtctccaaaa   34380
aaatgtatat atttaggtcc agtgattctc cagaactaaa tgtgttttgc ttttgttctt    34440
gtctgactcg cctggctgga cctgtctggg ccactccact gtcctctgcc tgaatctctg   34500
gtgcccggcg actgatgcct gttcctggat gggtccgcag gccactccca aagagacgg    34560 gggtggaact gcttggcagc ccggtggaag acacatcctg taagtttcca cgtccacaga   34620
agggcggaaa caggctcagt gtttccgggt ttcagccctg cctggggctg taactgtaga   34680
aatgtcagag gccacacacc gtgggtagaa tgttctgtcc tggggtctat ggtggaagtg   34740
gccgtggtgg gtgagagaca caatggatga tggcgctctc atgaagccag cacgctgtgt   34800
tgctgtgtgt ccctgtgcta gtcactcagc ctctctgtgc cccaatgcct catctactaa   34860
atgtaggtag cgagcttctc gcagaggggg catgtaagga ttaaatgagg tgatgccaaa   34920
tgccctggag gcacaaagtc agcacagcca agggtgcact gggaggctct gctatctgga   34980
gctctaaaca tatacatttt aatgtgtaat accttatatt agacccaaat atatacattt   35040
tttgggagac cgggtcacac tctgtcatcc aggctggagt gcagtggcgt gatcatggct   35100
cactgcagcc tcaacctcca gggctcaaga gatcctcctg cctcagcctt ctgagtagct   35160
gggactacag gtgcacacca ccatggctgg ctaattttgg tagttttgt agaaatggga   35220 tctagctatg ttgcccaggc tgctcttgaa ctcctgggct caagccatct tcttgcctca   35280
gcctcccaaa gtgctgggat tacgggcgtg agccaccacg cctggcatgt ttttcttca    35340 gcagaggaaa aaaatcataa tgtatcaggc tctgaagccc cagatcccgg ggatgggagt   35400
cctgggcggc cagaggagag ttttagccgt aacctggcga ttgcaacgtg cctccggagg   35460
cagggaaagg gcccaggttg gcaccgtggg gagaggtggg gtctggggag gacctggcag   35520
ccagccccac ttaacgacat tcagttaagc agaatatgga aaataaacct gtgagggcca   35580
aacaaaattt ttttggagac agagcctcac tgtatcgccc aggctggagt gcagtagcgt   35640
gatcatggct cactgcagcc tcaacctcct gggctcaaga gatcctcctg cctcagcctc   35700
ctgagtagct gggactacag gtacacacca ccatggctgg ttaattttg tagtttttg     35760 tagagatggg gtctcactat gttgcccagg ctgctcttga actcctgggc tcaagccatc   35820
ttcccacctt ggcctcccaa agtgttggga ttacgggcgt gagccactgc acccggccgc   35880
ctgtctctat ttaaaagaa aaaaaaaaa ggcaggtcac cgtggctcac gcctgtaatc     35940
ccagcacttt gggaggccga ggcgggcaga tcacgaggtc aggagtttga gaccaacctg   36000
gccaacatgg tgaagccccg tctctactaa agatacaaaa aaaaaaaaa aaaaaatta     36060 gccgggcatt gtggcacttg cctgtaatcc cagtcactca ggaggctgag gcatgaggat   36120
cgcttgaacc caggagacgg aggttgcagc aagctgagat tgtgccattg cactccagcc   36180
tgggtgacaa ggcgagactc tgtctaaaca aaacaaaaca aaaaagatt agtcgggctt    36240 ggtggcgcat gcctgtaatc ccagctactt gggaggctga ggtgggagaa tcacttgaac   36300
```

```
ctgggaggcg gaggttgcag tgagctgaga tcctaccatt gtactccagc ctgggtaacg    36360
gagtgagact ccatctcaaa aaataaata cataaataaa acaaaataaa ttagcagact    36420
ttggattaaa gcaggcagcc atctgtgatg tgggtgggcc tcatctaatc agttgaaggt    36480
tttaagagaa acagactgag gttcccccag gcagagacaa ttctgcctgc ggacggtttt    36540
gcaacatcaa ctcttcccta ggcgtcccgc ctgctggcct gccctgccga ttgaggactt    36600
gtcagtctct gtgatcacac gagctaattc cttaaaataa atttctccct ctctcttttt    36660
ttccatacat ataggaaaaa aatatgtata cacacacaca cacacacaca cacgtcctat    36720
tggatttgtt tccctggagc actctgatta aaataggaga ctatcctgga tcctgtatta    36780
tccaggtggc ctgacatcgt tacaggatcc tcatgagtgg agacaggagg gtgagagtca    36840
gagaaagcct agaagaagat gggctgcttt cacaatttgt ctgcacaaga gatatgtctc    36900
ttctccttta tttatttatt tatttatttt tgagatagag tttcactctg tcacccaggc    36960
tggagtgcaa tggtacgatc ttggctcact gtaacctccg cctcctgggc tcaagtgatt    37020
ctcctgcctc agactcccaa gcagctggga ttacaggcgc caccactgtg cccggctaat    37080 tttatattt ttagtagaga tggggttcg ccatgttggc caggctggtc tcgaactcct    37140
gacctcaggt gatctgcccg cctcggcctc caaagtgctg ggattacagg cgtgagccac    37200
cgcacccggc ccaaagtcag gctttgaact catgtctgcc caatgtccaa gcatccatcc    37260
ccttaatctc tgaggcttgc ccacaggaca gaggttataa cattcacccc tgtcaggatg    37320
atgtcggttt aattctgccc accccgcca atggcatgga tacagaaggg agcccaccct    37380
ctcttcccat tcctgcatga tgaaacagct tccaccaggt aggaaaatgg ggggaaggta    37440
aaagagagaa agcaaagatg ttttccattt ttctcatttc cctgcagctc ctcccaacac    37500
gctaaatttc aacggagcgc atcgtaagag gaagacgctg gtggcccag agatcaacat    37560 ttctctggat cagagtgagg ggtccctgct gtccgatgac ttcttggata ccctgatga    37620 cctggatatt aacgtggatg acatcgagac ccccgatgag accgactcgc tggagttcct    37680
ggggaatggc aacgaactgg agtgggaagg taaagttcag ggtctctctg ggcctgctg    37740 gagcccaccc ccccacccc acctttccgt ctctggattc ccataggctc agagagtcac    37800
aagtggggca ggggctctaa gcagtctagc cttaaaccca ggagatcaag actgcagtga    37860
gacgtgatca tgccactgca ctccagcctg gacaacagag tgagaccctg tctcaaaaat    37920
aaaattttta aaaagagag aggtggctgg gcgcagtggc tcatgcctgt aatcctagca    37980 cttttgggagg ccgaggcggg cagatcacga ggtcaggaga tcgagaccat cctggctgac    38040
acagtgaaac cccgtctcta ctaaaataca aaaaattagc caggcatggt ggcgggcacc    38100
tgaagtccca gctactcagg aggctgaggc aggaaacgg tgtgaaccca ggaggccgag    38160
cttgcggtga ccaagattg tgccactgca ctccagcctg gcgacagag cgagactccg    38220 tctcaaaaaa aaaaaaaag agagagagag gttggtgaat gggtaccaac atacagttag    38280
acagaaggaa taagttctat tgttcgatag cagaatagga ggggtgccag gaggagggtc    38340
catccgctcc tgcgactgtt ttttttttt ttttgagaca gagtctcact ctgttgccca    38400
ggctggagtg cagtggtgtg atctcagctc actgcatcct ccacctcccg ggttcaagcg    38460
attcttttgc ctcagcctcc cgagtagctg ggattacagg catgcactac cacttccggc    38520
tgatgtttat attttttagta gagatggggt tttcccatgt tgcccaggct ggtctcaaac    38580
tcctgacttc aagtgataca cccacctcgg cctcccaaag tgctgggatc acaggtgtga    38640
gccacggcgc ccagcctgcc cctgcaattt gatgcatatt tttcttgtgg gcttgtgaat    38700
```

```
ttttctgcag aacgtggctt tcatcagaat ctcaaaggcg accaagatcc caacaaactg   38760
ccctcgatgt atgcaacaaa tacttttttga ccatttactc cagggcaagt cctgattcag   38820
gcgtggggta tatggcaggg ctatgataag aagagatggt cctggtccct acctgcacac   38880
acagatcatc agaaagacag accacgaaag gccaggcgca gtgactcacg cctgtaatcc   38940
cagcactttg ggaggctgag gtgggcagat cacctgaggt caggagtttg agaccagcct   39000
ggccaacatg gtgaagctcc atctctacta aaaatacaga aattagccgg gcatggtggc   39060
gtgcgtagtc ccagctactc gggaggctga ggcaggagaa tcgcttgaac tctggaggca   39120
gaggctgcag tgagcagaga tcgcaccact ccactccagc ctgggcgatg aacaagact   39180 ctctcaaaaa aaaaaagaa agaaaaaaaa aaattaagga caatgtagtg gctcattcct   39240
gtaatcccag agcttcggga ggccagggta ggaggatcgc ttaaggccag gagtttgaga   39300
ccagcctggg caacatattg aaaccccatc tctacaaaaa tataaaaatt agctgggtgt   39360
ggtggtgcac aactgtagtc ccaggtatct gggaggctga ggcaggagga ctgctctctg   39420
tgtgccaggc tcctgggaga gtaaaaacca agcatgcatg ccccgagtat cctcgtggtt   39480
tgatgaagca gatgcattca ccagctctga gaagctccag gacacaggtc cttaaccaac   39540
agagtgccct gggaggccag caaagggaat gtccagaaag gcttcctgga ggaggcggca   39600
tttgagccag gccttgaaag gggagtagga gaggaaaatg ggtcagcagg gcagccaggt   39660
ggggagaagc gaaggacttg tgggtcccgg cagcgaggga ggtgggagag gggaaggaag   39720
gctgagcagg agggcaggag atatccggac tctggcgtcc atgcgactct ccgccacctg   39780
cttctagacg acaccccgt ggccaccgcc aagaacatgc cggggacag cgcggatcta   39840 tttggggacg gcacgacgga ggacggcagc gccgccaacg ggcgcctgtg gcggacagtg   39900
atcatcgggg agcaagagca ccgtatagac ctgcacatga tccggcctta catgaaagtg   39960
gtcacccacg gaggtgagac ccgcccccg gtgccccctt ggggctccag cccggcccac   40020
tgggcaacag ggggttcgtc agtgcccctc tctgatgcac ggggatgtta agccgtcaac   40080
tcgcttcggg tggacggact gtgggcaagg cgtgcatggt cagggaggcg cactgggggc   40140
ccctgatggt cgctgtcact cctcagcgaa ggcagagact ggctaagggg tcgccggctg   40200
ctgtggctcg gagccatgcc ctcccgagcg tgtgggcacc gggacgtggt gggtggtgcg   40260
cgggaggcag ctcagggctg ggagaggact ctgacgttgc cgatcggctg cctctcctca   40320
gggtactacg gcgaaggcct caacgccatc atcgtcttcg cagcctgctt ccttccagac   40380
agcagcctcc ccgactacca ctacatcatg gagaacctct tcctgtgagt ccccgcccgc   40440
ggcgagcagc ctcgggccag ctctgatgcc tccctggcca caggggcacc aggctgcaag   40500
gattgcattg tggccctagg aagcctgcct ggcaccaggg aagggcgtgg tggccacaga   40560
ccttgatctg agtccctgct ggccctgagg ctcacagtgg ccttccctct gggccaccct   40620
gttctcctcc ccgtcctcct cctcctcctc ttcctcctcc ttccctcct cctcactgtc   40680 ctcctcctcc tccccttctt cctcccccctt cccctttctt ctcctccttc tcctcccctt   40740
cttcctcccc cctcctcctc ccttttctcc tcctcctccc cttccctctc ctcctccccc   40800
tcttcccctt ccctctcctc ctccccctc ttccttctcc tcctcttcct ccccttttctc   40860 cacctcatcc tctttctctt cctcccctttt tccccccctt cctcctcctt ctcctccttc   40920
cctcatcttc ctctccttcc ctcctcctcc cctcccccatc ctcctcctcc ccatcctctt   40980
ccccttcctc ctcctcttcc cgctctgaga tggcaccact gcactccagc ctgggtgaca   41040
```

```
gagtgagaac ctgtctcaaa aaaaaaaaaa aaaaaaaaaa gcaaggccta gagaccagcc   41100
tggccaacat agtgaaatcc tgcctctact aaaactacaa tttagctggg ctcggtggca   41160
ggcgcctgta atcccagcta ctagggaggc tgtggcagga gaatggcgtg aacctgggag   41220
gcggagcttg cagtgagccg agatcgcacc actgcactct agcctgggca acagagcgag   41280
attccgtctc aaaaaaaaaa aacgactcaa taaaagagta actgccctat gaggatgccc   41340
gctgacactc atgtggagtg tgctgggatc atccacgtcc tctcccaccc tgcagtccgc   41400
caggacagca gacaacacct ggaccagtgg ggctgaccca gccagcggca ggagtggagg   41460
caggcagggt cggcaccgca ggtgtcctga ccctggaccc ctccatgttg ggtccctgcc   41520
ttctgtgccc cgtgagcagg tacgtcatca gcagcttaga gctcctggtg gctgaggact   41580
acatgatcgt gtacctgaac ggtgccacgc cccggcggag gatgcctgga atcggctggc   41640
tgaagaagtg ctaccagatg atcgaccgga ggtgaggtgg ggatgcctca ggaagcacag   41700
tgggggcatg aaaatcacac aggggctgg  acatggtggc tcacacctgg aatcccagca   41760
cttcgggagg ctgaggtggg aaggtccctt gagcccagga gtttgagacc agcctgggca   41820
acgcagccag cactttggga ggccaaggtg ggtggatcac ctgaggtcag gagttcaaga   41880
ccagcccggc caacatatag tgaaacccca tctctactaa aaaaattcaa aaattagctg   41940
ggcgtggtgg cgcatgcctg tagtcccagc tacttgggaa gctgaggcag gagaatcact   42000
tgaacccagg aggtggaggt tgcagtgagc cgagatcatg ccactgcact tcagcctggg   42060
caacagagcg agactctgtc cccatgaaac actcactccc tattccttct ccccaggctc   42120 cggcacccccc atcctactt tctgtctctg taaatctgat gactctaggg acctcctagg   42180
actggaatca cacaggattt gtccttttgt gtctggcttt cctcactgag tgtgatgtcc   42240
tcagggtgca tccacattgt agcctgtgtc agagcctcct tccttttcat ggctgcataa   42300
tattccactg tatggacata ccacatttgg tttgtccatt ccattcatct cttgatggac   42360
atgggttgct tccacccctg agttattgta aatagcctca gagtgacatt aaaattgagc   42420
cagccaatcc atccttgcac ccaggttagt ggagggaggc tccaaggaca ggctggtccc   42480
tcctagggca ttaggtggtg aaaatacaat cttggctgct caaataacta ccaacctggt   42540
tcacctgctc tgcaccatgg ggtctctacc tacctcatcc acctgagggt cttagggact   42600
caaagggtgt gtctttatcc caccatagga cccccatgtc ttggatgggg gcagggattt   42660
gacaggtacc tggagaccac acgtggaatg agcagagtga cgaatgcttg cttgtggctc   42720
tcccgtccca cccagctcct ccctccccag ggctcgcccc aggagcccat cttgcttcct   42780
ttgcggcccc acacaggttg cggaaaaacc tgaagtcctt gatcatcgtc cacccctcgt   42840
ggttcattcg gactgtgctg gccatctctc gcccttttcat caggtgagac ggggaggctg   42900
caacccaagt ccagtggcct cagtgtgcgt gtgtgcgtgt gtgtatgcat gcatttgtgt   42960
gtgcatgtgt gcacgtgtgt gcgtgtgtgc atctgtgtgt gtgtgcatcc atgtgtgtgt   43020
ttgatgtgca tgttccagct tctctatgat gaatacatat tattgcttta aacagtttta   43080
aattgcacac agccaggcac agtggctgac acctgtaatc ccagctactc agaaggctga   43140
ggtgggagga tcgtttgagg ccagcctgag caacatagca aaacccccat ctctacaaaa   43200
aatacaaaaa ttagcaggac gtggtggtgc acacctgtag tttcagctac ttgggaggct   43260
cacgtgggag gatggcttga gcccaggaga tcaaggctgc aatgagccgt gatcgagcca   43320
ctgtactcca gcctggatga cagagtgaga ccctgtctca aaagaaaatc agtcatgcat   43380
ggcatcacat gcctgtagtc ccagctactc aggaggctga ggcaggagga tcacttgagc   43440
```

-continued

```
ccaggaggta gaggctgcag tgagctatga tcactccact gcactccagc ctgggagaca    43500
gagcaaaaca accctgtctc taaaaataaa atatatatat atgtatgtat aaataaataa    43560
ataatatgac taataaattt aaaatttaaa actacatata ttctataatg tatatcatat    43620
atagttacta tattaaacat atagtaaaac agatcaagtg aaataaaatt aggcatgtta    43680
aatgccctat tcaatccaat aaaatgtcat gcaaatttaa tttaatctaa tgcaaaacat    43740
tgaattgaat aaagattcct aatgttcacg ttcccagtta caaatctggg atgagcgaaa    43800
gagacgaggg cttcactttc ccttgaacaa caggacacat tcacagcagg cccgattttc    43860
aaggaagact cttttaaacat gctgtttttca aggactgcta agtaccctga aggggcttat    43920
ttgcatatta gcgaaatgag atgaggaata cactaattat ggatcatttt agctaataat    43980
gaatcaacag gcaaaacggt aaacacgcat ttcagtctaa gataattgca tttgctcctc    44040
tatattccag aattcagtaa catagactac ctttgccttt aatgtagata ttaggatggt    44100
gcaaaaataa ttgaggttct tgccatattt tcattacaaa aactgcaatc actcttgcac    44160
gaacccaata attctgtcac tcttcaccgg tcgccatggc tcacacctgt aatcccaaca    44220
ctttggaagg tcgagatgag aggatcgctt gagcccggga gttcgagacc agcctgggtg    44280
acatagcgag accctgtctc tacaaaaaaa aattttttttt tttttcagac ggagtctcac    44340
tctgtcgccc aggctggagt gcagtggcgc gatctcagct cactgcaagc tccgcctccc    44400
gggttcacgc tattctgcct cagcctcccg agcagctggg actacaggcg cccgccacca    44460
ggcccagcta acttttttgta tttttagtag agatgggggtt tcatcgtgtt agccaggatg    44520
gtctcgatct cctgacttcg tgatccgcct gccttggcct cccaaagtga aaaaaatttt    44580
tttttaaata cggccaggtg tggtgaccca ggcttgtaat cccagcactt tgggagaccg    44640
aggcaggagg atcgcttgag gccaggagtt gaagaccagt ctgggcaaca tagcaagacc    44700
tccatctcta caaaaaaaaa tttttttttaa ttagccaggc ctggtggcgc gcacctgtga    44760
tcccagctac tcagaggctg agggaggagg atcacttgag cccaggaggt cgaggctgta    44820
gtgagccatg attacaccac tgcactccag cctgggtgac agagtgagac tctgtctctt    44880
aaaaaaaaaa taccatgaag tgctggtgat gaaacaccac atggtatcag atggccagaa    44940
ttcaggattg gaagggaaag aagggaaaga accattcatc cctgaaaaac agagaattgg    45000
gccaggcagg gtagctcatg actgtaatcc cagcactttg ggagttagag gcaggcagat    45060
cacatgaggt caggagttgg agactagcct ggccaacatg atgaaacccc atctccatta    45120
aaaatacaaa attagccgag agtggtggtg catgcctgta gtcccagcta ctcgggaggc    45180
tgaggcaggg aaaatcgctt gaaccggggga ggcggaggtg gcagtgagcc gagatcacac    45240
cactgcactc cagcctgggt gaagagcaag actctgtgtc aaaaaataac aataacagag    45300
aatcaatggg cagcccgtg tgccccttc ttgtgcccag ctgagtgttg gctgtgccgt    45360
cctgtgcggt gacatggaga gaaagcatcc ctgggaaaaa ttaacacaga ggagcaactt    45420
ttagagatga tgggaaaaca gcctgtagag tctaagacaa tctcccccacc tcctgacttc    45480 cttccaacaa gatcctcatt gcagggaccc atgtcaggtg catggccctg cttgcaaggg    45540
cctcggcgca gacccggggt ctccactcca tgcatggggt gcaagataat taaggctgtc    45600
atcgggcggg agggaggtgt cgtcgtctgc actgggcat cctggagtgg ggtcctgtgg    45660
ggatccctgt cgccatggct ctgtctggac ctaggtaacc cccacccat gggttgcatt    45720 tcagacctct ccctccttct cccccccgcca gcgtcaagtt catcaacaag atccagtacg    45780
```

-continued

```
tgcacagctt ggaagacctg gagcaactca tccctatgga acacgtccag atcccagact    45840
gcgtcctgca gtgagtggcc ccacagtcca ccccgccgta ttagtctgtt ttcgtgctgc    45900
tgataaagac acacctgaga cagggcaatt tacaaaagag gtttaagggg ccgggcgcgg    45960
tggctcctgc ctgtaatccc agcactttgg gaggctgagg cgggcggatc acgaggtcag    46020
gggatcgaga ccatcctggc taacatggtg aaaccccgtc tctactaaaa atacaaaaaa    46080
ttagccgggc gtggtggcgg cgcctgtag tcccagctac tcaggaggct gaggcaggag     46140
aatggcgtga accccggagg cggaggttgc agtaagctga gatcgcgcca ctgcactcca    46200
gcctgggcca cagagcgaga ctccatcgca aaaaaaaaa aaagggcta acggactcac      46260
aattccatgt ggctggcaac gcctcccaat cacggtggaa ggcaaaaggc acgtctccca    46320
tggcggcaga gaagagaagg aaatttgtac aggcaaattc ccctttataa aaccatcaga    46380
tctcatgaga cttactcact gtcgcgagaa tagcacagga aagacctgcc cccatgattc    46440
agtgacctcc caccaggtca ctcccacaac aggagggaat tatgggagct acaattcaag    46500
atgagatttg ggtgaagaga ccaggcaagg tggctcacac ctataatccc agcactgtaa    46560
tcccagcatt ttgagaggct gagacaggca gatcacttga ggtcaggagt tcgagactag    46620
cctggccaag atggtgaaac cctgtctctc ctaaaaatac aaaaattagc caggtgtggt    46680
ggtgcatgcc tgtaatccca gatactgagg aggctgaggc aggagaatcg cttgaacctg    46740
ggaggcagag gttgtggtga gccgagatcg caccactgca ctccagcctg gcaacaaga    46800
gtgaaactcc gtctcaagaa aaaaaaaaa agatttgggt ggagatacag tcaaaccctg    46860
tcaccccaa caccccccca ccgggtcccc ctggctacca ggagccagca atgaggggaa     46920
acgcagactt ggaagggagg aactagaacc caccccatttt atttcctgga gccccctcagg   46980
gacccccgg agcttgggga agggatgggc agcttcaagt cctgttgttt ttcactgaat     47040
gtcatatcat cggcacctcc cctaggttca tgctgcaaaa atctccttaa acgtacattt    47100
ttttattgtg gtaaaataca cgtaacatag aacttcccat cttagccatt ccttttttaa    47160
ttttatttat ttatttattt tttgagaagg agtttcactc ttgttgccca ggctggagtg    47220
caatggcgcc atctcggctc accacaacct ccgcctcccg ggttcaagcg attctcctgc    47280
ctcagcctcc caactagctg ggattacagg catgagccgc catgcctggc taatttttttt   47340
ttttttttttt gtattttag tagagacagg gtttctccat gttcgtcaag ctggtctcaa    47400
acccctgacc tcagatgatc taccggcctc ggcctcccaa agtgctggga ttacaggcgt    47460
gagccactgc gcccggccta tcttagccat ttctaaaagc acattcgcat atttgtgcag    47520
ccatcaccac catcctctcc agacctttct ttttttttt tttgagatgg agtcttgctc     47580
tgttgcccag gctggagtgc agtggcacga tctcgggtca ctgcaacctc cacctcctgg   47640
gttcaagtga ttctcctgcc tcagcctccc cagtagctgg gattaaggca cccaccacca    47700
tgcccagcta atttttttt ttttttttttt tgagatggag tttaactctt gttgcccagg   47760
ctggtctcga actcccgacc tcaggtgatc cgcccacctc agcctcccaa agtgctggga    47820
ttacaggcgt gagccaccac gcctggccga ttttttgtatt tttagtagag acggagtttt   47880
gtcatgttgg ccaggctggt cttgaactcc tgacctcagt tgatctgcct ggctcggcct    47940
cacaaagtgc tgggattaca ggcatgagcc actgcacccg gccctctcca gaacgttctc    48000
atcttcccaa actgaaactc tgtctccatg aaacactcac tccccattcc acatcccaac    48060
cctggcagcc cccatcctac tttctgtctc tgggagtctg acgactctag ggacctccta    48120
ggaatggatc cacacaggat ttgtcctttt gtgtctgacg tctctcactg agcgtgacat    48180
```

```
cctcaaggtg catccacatt gtagcctgtg tcagaatgtc cttccttttc atggctgaat    48240
aatattccat tgcgtgaatg gaccacattt tgtcaatcca tttgtccatc aatggacaat    48300
tgggttgttt ccaccttttg gctcttgtga atagtcatgt tatttatatg ctactcacct    48360
atgaccgtag atgtacaaat atctctgtaa gaccctactt tcaattctaa tgagtatata    48420
cccaaaagtg gaattgctga taattctgtt tttttgagga accaccatac tgttttgttt    48480
tgttttgctt tgctttgctt ttttgagacg gagtctcact ctgtcaccca ggctggagtg    48540
cagtggcgct atcttggctc gctgcaacct ccacctcccg ggttcaagca actctcctgc    48600
ctcagcctcc cgagtagctg ggactacagg cgcccaccac cacacccaga taatttttt    48660 gtattttag tagagatggg gtttcaccat gttggcctgg ctggtctcaa actccccacc    48720
tcagcctccc aaagtgctgg gattacaggc gtgagccatc gcacccagcc tgttttttgt    48780
tgttgttgtt ttgttggggt ttttctggtt ttttttttta gacagagtct cactctgttg    48840
cctacgctgg aacgcaatgg cgcaatctcg gctcaccata tcctccagct tctacgttca    48900
agggattctc gtgcctcagc ctcccgaata gctgggatta caggcacctg ccaccacgcc    48960
cagctaattt ttgtatttt agtagagata gggtttcacc atgttggcca ggatggtctc    49020
agtctcctga actcagtgat ctgcccgcct cggcctccca aagttctggg attataggcg    49080
tgagccaccg tgctcagcca annnnnnnnn nnnnnnnnnn nnnnnnnnnn nnnnnnnnnn    49140 nnnnnnnnn nnnnnnnnnn nnnnnnnnnn nnnnnnnnnn nnnnnnnnnn nnnnnnnnnn    49200
naaaatgcat ctatgggcca ggtgtggtgg ctcatgcctg taatcccagc actttgggag    49260
gctgaggcca gaggatcgct tgagcccagg agttggaggc tacaagtgag ttcatgccac    49320
tgcactccag tctgggctat gacagaatga gaacctgtct aaaaaaaaga gaagaggccg    49380
ggcgcggtgg ttcgcgcctg taatcccagc actttgggag gccgaggtgg gtggatcatg    49440
aggtcaggag tttgagacca gccaggccaa catagggaaa ccccgtctgt actaaaaata    49500
caaaaaatta gctgggcgtg gtagcaggtg cctgtaagtc ccagctactc ggaggctga    49560 ggcagcagaa tcactcaaac cggggaggtg gaggttgcag tgagccaaga tcgcaccact    49620
gcactccagc ttgggcgaca gtgcaagact ccatctcaaa aaaaaaaaa aaaaaaaaa    49680 aaaggaagaa gaagaagaag aaaagaaaga aaaagagag cttgtttctc tgcttgaaaa    49740
ggaaagggat ttccccaaaa agtatatctc aggggaaagg aaggttgtgt ctgacatctt    49800
tttctttctt tcagatacga agaggaaaga ctgaaggcca ggagggagag gtgtgtgcag    49860
agtggtttct gctggggctg ggtcggggca gcgggggct gagctgaact ctcagttagg    49920
gcaacccggt gacttctggg cagcaggac cattgtcctg tgcagggctc aagacgctgc    49980
ccttctggca aggactttaa actcagacct gggttcaaat actggctccc gcattgagct    50040
gcaaggtaac attaagcaaa taaaagcta acaaccacct tggaggttat tgtgcaagat    50100
gaggcaccct tggcaaaaaa ggttgagcac agacttcacg ctccataaag cataaaagtc    50160
aagacgggcg cggtggctca cccagcactt tgagaggctg taatcccagc actttgggag    50220
gctgaggcag gaggattgtg tgaggtcagg agttggagaa caacctggac aacatggcgt    50280
aactccgtct ctaccaaaaa tacaaaaatt agccaggcgt ggtggtgcgt gcctgtaatc    50340
ccagctactt gggaggctga gccaggagaa tcacttgaac ctgggaggcg gaggttgcag    50400
tgagccgaga tcatgccact gcactccagc gtgggtgaca gagcaagact ctgtctcaaa    50460
aaaaaaaaaa aataaattag ccaggtgtgg tggcatgcgc ctgtagttca gctacttgca    50520
```

```
gggagactga atcgggacga ctgcttgagc ccaggaagtt gaggctgcag tgagccatga    50580
ttgtaccatt gcactccagc ctgggcaaca gagcaagatc ctgtctcaaa aaaaaaaaca    50640
aaaaaaaaca gcctttatca tgccaggtcc aatgccagct ttgagggaaa cagaggcaaa    50700
taagacagag tcttggtccc agaagttttc tcaaatagca aaggcaggga acatctcact    50760
ggtttggaaa acaggtccca ggggacagga aaccagaga ggccagtact agctgagagc    50820
ccaccccttg gcctggctgg gctagtcacc cttgtcacct cgttctctct gtccacagcg    50880
cgaggcccca gccggagttt gtgctgccca ggtctgaaga aagccagag gtggcaccag    50940 tggaaaacag gtaggtgtgc aggggaccat gggcagagag ctgacagtca cgggaggctg    51000
cctactccct tgggggaggc tagagaggaa gatgggtcct tgttcaggga cagaaaatgg    51060
aactaagtgg ccgccatgg tggctcacgc ctgtaatccc agcactttgg gaggccgagg    51120
tgggcagatc acatgaggtc aggagttcga gaccagcctg gccagcatgg tgaaacctca    51180
tctctactaa aaatacaaaa attagctgga catggtggct cacatctgta atcccagcta    51240
cttgggaggc cgaggcagga gattcgcttg aacccagggg gcagaggttg cagtgagccg    51300
agatagtacc actgcactcg gcgacaaagt gagactccat ctcaaaaaaa taaataaaca    51360
aataaaataa aaataaaaat tatcggccgg gtgtggtggc tcacgcctgt aatcccagta    51420
gtttgggagg ctgaggtggg ccgatcacaa ggccaagaga tcgagaccag cctgccaac    51480 atggtgaaac cccatctctt ctaaaaatac aaaaattagc tgggcatggt ggctcgtgcc    51540
tgtagtccca cctacttgga aggctgaggc aggagaatca cttgaacctg ggaggcggag    51600
gttgcagtga gccgagatca gaccactgca ctccagcctg gcgacagaat gagattctgt    51660
ctcaaaaata aataaataaa taaatatcat ccaggtgtgg tgatgtacac ctctagtcca    51720
gctactcaga agggtgaggc aggcagatgg ctggagccca ggaggtcaag gctacagcaa    51780
gctatgactg cactccagcc tgggcaacag agcaagaccc tgtctcaaaa aaaaaaaaa    51840 agttatcatg atgttctcat attatcgcaa tctcaatgtt atcataatga tgaaaggtga    51900
cctttgtcca ggtcccagca ggtagattca gactccccca atccagtaga ccctgagcaa    51960
cattattggc ttcattttat gttagtgaag ggccttggcc aatttcctca aaactgtctg    52020
tttgggctca tttgttacgc agcagatgca cgctgacatc tgttttgtac cagatacagc    52080
agtgtcggtc ctcatagggc ttacagcctc cacgaacagg tagaaaatgc ccaagaatgg    52140
gcactgtggc tcacgcctgt aatcccagca ctttcggagg ccaaagcagg aggaccattt    52200
gaggtcagga gttcgagacc aacttgggca acatattgag actccatctc tacaaaaagt    52260
ttaaaagtta gccaggcatg atggtgtata ccttgtagtc ccagctactt gggaggctga    52320
ggtgggagga tcacttgagc ccggagctgg aagctgcagt gagccatgat tgcaccactg    52380
ccctccagcc tgggcaacat aacaagaccc tgtatctttt tttttttttt aagacagatt    52440
ttcactcttg tcgcccaggg gccagagtgc aatggtgcga tcttggctca ctgcaacctc    52500
cacctcccgg gttcaagcga ttctcctgcc tcagcctccc gagtagctgg gattacaggc    52560
acccaccacc acacccggct aattttttgta tttttagtag agacagggtt ttaccatgtt    52620
ggccaggctg gtctcgaact cctgacctca gtgatccac ccacctcagc ctcccaaagt    52680
gctgggatta taggcatgag ccactgcacc cagccaagac cctgtatctt aataataata    52740
aataaataaa aataaaataa gttaaagaaa aaaagggaa aatgcccagg ctcccaaaaa    52800
taagcaaata acgcccagtc tccgtctctc ctccacaggt ctgctctggt ctcagaagat    52860
caggaaacaa ggtgggtgtg atgcagagtg gtcttcgtgc tgttttcaaa atgtccttca    52920
```

```
tggacctgta ttagtcaggg ttctctagaa ggacagaaaa tcaaaccagc tgccagcaaa    52980
tataaagcag gcagggatcc taatcccagg aaaactgccc catgacttat cgggagtggg    53040
ggatacggca ccgggaaggc agggaggtag tggttcccct taaccagtca gccgtccttg    53100
cacaactcca gggggcacc attacctaga ccaggatgca aatgaggccc cagagttatg    53160
cagtggagcg gccctcaggg aaaaacccac acagagccaa gctccctgaa gcccaggata    53220
tgataccaca aaagggtaga ctgtccacgc tctgcctccg attctccacc tggttctgga    53280
tgccaagaaa agcctccctg tggccgggcg cagcgtctca cgcctgtaat cccagcactt    53340
tgggaggccg aggcaggcgg atcatttgag gtcaggagtt caagaccagc ctgggcaaca    53400
tggcaagacc ccgtccctaa aaaaaataca aaaattagcc aggtgagcca agatcgtacc    53460
actgcactcc acagcctggg caatagggct agactttgtc tcaaaaaaag aaaaaaaaaa    53520
ggaaagaaaa gaaaagcctc cctgtgtgtt gatgtccaag ggtatcctca ggcacaatgg    53580
tttgccagaa ggactcacag agctcagcaa agctgtcata ctcacagtta tggtttatca    53640
cagtggcatg gtttattaca gtagaagggt acagttaaaa atcagcagag ttgggtgtgg    53700
tggctcatgc ctgtaatccc agcactttgg gaggccgagg caggtggatc acttgaaatc    53760
aggaattcaa gaccagcctg gccaatatgg tgaaaccccca tctctactaa aaatataaaa    53820
ttagctgggt gtggtggcac acacctgtag tcccagctac tcaggaggct gaggcaagag    53880
aattgcttga acctgggagg cggaggttgc agtgagctga gattgcacca ttgcattcca    53940
gcctgggcaa cagagcaaga ctctgtttaa aaaaaaaaa acaaaaaaac aaaaaactta    54000
acaaaaggaa gaggtgcata gggctggatc caggagagat cgggtggaag cctgcaagtg    54060
tcctctccca gtggggttgt gtggacagcc tttatttctc ccagcaggga tgtgtggcaa    54120
aacacacaaa gtgctgccaa ctagagaagc tgacccaagc cttctagcc agggtgttta    54180 tagagagtca actacataca cctggctgac tgtctgcatg gctttctta gcctccagcc    54240 cctgcacaga tcaagctgat gccacgtggc ccaagttcca accctaagtc acgttgtgag    54300
tgttattagt ccattctcat gctgctatga agaaataccc aagaccgggt aaattataaa    54360
gaaaagaggt ttaattgact cacagttctg catggctggg gaggccccgg gaatttata    54420 atcctggcgg aagccacctc ttcaccaggc agcaggagcg agaagtgctg agcaaagggg    54480
ggaaagcccc ttataaaacc atcagatctc gtgagaactc actaccacga gaacagcatg    54540
gaggtagccg cccccatggt tcagttacct cccactgagt accgcccacg acaagtgggg    54600
ttatgggaac tacaattcaa gatgagattt gggtggggac acagcccaac catatcagtt    54660
agcatagact atctggcatg acccacatag acactccagc caggatgctc caagagttta    54720
gaagttaatc ccaggagcca gggaaggacc aaacttttct ttagaatgtg tgggatttat    54780
ccttgaccac acagtttttt tgttttgttt tgttttttgtt gttgttgttg ttttttgagat    54840 ggagtctcgc tctgtcgccc aggctggagt gcagtggcat gatcttggct cactgcaagc    54900
tccgcctccc agggtcactc cagtctcttg cctcagcctc ccaagtagct gggactacag    54960
gcgtctgcca ccacacccag ctaatttttt gtattttta gtagagacgg gtttcacca    55020 tgttagccgg gatggtctcg atctcctgac ctcgtgatcc acccgcttcg gcctcccaaa    55080
gtgctgagat tacaggcgtg agccaccatg cccagctgac cacacagttt tatacaaatc    55140
tataagatgg cctggccaca tgccttacta cccatgtgac ccaggaagct ccaagctaag    55200
aaataaacat caaaaatggc cttagaccag tgctgcttaa ggggcactga gtaaaagttc    55260
```

```
tcaatgtatt tctgaaaaga ccacctcaac ccaagctctc tggagatgag ttcacatata  55320
cagacagaaa acacaaggaa atcatccacc atgagcaaaa gacagcagag acaacaaaca  55380
gcagaattag atcttgcctg gagatcctta ggtggataag atataataag catgttttaa  55440
caattaaaaa cacaaaagaa ggaattgtaa gaagcaatag atgaatggat gaatggatag  55500
gtggataaat ggatggatgg atggatgagt ggatggatgg aaggatgttt ggatgatggg  55560
tggatagata gatgaatgaa tgagtggagg gatgggagga tagatggatg ataggtggat  55620
ggatggatgg ataaatggat ggatggatgg atgggtgaag gttnnnnnnn nnnnnnnnnn  55680
nnnnnnnnnn nnnnnnnnnn nnnnnnnnnn nnnnnnnnnn nnnnnnnnnn nnnnnnnnnn  55740
nnnnnnnnnn nnnnnnnnnn nnngagtggg tgggtggatg gatggatgga tggatggatg  55800
gatggatgga cagatggatg agtgggtgga tggatgggtg ggcagatgga tcaatggata  55860
ggtgggtgga tggatggatg gatggttgaa tagatggatg agtggaggga tggatggatg  55920
aatggatgga tgtgtgggtg ggtggatggg tggatggacg gatgagtgag tggctggatg  55980
ggtgggcaga gggatgaatg gatccctcca ttgagtgaat ggatgggtga gtgagtgtgt  56040
ggatggatgg atggatggat ggatggatgg atggatgggt ggatggatag atgtgtgggt  56100
ggttgtatgg ttggttagtt gggggtgggg ttgaagcctc cctccaggct gattgaggtt  56160
gccagtctcc agggcctgtt ctgctgaggc accaggaagg aggccctcag agccacactt  56220
agaaagtggg tggcaggagc cgggccctga agggcatgtg ccactcttgc tgctgggagt  56280
tcacccacgc tgggtgggat cattgttttg gattacatac atgtagaagc gcattttgca  56340
cttttaacat taacagcaat aacttggcct gtgtctttcc ctccctagca tgtcctgagg  56400
cgacgtgagc ataacaaagg acatggaaga agattccaga tgccagaaaa cctctgtcag  56460
acgcccactg gccccagatc tcatcctgcc tcatcctgag tcccaatctt ccaagggtgc  56520
cagcccctcc gttcatctct gaaacccagc atccttttca gctgcttgaa acattgtat  56580 tttttttttt taacgatgca gtatttgtgc gttccagaaa agggcccagc tctgagcccc  56640
tcacccttcc acactcacga actctcagcc gaggaaggca agaagcgcag ggggtggccc  56700
gcgtggcgtc ggtggcctcc gctcctgctc gcagcctctg tggtcagagc tggatacaag  56760
attcaagacc cttctcttgc ttgtcacccg ctccaggttg gagccacaga cacccaccgc  56820
caccccggct gggtctgcgt cctttcctgt gcctttccct ccagaatgcg gcctcagacc  56880
tagaagctca accccctat gagggccacg tcctgggta gctcctgacc tccgaccta  56940 tgtccaaatt tcacacccat ggttttcat ttgacccgcc cccttctcgc tcataatgac  57000
acccagctcc tttgagagga tcagagccca ttgcacaaga agagccgctg ccaaccatcc  57060
ttgtcctccg attgcaaaat gacaccccag taatctagaa cattctcaag cccctttaac  57120
tcagatgtca agccaccggg caaacccgt caatacctcc caccaaggaa tgagatatgt  57180
ggacctcact gctcccccaa cccagcgtca ggctgggaca cgccaacgct gttccgggtt  57240
ggaacagcag aggctcagaa actggctctg aaataggcag acctagcaag aggaagatac  57300
agggtatcgg gcgtttgagt gtttcagaag tcattcggga agataaatcc agtgcgctgg  57360
ccgcagccac ctgcattcaa agcttggacc agcgggttct tgttcgggag gcaaatttcc  57420
ctaggaaaaa gaagacagac ttttctaatg tggtccaaat gcggatcact ggtcagatgg  57480
actctagaag cactgagctc cctgtctctg gaagtattta agaaaaggct gggccaggca  57540
cgatggctca cgcctgtaat cccagacttt ggaggccga gcaggcgga tcacctgagg  57600 tgaggagttt gagaacagcc tggccaacat ggtgaaacct catctctact aaaaatacaa  57660
```

-continued

```
aaattagcca ggcgtggtgg caggtgcctg taatcccagc tacttgggag gctgaggcat    57720
gagaatcact taaacctgag aggcagaggt tacagtgagc caagatcgtg ccactgcatt    57780
ccagcctggg cgacagagca agactctgtc tcaaaaaaaa taaaaaataa tcagggcaca    57840
gtggctcatg cctgtaatcc cagcactctg ggaggctgag gtgggtggat cacctgaggt    57900
caggagttca agaccagcct ggtgaacatg gcgaaacccc gtctctaata aaaatacaaa    57960
aattagccgg gcatggtggt gcatgcctgt aatcccagct actcgggagg ctgaggcagg    58020
agaactgctt gaacccagga ggcagaggtt gcagtgatcc aagatcatgc cactgcactc    58080
cagcctgggc aacaagagca aaactccgtc tcaaaataaa aagaaaagaa aagaatggac    58140
agtgtttgca gagagttgct cacgagtttc cctctaatcc taaatgtctt catgtctatc    58200
agtctgagca gacggtgagt agggcgggca cattctccag gccttcttc ctagctctgt    58260 ggttgacctc tcagcaagtg ctatccaggc tgggccaacc agaccacaa ttaactgagc    58320 ctcagtgaaa gcgtccagtg catcttgacc tgagacagca aggaattgca tttggggtta    58380
ttccaacgat gatggcaggg aactggtggt atttagtgct gaggggcagt gatacagaaa    58440
gatttgccct gtgggacagg gtcctgcgcg agtcccatcc ccaaaagcca gcagctcctg    58500
ccatgaggaa gacggggttt ctgagcaggc ttatgcctgc aggttcctgt ggagccaccg    58560
gctgtgacgg gacacctctg ggtctcagca ttgccctggg gaggctggga catttaggga    58620
catggtaggg ttttaacatt tgtttcccaa atgtcaaatc ccgggcacag ggcaagacc    58680 ctgtcccgaa ttcccacccc agtgaatggt gtcgctgcca aagccaacac aagatgacaa    58740
aagtggctgg gtacggtggc tcacgcctat aatcccagca ctttgggaga ccgagacagg    58800
tggatcacct gaggtcagga gttcgagacc aggctggcca acatggtgaa accccatctc    58860
tactaaaaat acaaaaatta gctgggtgtg gtggcgcgca cctgtagtcc cagctactca    58920
ggaggctgag gtagaagaat agctggaacc caggaggcag agattgcagt cagccgagat    58980
tgcaccactg cactccagcc tgggagacag agcaagactg actcaaaaga aaaaaaatga    59040
cagaagcctg attatcagac tgcccggagg agacaggctc cagcagatag atgccagcca    59100
ggcccagctg ccacgatttg tcccaggtga ccaaaggcac gcagctccag catgaatcgt    59160
tctaacccaa cagtgacaag aactgctggg ccttaaccgt catggaagac tggggccgct    59220
tccaagtcac agacaggaga cggggacagg aaagaactca ttccacccaa tcggacacct    59280
aataattgag tgtctacagc agcaatcaag tgacaagtga ggccctacct gacccagaag    59340
gtgcctgccg gctaaacatt ctgcccccac cagaaactcc aggggtccg cccgttatgc    59400 cgtggcccac ccacgcccct ttggatcacc agcagtcaca gacaacaggc aggcgaaact    59460
gaagacccca actcagcccc agcggaccct ccagagcaaa agaggcccc ggcgaggcca    59520 cctgtcggca ggcatgccga ggtcaaacag ccggggccac cgttcccagc tgggccacga    59580
cctgcaccgt ccacagatgg gctttgagat ggatttgtat cagggtgggg ggtgtggttt    59640
ggccaaaatg caatggaccc cgaccctcc tcgtaaaagg atgttgggtt tccctctggt    59700
gacacatggg atgcgtcata aaccctcccc caaagtcctg gtcagcagcc catccttcca    59760
acgatgagtt ttgcggtttt tcagaacaga aatgatcact acgattgacg acggtcgtga    59820
tgttaagacg tcgtctccat gagctttggg gggacttta tgtggaataa agaaactatc    59880
actg                                                                59884
```

<210> SEQ ID NO 12

-continued

<211> LENGTH: 21
<212> TYPE: DNA
<213> ORGANISM: Artificial Sequence
<220> FEATURE:
<223> OTHER INFORMATION: Synthetic

<400> SEQUENCE: 12
gagaacgtga ttgccctcat c                                          21

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
ggaggtgtga atcttatctt c                                          21

<210> SEQ ID NO 14
<211> LENGTH: 307
<212> TYPE: PRT
<213> ORGANISM: Homo sapiens

<400> SEQUENCE: 14

Met Gly Thr Thr Glu Ala Thr Leu Arg Met Glu Asn Val Asp Val Lys
1               5                   10                  15

Glu Glu Trp Gln Asp Glu Asp Leu Pro Arg Pro Leu Pro Glu Glu Thr
            20                  25                  30

Gly Val Glu Leu Leu Gly Ser Pro Val Glu Asp Thr Ser Ser Pro Pro
        35                  40                  45

Asn Thr Leu Asn Phe Asn Gly Ala His Arg Lys Arg Lys Thr Leu Val
    50                  55                  60

Ala Pro Glu Ile Asn Ile Ser Leu Asp Gln Leu Asp Ile Asn Val Asp
65                  70                  75                  80

Asp Ile Glu Thr Pro Asp Glu Thr Asp Ser Leu Glu Phe Leu Gly Asn
                85                  90                  95

Gly Asn Glu Leu Glu Trp Glu Asp Asp Thr Pro Val Ala Thr Ala Lys
            100                 105                 110

Asn Met Pro Gly Asp Ser Ala Asp Leu Phe Gly Asp Gly Thr Thr Glu
        115                 120                 125

Asp Gly Ser Ala Ala Asn Gly Arg Leu Trp Arg Thr Val Ile Ile Gly
    130                 135                 140

Glu Gln Glu His Gly Gly Tyr Tyr Gly Glu Gly Leu Asn Ala Ile Ile
145                 150                 155                 160

Val Phe Ala Ala Cys Phe Leu Pro Asp Ser Ser Leu Pro Asp Tyr His
                165                 170                 175

Tyr Ile Met Glu Asn Leu Phe Leu Tyr Val Ile Ser Ser Leu Glu Leu
            180                 185                 190

Leu Val Ala Glu Asp Tyr Met Ile Val Tyr Leu Asn Gly Ala Thr Pro
        195                 200                 205

Arg Arg Arg Met Pro Gly Ile Gly Trp Leu Lys Lys Cys Tyr Val His
    210                 215                 220

Pro Ser Trp Phe Ile Arg Thr Val Leu Ala Ile Ser Arg Pro Phe Ile
225                 230                 235                 240

Ser Val Lys Phe Ile Asn Lys Ile Gln Tyr Val His Ser Leu Glu Asp
                245                 250                 255

Leu Glu Gln Leu Ile Pro Met Glu His Val Gln Ile Pro Asp Cys Val

```
                   260                 265                 270
Leu Gln Tyr Glu Glu Arg Leu Lys Ala Arg Arg Glu Ser Ala Arg
            275                 280                 285

Pro Gln Pro Glu Phe Val Leu Ala Leu Val Ser Glu Asp Gln Glu Thr
        290                 295                 300

Ser Met Ser
305

<210> SEQ ID NO 15
<211> LENGTH: 307
<212> TYPE: PRT
<213> ORGANISM: Macaca fascicularis

<400> SEQUENCE: 15

Met Gly Thr Thr Glu Ala Thr Leu Arg Met Glu Asn Val Asp Val Lys
1               5                   10                  15

Glu Glu Trp Gln Asp Glu Asp Leu Pro Arg Pro Leu Pro Glu Glu Thr
            20                  25                  30

Gly Val Glu Leu Leu Gly Ser Pro Val Glu Asp Thr Ser Ser Pro Pro
        35                  40                  45

Asn Thr Leu Asn Phe Asn Gly Ala His Arg Lys Arg Lys Thr Leu Val
    50                  55                  60

Ala Pro Asp Ile Asn Ile Ser Leu Asp Gln Leu Asp Ile Asn Val Asp
65                  70                  75                  80

Asp Ile Glu Thr Pro Asp Glu Thr Asp Ser Leu Glu Phe Leu Gly Asn
                85                  90                  95

Gly Asn Glu Leu Glu Trp Gly Asp Asp Thr Pro Val Ala Thr Ala Lys
            100                 105                 110

Asn Met Pro Gly Asp Ser Ala Asp Leu Phe Gly Asp Gly Thr Thr Glu
        115                 120                 125

Asp Gly Ser Ala Ala Asn Gly Arg Leu Trp Arg Thr Val Ile Ile Gly
    130                 135                 140

Glu Gln Glu His Gly Gly Tyr Tyr Gly Glu Gly Leu Asn Ala Ile Ile
145                 150                 155                 160

Val Phe Ala Ala Cys Phe Leu Pro Asp Ser Ser Leu Pro Asp Tyr His
                165                 170                 175

Tyr Ile Met Glu Asn Leu Phe Leu Tyr Val Ile Ser Ser Leu Glu Leu
            180                 185                 190

Leu Val Ala Glu Asp Tyr Met Ile Val Tyr Leu Asn Gly Ala Thr Pro
        195                 200                 205

Arg Arg Arg Met Pro Gly Ile Gly Trp Leu Lys Lys Cys Tyr Val His
    210                 215                 220

Pro Ser Trp Phe Ile Arg Thr Val Leu Ala Ile Ser Arg Pro Phe Ile
225                 230                 235                 240

Ser Val Lys Phe Ile Asn Lys Ile Gln Tyr Val His Ser Leu Glu Asp
                245                 250                 255

Leu Glu Gln Leu Ile Pro Met Glu His Val Gln Ile Pro Asp Cys Val
            260                 265                 270

Leu Gln Tyr Glu Glu Arg Leu Lys Ala Arg Arg Glu Ser Ala Arg
        275                 280                 285

Pro Gln Pro Glu Phe Val Met Ala Pro Val Thr Glu Asp Gln Glu Thr
    290                 295                 300

Ser Met Ser
305
```

```
<210> SEQ ID NO 16
<211> LENGTH: 308
<212> TYPE: PRT
<213> ORGANISM: Mus musculus

<400> SEQUENCE: 16

Met Gly Thr Thr Glu Ala Thr Leu Arg Met Glu Asn Val Asp Val Arg
1               5                   10                  15

Asp Glu Trp Gln Asp Glu Asp Leu Pro Arg Pro Leu Pro Glu Asp Thr
            20                  25                  30

Gly Val Glu Arg Leu Gly Gly Ala Val Glu Asp Ser Ser Ser Pro Pro
        35                  40                  45

Ser Thr Leu Asn Leu Ser Gly Ala His Arg Lys Arg Lys Thr Leu Val
    50                  55                  60

Ala Pro Glu Ile Asn Ile Ser Leu Asp Gln Leu Asp Ile Asn Val Asp
65                  70                  75                  80

Asp Ile Glu Thr Pro Asp Glu Thr Asp Ser Leu Glu Phe Leu Gly Asn
                85                  90                  95

Gly Asn Glu Leu Glu Trp Glu Asp Asp Thr Pro Val Ala Thr Ala Lys
            100                 105                 110

Asn Met Pro Gly Asp Ser Ala Asp Leu Phe Gly Asp Gly Ser Ala Glu
        115                 120                 125

Asp Gly Ser Ala Ala Asn Gly Arg Leu Trp Arg Thr Val Ile Ile Gly
    130                 135                 140

Glu Gln Glu His Gly Gly Tyr Tyr Gly Glu Gly Leu Asn Ala Ile Ile
145                 150                 155                 160

Val Phe Ala Ala Cys Phe Leu Pro Asp Ser Ser Pro Asp Tyr His
                165                 170                 175

Tyr Ile Met Glu Asn Leu Phe Leu Tyr Val Ile Ser Ser Leu Glu Leu
                180                 185                 190

Leu Val Ala Glu Asp Tyr Met Ile Val Tyr Leu Asn Gly Ala Thr Pro
            195                 200                 205

Arg Arg Arg Met Pro Gly Ile Gly Trp Leu Lys Lys Cys Tyr Val His
210                 215                 220

Pro Ser Trp Phe Ile Arg Thr Val Leu Ala Ile Ser Arg Pro Phe Ile
225                 230                 235                 240

Ser Val Lys Phe Ile Ser Lys Ile Gln Tyr Val His Ser Leu Glu Glu
                245                 250                 255

Leu Glu Arg Leu Ile Pro Met Glu His Val Gln Leu Pro Asp Cys Val
            260                 265                 270

Leu Gln Tyr Glu Glu Gln Arg Leu Arg Ala Lys Arg Glu Ser Thr Arg
        275                 280                 285

Pro Pro Gln Pro Glu Phe Leu Leu Ala Glu Ala Thr Glu Asp Gln Glu
    290                 295                 300

Thr Ser Met Ser
305

<210> SEQ ID NO 17
<211> LENGTH: 263
<212> TYPE: PRT
<213> ORGANISM: Homo sapiens

<400> SEQUENCE: 17

Glu Asp Val Gly Met Asp Ile Pro Phe Glu Glu Gly Val Leu Ser Pro
1               5                   10                  15
```

```
Ser Ala Ala Asp Met Arg Pro Glu Pro Pro Asn Ser Leu Asp Leu Asn
            20                  25                  30

Asp Thr His Pro Arg Arg Ile Lys Leu Thr Ala Pro Asn Ile Asn Leu
        35                  40                  45

Ser Leu Asp Gln Ile Asp Ile Asn Val Asp Glu Leu Asp Thr Pro Asp
    50                  55                  60

Glu Ala Asp Ser Phe Glu Tyr Thr Gly His Glu Asp Pro Thr Ala Asn
65                  70                  75                  80

Lys Asp Ser Gly Gln Glu Ser Glu Ser Ile Pro Glu Tyr Thr Ala Glu
                85                  90                  95

Glu Glu Arg Glu Asp Asn Arg Leu Trp Arg Thr Val Val Ile Gly Glu
            100                 105                 110

Gln Glu Gln Gly Gly Tyr Tyr Gly Asp Gly Leu Asn Ala Ile Ile Val
            115                 120                 125

Phe Ala Ala Cys Phe Leu Pro Asp Ser Ser Arg Ala Asp Tyr His Tyr
    130                 135                 140

Val Met Glu Asn Leu Phe Leu Tyr Val Ile Ser Thr Leu Glu Leu Met
145                 150                 155                 160

Val Ala Glu Asp Tyr Met Ile Val Tyr Leu Asn Gly Ala Thr Pro Arg
                165                 170                 175

Arg Arg Met Pro Gly Leu Gly Trp Met Lys Lys Cys Tyr Val His Pro
            180                 185                 190

Ser Trp Phe Ile Arg Thr Ile Leu Ala Val Thr Arg Pro Phe Ile Ser
    195                 200                 205

Ser Lys Phe Ser Ser Lys Ile Lys Tyr Val Asn Ser Leu Ser Glu Leu
    210                 215                 220

Ser Gly Leu Ile Pro Met Asp Cys Ile His Ile Pro Glu Ser Ile Ile
225                 230                 235                 240

Lys Leu Asp Glu Glu Leu Arg Glu Ala Ser Glu Ala Ala Lys Thr Ser
                245                 250                 255

Cys Leu Tyr Asn Asp Pro Glu
            260

<210> SEQ ID NO 18
<211> LENGTH: 259
<212> TYPE: PRT
<213> ORGANISM: Mus musculus

<400> SEQUENCE: 18

Met Asp Ile His Phe Glu Glu Gly Val Leu Ser Pro Ser Ala Ala Asp
1               5                   10                  15

Met Arg Pro Glu Pro Pro Asn Ser Leu Asp Leu Asn Gly Ser His Pro
            20                  25                  30

Arg Arg Ile Lys Leu Thr Ala Pro Asn Ile Asn Leu Ser Leu Asp Gln
        35                  40                  45

Ile Asp Ile Asn Val Asp Glu Leu Asp Thr Pro Asp Glu Ala Asp Ser
    50                  55                  60

Phe Glu Tyr Thr Asn His Glu Asp Pro Thr Ala Asn Lys Ser Ser Gly
65                  70                  75                  80

Gln Glu Ser Glu Ser Ile Pro Glu Tyr Thr Ala Glu Glu Arg Glu
                85                  90                  95

Asp Asn Arg Leu Trp Arg Thr Val Val Ile Gly Glu Gln Glu Gln Gly
            100                 105                 110

Gly Tyr Tyr Gly Asp Gly Leu Asn Ala Ile Ile Val Phe Ala Ala Cys
            115                 120                 125
```

```
Phe Leu Pro Asp Ser Ser Arg Ala Asp Tyr His Tyr Val Met Glu Asn
        130                 135                 140

Leu Phe Leu Tyr Val Ile Ser Thr Leu Glu Leu Met Val Ala Glu Asp
145                 150                 155                 160

Tyr Met Ile Val Tyr Leu Asn Gly Ala Thr Pro Arg Arg Met Pro
                165                 170                 175

Gly Leu Gly Trp Met Lys Lys Cys Tyr Val His Pro Ser Trp Phe Ile
            180                 185                 190

Arg Thr Ile Leu Ala Val Thr Arg Pro Phe Ile Ser Ser Lys Phe Ser
            195                 200                 205

Ser Lys Ile Lys Tyr Val Thr Ser Leu Ser Glu Leu Ser Gly Leu Ile
        210                 215                 220

Pro Met Asp Cys Ile His Ile Pro Glu Ser Ile Ile Lys Leu Asp Glu
225                 230                 235                 240

Glu Leu Arg Glu Ala Ser Glu Ala Ala Lys Thr Ser Cys Leu Tyr Asn
                245                 250                 255

Asp Pro Glu

<210> SEQ ID NO 19
<211> LENGTH: 263
<212> TYPE: PRT
<213> ORGANISM: Homo sapiens

<400> SEQUENCE: 19

Met Glu Gly Val Glu Leu Lys Glu Glu Trp Gln Asp Glu Asp Phe Pro
1               5                   10                  15

Ile Pro Leu Pro Glu Asp Asp Ser Ile Glu Ala Asp Ile Leu Ala Ile
                20                  25                  30

Thr Gly Pro Glu Asp Gln Pro Gly Ser Leu Glu Val Asn Gly Asn Lys
            35                  40                  45

Val Arg Lys Lys Leu Met Ala Pro Asp Ile Ser Leu Thr Leu Asp Pro
        50                  55                  60

Gly Glu Ile Asp Leu Asp Gly Leu Asp Thr Pro Ser Glu Asn Ser Asn
65                  70                  75                  80

Glu Phe Glu Trp Glu Asp Asp Leu Pro Lys Pro Lys Thr Thr Glu Val
                85                  90                  95

Ile Arg Lys Gly Ser Ile Thr Glu Tyr Thr Ala Ala Glu Glu Lys Glu
                100                 105                 110

Asp Gly Arg Arg Trp Arg Met Phe Arg Ile Gly Glu Gln Asp His Gly
            115                 120                 125

Gly Tyr Tyr Gly Asp Gly Leu Asn Ala Ile Val Val Phe Ala Val Cys
        130                 135                 140

Phe Met Pro Glu Ser Ser Gln Pro Asn Tyr Arg Tyr Leu Met Asp Asn
145                 150                 155                 160

Leu Phe Lys Tyr Val Ile Gly Thr Leu Glu Leu Leu Val Ala Glu Asn
                165                 170                 175

Tyr Met Ile Val Tyr Leu Asn Gly Ala Thr Thr Arg Arg Lys Met Pro
            180                 185                 190

Ser Leu Gly Trp Leu Arg Lys Cys Tyr Val His Pro Ser Trp Phe Ile
        195                 200                 205

Arg Thr Leu Leu Ala Val Thr Arg Pro Phe Ile Ser Ser Lys Phe Ser
    210                 215                 220

Gln Lys Ile Arg Tyr Val Phe Asn Leu Ala Glu Leu Ala Glu Leu Val
225                 230                 235                 240
```

-continued

Pro Met Glu Tyr Val Gly Ile Pro Glu Cys Ile Lys Gln Val Gln Glu
                245                 250                 255

Leu Asn Gly Lys Gln Asp Glu
            260

<210> SEQ ID NO 20
<211> LENGTH: 274
<212> TYPE: PRT
<213> ORGANISM: Mus musculus

<400> SEQUENCE: 20

Met Glu Gly Val Glu Leu Lys Glu Glu Trp Gln Asp Glu Asp Phe Pro
1               5                   10                  15

Ile Pro Leu Pro Glu Asp Asp Ser Ile Glu Ala Asp Thr Leu Asp Gly
            20                  25                  30

Thr Asp Pro Asp Arg Gln Pro Gly Ser Leu Glu Val Asn Gly Asn Lys
        35                  40                  45

Val Arg Lys Lys Leu Met Ala Pro Asp Ile Ser Leu Thr Leu Asp Pro
    50                  55                  60

Gly Glu Val Asp Leu Glu Gly Leu Asp Thr Pro Ser Glu Asn Ser Asp
65                  70                  75                  80

Glu Phe Glu Trp Glu Asp Asp Leu Pro Lys Pro Lys Thr Thr Glu Val
                85                  90                  95

Ile Arg Lys Gly Ser Ile Thr Glu Tyr Thr Ala Thr Glu Glu Lys Gly
            100                 105                 110

Asp Gly Arg Arg Trp Arg Met Phe Arg Ile Gly Glu Gln Asp His Gly
        115                 120                 125

Gly Tyr Tyr Gly Asp Gly Leu Asn Ala Ile Val Val Phe Ala Val Cys
    130                 135                 140

Phe Met Pro Glu Ser Gly Gln Pro Asn Tyr Arg Tyr Leu Met Asp Asn
145                 150                 155                 160

Leu Phe Lys Tyr Val Ile Gly Thr Leu Glu Leu Leu Val Ala Glu Asn
                165                 170                 175

Tyr Met Ile Ile Tyr Leu Asn Gly Ala Thr Thr Arg Arg Lys Met Pro
            180                 185                 190

Ser Leu Gly Trp Leu Arg Arg Cys Tyr Val His Pro Ser Trp Phe Ile
        195                 200                 205

Arg Thr Leu Leu Ala Val Thr Arg Pro Phe Ile Ser Ser Lys Phe Ser
    210                 215                 220

Gln Lys Ile Arg Tyr Val Phe Asn Leu Ala Glu Leu Ala Glu Leu Val
225                 230                 235                 240

Pro Met Glu Tyr Val Gly Ile Pro Glu Cys Ile Lys Gln Tyr Glu Glu
                245                 250                 255

Glu Lys Phe Lys Lys Arg Val Asp Gln Glu Pro Leu Asn Gly Lys Gln
            260                 265                 270

Glu Pro

<210> SEQ ID NO 21
<211> LENGTH: 153
<212> TYPE: PRT
<213> ORGANISM: Drosophila melanogaster

<400> SEQUENCE: 21

Tyr Thr Ala Ala Glu Glu Arg Arg Asp Ser Arg Asn Trp Gln Lys Ile
1               5                   10                  15

-continued

```
Thr Leu Pro Asp Gly Arg Thr Gly Tyr Gly Gly Gln Asn Ala Ile
            20                  25                  30

Val Ile Phe Cys Ala Cys His Leu Pro Asp Arg Ser Arg Ala Arg Tyr
            35                  40                  45

Ser Tyr Val Met Asp Asn Leu Phe Leu Tyr Val Val Lys Thr Leu Glu
 50                  55                  60

Gln Leu Val Thr Asp Asp Tyr Val Leu Ile Tyr Leu His Gly Gly Ser
 65                  70                  75                  80

Asn Arg Arg Asn Val Pro Pro Phe Pro Trp Leu Lys Arg Cys Tyr Val
                 85                  90                  95

His Pro Thr Phe Trp Ile Lys Ser Leu Val Trp Met Ala Arg Pro Phe
            100                 105                 110

Val Ser Thr Lys Phe Trp Arg Lys Leu Val Tyr Val Lys Ser Leu Glu
            115                 120                 125

Glu Leu Gly Met His Val Val Val Glu Lys Ala Ala Ile Pro Glu Lys
            130                 135                 140

Val Lys Gln Tyr Asp Ala Lys Arg His
145                 150
```

<210> SEQ ID NO 22
<211> LENGTH: 13
<212> TYPE: DNA
<213> ORGANISM: Artificial Sequence
<220> FEATURE:
<223> OTHER INFORMATION: Synthetic

<400> SEQUENCE: 22
ccagctctca tgg        13

<210> SEQ ID NO 23
<211> LENGTH: 13
<212> TYPE: RNA
<213> ORGANISM: Artificial Sequence
<220> FEATURE:
<223> OTHER INFORMATION: Synthetic

<400> SEQUENCE: 23
gccgccacca ugg        13

<210> SEQ ID NO 24
<211> LENGTH: 70
<212> TYPE: PRT
<213> ORGANISM: Mus musculus

<400> SEQUENCE: 24

```
Pro Ser Ser Asp Ala Glu Ser Ala Pro Ala Ser Ile Leu Phe Leu Leu
 1               5                  10                  15

Gly Ser Glu Gly Pro Gly Ser Val Ser Asp Ala Gln Leu His Pro Gly
            20                  25                  30

Arg Ala Arg Leu Cys Leu Pro Val Arg Arg Gly Cys Leu Ser Cys
            35                  40                  45

Arg Gly Val Ile Pro Ala Ser Ser Gln Cys Leu Phe Pro Ala Pro Met
 50                  55                  60

Gly Thr Thr Glu Ala Thr
 65                  70
```

<210> SEQ ID NO 25
<211> LENGTH: 55
<212> TYPE: PRT
<213> ORGANISM: Homo sapiens

```
<400> SEQUENCE: 25

Ala Ser Phe His Gln Ala Pro Arg Leu Gly Thr Ile Glu Lys Cys Pro
1               5                   10                  15

Pro Leu Cys Pro Ser Asp Ser Ala Glu Ala Ala Ser Ala Thr Glu Ile
            20                  25                  30

Ile Phe Trp Val Thr Arg Val Ser Arg Pro Leu Leu Phe Pro Ala Leu
        35                  40                  45

Met Gly Thr Thr Glu Ala Thr
    50                  55

<210> SEQ ID NO 26
<211> LENGTH: 314
<212> TYPE: PRT
<213> ORGANISM: Homo sapiens

<400> SEQUENCE: 26

Met Glu Gly Val Glu Leu Lys Glu Glu Trp Gln Asp Glu Asp Phe Pro
1               5                   10                  15

Ile Pro Leu Pro Glu Asp Asp Ser Ile Glu Ala Asp Ile Leu Ala Ile
            20                  25                  30

Thr Gly Pro Glu Asp Gln Pro Gly Ser Leu Glu Val Asn Gly Asn Lys
        35                  40                  45

Val Arg Lys Lys Leu Met Ala Pro Asp Ile Ser Leu Thr Leu Asp Pro
    50                  55                  60

Ser Asp Gly Ser Val Leu Ser Asp Leu Asp Glu Ser Gly Glu Ile
65                  70                  75                  80

Asp Leu Asp Gly Leu Asp Thr Pro Ser Glu Asn Ser Asn Glu Phe Glu
                85                  90                  95

Trp Glu Asp Asp Leu Pro Lys Pro Lys Thr Thr Glu Val Ile Arg Lys
            100                 105                 110

Gly Ser Ile Thr Glu Tyr Thr Ala Glu Glu Lys Glu Asp Gly Arg
        115                 120                 125

Arg Trp Arg Met Phe Arg Ile Gly Glu Gln Asp His Arg Val Asp Met
    130                 135                 140

Lys Ala Ile Glu Pro Tyr Lys Lys Val Ile Ser His Gly Gly Tyr Tyr
145                 150                 155                 160

Gly Asp Gly Leu Asn Ala Ile Val Val Phe Ala Val Cys Phe Met Pro
                165                 170                 175

Glu Ser Ser Gln Pro Asn Tyr Arg Tyr Leu Met Asp Asn Leu Phe Lys
            180                 185                 190

Tyr Val Ile Gly Thr Leu Glu Leu Leu Val Ala Glu Asn Tyr Met Ile
        195                 200                 205

Val Tyr Leu Asn Gly Ala Thr Thr Arg Arg Lys Met Pro Ser Leu Gly
    210                 215                 220

Trp Leu Arg Lys Cys Tyr Gln Gln Ile Asp Arg Arg Leu Arg Lys Asn
225                 230                 235                 240

Leu Lys Ser Leu Ile Ile Val His Pro Ser Trp Phe Ile Arg Thr Leu
                245                 250                 255

Leu Ala Val Thr Arg Pro Phe Ile Ser Ser Lys Phe Ser Gln Lys Ile
            260                 265                 270

Arg Tyr Val Phe Asn Leu Ala Glu Leu Ala Glu Leu Val Pro Met Glu
        275                 280                 285

Tyr Val Gly Ile Pro Glu Cys Ile Lys Gln Val Asp Gln Glu Leu Asn
    290                 295                 300
```

```
Gly Lys Gln Asp Glu Pro Lys Asn Glu Gln
305                 310

<210> SEQ ID NO 27
<211> LENGTH: 314
<212> TYPE: PRT
<213> ORGANISM: Mus musculus

<400> SEQUENCE: 27

Met Glu Gly Val Glu Leu Lys Glu Glu Trp Gln Asp Glu Asp Phe Pro
1               5                   10                  15

Ile Pro Leu Pro Glu Asp Asp Ser Ile Glu Ala Asp Ile Leu Ala Ile
            20                  25                  30

Thr Gly Pro Glu Asp Gln Pro Gly Ser Leu Glu Val Asn Gly Asn Lys
        35                  40                  45

Val Arg Lys Lys Leu Met Ala Pro Asp Ile Ser Leu Thr Leu Asp Pro
50                  55                  60

Ser Asp Gly Ser Val Leu Ser Asp Asp Leu Asp Glu Ser Gly Glu Ile
65                  70                  75                  80

Asp Leu Asp Gly Leu Asp Thr Pro Ser Glu Asn Ser Asn Glu Phe Glu
                85                  90                  95

Trp Glu Asp Asp Leu Pro Lys Pro Lys Thr Thr Glu Val Ile Arg Lys
            100                 105                 110

Gly Ser Ile Thr Glu Tyr Thr Ala Ala Glu Glu Lys Glu Asp Gly Arg
        115                 120                 125

Arg Trp Arg Met Phe Arg Ile Gly Glu Gln Asp His Arg Val Asp Met
130                 135                 140

Lys Ala Ile Glu Pro Tyr Lys Lys Val Ile Ser His Gly Gly Tyr Tyr
145                 150                 155                 160

Gly Asp Gly Leu Asn Ala Ile Val Val Phe Ala Val Cys Phe Met Pro
                165                 170                 175

Glu Ser Ser Gln Pro Asn Tyr Arg Tyr Leu Met Asp Asn Leu Phe Lys
            180                 185                 190

Tyr Val Ile Gly Thr Leu Glu Leu Leu Val Ala Glu Asn Tyr Met Ile
        195                 200                 205

Val Tyr Leu Asn Gly Ala Thr Thr Arg Arg Lys Met Pro Ser Leu Gly
210                 215                 220

Trp Leu Arg Lys Cys Tyr Gln Gln Ile Asp Arg Arg Leu Arg Lys Asn
225                 230                 235                 240

Leu Lys Ser Leu Ile Ile Val His Pro Ser Trp Phe Ile Arg Thr Leu
                245                 250                 255

Leu Ala Val Thr Arg Pro Phe Ile Ser Ser Lys Phe Ser Gln Lys Ile
            260                 265                 270

Arg Tyr Val Phe Asn Leu Ala Glu Leu Ala Glu Leu Val Pro Met Glu
        275                 280                 285

Tyr Val Gly Ile Pro Glu Cys Ile Lys Gln Val Asp Gln Glu Leu Asn
290                 295                 300

Gly Lys Gln Asp Glu Pro Lys Asn Glu Gln
305                 310

<210> SEQ ID NO 28

<400> SEQUENCE: 28

000
```

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
ctggaactac aggaatgtac c                                              21

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
tgtgttcacc tactacctac                                                20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
aaatgcatcc tgctgccttc                                                20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
caccagtgca gagaatcctt                                                20

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
atgacaagca ctccagcctg a                                              21

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
gccgtttgac gtgcattgtt                                                20

<210> SEQ ID NO 35
<211> LENGTH: 19
<212> TYPE: DNA
<213> ORGANISM: Artificial Sequence
<220> FEATURE:
<223> OTHER INFORMATION: Synthetic

```
<400> SEQUENCE: 35
gactcctagt tgtctccct                                              19

<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
agacagagta agacaaaaac acc                                         23

<210> SEQ ID NO 37
<211> LENGTH: 17
<212> TYPE: DNA
<213> ORGANISM: Artificial Sequence
<220> FEATURE:
<223> OTHER INFORMATION: Synthetic

<400> SEQUENCE: 37
tggcttattt tctcatc                                                17

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
gcacgaaaac agactaatac gg                                          22

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
ccgatggatc tacagttgca                                             20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
ttacaggagt gagccaccat                                             20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
ttgtactcac tgtgtgccag                                             20

<210> SEQ ID NO 42
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 42
ttagaagccc gtgttggaac                                              20

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
tagtccaggg attggcaa                                                18

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
agccctaata ctcgcttctg                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
tctgctgtag tatcctcttc                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
tttctgctct tgcttcacgg                                              20

<210> SEQ ID NO 47
<211> LENGTH: 19
<212> TYPE: DNA
<213> ORGANISM: Artificial Sequence
<220> FEATURE:
<223> OTHER INFORMATION: Synthetic

<400> SEQUENCE: 47
aaagaccaaa gtctggcag                                               19

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
```
gatccaatgt gacatgccac 20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
tctctgggct gtgtgagagc 20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
agcttgcagt gagccgagat 20

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
agcaatatcc gctcttcctg 20

<210> SEQ ID NO 52
<211> LENGTH: 19
<212> TYPE: DNA
<213> ORGANISM: Artificial Sequence
<220> FEATURE:
<223> OTHER INFORMATION: Synthetic

<400> SEQUENCE: 52
cacacatagg gacaaagag 19

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
gatttgagaa gatgtcagtt t 21

<210> SEQ ID NO 54
<211> LENGTH: 18
<212> TYPE: DNA
<213> ORGANISM: Artificial Sequence
<220> FEATURE:
<223> OTHER INFORMATION: Synthetic

<400> SEQUENCE: 54
cacttgtgct gagactct 18

<210> SEQ ID NO 55
<211> LENGTH: 20
<212> TYPE: DNA

<213> ORGANISM: Artificial Sequence
<220> FEATURE:
<223> OTHER INFORMATION: Synthetic

<400> SEQUENCE: 55
gttgcatttc agacctctcc                                                      20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
tcttggatga gaaccaactc                                                      20

<210> SEQ ID NO 57
<211> LENGTH: 18
<212> TYPE: DNA
<213> ORGANISM: Artificial Sequence
<220> FEATURE:
<223> OTHER INFORMATION: Synthetic

<400> SEQUENCE: 57
aggactcaca agtggtttg                                                       18

<210> SEQ ID NO 58
<211> LENGTH: 21
<212> TYPE: DNA
<213> ORGANISM: Artificial Sequence
<220> FEATURE:
<223> OTHER INFORMATION: Synthetic

<400> SEQUENCE: 58
tagtaagcca agatcactcc c                                                    21

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
ctgtgatttg tggagtgtgg                                                      20

<210> SEQ ID NO 60
<211> LENGTH: 19
<212> TYPE: DNA
<213> ORGANISM: Artificial Sequence
<220> FEATURE:
<223> OTHER INFORMATION: Synthetic

<400> SEQUENCE: 60
gaagacgtaa catgtccag                                                       19

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
gcaggttgca gaataccttg                                                      20

-continued

```
<210> SEQ ID NO 62
<211> LENGTH: 19
<212> TYPE: DNA
<213> ORGANISM: Artificial Sequence
<220> FEATURE:
<223> OTHER INFORMATION: Synthetic

<400> SEQUENCE: 62
gactatgaag ggagaagta                                               19
```